United States Patent [19]
Drolet

[11] Patent Number: 5,620,463
[45] Date of Patent: Apr. 15, 1997

US005620463A

[54] ELECTROPHYSIOLOGICAL CONDITIONING SYSTEM AND METHOD

[75] Inventor: Roland A. Drolet, Quebec, Canada

[73] Assignee: Free World Trust, Phoenix, Ariz.

[21] Appl. No.: 256,015

[22] PCT Filed: Dec. 9, 1992

[86] PCT No.: PCT/CA92/00538

§ 371 Date: Aug. 30, 1994

§ 102(e) Date: Aug. 30, 1994

[87] PCT Pub. No.: WO93/12835

PCT Pub. Date: Jul. 8, 1993

[30] Foreign Application Priority Data

Dec. 20, 1991 [CA] Canada ................................. 2058179

[51] Int. Cl.$^6$ ................................. A61N 1/18; A61N 2/04
[52] U.S. Cl. ................................................................ 607/3
[58] Field of Search ......................... 607/3, 65, 72

[56] References Cited

FOREIGN PATENT DOCUMENTS

| 1150361 | 7/1983 | Canada . |
|---|---|---|
| 0104793 | 4/1984 | European Pat. Off. . |
| 0160703 | 11/1985 | European Pat. Off. . |
| 0189620 | 8/1986 | European Pat. Off. . |
| 0244784 | 11/1987 | European Pat. Off. . |
| 2156679 | 10/1985 | United Kingdom . |

Primary Examiner—William E. Kamm
Assistant Examiner—Scott M. Getzow
Attorney, Agent, or Firm—Longacre & White

[57] ABSTRACT

Electrophysiological conditioning system including conditioning applicators transmitting electromagnetic conditioning signals capable of producing basis physiological effects of relaxation of the nervous system, stimulation of the blood circulation and stimulation of normal cell repair and regeneration, and capable of enhancing the natural self-defense and healing mechanisms of man and animals. The method of use is also disclosed.

30 Claims, 66 Drawing Sheets

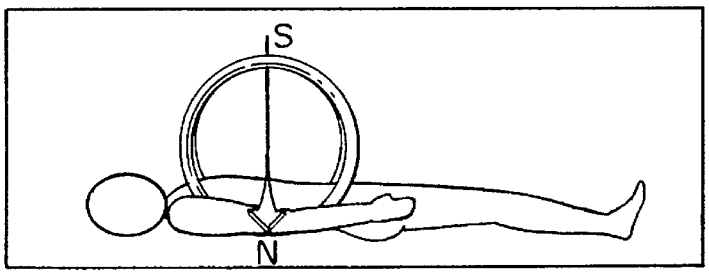
Fig. 1g
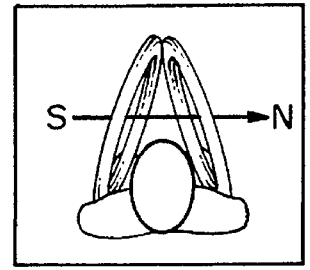
Fig. 1g²
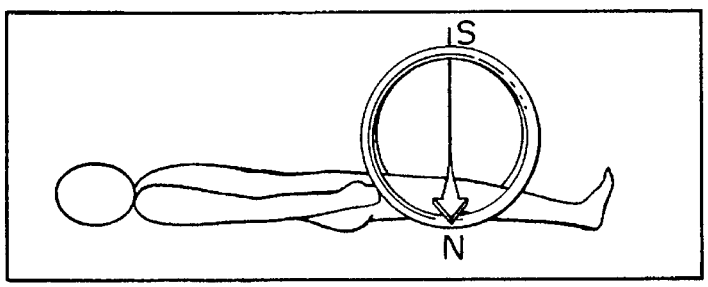
Fig. 1h
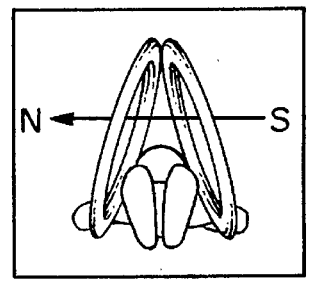
Fig. 1h²
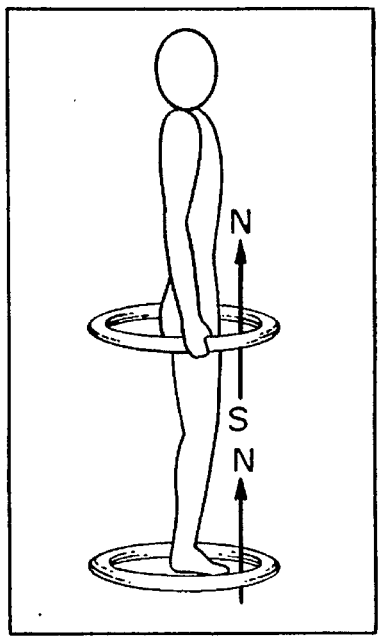
Fig. 1i
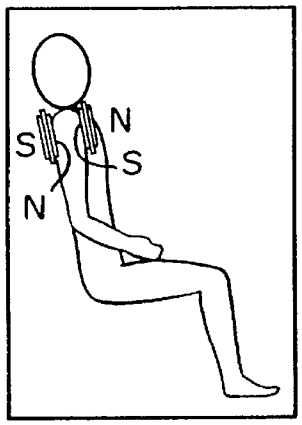
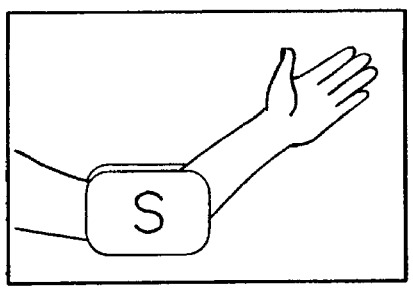
Fig. 1j
Fig. 1k

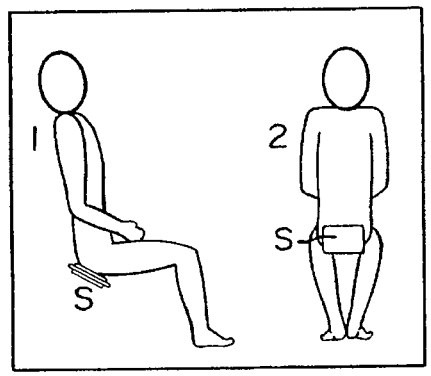
Fig. 1ℓ
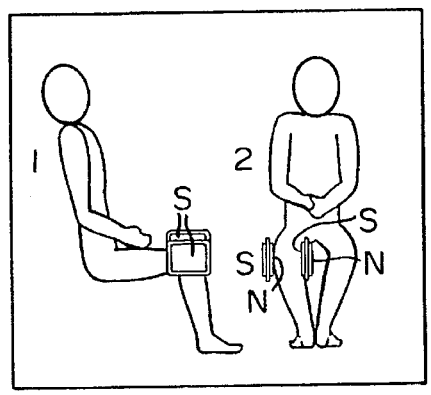
Fig. 1m
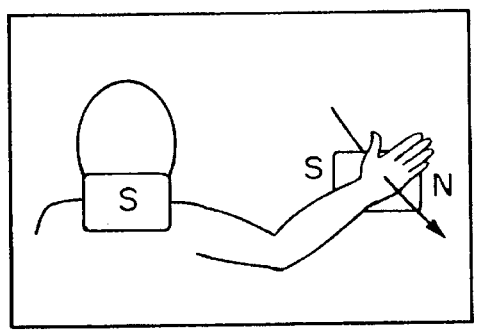
Fig. 1n
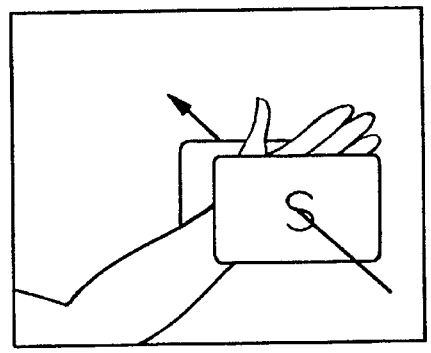
Fig. 1o
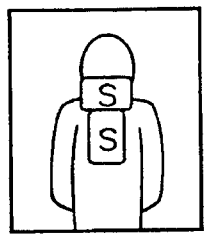
Fig. 1p
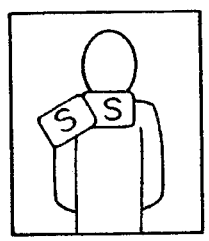
Fig. 1q
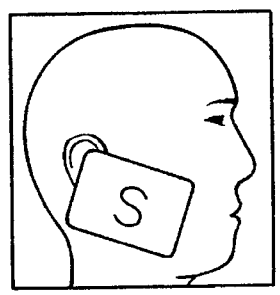
Fig. 1r

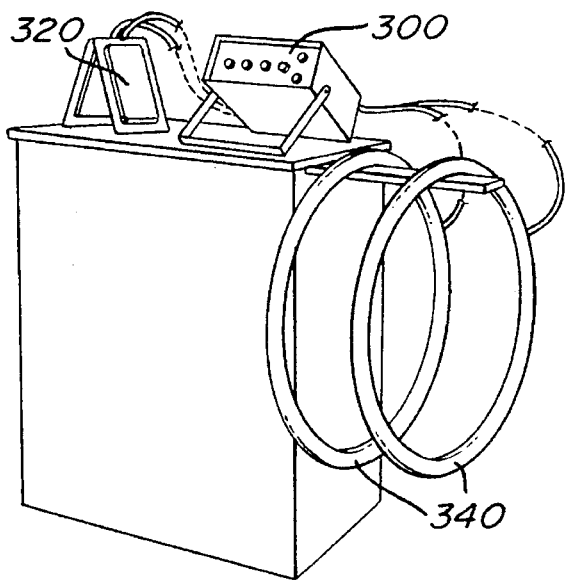
Fig. 2f
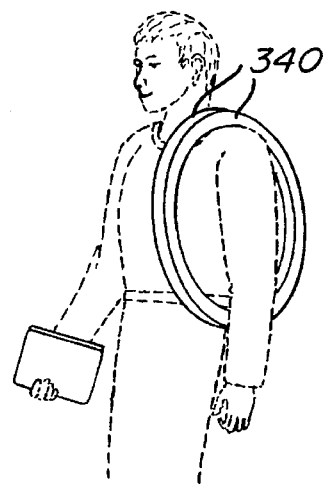
Fig. 2g
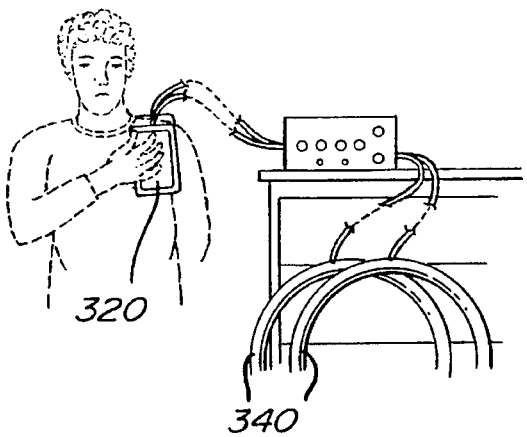
Fig. 2h¹
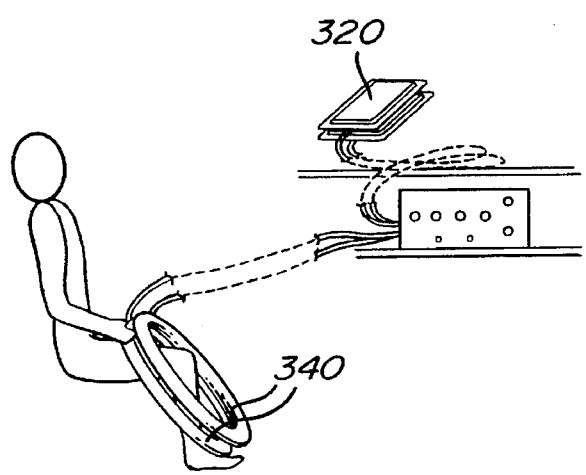
Fig. 2h²

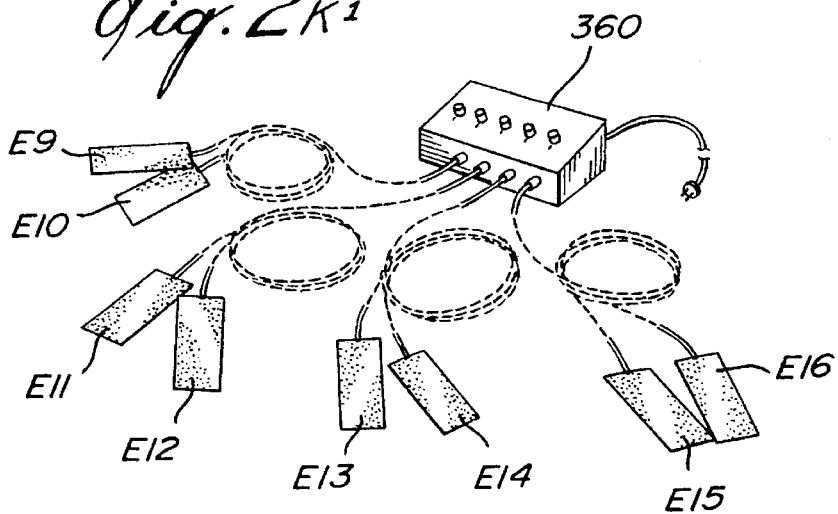
Fig. 2K1
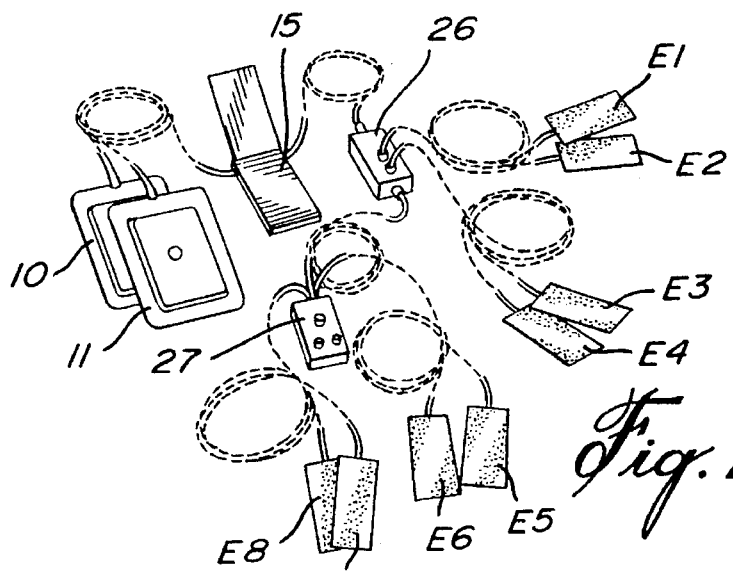
Fig. 2K2
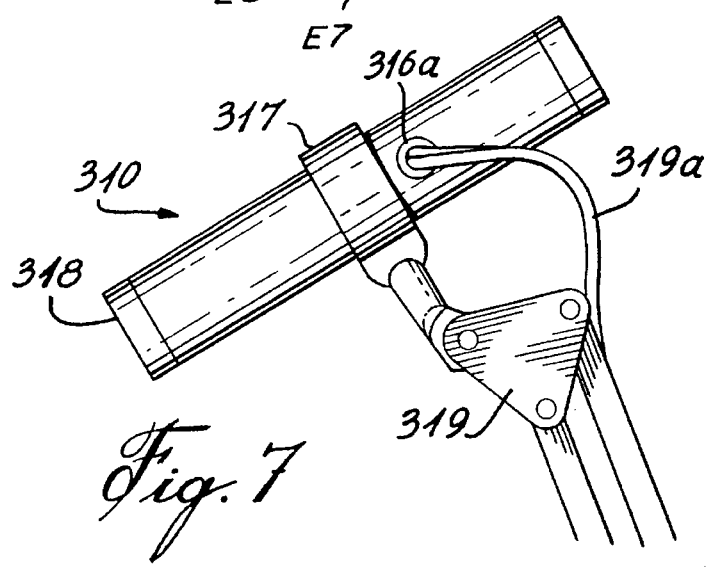
Fig. 7

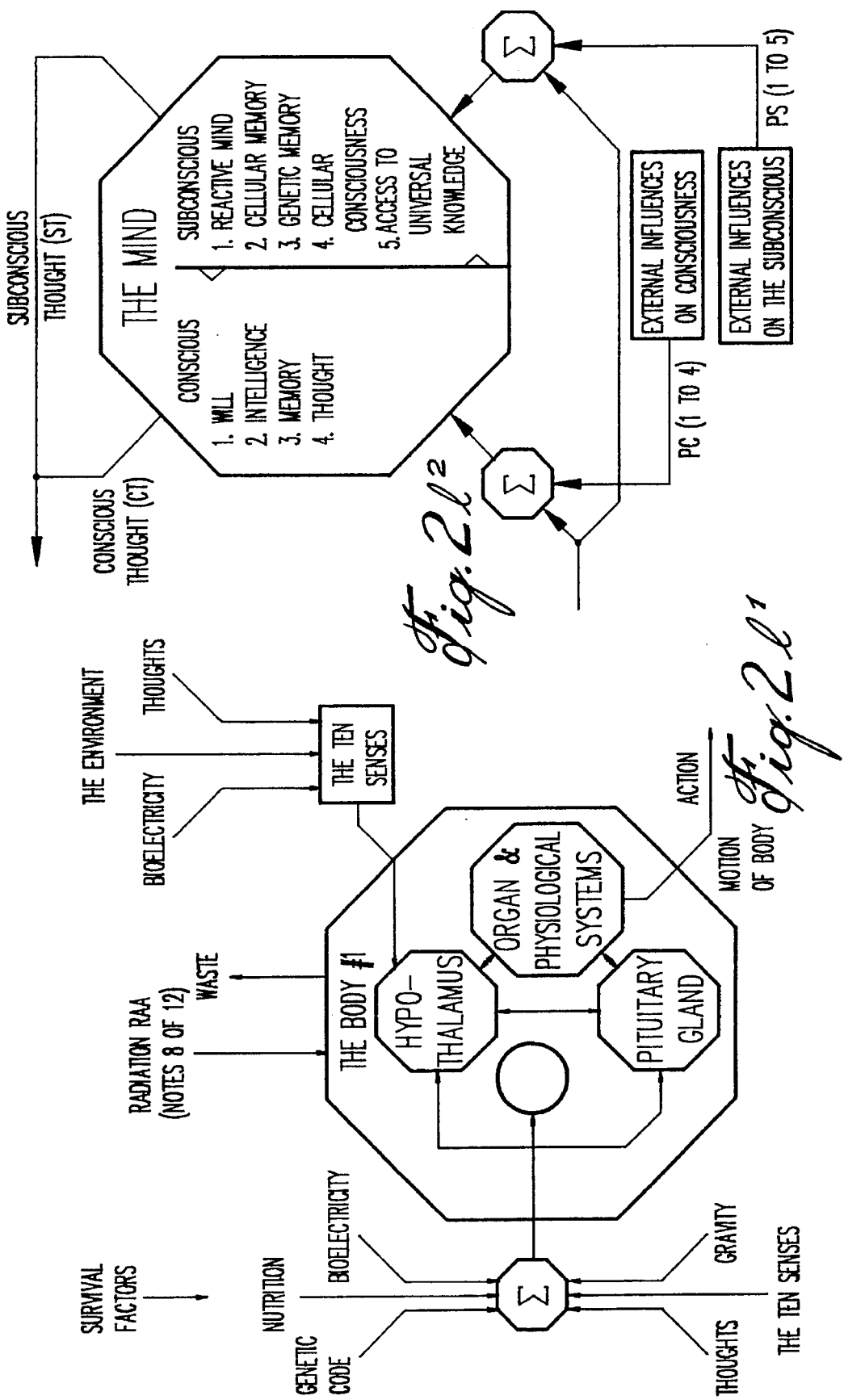

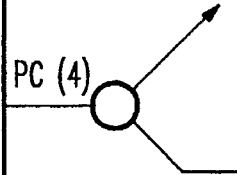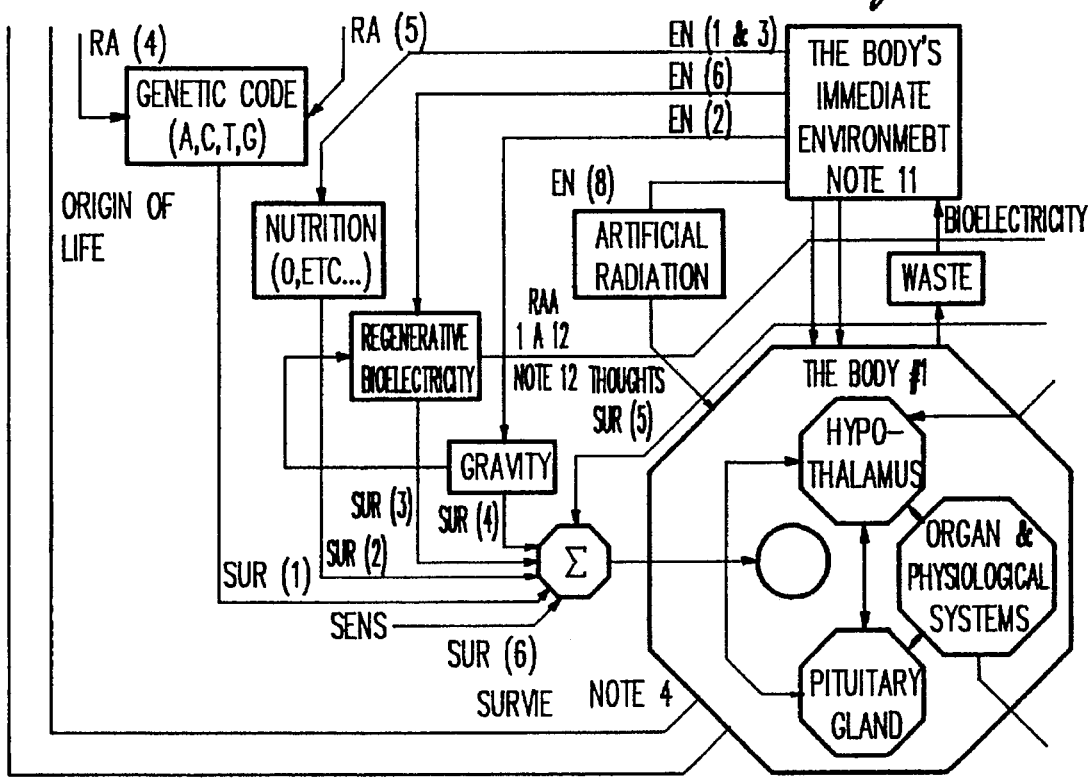

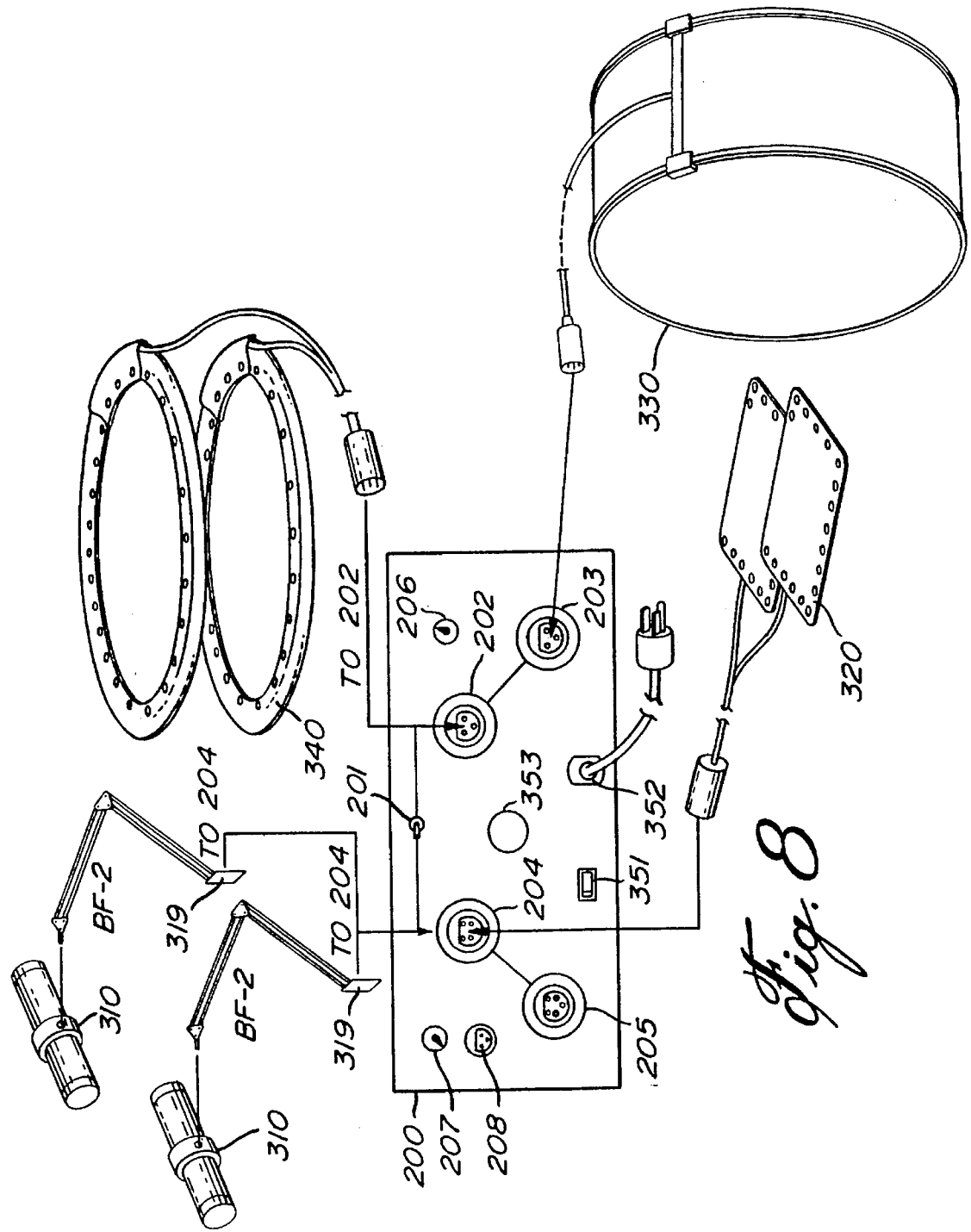

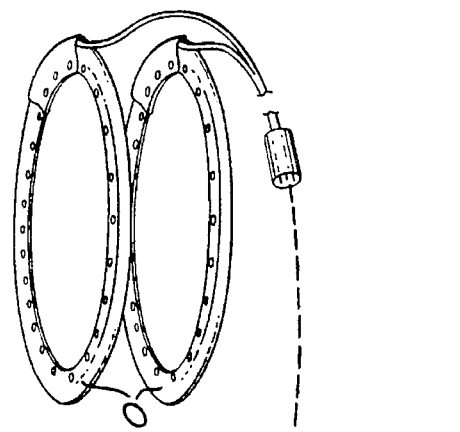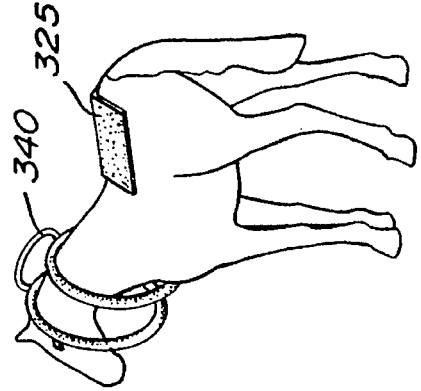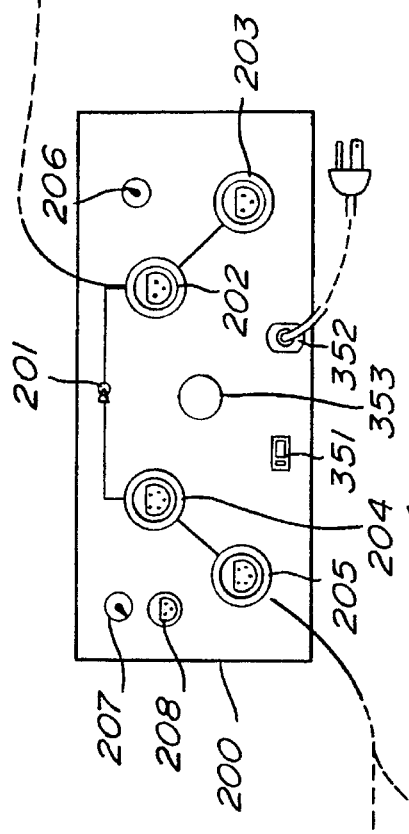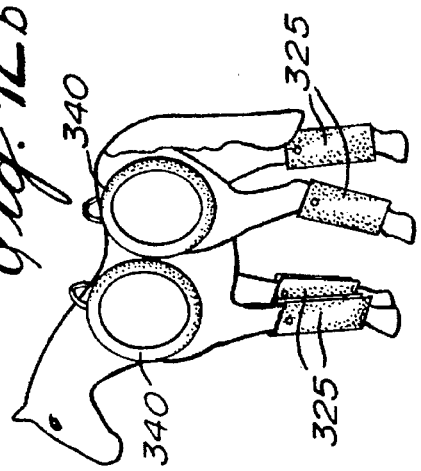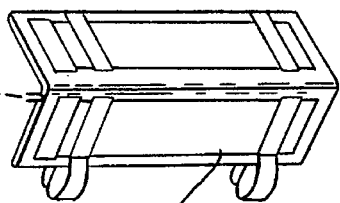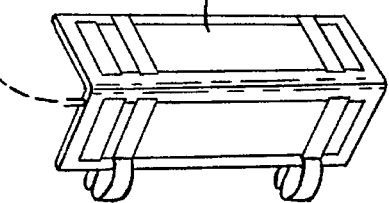
Fig. 12
Fig. 12a
Fig. 12b

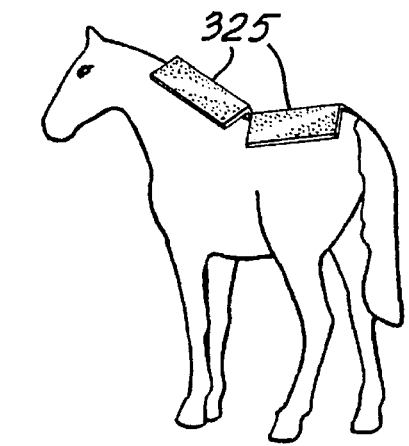
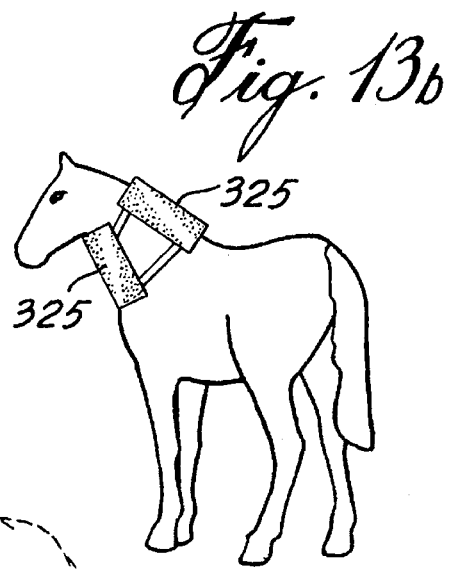
Fig. 13a
Fig. 13b
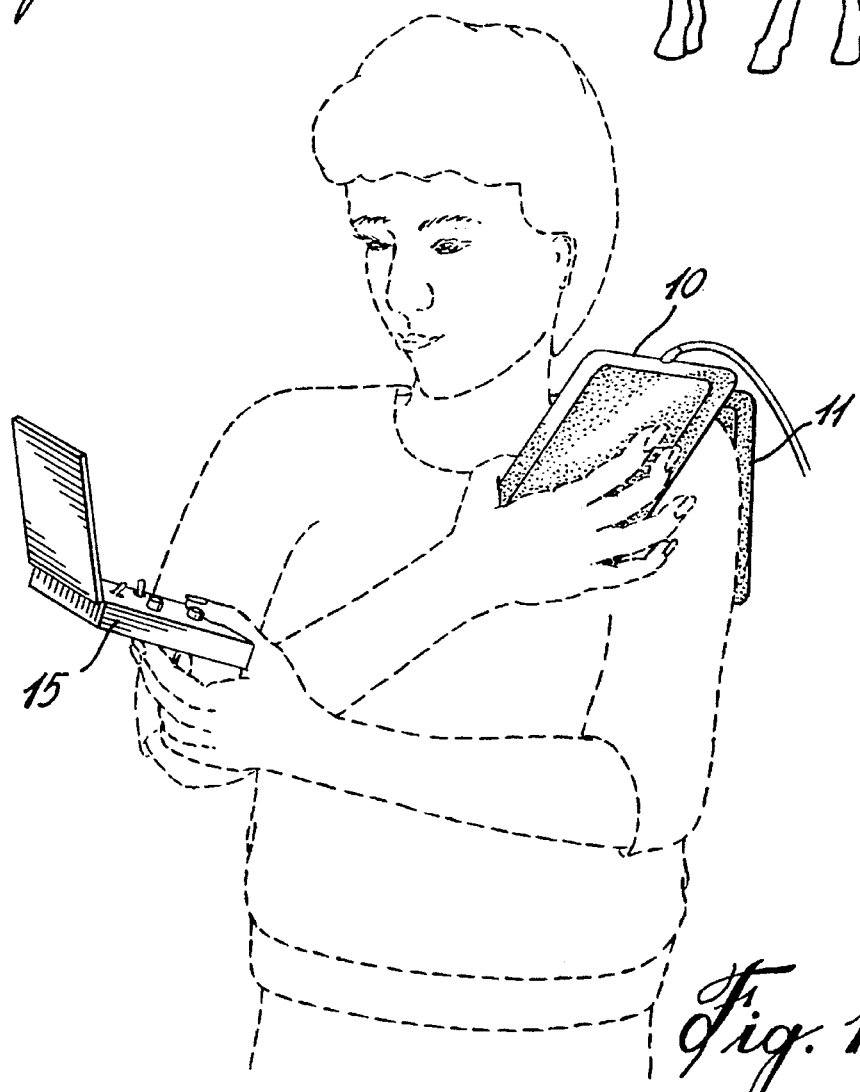
Fig. 15

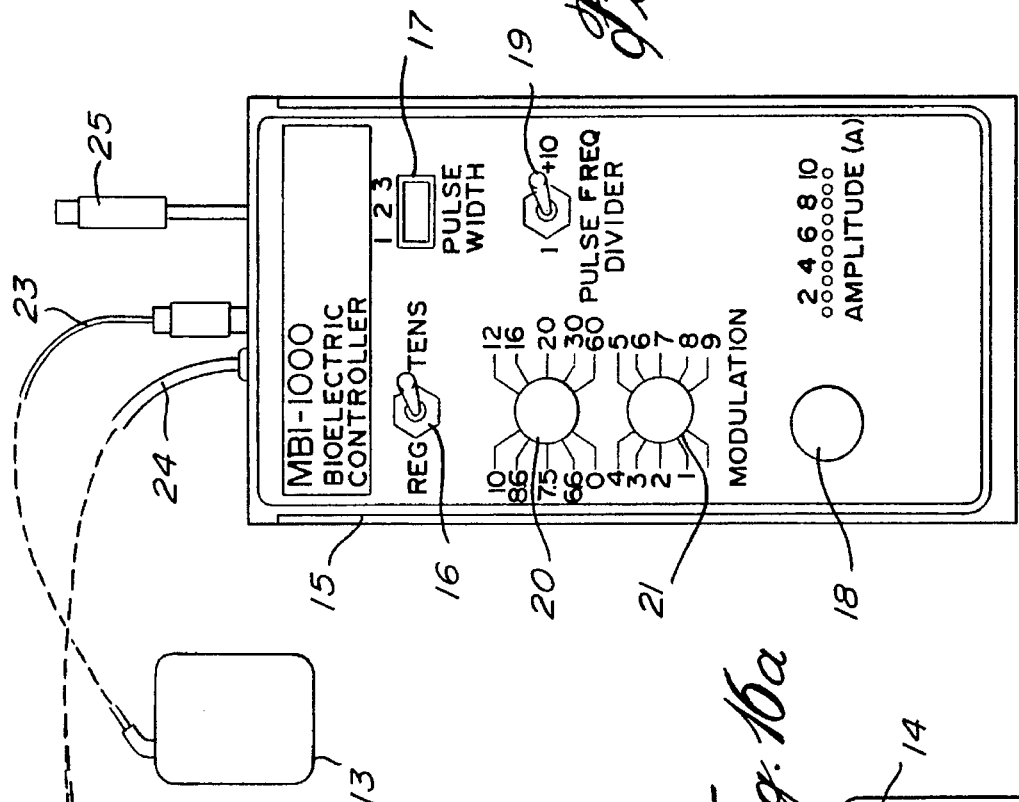
Fig. 16
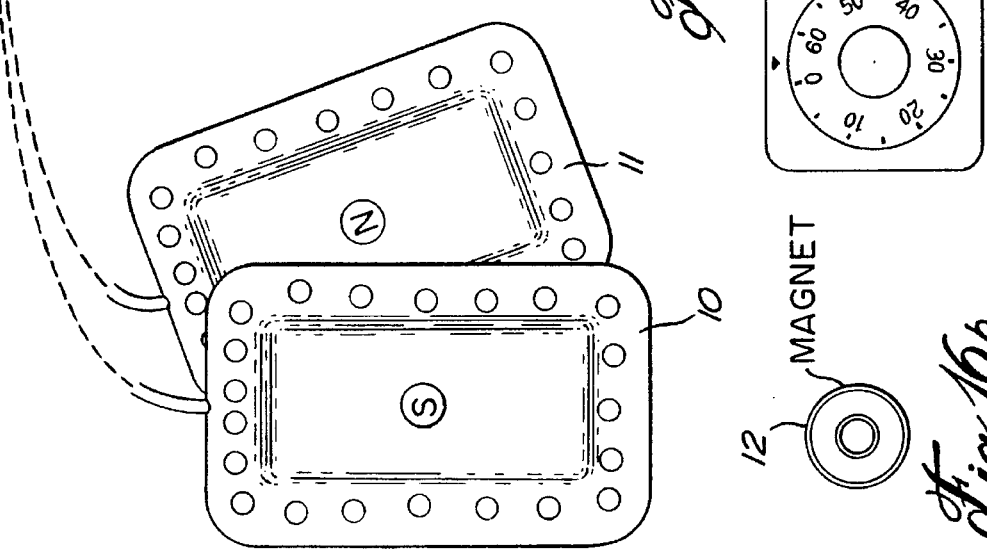
Fig. 16a
Fig. 16b

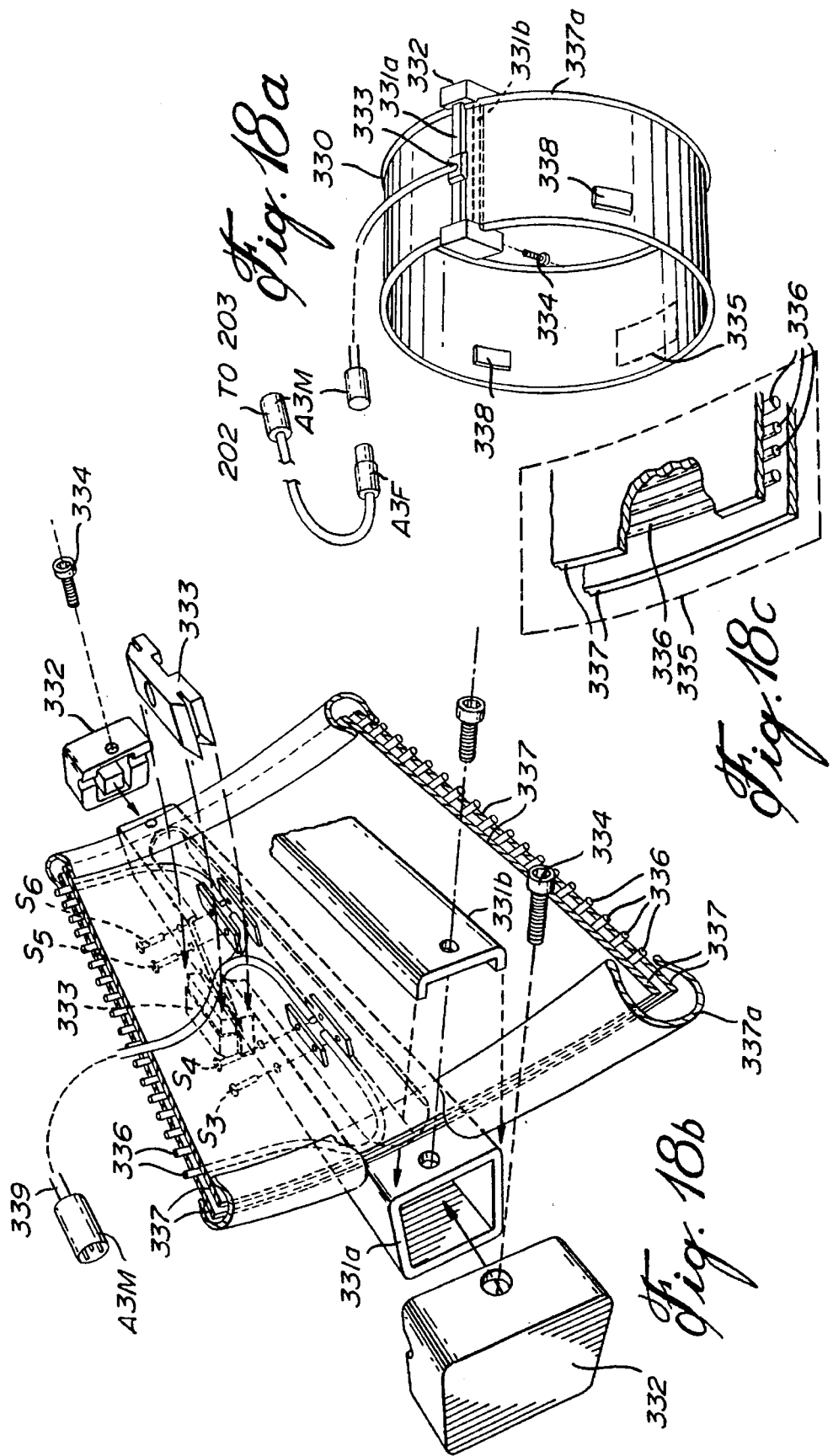

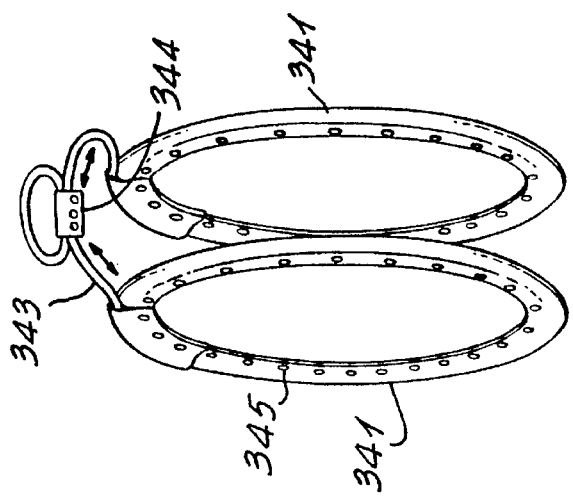
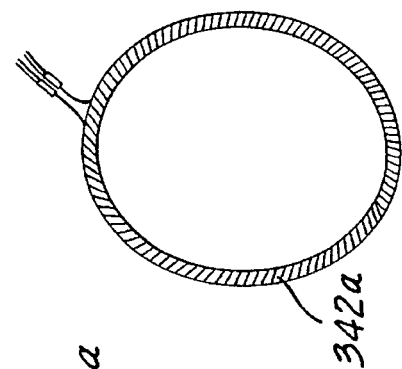
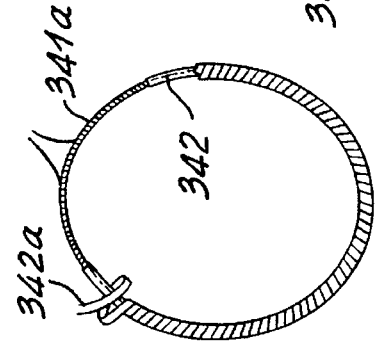
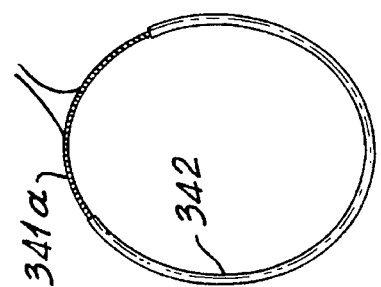
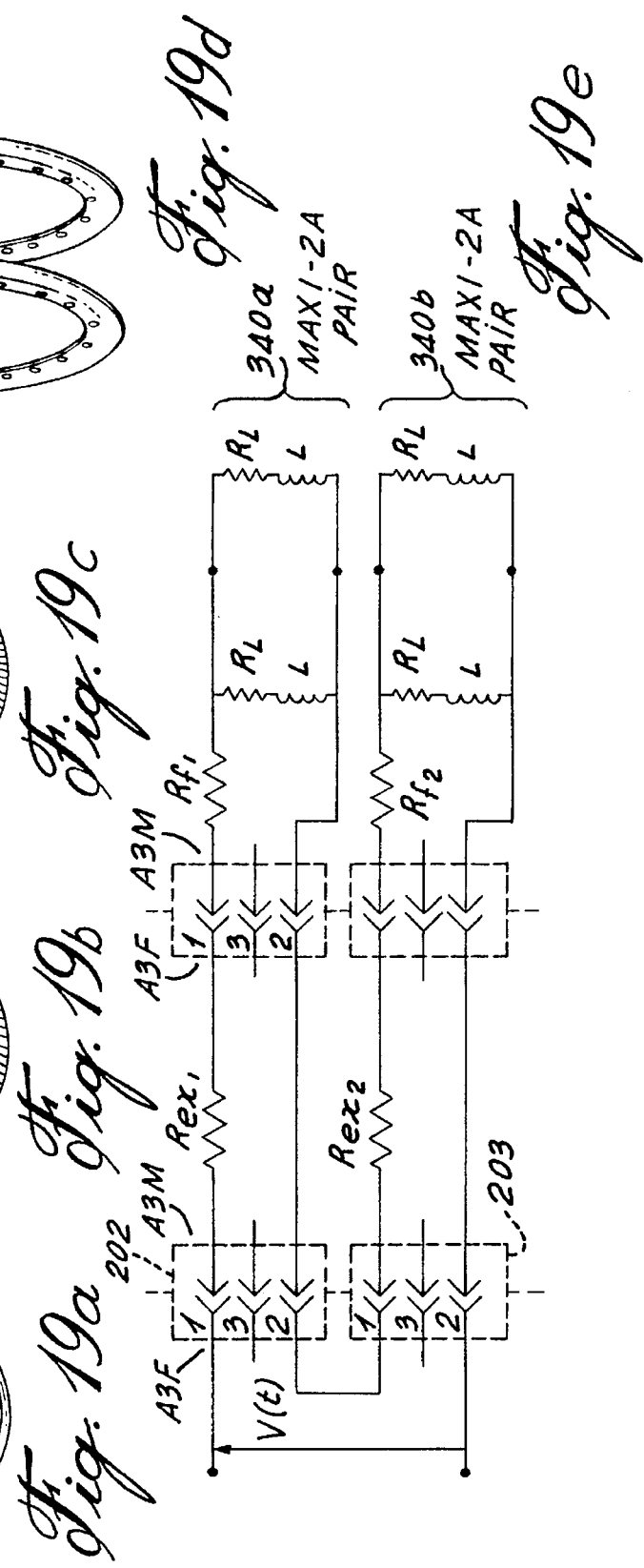

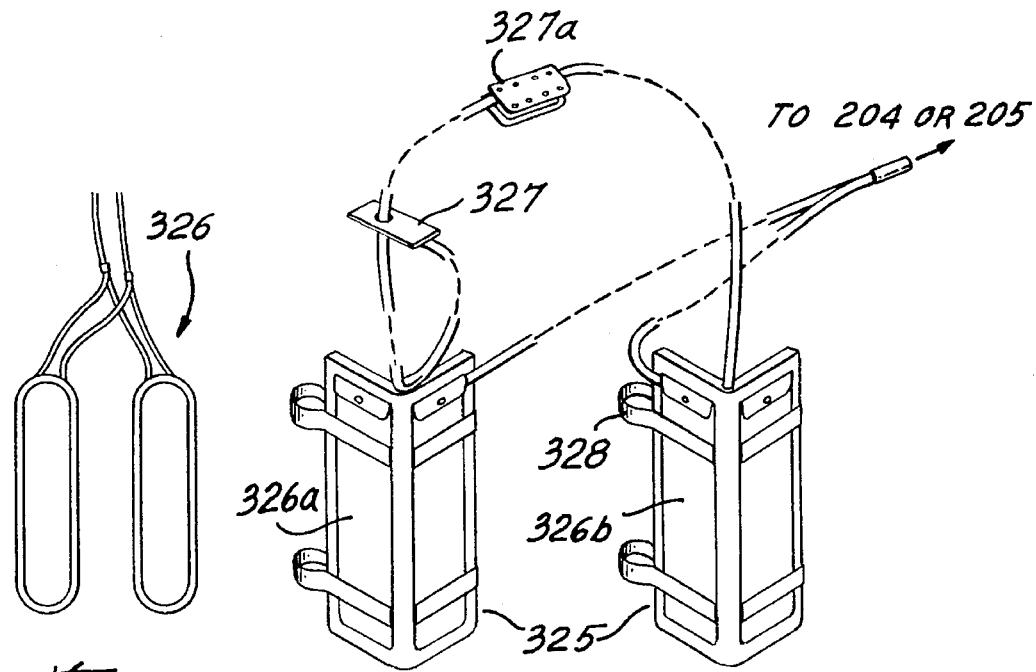
Fig. 20b    Fig. 20a
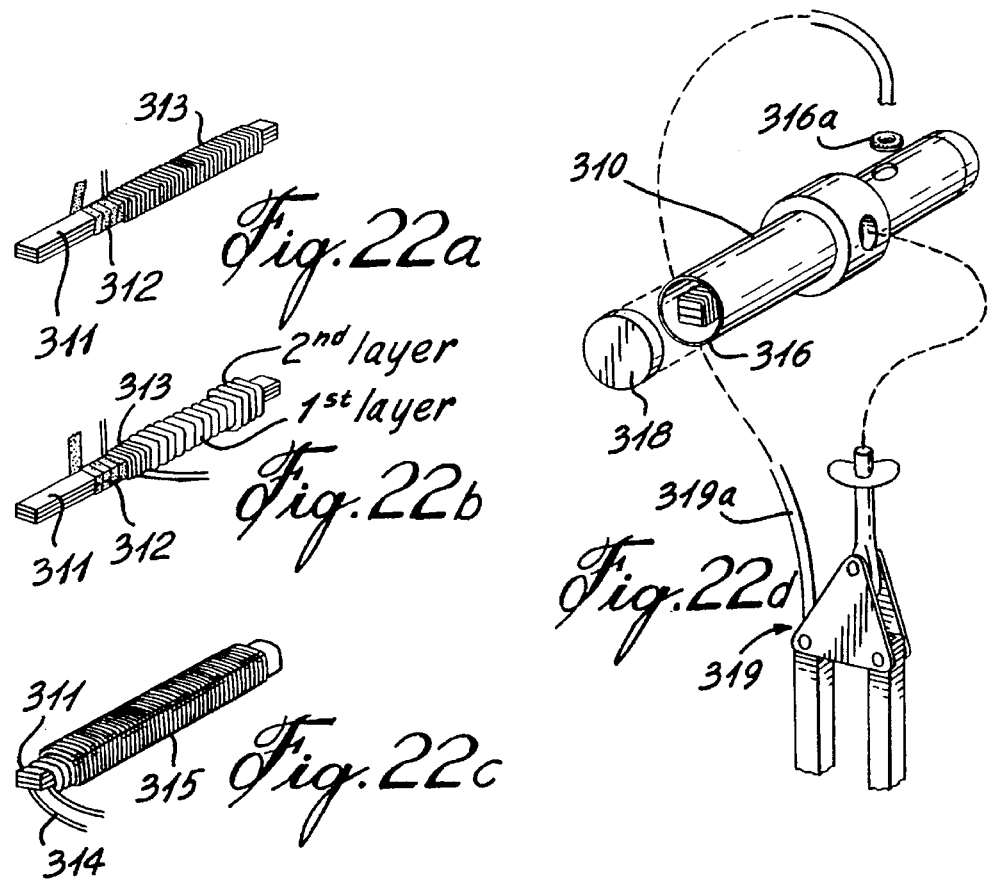
Fig. 22a
Fig. 22b
Fig. 22c
Fig. 22d

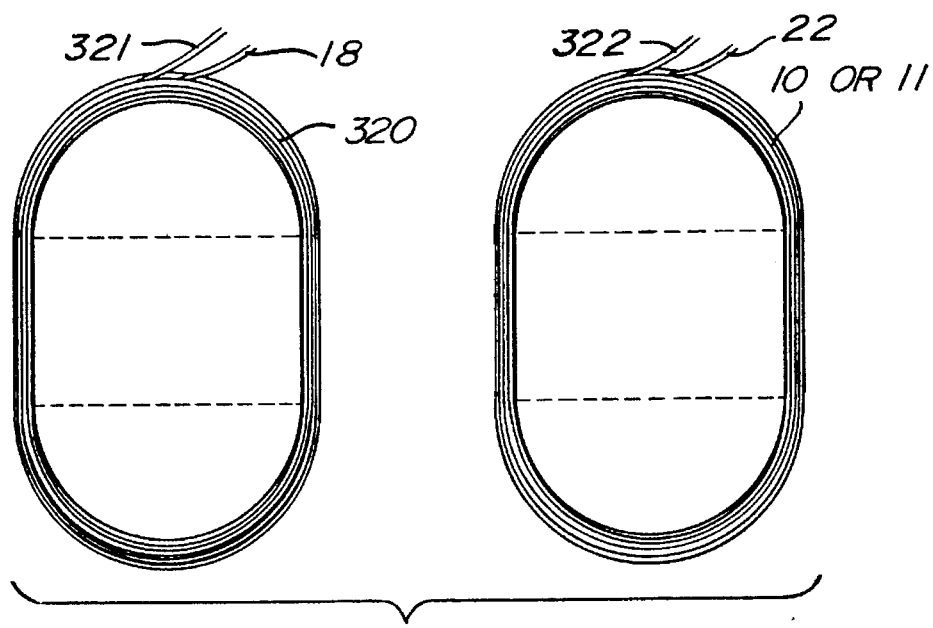
Fig. 21b
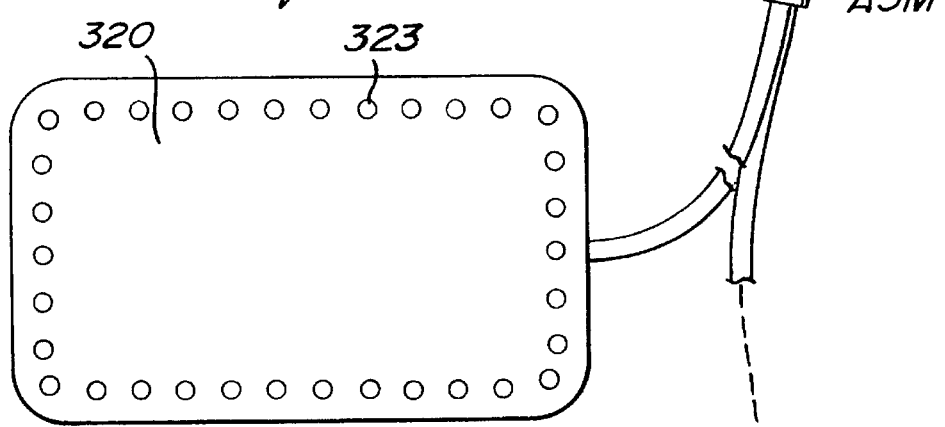
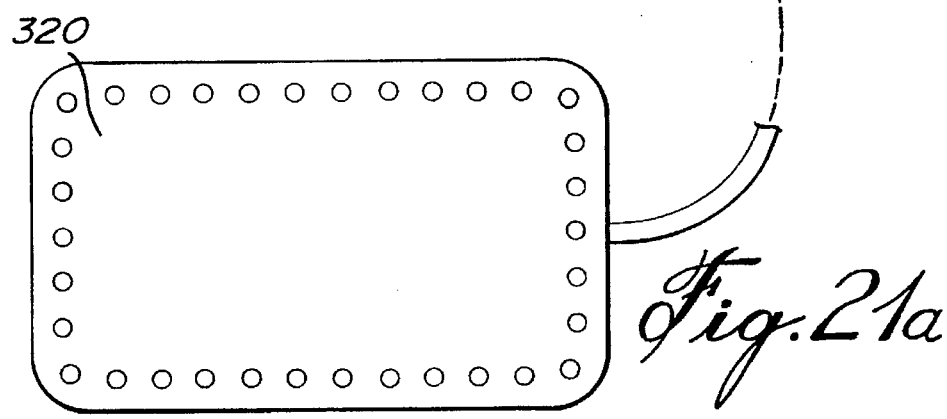
Fig. 21a

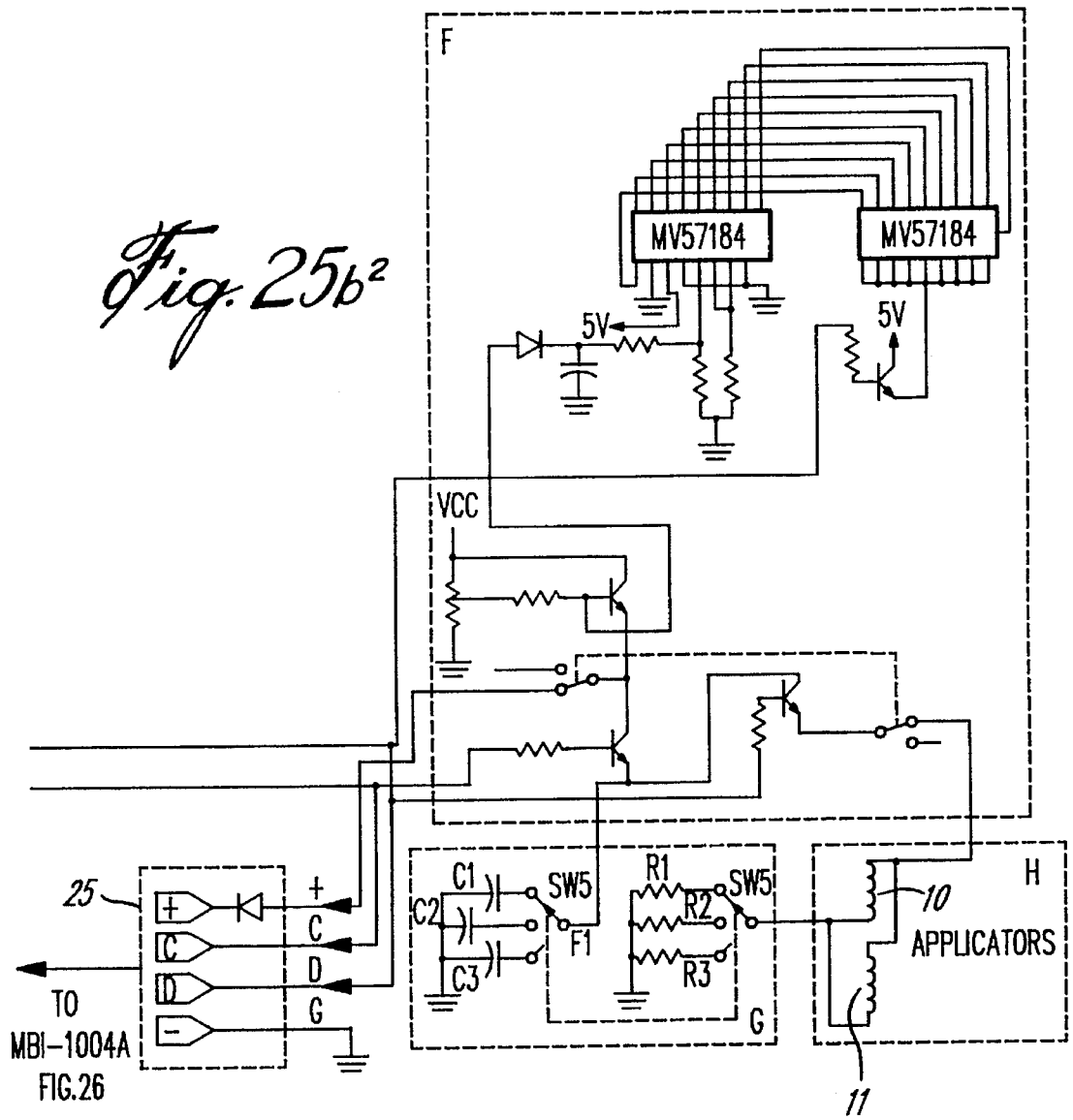

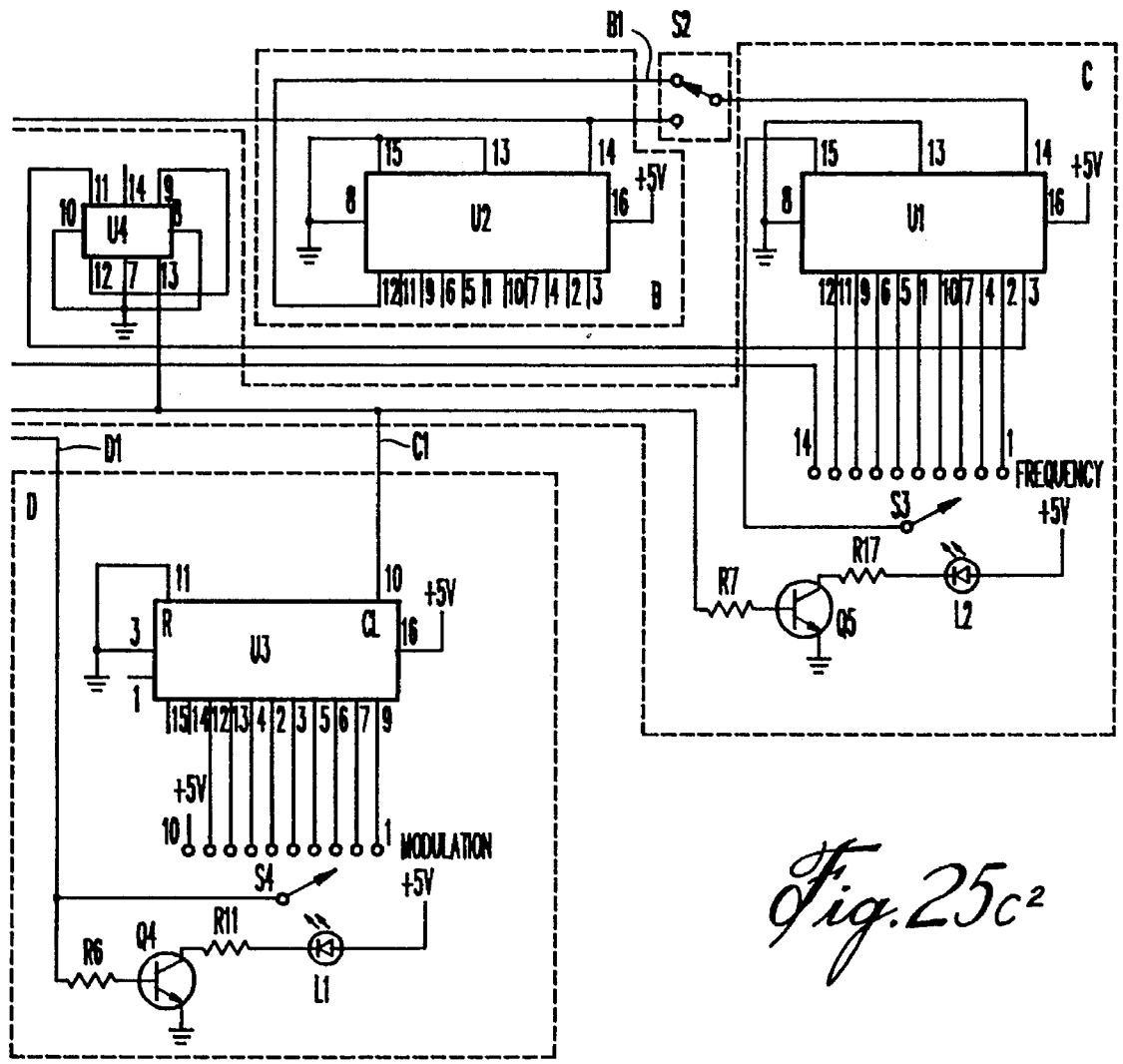
Fig. 25c²
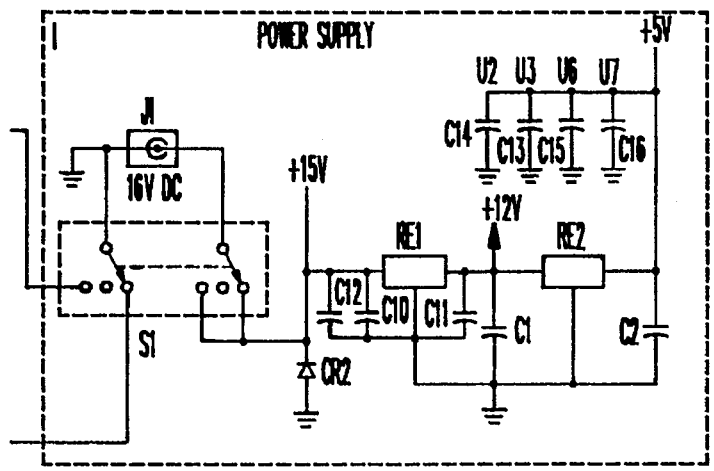

CURRENT IN 6.2Ω RESISTOR
FOR P.W.=0.1 MSEC POSITION
(OTHER PARAMETERS AS FOR FIG.26d)

MBI-1004A OR MBI-1004B
OUTPUT VOLTAGE ON E1 TO E8, BY
PAIRS, FOR P.W.=0.1 MSEC POSITION;
$f_b$=60pps; A=10 (ON MBI-1000);
$V_{out}$=MAX (ON MBI-1004)
WITH A 10kΩ LOAD RESISTOR.

MBI-1004A OR MBI-1004B
OUTPUT VOLTAGE ON E1 TO E8, BY PAIRS
FOR P.W. = 0.2 MSEC POSITION;
Fb=60pps; A=10 (ON MBI-1000);
Vout = MAX (ON MBI-1004);
WITH A 10 kΩ LOAD RESISTOR.

CURRENT IN THE 2.7Ω RESISTOR
FOR P.W. = 0.2 MSEC POSITION;
(OTHER PARAMETERS : SEE FIG.26f)

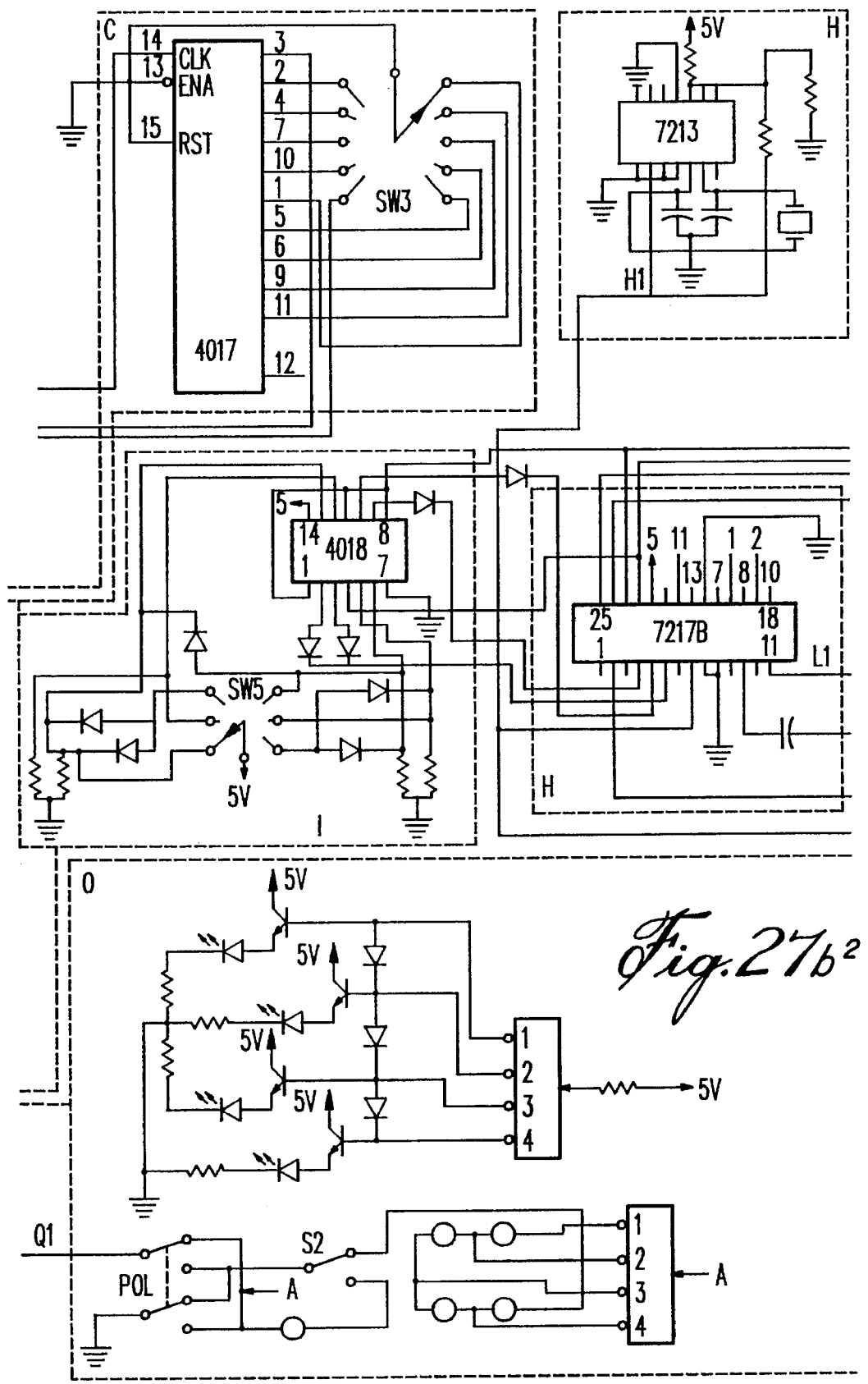
Fig. 27b²

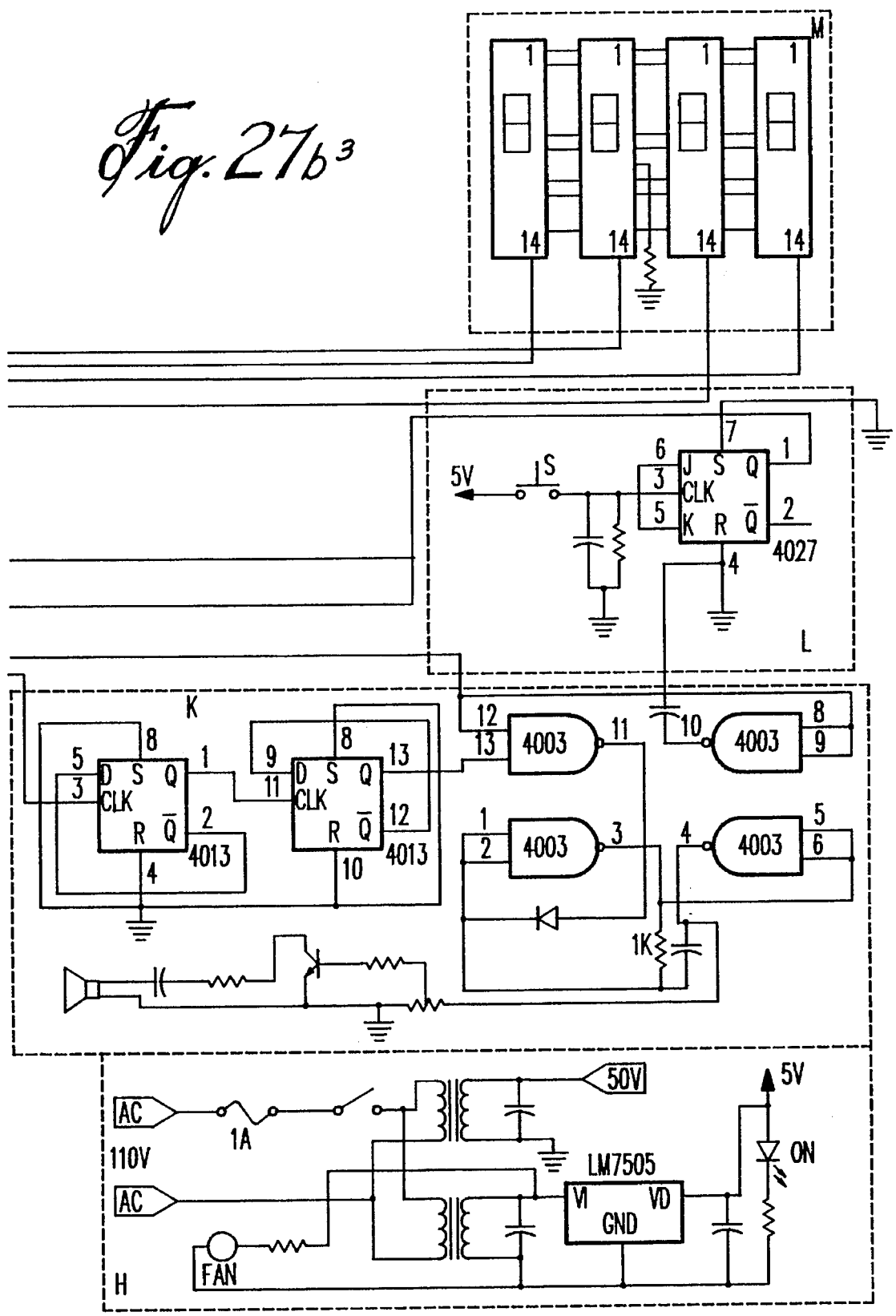
Fig. 27b³

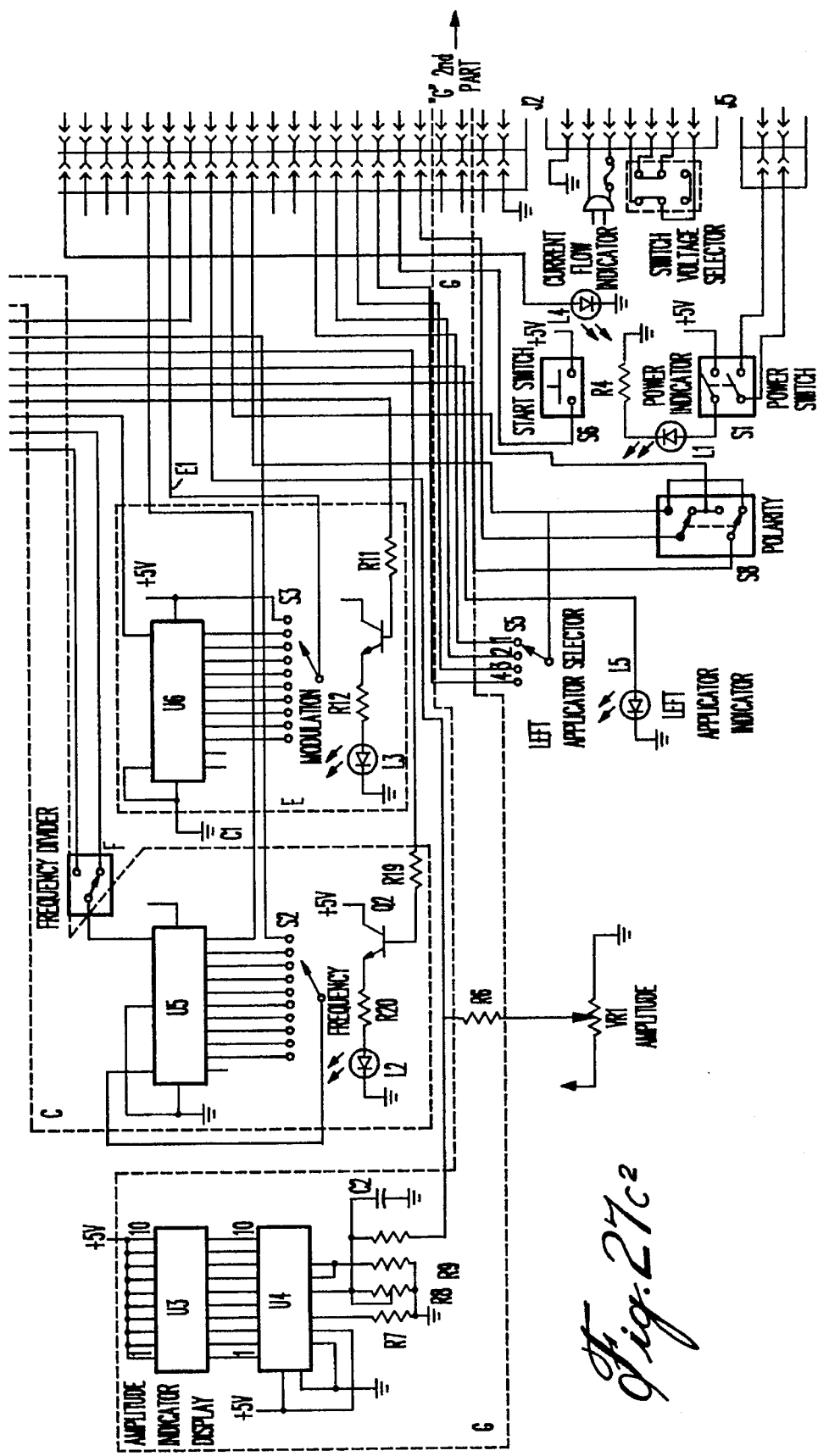
Fig. 27c²

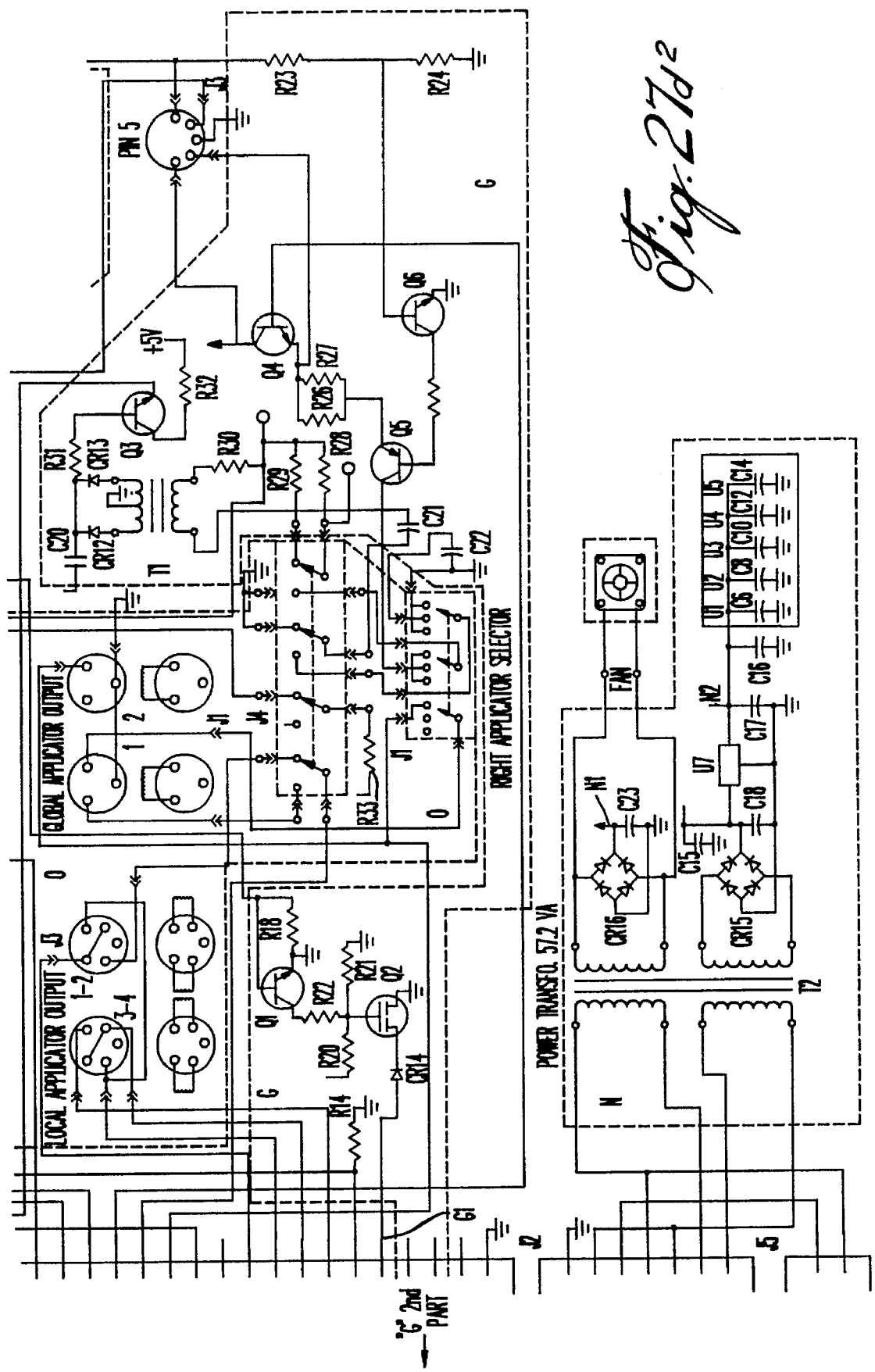
Fig. 27d²

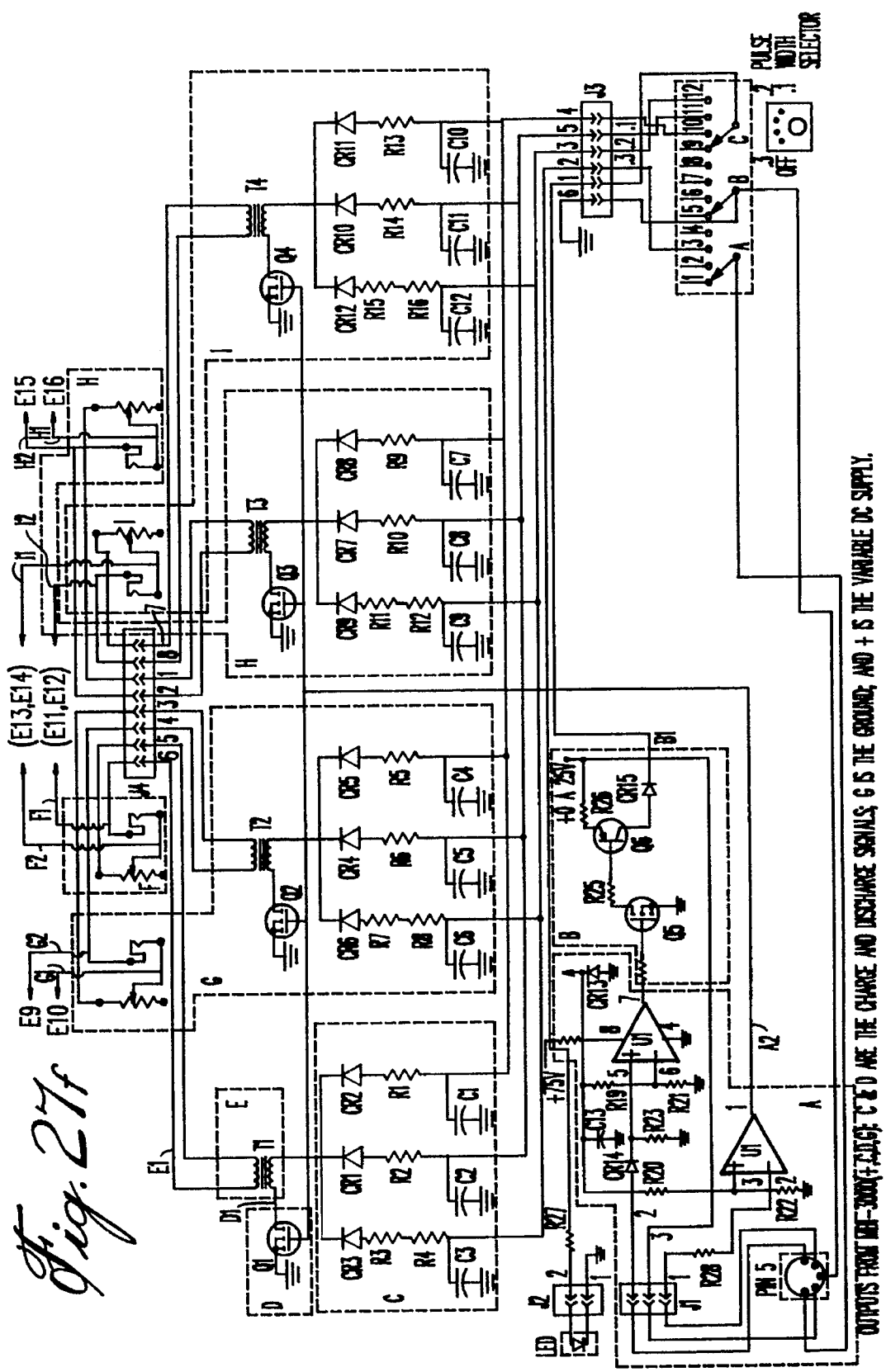

MBI-3004
OUTPUT VOLTAGE ON E9 TO E16, BY PAIRS OF ELECTRODES, FOR P.W.=0.2 MSEC POSITION, $f_b$=60pps; A=10 (ON MBI-3000); $V_{out}$ =MAX (ON MBI-3004) WITH A 10KΩ LOAD RESISTOR.

CURRENT IN THE 120Ω RESISTOR FOR P.W. = 0.2 MSEC POSITION (OTHER PARAMETERS: SEE FIG.27i)

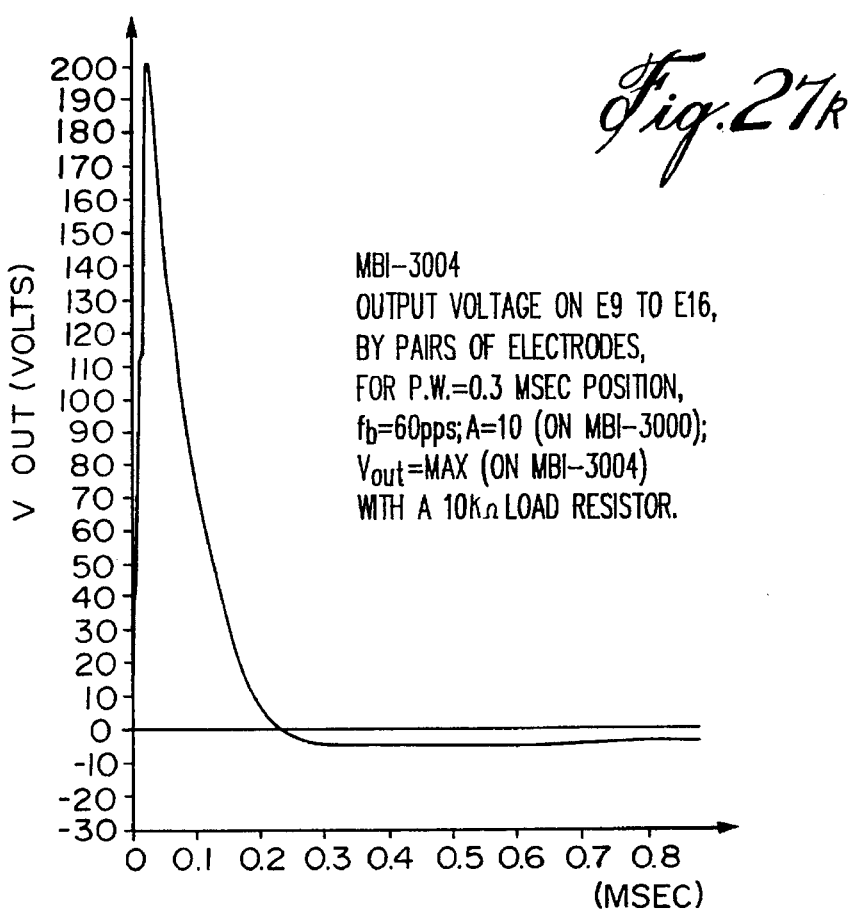
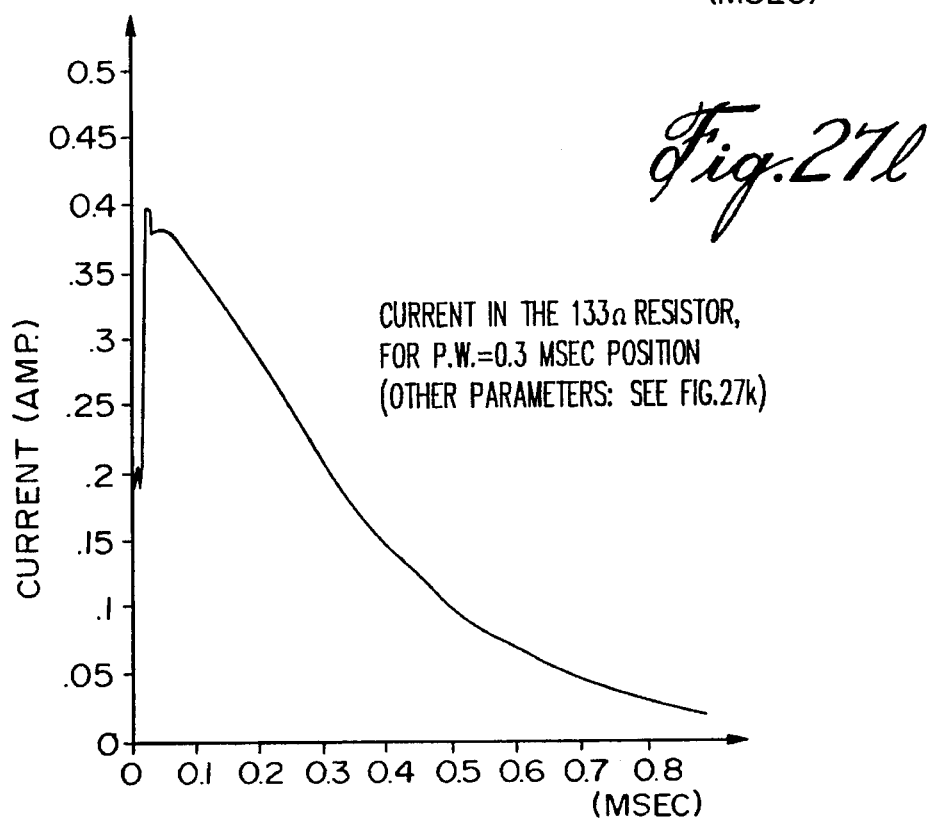

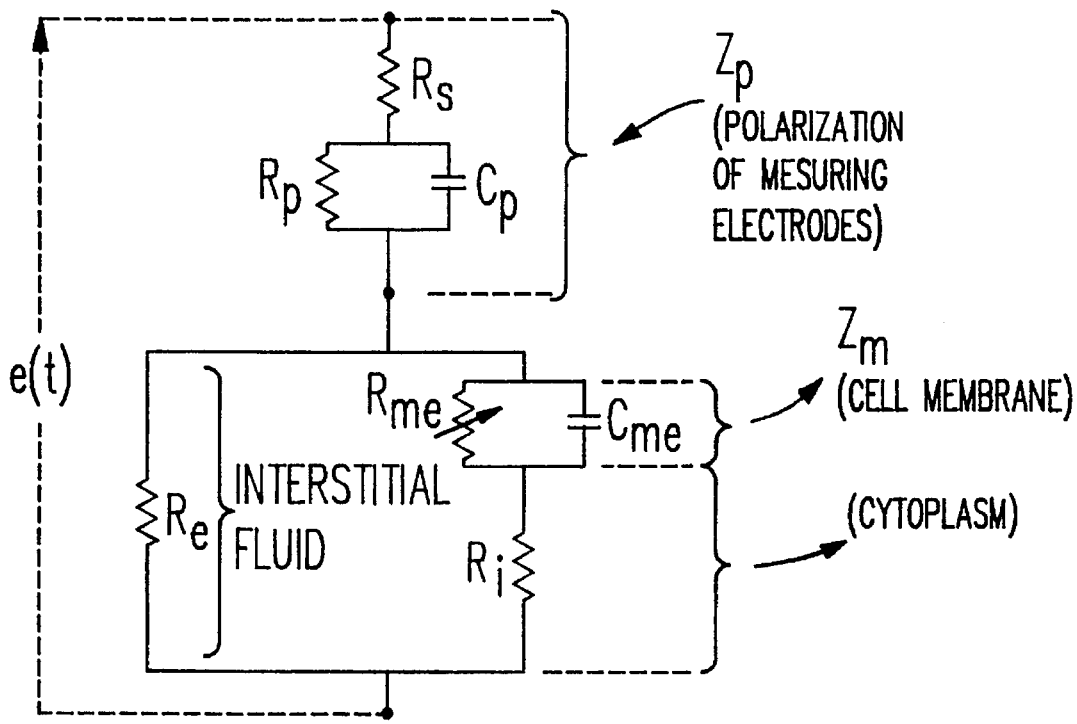

Fig. 29

$Z_p$ : ELECTRODE POLARIZATION IMPEDANCE $R_{me}$ AND $C_{me}$ : EQUIVALENT ELECTRIC RESISTANCE AND CAPACITANCE OF ALL CELL MEMBRANES IN THE INDUCTION CIRCUIT;

$R_i$ : EQUIVALENT INTRACELLULAR ELECTRIC RESISTANCE OF ALL LIVING CELLS IN THE BIOLOGICAL INDUCTION CIRCUIT;

$R_e$ : EQUIVALENT ELECTRIC RESISTANCE OF THE INTERSTITIAL FLUID IN THE BIOLOGICAL INDUCTION CIRCUIT;

$e(t)$ : BIOELECTRIC POTENTIAL INDUCED IN A LOOP OF THE BIOLOGICAL INDUCTION CIRCUIT;

$Z_m$ : EQUIVALENT ELECTRIC IMPEDANCE OF ALL CELL MEMBRANES.

ELECTROPHYSIOLOGICAL CONDITIONING SYSTEM AND METHOD

(A) TECHNICAL FIELD

The present invention relates to an electrophysiological conditioning system and method to help people and certain animals maintain and improve their health by reinforcing the body's natural defense and healing mechanisms by inducing physiological effects by the use of bioelectric impulses similar to those of the human nervous system. Briefly, the method of this invention uses three basic factors (motivation of user, help of his mentor and the new electrophysiological Conditioning system described herein) acting together, using the initial Conditioning parameters suggested herein and the holistic method of the present invention, to adapt the conditioning parameters to individual needs. In short, this invention is a new auto-health or self-health system.

BACKGROUND ART

The mode of operation of this invention is based on the electrophysiology of the human nervous system and is herein referred to as the "RHUMART" system. The words "RHUMART", "RESC," "SCIENTIFIC-PHILOSOPHY," "AUTO-HEALTH," AUTO-SANTÉ, ULTIMA-SANTÉ, ULTIMA-100T, OPTIMA-SANTÉ or "SELF-HEALTH" are Trade Marks used respectively for the new method of the present invention and the RHUMART or RESC conditioner, the AUTO-HEALTH, AUTO-SANTÉ, ULTIMA-SANTÉ, OPTIMA-SANTÉ or SELF-HEALTH SYSTEM are also Trade Marks.

The RHUMART technique subjects living cells to "smooth" physiological exercises. In fact, the cells receive specific impulses, which recall the human nerve impulses. And, since the human neural impulses govern most of the body functions, this method, induces important physiological effects on biological cells found in the human body and animals.

The present invention induces three specific physiological effects: (1) Stimulation of blood circulation; (2) Relaxation of the nervous system, producing anti-inflammatory and pain killing effects; and (3) Stimulation of normal cellular repair and regeneration.I The system of this invention is not intended to be a medical device or instrument under any legal system in the world and is not presently thought in any medical department of any university. More over, this system is not designed or intended for hospitals or clinics of any kind. It is rather a SELF-HEALTH SYSTEM which can be classified as a Basic Electrophysiological Conditioning System. Governments are starting to encourage people to accept responsibility for their own health, thereby helping to reduce the spiralling health costs that governments have had to assume themselves in the past.

This technique acts on the stress related to most diseases or health problems. It is mainly because it induces the three basic physiological effects mentioned above, that it is very useful to help people resolve or improve many of their own diseases or health problems without acting specifically on any of these, but acting on the stress related to most health problems.

For example, by controlling the pain and improving sleep duration and quality, this method can help by reinforcing the body's natural defense and healing mechanisms.

This invention is basically a Self-Health-System (AHS) or a basic Physiological Conditioning System which gives far greater and more reliable results in the hands of the end users themselves. Indeed, the conditioning parameters must be chosen and adapted by each individual user for best results.

The bioelectric impulses emitted by this method are very similar to those emitted by the nervous system.

"The impulses help people to heal themselves by producing the same three physiological effects produced by walking and other physical exercise," "Blood circulation is improved and there is a relaxing effect which leads to a reduction in pain and inflammation. The improved blood circulation also stimulates cell repair and regeneration."

When you haven't exercised in a long time, you become stiff and you may suffer from such ailments as arthritis or rheumatism. You may become overweight and in pain, and it is then difficult to exercise. It's a vicious circle, because physical exercise is essential to physical and "'mental'" fitness.

The three effects produced by this method play a similar role; they REINFORCE THE BODY'S self-defense system, which is thus better able to protect the organism from all kinds of health problems.

Since pain is diminished, people are once again able to exercise; they are more relaxed and so they sleep better at night. They feel so much better that they regain confidence in their own bodies and minds.

Briefly, this invention is very useful to help people improve their own physical as well as mental health and Quality of Life when properly used as described herein.

DESCRIPTION OF PRIOR ART

The closest prior art is my canadian patents No 1150361 and 1113156.

As background information, reference is made to Dr. Tom Ferguson, chief editor of a Self-Care journal (in the U.S.) and his seven laws for self-health. These are:

1) Each person is already his or her own doctor. People already solve 80% to 98% of their health problems by themselves. So why not continue this trend?
2) Non-professionals could do a lot for themselves if they had access to everything that is already available in terms of tools, skills, support and information. Collectively, we now know more than ever about the means of positively influencing our health. However this knowledge is not made easily available to the public.
3) Spouses, families, friends and our social and community networks are our best health resources.
4) Health is not the absence of diseases. We live from day to day a continuum whose two poles are perfect health and mortal illness—throughout our lives we are always situated somewhere between these two extremes.
5) What works best for the health of an Individual depends at least partially on his or her beliefs. The remedies in which a person believes are much more likely to succeed than those in which he has no faith.
6) The primary goal of a health-care system should be to help people to look after themselves.
7) Health is a regenerative process. The recuperative and healing powers of the human body are absolutely astonishing, but to function most efficiently they must be carefully nourished and maintained with good eating habits, regular exercise, a suitable environment, the support of others, a meaningful life and self-knowledge.

Health is like the soil: if you take good care of it over the long term, it can renew itself and perform far beyond your expectations. But if it is neglected, overworked and exploited, it will soon lose the ability to support life.

The following is extracted from a report on a research project headed by Dr. Benjamin Lau, M.D., Ph.D., associated professor of microbiology and immunology, published in LOMA LINDA University's newspaper. The OBSERVER (Thursday, Aug. 27, 1981):

"Although high intensity, high frequency electromagnetic energy has been shown in the literature to impair normal immune responses, his preliminary studies in animal models have demonstrated an enhancing immune response with low-dose electromagnetic energy.

In the European literature, low dose electromagnetic energy has been shown to increase blood flow and tissue oxygen supply and to hasten nerve regeneration."

In an article discussing this research, Dr. Benjamin Lau also concluded that the improvement in blood circulation produced by the low-frequency waves, is not due to an increase in heart rate nor to an increase in blood pressure, but rather to a real decrease in peripheral resistance caused by peripheral vasodilation (itself caused by a relaxation of the nervous system).

Most of the known electromagnetic systems were designed to help certain diseases and health problems specifically. Much of the prior an in this field is described in Vol. 238 of the Annals of the New York Academy of Sciences, Oct. 11, 1974, and entitled "Electrically Mediated Growth Mechanism in Living Systems."

As background information, reference is made to Magnetotherapy as defined by Solov'eva and summarized in his paper, Solov'eva (1975). EFFECTS OF MAGNETIC FIELD ON INFLAMMATION, Experientia, Vol. 31, 12. Solov'eva concluded, already in 1975, that the effectiveness of magnetotherapy is beyond any doubt in numerous human applications. However, the results obtained by various clinicians using magnetotherapy with previous apparatus are not uniform and very limited to a few specific health problems. Usually, the clinician select the "treatment" parameters for the patient based on a predetermined set of parameters for each disease or health problems. These parameters were not adapted or selected for each individual user.

Also the previous low-frequency electro-magnetic systems did not use the best type of impulses, as compared to those of the present invention.

Prior studies have shown that the direction in which new nerve processes grow can be controlled by weak electric fields which may influence regeneration by directing nerves into the region where they influence blastema formation (R. B. Borgens, 1979, Bio-Electricity and Limb Regeneration, Encyclopedia Science, Suppl. 1979, pp 89–93 (Biology) Grolier Ltd., Toronto, Canada).

Several authors who investigated Low-Frequency Electro-Magnetic Fields reported numerous beneficial effects on living systems:

- anti-inflammatory effects (Solov'eva, 1975, up cit.);
- normalization of arterial pressure;
- diuretic action;
- normalization of transmembrane electrical potential of living cells;
- stimulation of osteogenesis and bone repair and maintenance;
- alteration of the amount and rate of calcium influx-efflux at the cellular level;
- improvement of sleep and pain relief in many kinds of arthritic diseases.

Furthermore, several authors have noted the advantages of magnetotherapy over UHF therapy and induction heating, indeed it was reported that deep joint heating associated with UHF fields and diathermy apparatus, used in many clinics and hospitals (still in 1991), can cause severe side effects and can accelerate cartilage degeneration (Fiebel et al., Deep Heating of Joints: A Reconsideration, Arch. Phys. Med. Rehabil., Vol. 57, November 1976).

Our first investigation in this broad field was in 1969 (Drolet, R. and Kunov, H., 1969, Physical Interpretation of Biological Impendances with Applications to Electro-Stimulation, 2nd CMBES Conference, Halifax), (Talibi, M. A., Drolet, R. etal., 1970, A Model for Studying the Electrical Stimulation of the Urinary Bladder of Dogs, British J. Urol., Vol. 42, 56–65) and it was concerned with the evacuation of the bladder of paraplegic patients. We have studied the optimal parameters for the electromagnetic evacuation of the urinary bladder including electrode characteristics and different electrical current characteristics.

The patent literature is well summarized by Drolet (Can. Patent No. 1150361). Various types of non-biological waveforms were used in the prior art in contrast with the present invention.

To name just three important books recently published on the broad field of BIOELECTRICITY let us mention the following:

1. *The Body Electric*: electromagnetism and the foundation of life, Becker, R. O., and Selden, G., Published by William Morrow, (A pioneering book in the field of "Regeneration and its relationship to electrical currents in living things), 1985.
2. *Cross Currents*, Becker, R. O., Published by Jeremy P. Tarcher, Inc. , (including "Exciting Insights into How to Use the Body's Inherent healing abilities . . . "), 1990.
3. *Electromagnetics in Medicine and Biology*, Carl T. Brighton, M.D., Ph.D. and Solomon R. Pollack, Ph.D. (Editors), published by San Francisco Press, Inc., This book contains papers presented at the tenth annual meeting of the Bioelectrical Repair and Growth Society, held in Philadelphia on 14–17 October 1990. Briefly, this book reveals that ". . . applied electro magnetic fields have been found to have profound effects on many cellular events, such as proliferation, macromolecular synthesis, and cell membrane transport; and on molecular biosynthesis, such as transcription, translation, and signal transduction") 1991.

A groundbreaking new book is now being written by Dr R. A. Drolet, Ph.D., under the title *"Self-Health and Bioelectricity: a New Approach to Lengthen Life Expectancy and Reduce Public Health Costs"*.

OBJECT AND SUMMARY OF THIS INVENTION

In contrast to the prior inventions, this invention is concerned with an original compact, miniaturized, portable, and modular self-health system (AHS) or electrophysiological Conditioning System for living cells which induces in the body unique bioelectric impulses in the range of from 0.1 to 100 $\mu A/cm^2$ for regeneration modes (and from 0.1 to approximately 200 $\mu A/cm^2$ with muscular modes) of the type and intensity of calcium Ion ($Ca^{++}$) current Impulses involved in the human nervous system and which are absolutely essential for the proper operation of the human nervous system. In fact, the cells receive specific impulses, which recall the human nerve impulse. And since the human neural impulses govern most of the body functions, this electrophysiological method induces important physiological effects on biological cells found in the human body and in animals.

The present invention can also be described as an electrophysiological conditioning system comprising generator means for producing conditioning pulses having a critical damping or nearly critical damping waveform, adjustable control means for selecting a desired intensity of said conditioning pulses in the range of from 0.1 to 100 $\mu A/cm^2$ (when using coil applicators, and from 0.1 to approximately 200 $\mu A/cm^2$ when using flexible conductive electrodes) which pulses are similar to calcium ion current impulses present in synaptic transmission of biological control signals of the human nervous system, said desired intensity and pulse waveform being determined by a selected one of one or more conditioning applicators, said conditioning applicators including one or more electromagnetic coil applicators or one or more pairs of flexible conductive rubber electrodes connected to one or more of said generator means through predetermined interlace circuit means dependent on a selected one or more of said conditioning applicators, said conditioning applicators transmitting electromagnetic conditioning signals capable of producing basic physiological effects of relaxation of the nervous system. stimulation of blood circulation and stimulation of normal cell repair and regeneration, and capable of enhancing the natural self-defense and healing mechanisms of man and animals.

DISCLOSURE OF INVENTION

This invention also includes a method of producing electromagnetic and electrophysiological conditioning signals capable of producing physiological effects of relaxation of the nervous system, stimulation of blood circulation and stimulation of normal cell repair and regeneration, and capable of enhancing the natural self-defense and healing mechanisms of man and animals, said method comprising the steps of:

i) producing pulsating conditioning signals each having a critical damping or nearly critical damping waveform and wherein the value and nature of components of a circuit or a computer means generating the said waveform can be varied so as to decrease the maximum intensity of said conditioning signals by not more then 75% of that generated with critical damping conditions, or a waveform defined by the derivative with respect to time of said critical damping or nearly critical damping waveform.

ii) selecting one or more conditioning applicators to transmit said conditioning signals, said applicators being selected from one or more electromagnetic coil applicators and/or one or more pairs of electrodes connected to one or more controller generator means through predetermined interlace circuit means dependent on a selected one or more of said conditioning applicators, iii) adjusting the intensity of said conditioning pulses to a selected intensity in the range of from 0.1 to 100 $\mu A/cm^2$ (when using coil applicators, and from 0.1 to approximately 200 $\mu A/cm^2$ when using flexible conductive electrodes) which pulses are similar to biological impulses present in the human nervous system.

iv) adjusting the basic frequency or pulse rate of said conditioning signals to a selected frequency or pulse rate in the range of 0.55 Hz or 0.55 pulse per second to 180 Hz or 180 pulses per second, according to the desired physiological effect and the user's needs, tolerance and response to said conditioning, v) selecting the modulation of said conditioning signals according ro the desired physiological effects and the user's tolerence to said conditioning, vi) selecting the duration of said conditioning according to the desired physiological effects and the user tolerance to said conditioning, and vii) selecting the polarity of said conditioning signals from each said conditioning applicator or pairs of said applicators.

A few important characteristics of the embodiments and "modes" of this invention This invention includes many mechanically and electronically compatible constituents including two field Controller-generators, one is miniaturized and the other is very compact and versatile, both of which can generate continuous or periodically interrupted bioelectric pulse trains (bundles) of specific characteristics.

This invention also includes many modes (one mode includes one or more coil applicators or muscular electrodes and the proper controller-generator) named the MINI-4A, REBONE-4A, REBONE-PM, JAM-8A, MAXI-2A, and MAXI cellular or regeneration modes and muscular modes (MBI-1004A, MBI-1004B and MBI-3004 modes). (The expression MBI-1004A.B is used to name the combination of the MBI-1004A and MBI-1004B together). The miniaturized constituent of the present invention (AHS-M) also comprises a small AC to DC voltage converter, a battery pack, a known chronometer and a small known magnet to detect the presence and intensity of the field.

All these modes or embodiments of the present invention are properly described herein, including various examples of their use.

This invention also includes a special directional field detector named the MBI-101 which is a low cost and versatile miniatunsed device which is very useful for the quality control of said bioelectric impulses.

The MBI-1000 Controller-generator described herein can be used n combination with the REBONE-PM coil applicators (this mode is named the REBONE-PM CELLULAR MODE), or with the MBI-1004 A.B MUSCULAR mode. Examples of use of these modes are given herein.

The MBI-3000 Controller-generator described herein can be used in combination with the MINI-4A, REBONE-4A, JAM-8A, MAXI or MAXI-2A, (called the MBI-3000 Cellular Regeneration modes) or with the MBI-3004 Muscular mode. Various examples of use of these modes are also given herein.

The said MBI-101 field detector and a the known magnet are used in combination with either the said MBI-1000 or the MBI-3000 generator and any said coil applicator.

How and when to use various "modes" of this invention (briefly)

Generally, the method of this invention starts by using the MBI-3000 CELLULAR CONDITIONING mode with the said MAXI or MAXI-2A applicator described herein for global physiological Conditioning and relaxing the whole body as described herein.

Then one would use the said REBONE-4A or the MINI-4A Cellular mode to condition particular areas or specific spots of the body which are the sites of new and/or old STRESS induced by various known and/or unknown causes and which maintain continuous or intermittent health disturbances such as pain and/or inflammation and/or perturbed sleep. If the stressed or painful area is large enough, one could use the JAM-8A Cellular mode described herein.

The said MINI-4A mode is used for well localized pain and/or stress focuses, as compared to the said REBONE-4A which is used for A SMALL REGION of the body like, for example, an ankle, a knee, an area of the spine, a wrist, an elbow or a shoulder; with Conditioning parameters as suggested in examples of use given herein to start with and which can be adapted by the user in successive applications, as described herein.

Generally, it is the size of the area or region to be conditioned that will determine which is the best applicator or mode to use. Except that the said REBONE-4A mode is much more powerful than the said REBONE-PM mode in terms of intensity of induced bioelectric impulses.

The said REBONE-PM mode of the said MBI-1000 is much more practical to use than the said REBONE-4A mode when a low intensity of impulses is required (in the head region for example, which is more sensitive), and during long distance trips where the small size and low weight of the said MBI-1000 mode are real advantages over the said REBONE-4A mode.

The said MAXI mode of operation is more practical and easy to use by a person lying in a bed, especially if that person cannot sit or stand up.

The said MAXI-2A mode on the other hand is more practical and easy to use by a person who wishes to take his conditioning sessions while sitting in a comfortable living-room type of seat or in any simple chair, preferably not made of ferromagnetic material so as not to perturbate the magnetic field impulses.

Generally, it is not recommended to use the said MAXI or the MAXI-2A mode directly centered on the head, except if the amplitude is kept very low, lower than 1.5 for example. On the head region, the said REBONE-4A mode should be used with amplitudes lower than 1.5 or 2.0 in most circumstances, except as suggested herein.

For SMALL CHILDREN, below the age of two (2) to three (3) years, the said REBONE-PM MODE iS often the best suited because of the SMALL SIZE of the different organs and parts of the child's body, and also because of the GREATER SENSITIVITY OF RESPONSE in general of children (partly due to their known higher regenerative capacity linked with their young age; this also applies to small and young animals.)

Generally, the said MBI-1004 A.B and the MBI-3004 Muscular modes are used after approximately two to three months of Conditioning with the said regeneration or CELLULAR CONDITIONING modes. The Muscular modes are very useful to strengthen various muscles and especially useful also to help reduce or eliminate newly formed or old oedemas. Especially in sports injuries for example, the Modulation n=2 of the cellular mode is used to help reduce pain; and the Modulation n=3 of the Cellular mode is used to help reduce severe or persistent oedemas. The said Muscular modes (MBI-1004 A.B or MBI-3004) can also be used to help eliminate oedemas as described herein.

The Muscular modes are also very useful to Condition specific muscles while other nearby muscles and/or pans of the body do need a rest in order to recuperate from various sports injuries and/or accidents. As for the use of the said magnet and the MBI-101 Field Detector, it is well explained in the examples of use of the MBI-101, the MBI-1000 and MBI-3000 controller-generators.

Generally, the said magnet is used to feel the approximate intensity and frequency of pulse trains (for experienced users). The said MBI-101 detector is essential to find the direction and intensity of the magnetic field impulses. It has five intensity scales (Gain scales) allowing for the measurement of the intensity of magnetic field impulses generated by all regeneration or cellular modes of the present invention. It is also very compact and versatile and is held in one hand for practical use as further described herein.

Previous detectors were not as compact and versatile to detect and quantitatively measure the physiological magnetic field impulses. With the highest sensitivity scale, each LED (Light Emitting Diode) lit in the so called BAR LED corresponds to one gauss ($10^{-4}$ Wb/m$^2$), a unit of magnetic field in the range of that of the earth.

Finding the Amplitude and Modulation "WINDOWS" for best results with this invention The biological effects which are induced with the present invention are dependent on the Amplitude and Modulation (or frequency of pulse bundles) values of these impulses and also on the duration (T) and frequency of conditioning sessions. In fact there are so called "Amplitude and Modulation-Frequency windows" for specific physiological effects to be induced; meaning that the same effects are not necessarily induced when the Amplitude and the Modulation values are below or higher than the limit values of the said windows.

In order to discover these Amplitude and Modulation windows, it is important to initiate conditioning with the low Amplitudes and Modulation frequencies suggested herein; and maintain reduce or gradually increase the said amplitude according to the method of the present invention.

If satisfactory results are not obtained after, say 15 or 20 conditioning sessions, always consider the use of a different Modulation frequency (n), duration and/or frequency of conditioning session; and this by taking the examples given herein into consideration along with your own experience.

Towards the end of a conditioning course, it is recommended to decrease the Amplitude and the duration of session (T) gradually in the last 2 or 3 sessions. That is when you do not feel that you need to take regular conditioning sessions, say, every other day or every third day.

The subjective feelings of the experimenter should always be used as indicators, for adapting the conditioning parameters to one's own needs.

Generally, the frequency of conditioning sessions will vary between one session per day to one per week, one session every other day being the most common.

Numerous unique features

The present physiological-Conditioning and Self-Health System has a wide range of applications also because of the following unique features:

wide range of controllable electrophysiological conditioning characteristics adapted for Self-Health uses;

whole body electrophysiological conditioning of one to four people simultaneously;

well localized conditioning in the affected areas of one to 24 people simultaneously;

simplified utilization procedure that makes it a true Self-Health System for non specialists and the layman;

induces the following three physiological effects:

improvement of blood circulation;

relaxation of the nervous system; producing anti-inflammatory and pain-killing effects;

stimulation of normal cell repair and regeneration;

enhances the body's natural defense and healing mechanisms;

non-thermal-cell-conditioning;

painless conditioning, when properly used;

conditioning without mechanical vibration;

conditioning applied without metallic electrodes;

induces unique bioelectric impulses in the range of 0.1 to 200 µA/cm² (limited to approximately 100 µA/cm² with said coil applicators) of the type and intensity of calcium Ion ($Ca^{++}$) current pulses involved in the synaptic transmission of the human nervous system;

specific bioelectric impulse patterns;

modular structure allowing for simultaneous use of several pairs of physiological applicators serially or parallel connected to the controller-generator means;

low weight and miniaturization;

choice of DC or various levels of AC power requirements (12–15 VDC, 115 or 230 VAC, 50 or 60 Hz);

portability and mechanical flexibility;

wide range of controllable field parameters (field intensity, direction, frequency and spatial gradient) generated by two different bioelectric controller-generators;

Critical-Damping-Design for the pulse-shaping-circuit of the two controller- generators, allowing for a great improvement of the field intensity and effectiveness for a given weight of field applicator and/or generator;

Combination of the MUSCULAR AND CELLULAR MODES of electrophysiological conditioning using a choice electrode interlace circuit means and/or a choice of one or more ELECTROMAGNETIC COIL APPLICATORS;

possibility of conditioning a group of up to 16 or 24 people with the electrode interface circuit means simultaneously with the application of the "cell regeneration" mode on two to four people (using the pulsating electromagnetic mode);

the system and method of the present invention can help people regain the autonomy that comes with being in good health;

When properly used, it can help improve the QUALITY OF LIFE of the subject being conditioned even if he has experienced long periods of malaise brought on by chronic ailments such as arthritis, arthrosis, stress, hypertension, ulcers, lesion and chronic pain, sport injuries, migraines, back pain, circulatory problems, and various other ailments.

The resonance of the impulses of the present invention with the human nervous system and living cells.

The shape of the bioelectric impulses induced in the body is practically identical to the one produced by the nervous system, and we know that this system controls just about all body functions, organs, glands and life processes. It is therefore recognized by the author of the present invention that this system can help control all life processes, from pain to blood pressure to cell repair and/or normal regeneration by means of electrophysiological effects. There remains, however, one very important question.

Why the range of induced micro-currents had to be in the range of 1 to 20 µA/cm² (peak value), for the cellular or regeneration mode while any currents much larger or much smaller were not producing the same results observed when this "magic range" of induced impulses was used.

This range of induced current density is lower than that required for NORMAL SENSORY PERCEPTION in most people, which is approximately 60 µA/cm², corresponding to approximately 3 mA "hand to hand" induced current.

The most useful current density for said impulses (20 µA/cm², peak value) is thus two or three times less than that of directly perceptible impulses, such as a muscle contraction in the arm, for example.

It is interesting to note that close to 50% of normal people, with no major arthritic or muscular inflammation, experience a VERY SLIGHT "PRICKLY" SENSATION when stimulated WITH THE SAID REGENERATION MODES. At this stage, we are one step closer to the fundamental scientific explanation of the RHUMART phenomenon by the author.

In an attempt to quantify the PHENOMENON OF THE PRESENT INVENTION, we measured the INTENSITY AND WAVE SHAPE Of the current induced in the arms of a man standing inside the whole body applicator (an empty cylinder 25 cm high and 50 cm in diameter, called the "MAXI").

All artifacts of measurement were reduced to a minimum, and THE SHAPE Of the induced pulses was found to be exactly that predicted by the MAXWELL electromagnetic theory as further described herein after.

As for the PEAK AMPLITUDE Of the induced microcurrents, we obtained a MEASURED VALUE Of approximately 20 µA/cm², a value we had been able to calculate using the electromagnetic laws of physiological cell conditioning described herein. In October 1982, Scientific American published an article entitled "CALCIUM IN SYNAPTIC TRANSMISSION: A current of calcium ions triggers the passage of signals from one nerve cell to another".

The waveform of an axon's electrical potential is almost identical to the said induced voltage waveform as described in the RHUMART physics section herein after. The wave of the calcium ion current that enables the passage of signals from one nerve cell to another is practically identical to the RHUMART wave. Mathematical calculations based on experimental data and the findings of Rodolfo R. Llinas (Sc. Am., October 1982) proves that the density of the current of calcium ions $Ca^{++}$ required to trigger synaptic transmission is in order of 20 µA/cm², or precisely that of the RHUMART induced micro-currents.

The giant synapse used by Rodolfo R. Llinas is cylindrical:

So that its surface, $S_{syn}$, is equal to:

$$S_{synapse} = \pi D \times L$$

$$S_{syn} = \pi \times 0.5 \times 0.7 \text{ mm}^2$$
$$S_{syn} \approx 1.1 \text{ mm}^2;$$

and the peak current of calcium ions flowing through this cylindrical synapse, as measured by Llinas* (Sc. Am., October 1982) is 200 nA.

Therefore, the current density ($j_{Ca^{++}}$) of Calcium ions impulses present in those giant synapse of the nervous system is,( as directly calculated from said Llinas' Scientific America article (1982):

$$j_{Ca^{++}} \approx \frac{200 \text{ nA}}{1.1 \text{ mm}^2} \approx \frac{20 \text{ µA}}{\text{cm}^2}$$

As further features of the present invention, the following parameters of the field can be selected or predetermined on this system:

Peak amplitude of magnetic pulsating field: it varies between zero to approximately (≈meaning approximately herein after) 20 GAUSS (peak) when using the said MAXI, 0 to ≈100 gauss (peak) with the said MINI-4A, 0 to ≈33 gauss (peak) with a parallel pair of said MAXI-2A applicators in same polarity orientation, 0 to ≈55 gauss (peak) with a pair of said REBONE-4A, and 0 to ≈50 gauss with the said leg pads (JAM-8A type) described herein.

Orientation and/or direction of the field with respect to the area to be conditioned. The orientation of the field can be in any desired direction depending on the selected one or more coil applicators and its (their) orientation with respect to the region to be conditioned.

The basic pulse frequency (in imp/sec), meaning the repetition frequency of pulses; can be selected as 6.6, 7.5, 8.6, 10, 12, 15, 20, 30 or 60 imp/see or ten times slower (0.66, 0.75, . . . 6 imp/sec);

The Modulation (n), meaning the repetition frequency of pulse bundles, can be selected as n=0, 1, 2, 3, 4, 5, 6, 7, 8, 9 which means that there are $2^{n-1}$ pulses per pulse bundle with a nul field for half of each cycle;

Duration of session (in minutes) is preselectable to 1, 2, 3, 5, 10 or 15 min. for the said MBI-3000 (and longer by reinitiating the conditioning session), and preselectable to any desired time for the said MBI-1000 using a known chronometer as described herein Polarity, meaning the orientation of the magnetic flux can be reversed on the said MBI-3000 generator, and can be reversed by choosing the other side of any coil applicator;

Pulse Width, (in msec), can be preselected to 0.1, 0.2, 0.3, 0.5 or 0.8 msec using different regeneration and muscular modes described herein.

Current and voltage control for the muscular modes: the peak voltage applied to each pair of flexible and conductive electrodes is adjusted between 0 to ≈200 Volts by varying the amplitude (A) on the selected controller (said MBI-1000 or MBI-3000) and the current applied to each electrode circuit by turning the desired current intensity control clockwise from 0 to approximately 6 mA (peak);

The spatial field gradient in the subject and/or region being conditioned can be preset by choosing the proper field applicator (named MINI-4A, REBONE-4A, MAXI-2A. etc.) and placing it at a proper distance and/or orientation with respect to the user and/or "treatment" region, with the guidance of the so called "Field-Pattern-Charts" described hereinafter.

The volume of the region to be conditioned, for a given range of magnetic field, from 20 to 50 gauss for example, can be preset in the same manner as that used for selecting the spatial field gradient as described above.

An important feature of the electromagnetic pulse shaping circuit is that the electronic components of this circuit are CHOSEN SO AS TO OBTAIN A CRITICAL OR "NEARLY CRITICAL" DAMPING OF THE CURRENT PULSE FLOWING THROUGH THE CONDITIONING COIL APPLICATOR. This "Critical Damping Condition" is defined by the simultaneous solution of the three following equations:

$$C_j = \frac{4L}{R_T^2} \; ; \tau_r = \frac{2L}{R_T} \; ; \text{and } i_m = -\frac{2V_o}{eR_T}$$

where $C_j$=capacitance of capacitor being discharged into the treatment coil through a damping resistor $R_{Damping}$;

L=inductance of the treatment coil applicator;

$R_T$=total series resistance in the discharging circuit of the capacitor; $R_T$ is equal to the sum of the damping resistor $R_{Damping}$ and the D.C. electrical resistance $r_L$ of the treatment coil winding;

$\tau_r$=time lapse between beginning of the current pulse and the time corresponding to the maximum current $i_m$, as illustrated in FIG. 3a, 3b and 3c herein;

$t_f$=period of time from the beginning of the current pulse to the time where the second derivative of the current in this pulse is equal to zero. (We have shown that $t_f=2t_m$);

$i_m$=maximum current flowing through the treatment coil;

$V_o$=initial voltage across the capacitor C, before discharging it into the treatment coil;

e=2.7182818 . . . , being the limit approached by the expression $(1+1/n)^n$ as n approaches infinity, also called the "base" of natural or neperian logarithm;

and it is intended that any of the components of this R, L, C circuit can be changed so as to cause the peak amplitude of the said current pulse to decrease by not more than 75% of that resulting from the "Critical Damping Conditions" defined above, without departing from the spirit and scope of the present invention. It can be shown that:

$$i = -(R_T/2L)^2 C_j V_o t \; e^{-(R_T/2L)t}$$

where t is the time and i the current flowing through the coil, for the critical damping design.

According to a broader aspect of the pulse shaping circuit, There is an equivalent circuit of the "N" identical electromagnetic applicators (or coils) serially or parallel connected to the said Controller-generator means. FOR THE SERIES CASE, $R_{eq}$ is defined as equal to $NR_L$, where $R_L$ is the DC resistance of the coil of one applicator, and $L_{eq}$ is defined as equal to NL, where L is the inductance of the said treatment coil (in one applicator). FOR THE PARALLEL CASE, the said $R_{eq}$ is defined as equal to $R_L/N$, and $L_{eq}$ as equal to L/N, where $R_L$ and L are defined just above. $R_F$ is the equivalent resistance of the extentions and leads interconnecting the applicators together. $C_j$ is the capacitive means being sequentially charged and discharged by the so called charge and discharge circuit means of the said Controller.

The actual magnetization circuit comprises a magnetization coil or a combination of "N" such identical coils connected in series or in parallel. The capacitive means, $C_j$, feeds the said coil or combination of coils with a Conditioning (or treatment) pulse current, $i_{eq}(t)$, to obtain a desired magnetic field characteristic when the said current pulse is discharged through the said coil or combination of such coils. A damping resistive means, $R_j$, is serially connected to the said coil or combination of coils (in series with the said $R_F$).

The current pulse has a rise time $\tau_r$ also named $T_j$ for reaching a maximum pulse current intensity, $i_m$ or $i_{max}$, delivered by the capacitive means $C_j$ and a damped fall time of a value such that the second derivative of the current waveform is null at a time twice the said rise time ($\tau_r$ or $T_j$).

The said current pulse waveform is expressed by the three equations:

$$i_{eq}(t) = -(R_T/2L_{eq})^2 C_j V_o t \exp(-R_T/2L_{eq});$$

$$i_{ns}(t) = i_{eq}(t) \text{ for "N" identical applicators in series;}$$

$$i_{np}(t) = i_{eq}(t)/N; \text{ for "N" identical applicators in parallel;}$$

WHERE:

$i_{eq}(t)$=current pulse delivered by the said generator/controller;

$i_{ns}(t)$=the current pulse flowing in any of the "N" applicators in series;

$i_{np}(t)$=the current pulse flowing in any of the "N" applicators in parallel;

$R_T$=total series resistance value including said damping resistance means $R_j$, the resistance of the extentions and leads and the equivalent D.C. resistance $R_{eq}$ of the said coil or combination of coils;

$L_{eq}$=equivalent inductance of the said coil or combination of "N" identical coils serially or parallel connected;

$V_o$=voltage to which the capacitive means $C_j$ is charged before being discharged in the said coil or combination of coils;

$C_j$=capacitance of the capacitive means;

exp=exponential function meaning "e" to the power, $$e = 2.712828 = \lim_{n \to \infty} (1 + 1/n)^n$$

And, with the following definition of SYMBOLS:

t: time;

t': $t/T_j$, where $T_j$ is defined below;

$k_n$: parallel or series factor: $k_n=N$ for N applicators in series, and $k_n=1/N$ for N applicators in parallel;

L: inductance of one applicator;

$L_{eq}$: $k_n L$;

$R_L$: DC resistance of the coil of one applicator;

$R_F$: resistance of the leads or wires to and from the applicator;

$R_{LF}$: $R_L+R_F$;

$R_{eq}$: $k_n R_{LF}$;

$R_j$: resistance to place in series with the applicators to obtain Critical Damping;

$R_T$: $R_j+R_{eq}=R_j+k_n R_{LF}=R_j+k_n(R_L+R_F)$ total damping resistance;

$C_j$: capacitance to place in series with the applicator to obtain Critical Damping;

$V_o$: value of the voltage on the charging capacitor at t=0;

$T_j=\tau_r$: time for which the current in the coil is at peak value $\left( \frac{di}{dt} = 0 \right)$ $T_{jc}$: time for which the voltage across the applicator crosses the zero voltage base line $I_{mj}$: value of the peak current in the applicator or combination of applicators;

$I_{mjs}$: value of the peak current in the applicator or combination of applicators when the voltage, $V_o$=10 Volts;

NOTE: For the MBI-1000, $V_o \approx 0$ to 11 volts ($V_o$ is proportional to the Amplitude 18, FIG. 16a) For the MBI-3000, $V_o \approx 0$ to 65 volts ($V_o$ is proportional to the Amplitude 302, FIG. 9A);

$(k_{\epsilon+}/k_{\epsilon-})$: quotient of the applicator voltage at t=0, over the voltage when $$\frac{d^2}{dt^2} [i_{eq}(t)] = 0$$

at the inflection point of the current curve;

$i_{js}(t)$: the standard current curve: for $V_o$=10 Volts;

$V_{aw}(t)=V_{coil(s)}(t)$: the voltage curve across the applicator(s);

$$V_{Leq}(t) = L_{eq} \left( \frac{di}{dt} \right):$$

the voltage curve across the pure $L_{eq}$ of the applicator(s);

i'(t): di/dt;

$T_{jj}$: $T_{jc}+T_j$;

The relationships between the "Critical Damping" parameters for the present general cases are as follows:

In the "CRITICAL DAMPING" equations below, there is a factor $k_n$ which is named the parallel or series factor. N is the number of identical applicators in series or in parallel. If the applicators are in parallel, the factor $k_n$ is equal to 1/N. If the applicators are in series, the factors $k_n$ is equal to N.

1) Time where the current in applicator(s) is maximum, ($T_j$):

$$T_j = \frac{2 L_{eq}}{R_T} = \frac{2 k_n L}{R_j + k_n R_{LF}}$$

2) Capacitance for the circuit, ($C_j$):

$$C_j = \frac{2 T_j}{R_T} = \frac{2 T_j}{R_j + k_n R_{LF}}$$

3) Peak current ($I_{mj}$) with the generator at amplitude ($V_o$):

$$I_{mj} = \frac{C_j V_o}{e T_j} = \frac{2 V_o}{e R_T} = 0.7357588 \frac{V_o}{R_T} = 0.736 \frac{V_o}{R_T}$$

4) First time dericative of applicators current at t=0:

$$\left( \frac{di}{dt} \right)_{t=0} = \frac{V_o}{L_{eq}} = \frac{V_o}{k_n L}$$

5) Time where the voltage across the applicator(s) crosses the zero value, $T_{jcoil(s)}$:

$$T_{jcoil(s)} = \frac{2 k_n L}{r_j - k_n R_{LF}} = T_{jc}$$

6) Quotient of the applicator(s) voltage at t=0, over the voltage when $d^2i/dt^2=0$; the inflection point of the current curve:

$$\left( \frac{k_{\epsilon+}}{k_{\epsilon-}} \right)_{coil(s)} = \frac{T_{jc}}{T_j} e^{(1+T_{jc}/T_j)}$$

7) Quotient of $T_{jc}$ and $T_j$ defined in (5) and (1) above:

$$\frac{T_{jc}}{T_j} = \frac{1 + (R_{eq}/R_j)}{1 - (R_{eq}/R_j)},$$

8) From equation (7) above, it can be shown that:

$$R_{eq} = R_j \frac{(T_{jc}/T_j - 1)}{(T_{jc}/T_j + 1)} ;$$

leading to an indirect method for measuring $R_{eq}$, from $T_{jc}$, $T_j$, $R_j$, at critical damping

BRIEF DESCRIPTION OF DRAWINGS

A preferred embodiment of the invention will now be described with reference to the accompanying drawings in which.

Figure 2A:
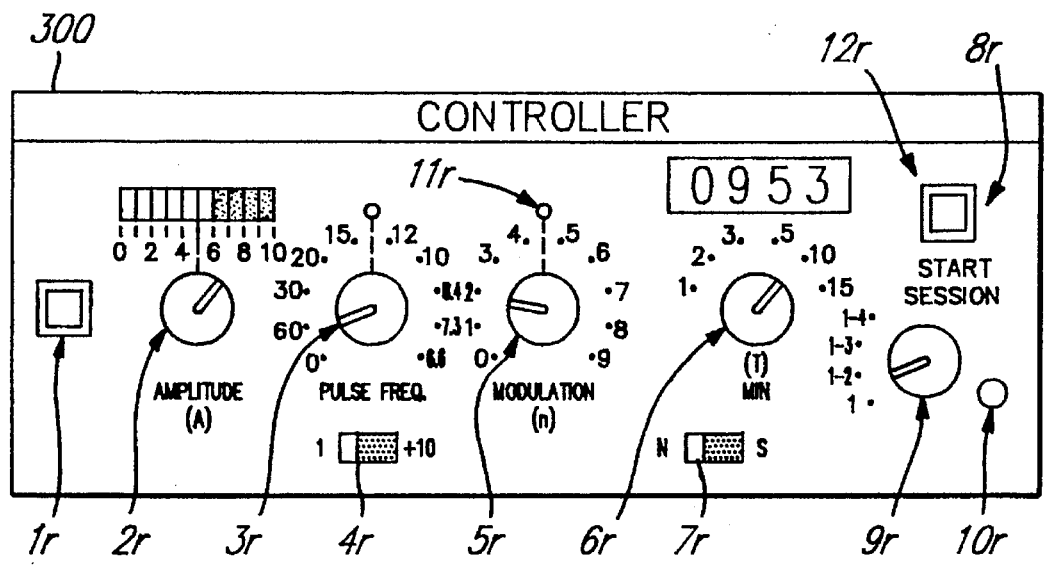
FIG. 2a, and 2b shows a simplified views of the front and rear panel of the said MBI-3000 controller/generator used in a brief description of a preferred embodiment of the invention and connection of the said MAXI-2A and REBONE-4A applicators of this invention.
Figure 2B:
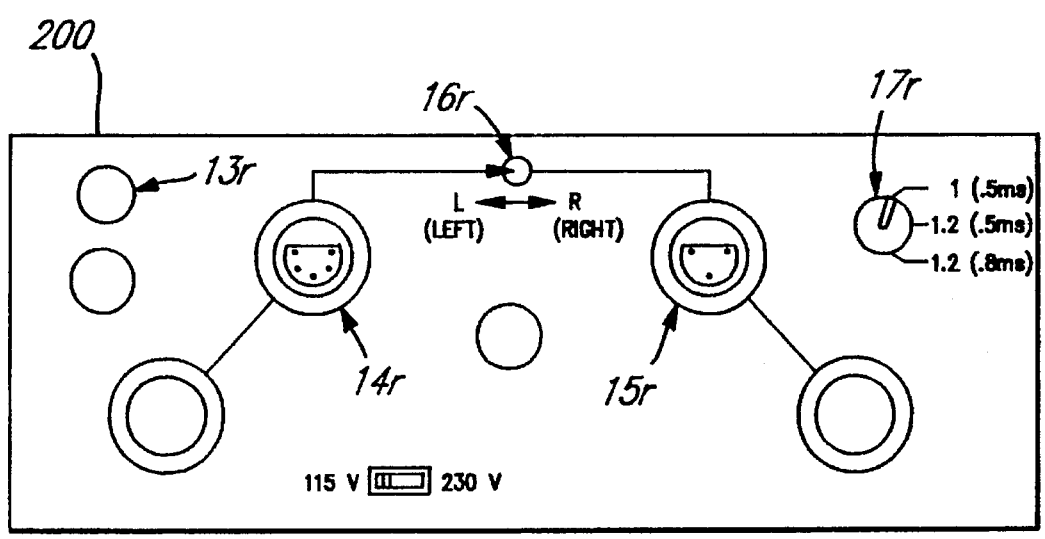
Figure 2C:
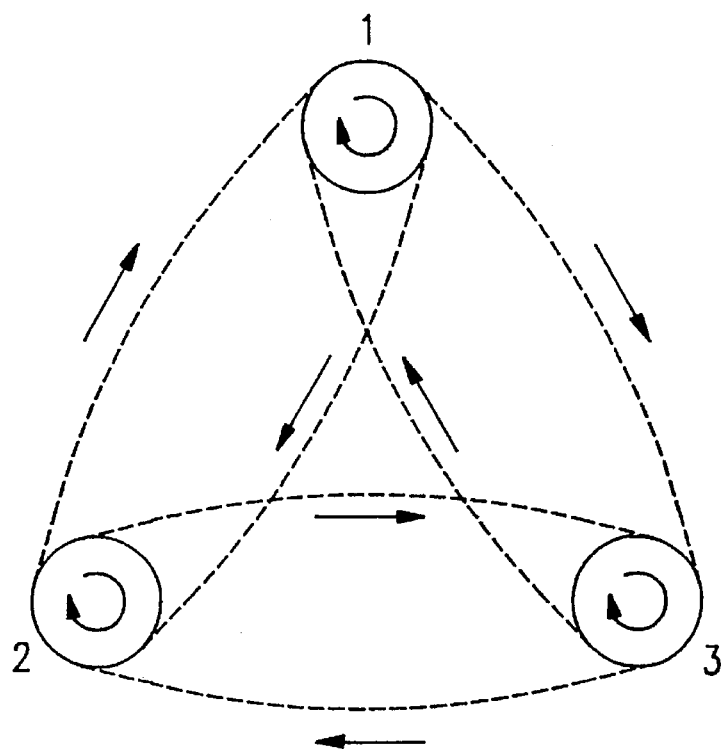
FIG. 2c shows the three factors involved in the holistic approach (named RESC) of the present invention.
Figure 2E:
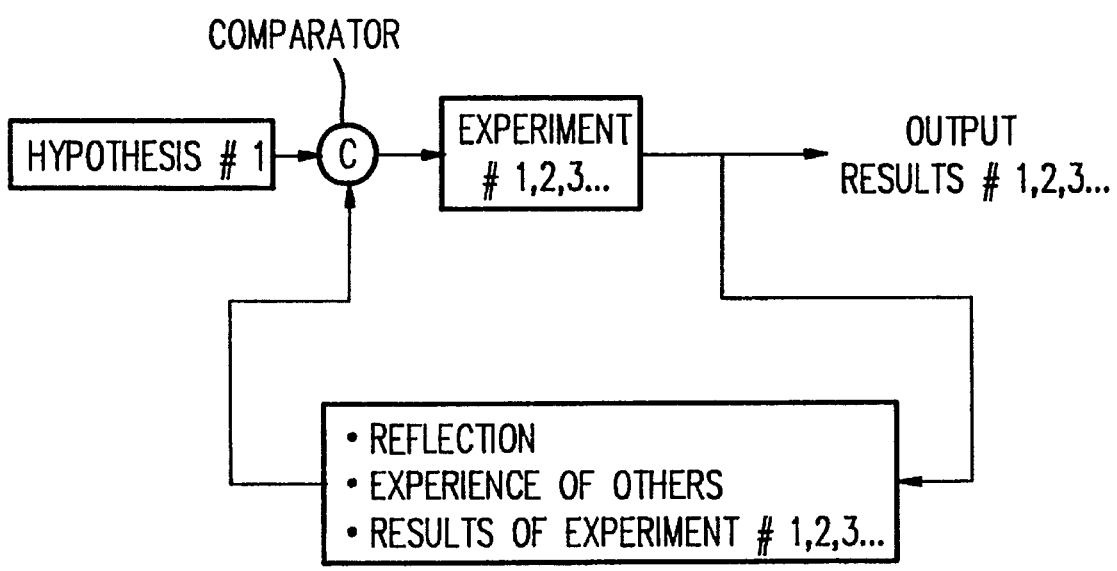
FIG. 2e is a block diagram which illustrates the RESC or RHUMART method.
Figure 2D:
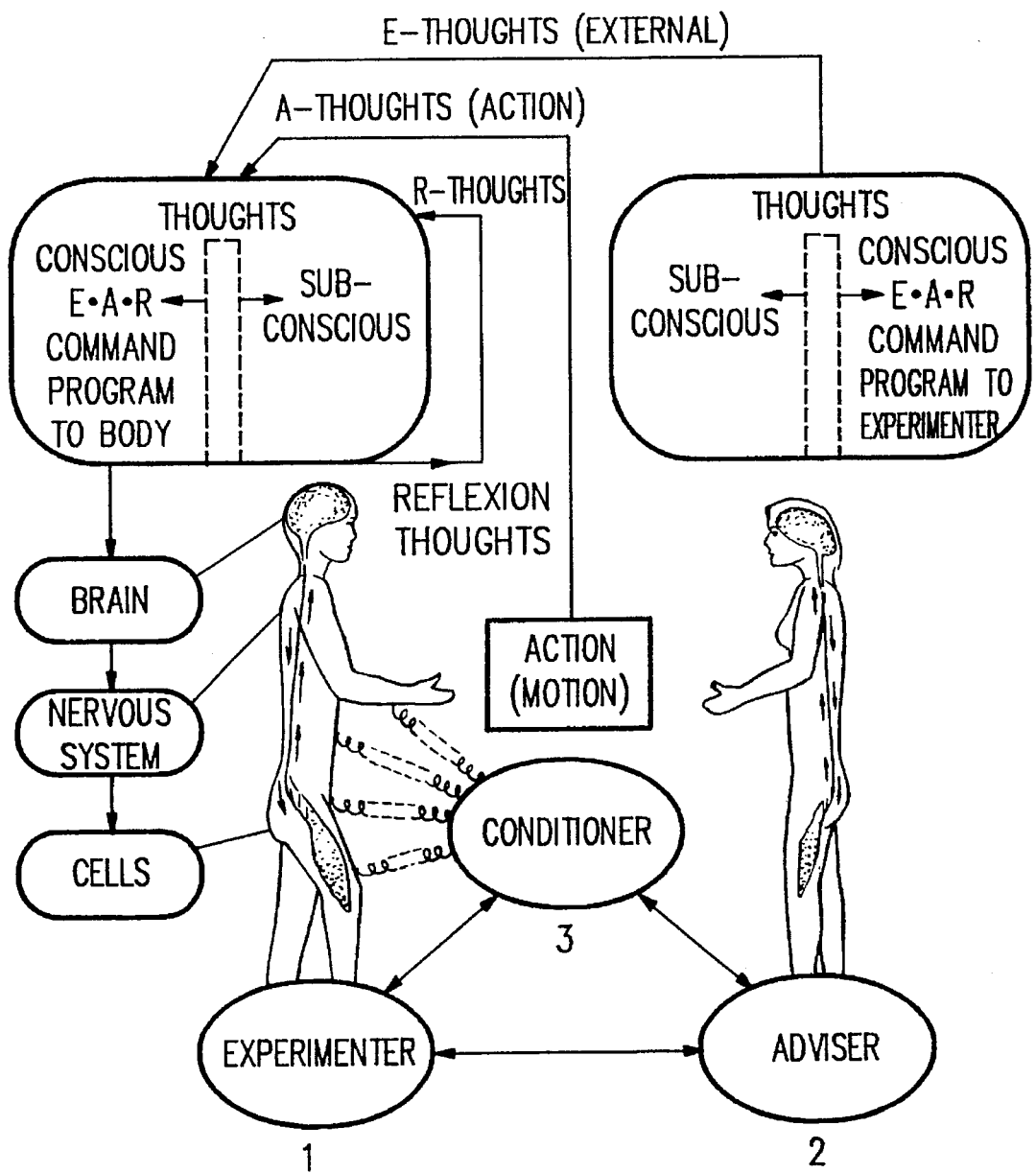
FIG. 2d illustrates the working principle of the RESC method involving the RESC experimenter, the advisor, teacher or mentor, and the said RHUMART or RESC conditioner.
Figure 2I:
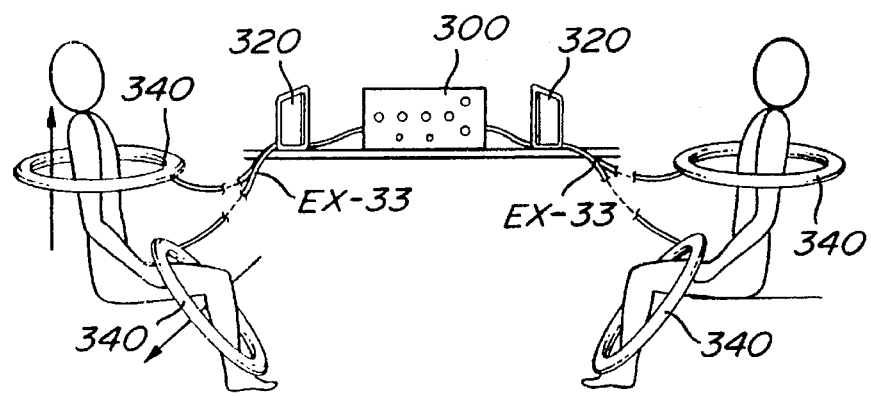
FIG. 2f shows an example of RHUMART Self-Health System, with optional table.
FIG. 2g shows a person carrying a Self-Health System in a handy suitcase and on a shoulder.
Figure 2J:
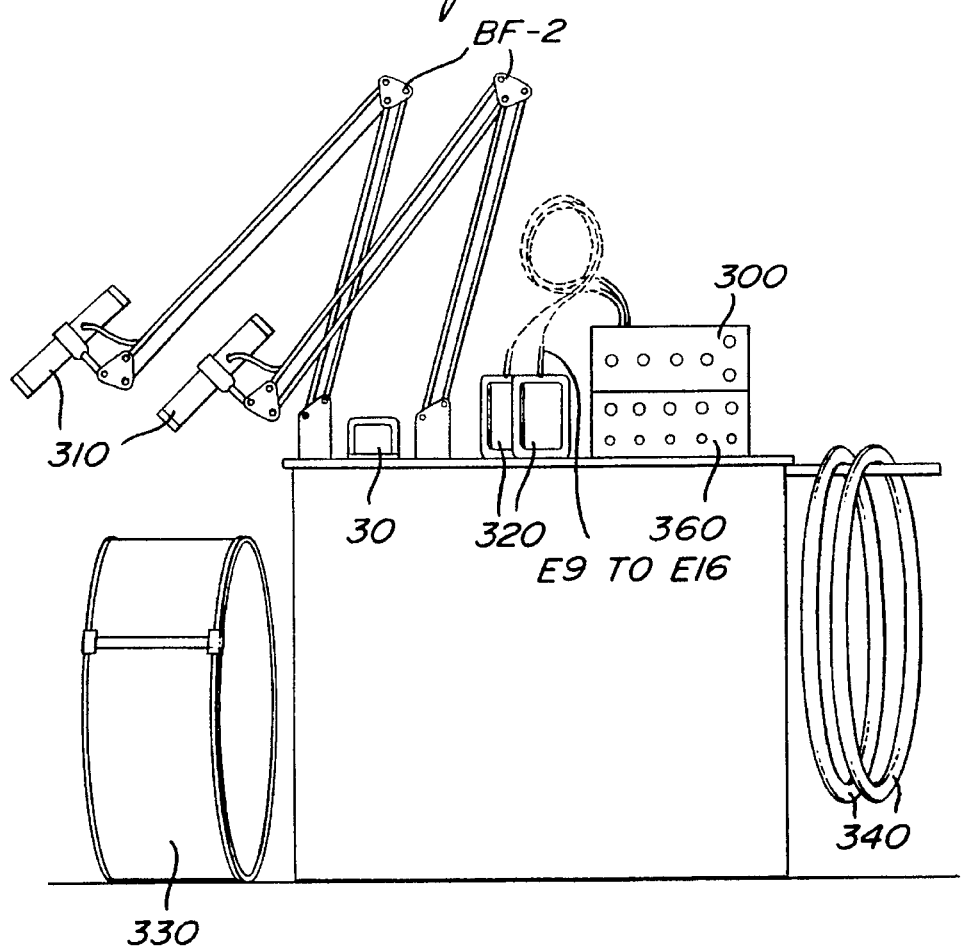
Figure 2M:
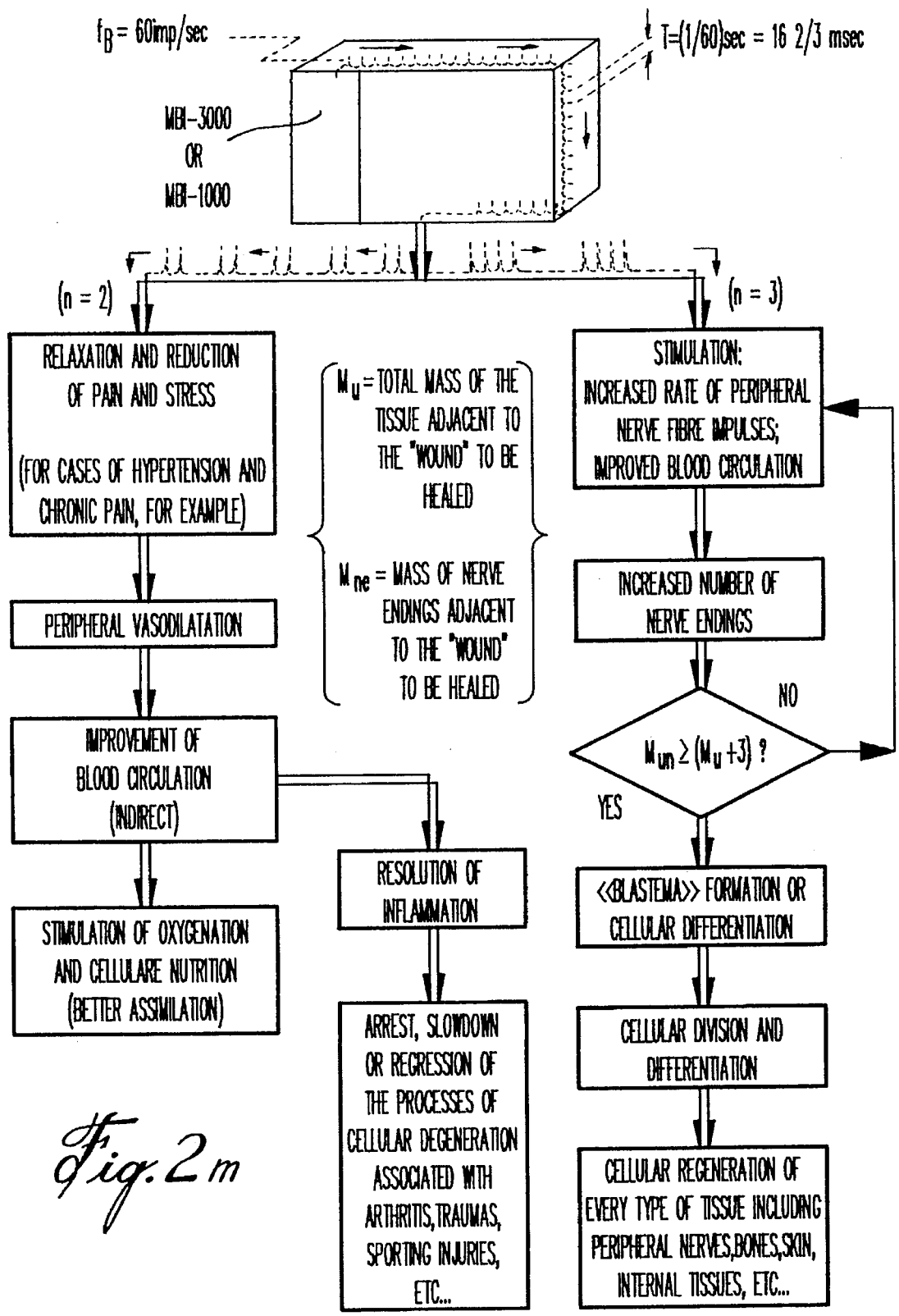
Figure 2N:
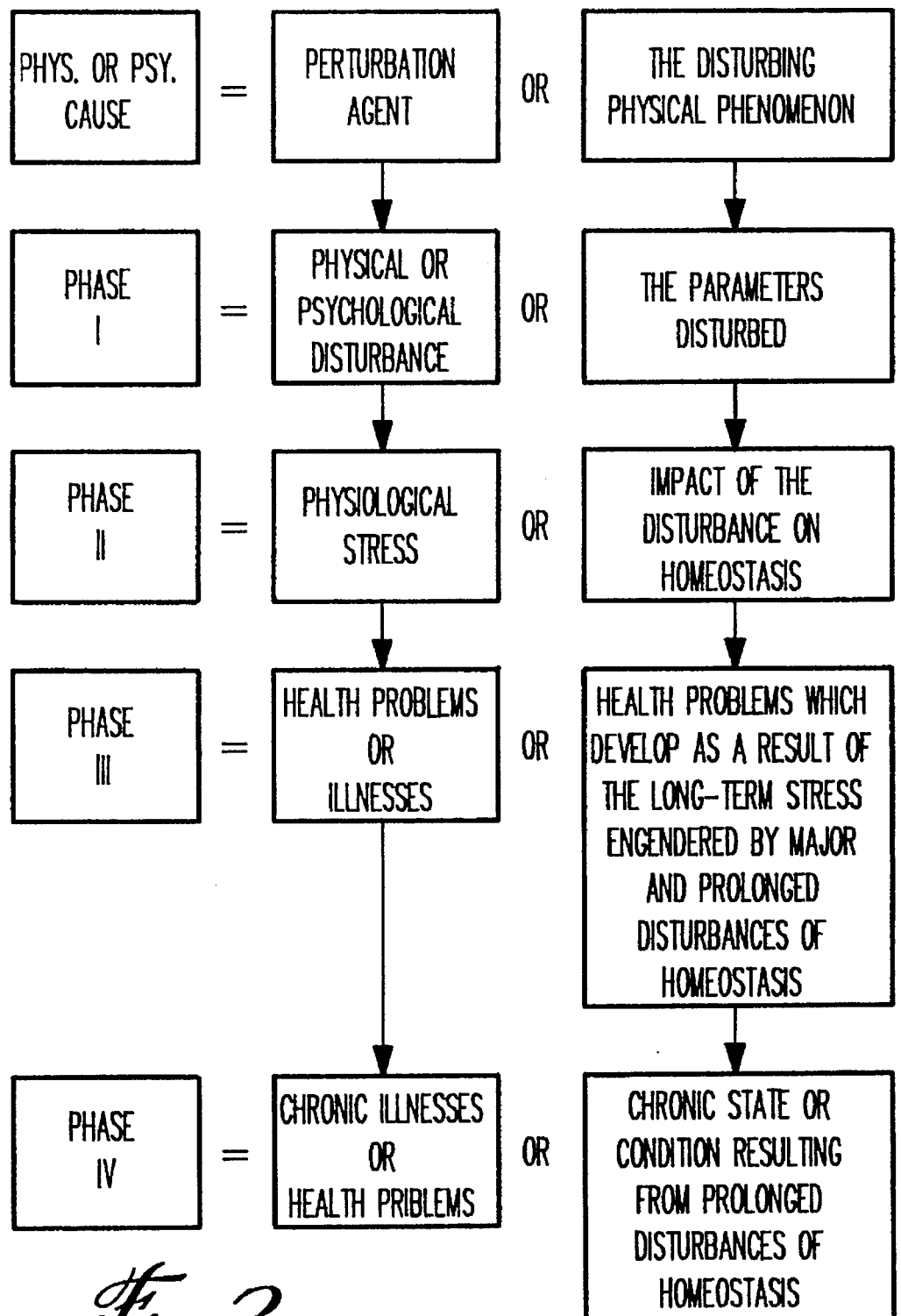
Figure 2P:
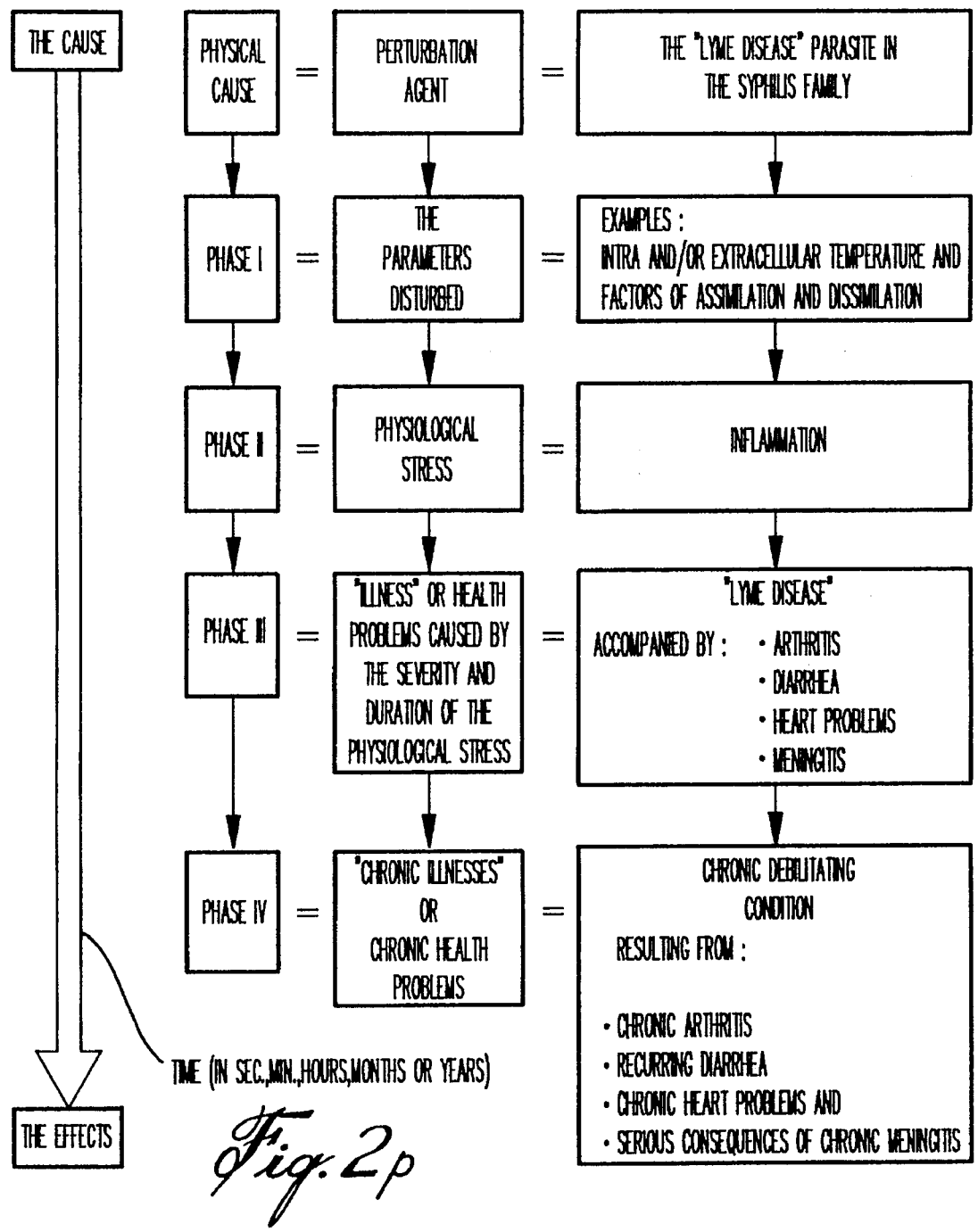
Figure 2R:
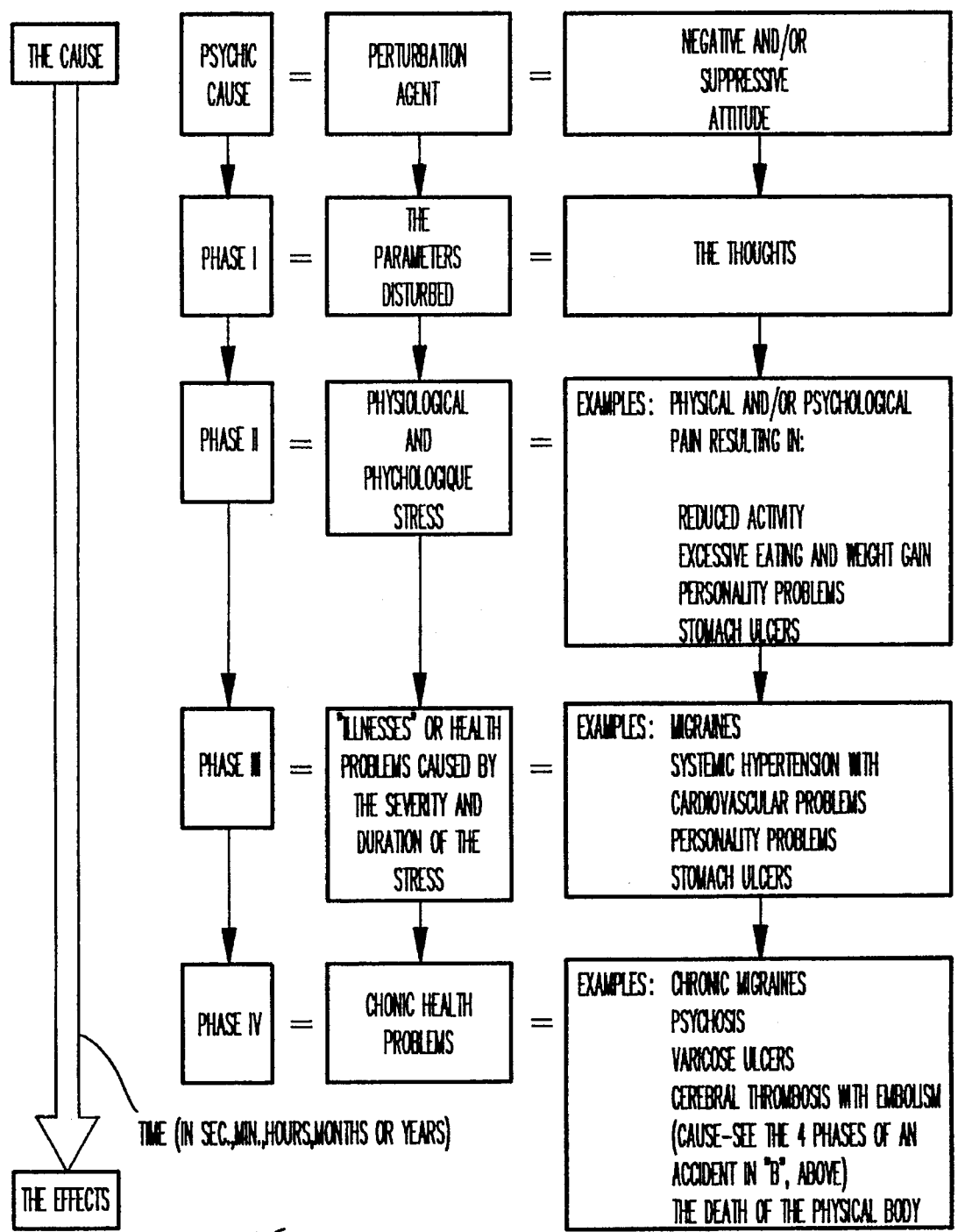
Figure 3A:
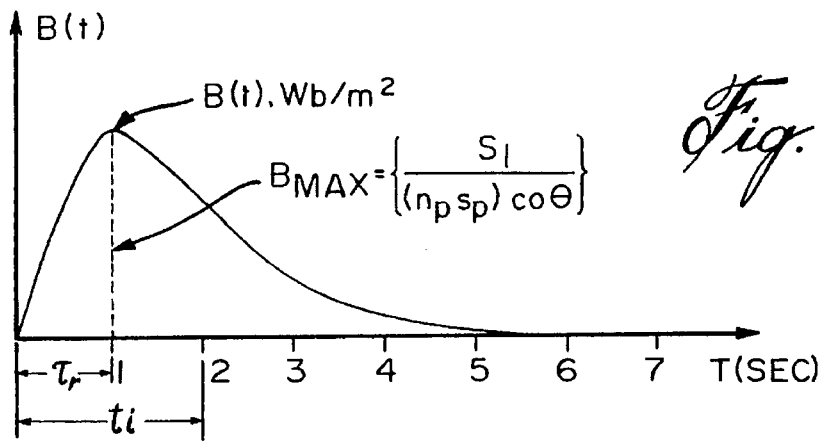
Figure 3B:
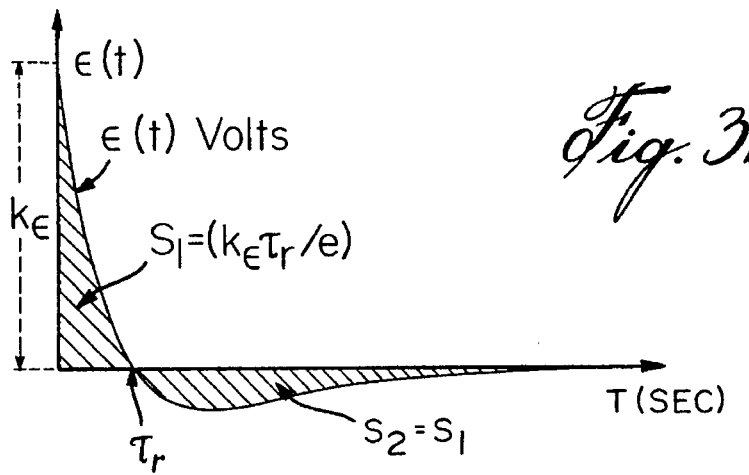
Figure 3C:
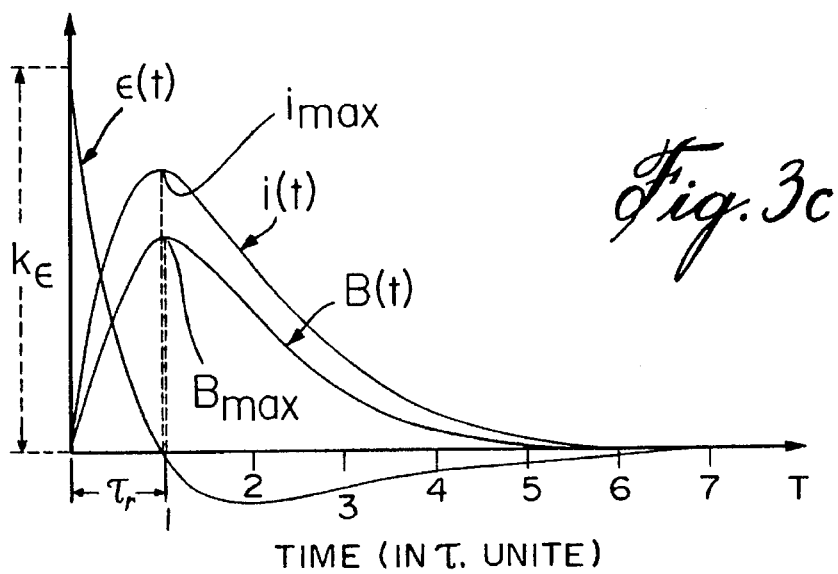
Figure 3D:
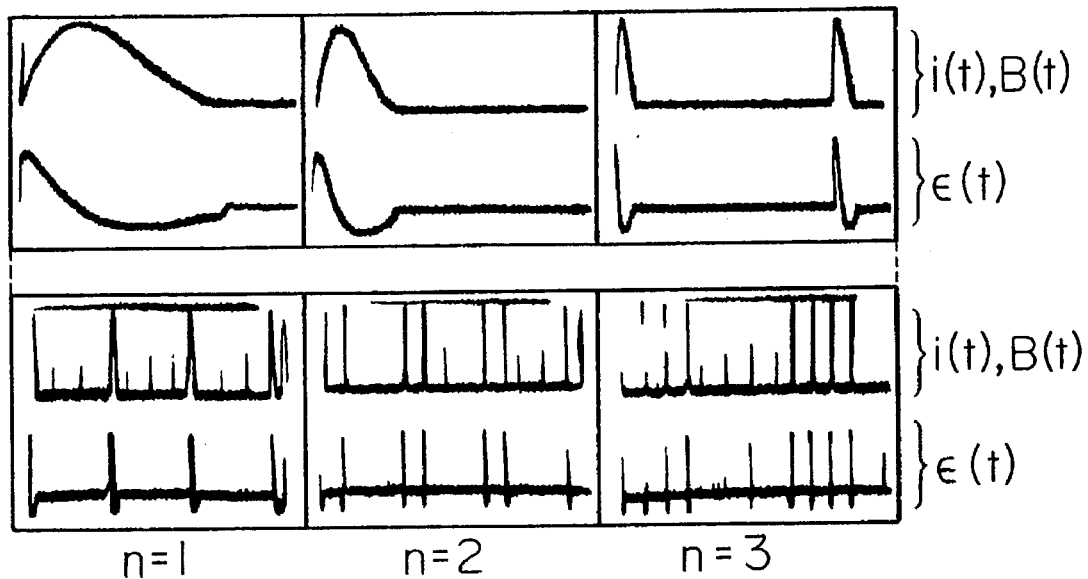
Figure 3E:
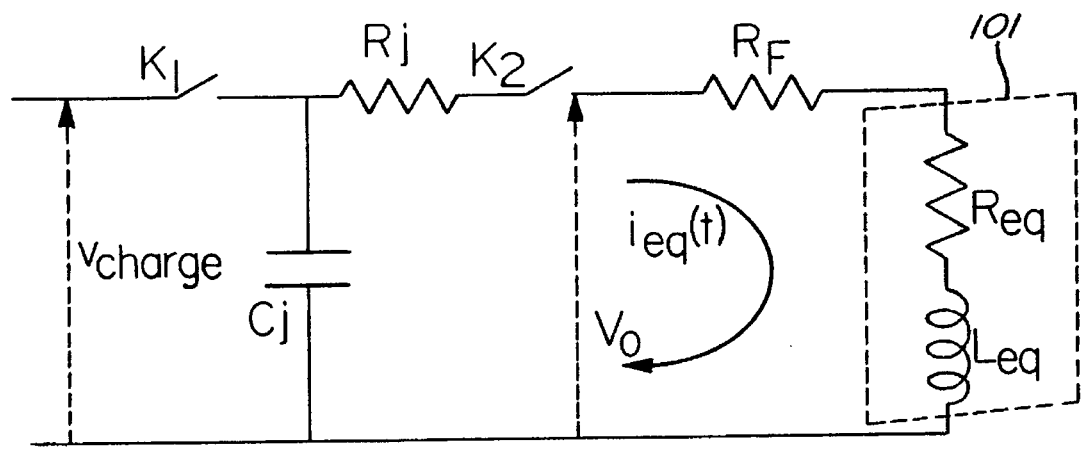
Figure 4:
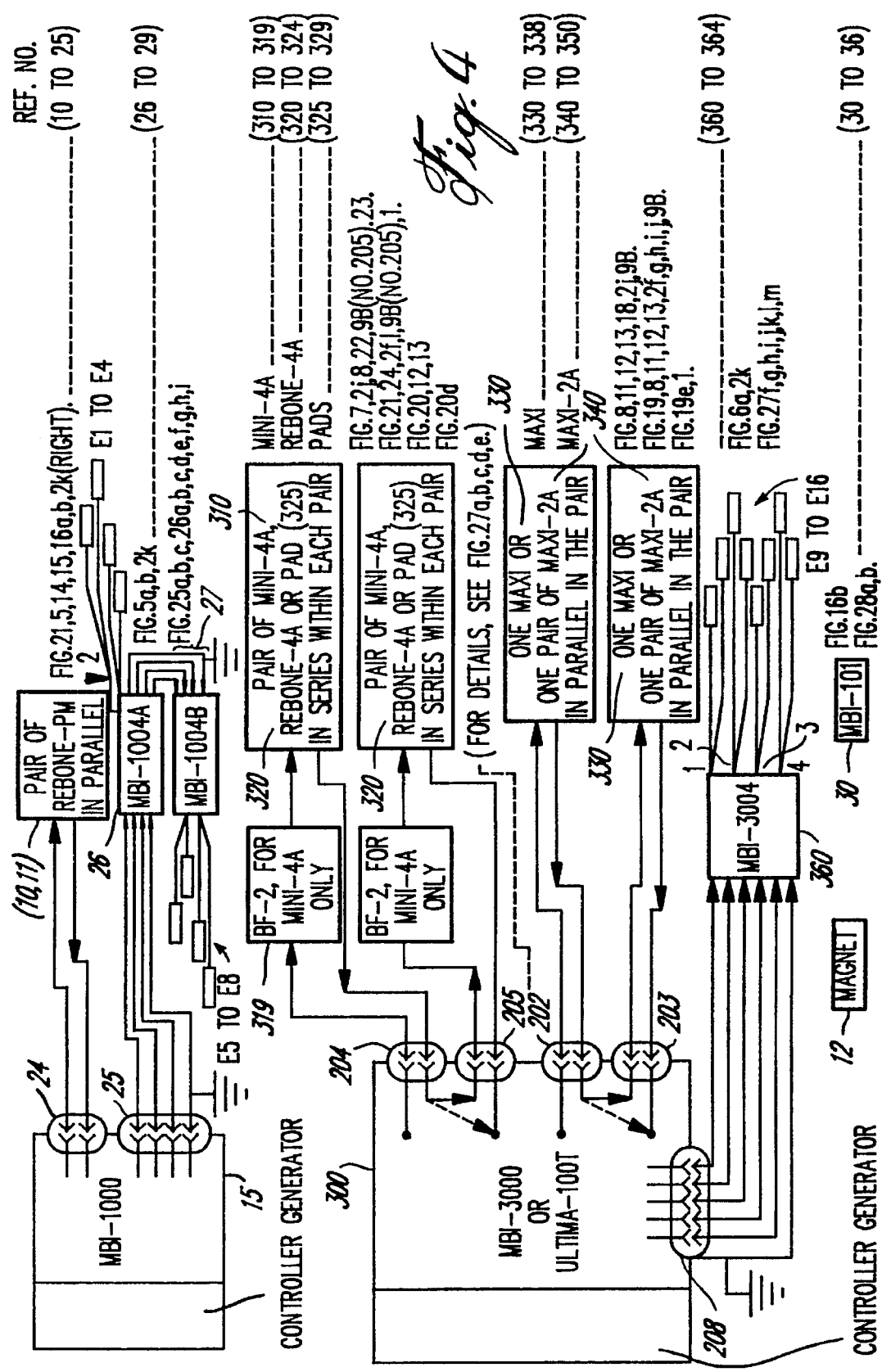
Figure 5:
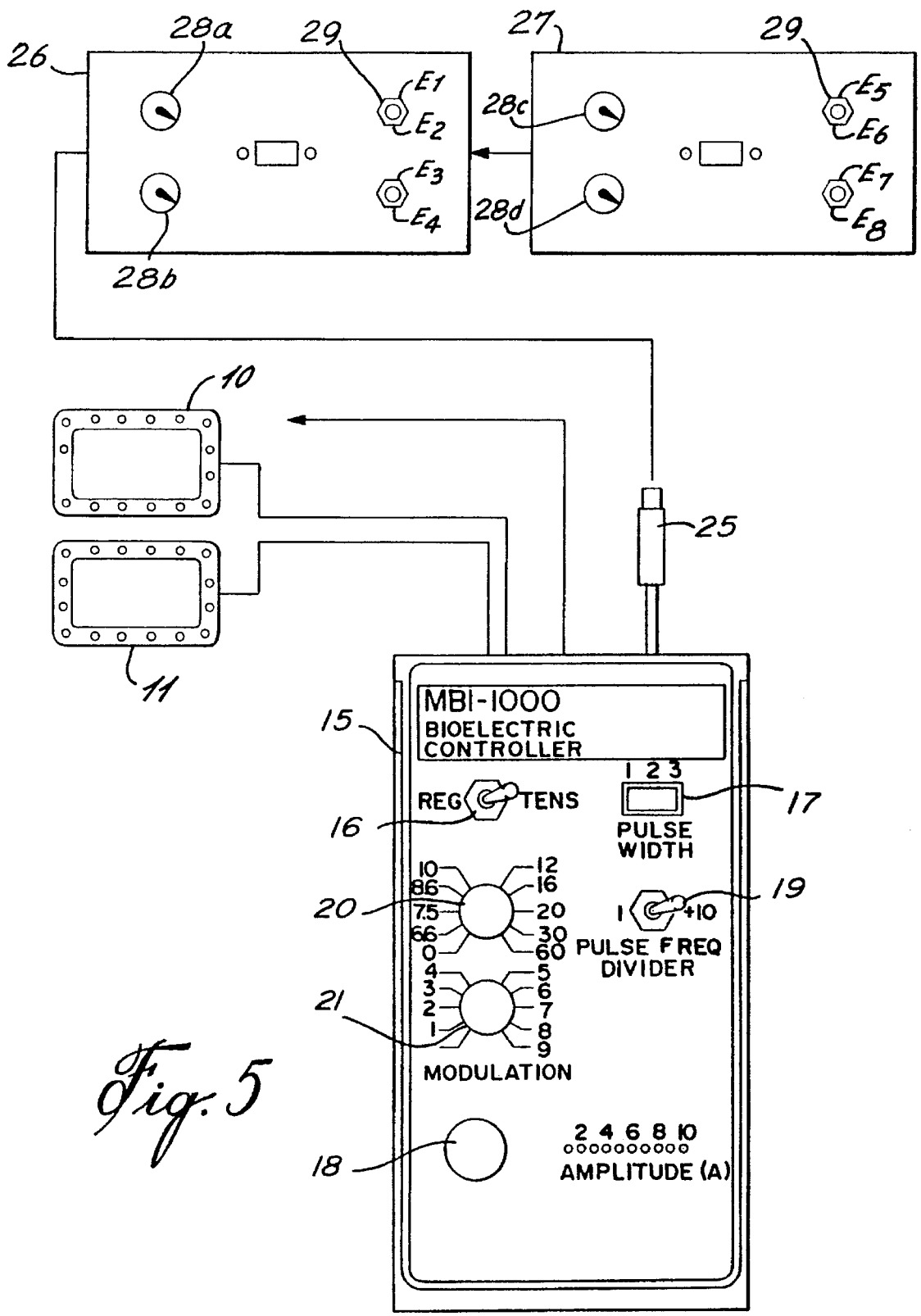
Figure 6A:
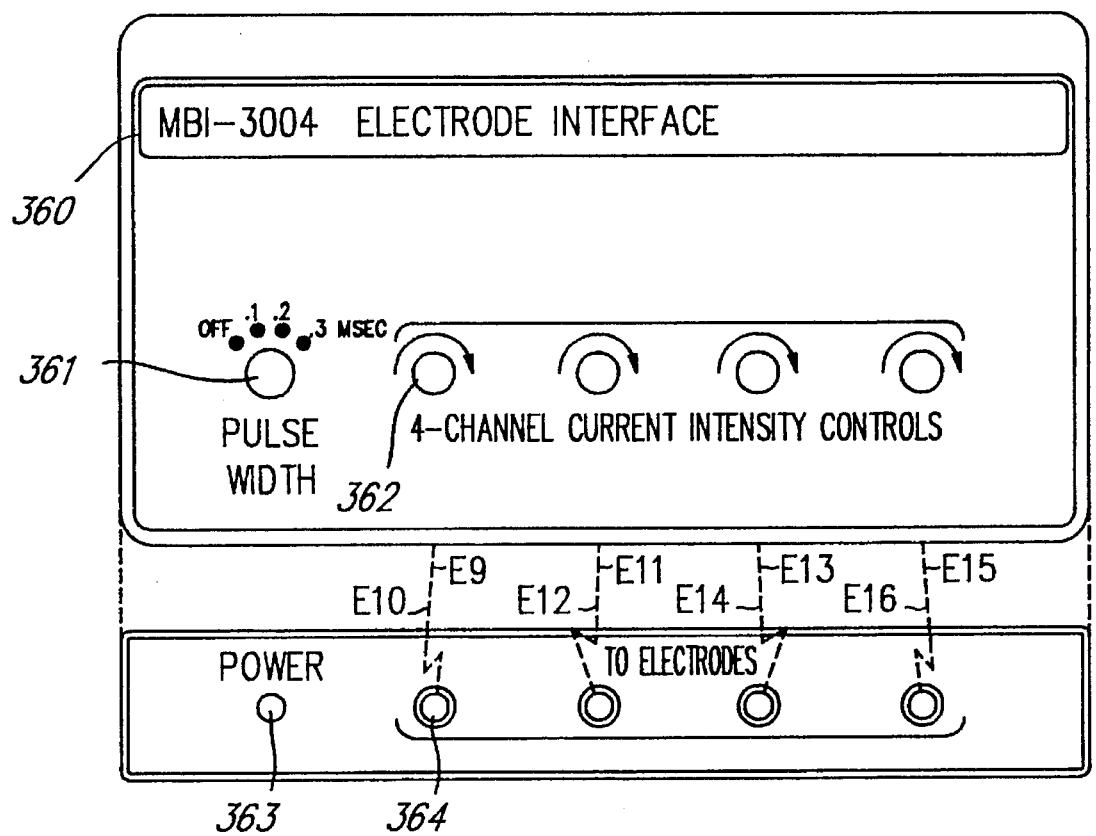
Figure 6B:
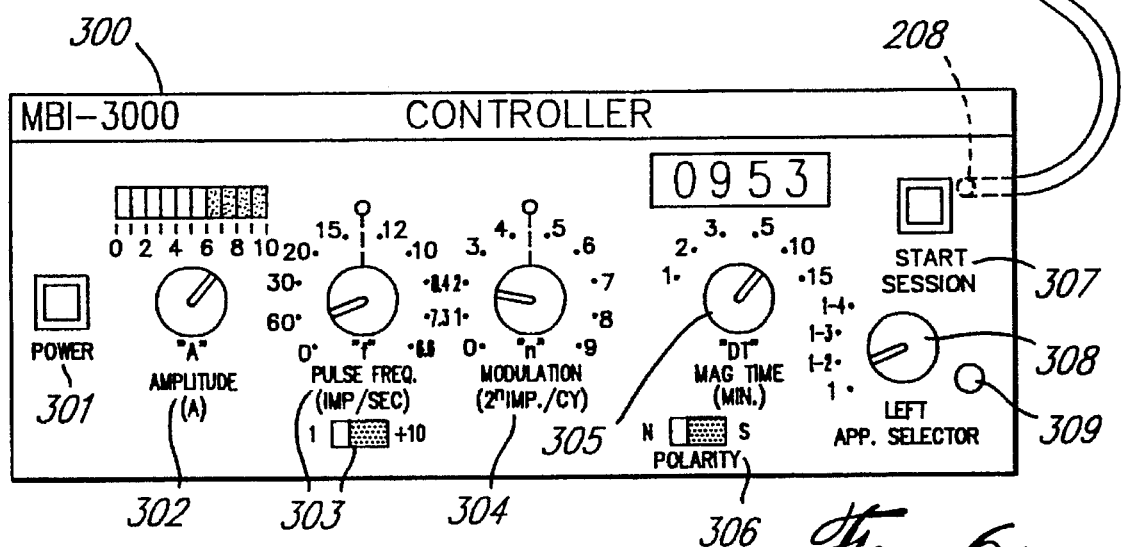

FIG. $2h^1$ and $h^2$ illustrates two examples of how to use a Self-Health System for global conditioning with the ring applicators, MAXI-2A, (left), and for local applications with the regional applicators, REBONE-4A, (right);

FIG. 2i illustrates the use of a RESC (or Rhumart) conditioner for couples. There is shown an example of global conditioning, simultaneously for two adults, with the double-ring applicators, MAXI-2A. The said MBI-3000 controller and two pairs of said REBONE-4A regional applicators are shown between the two users of this system;

FIG. 2j illustrates an other example of Self-Health System;

FIGS. $2k^1$ $2k^2$ illustrates two muscular modes of the present invention, the MBI-3004 with 4 pairs of flexible conductive electrodes (left) connected to the said MBI-3000 controller (not shown), and on the right, we can see the said MBI-3000 controller (with a cover) and a pair of said REBONE-PM local applicators, and on the right and lower right of this illustration, the said MBI-1004A-B (MBI-1004A plus MBI-1004B), muscular mode of the said MBI-1000 where 4 pairs of conductive and flexible, reusable muscular electrodes are shown;

FIG. $2L^1$ shows an exploded view of a portion of Man's diagram that is the body, the six survival factors (left),- and how the newly defined 10 senses, or sensorial activity, can influence man's actions (through the integrating hypothalamus, the organs and Physiological systems), the latter influencing man's thoughts by means of various actions as those shown in FIG. $2L^3$, including said RESC sessions and scientific experiments;

FIG. $2L^2$ shows an exploded view of a portion of Man's Diagram, that is the mind which processes action generated thoughts (and others) which in turn, will generate sensory feedback activity (biofeedback) induced by said RESC sessions and other means, as illustrates in FIGS. $2L^1$–$2L^4$;

FIG. $2L^3$ is a block diagram illustrating how the various types of action including said RESC sessions shown in this drawing interrelate the body and mind (illustrating the fact that "thoughts are the interiorization of the actions of man during his life";

FIG. $2L^4$ shows an enlarged view of a portion of Man's diagram, on the left, showing how the said six survival factors, including the regenerative bioelectricity of the type used in the present invention, the genetic code, nutrition, gravity, thoughts and the newly defined 10 senses;

FIG. 2m is a schematic illustration of the new RHUMART PHYSIOLOGY" described herein after, which shows how the present invention can induce the three basic physiological effects described herein and reinforce the defense and healing mechanisms of man kind and animals;

FIG. 2n shows the four stages of a disease or health problem which help illustrate the level at which the present invention induces its physiological effects;

FIG. 2p shows the four basic stages in the development of Lyme disease; this is indicative of how RHUMART can help control many health problems through its anti-inflammatory effect;

FIG. 2q is an illustration of the four phases of various types of accidents, from the perturbation agent to chronic health problems, still illustrating numerous health problems which can be helped through the anti-inflammatory and anti-stress effects of the present invention;

FIG. 2r shows examples of the four phases of through disturbances, from perturbation agents to chronic health problems, showing that the anti-stress effect of this invention can help in various problems developed from through disturbances;

FIG. 3a, b and c show graphical and mathematical representations of the impulse wave forms used in the present invention;

FIG. 3d shows a photographic reproduction of impulses and impulse bundles used in the present invention, as seen on the screen of an oscilloscope: for n=1, n=2 and n=3, n being the said modulation value, where there are $2^{n-1}$ impulses per impulse bundle;

FIG. 3e shows the equivalent pulse shaping circuit or the equivalent circuit of N identical applicators described herein, which are serially or parallel connected to the said generator or controller means;

FIG. 4 is a block diagram of the present invention where major constituents are identified by numbers (lo up), on the right hand side of this Figure, (see FIG. 8 and 9b) herein after for a detailed view of applicator connections; the Figure numbers relating to the various constituents of this system are also given on the right);

FIG. 5 is an illustration of the miniaturized MBI-1004A and MBI-1004B electrode interfaces of muscular modes including an illustrating of the miniaturized MBI-1000 bioelectric controller;

FIG. 6a illustrates the said MBI-3004 electrode interface of the muscular mode which includes the said MBI-3000 bioelectric controller shown in FIG. 6b;

FIG. 6b is a simplified view of the front panel of the controller MBI-3000.

Figure 9A:
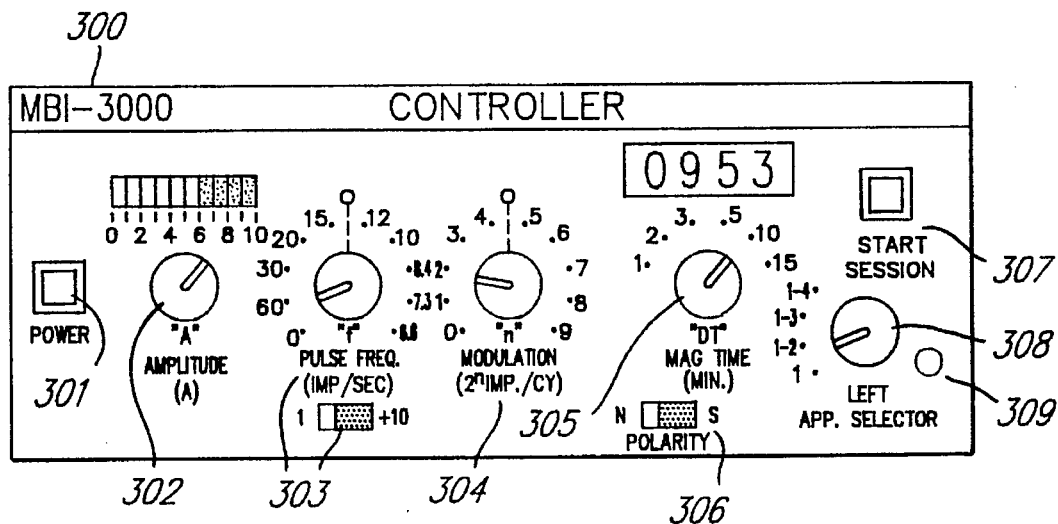
Figure 9B:
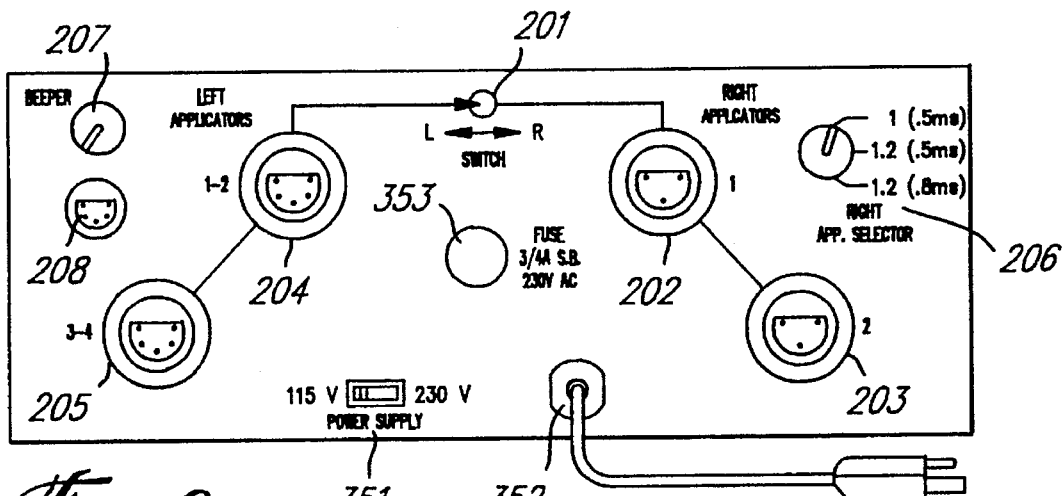
Figure 10:
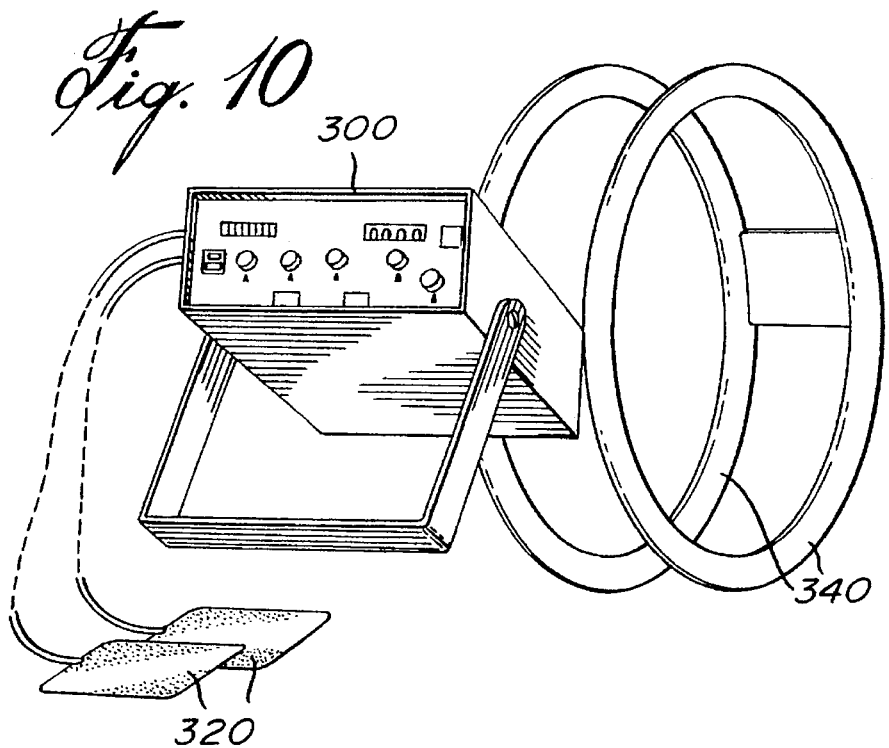
Figure 11:
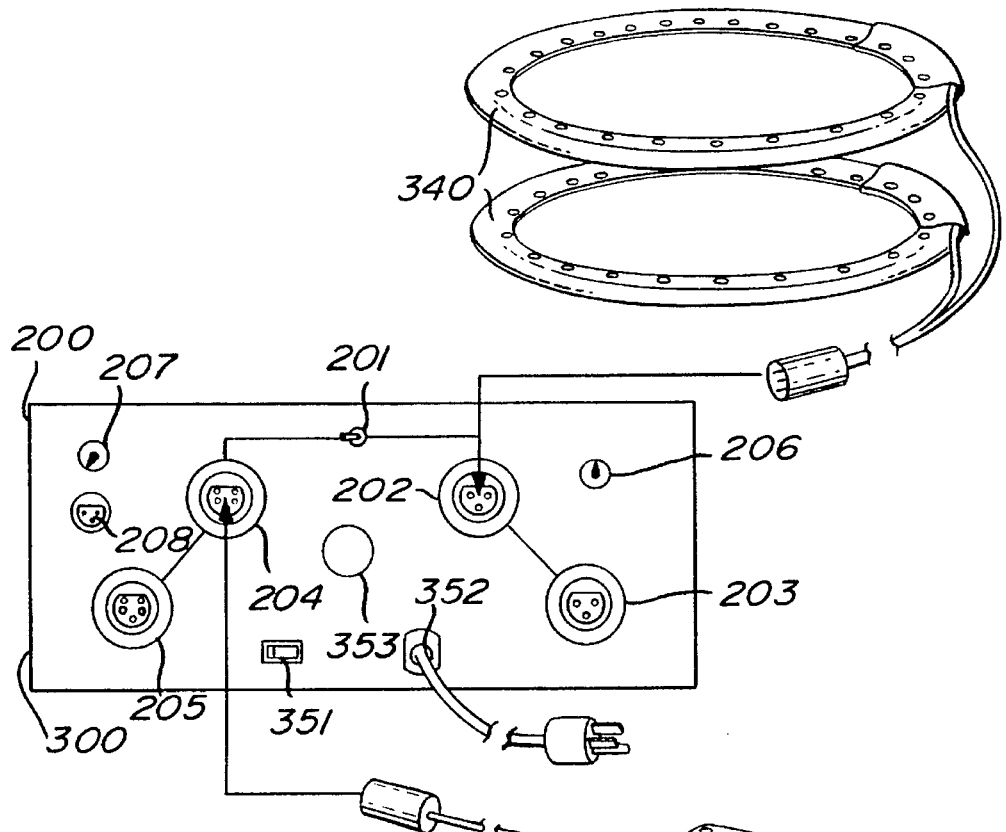
Figure 14:
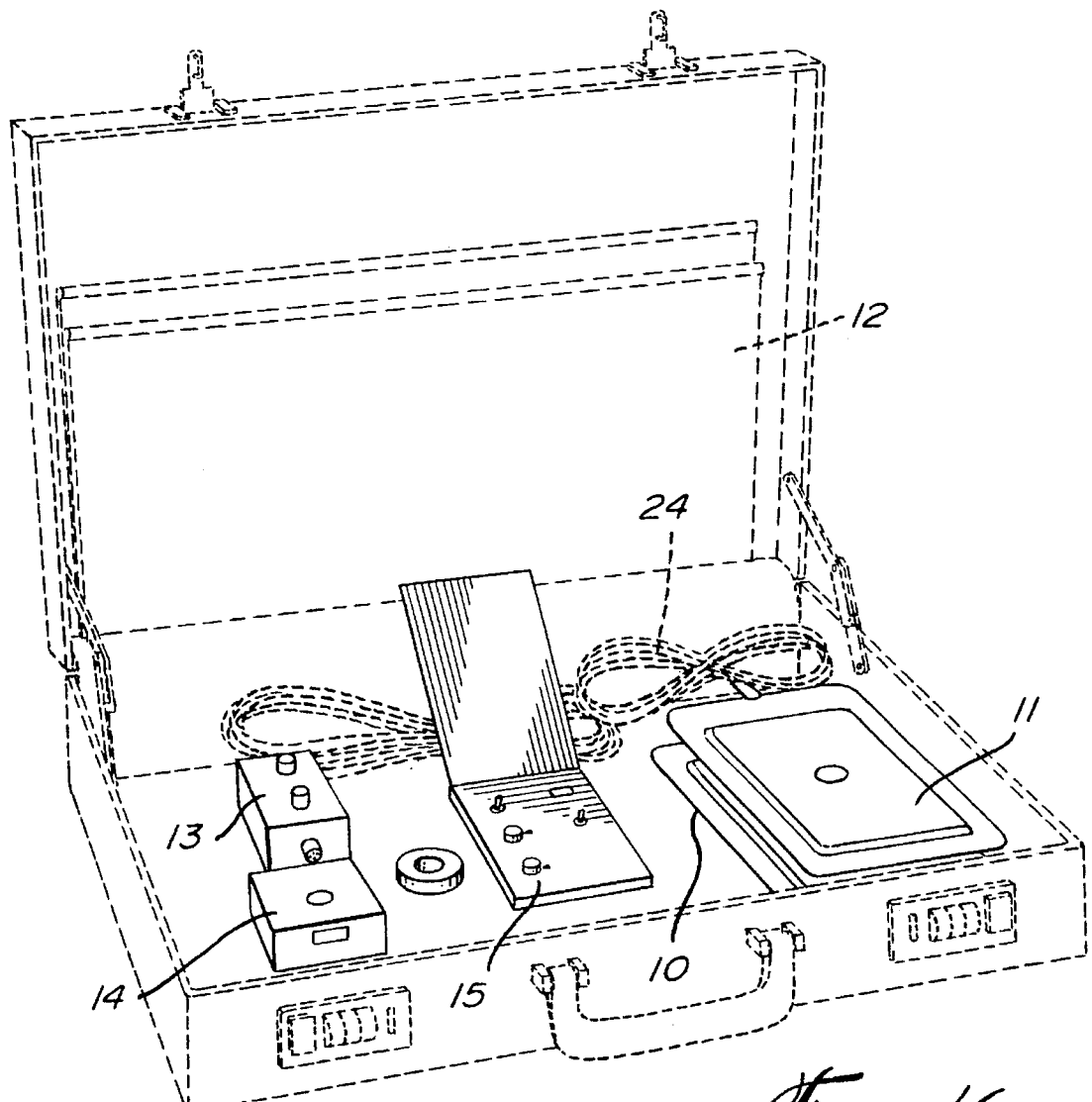
Figure 16C:
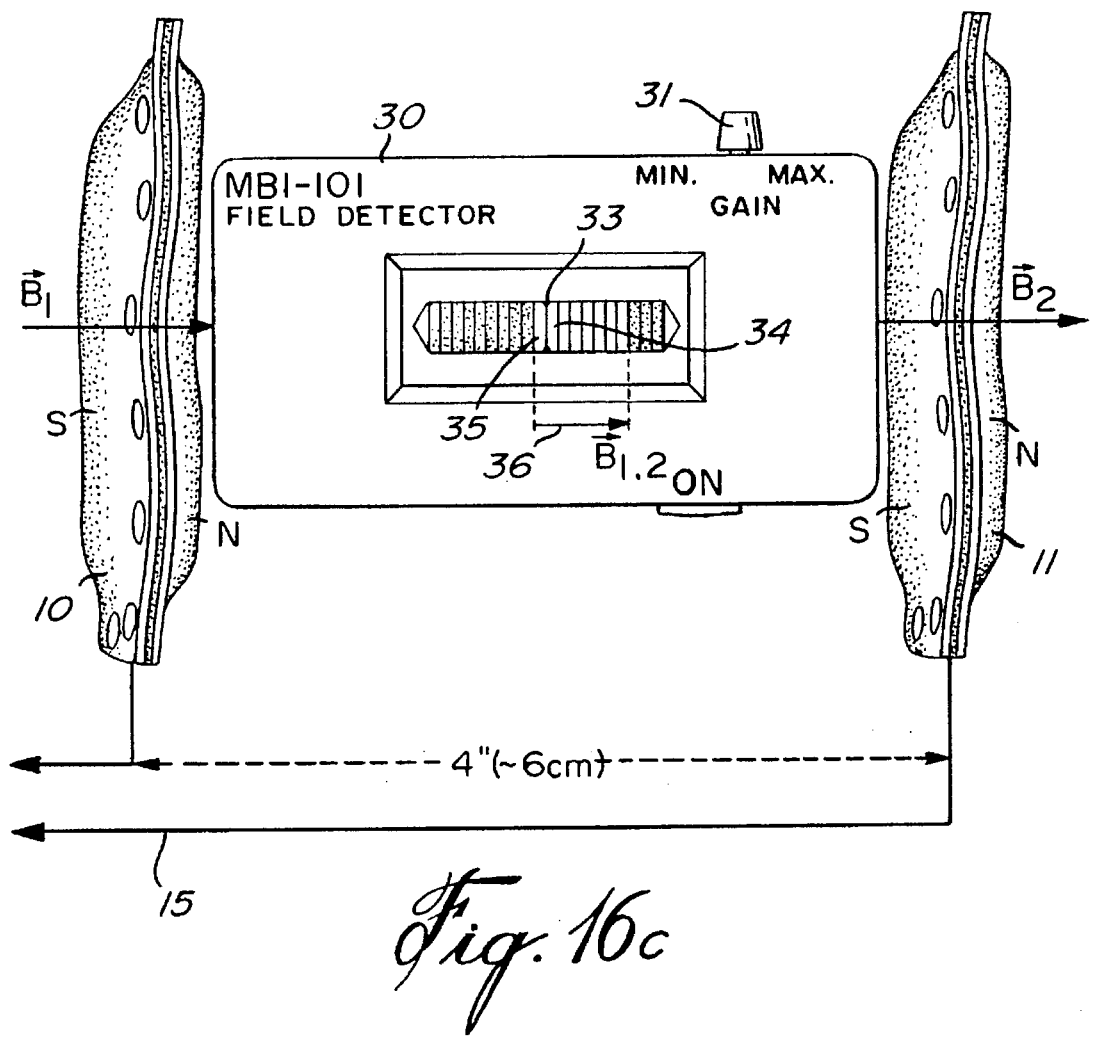
Figure 17:
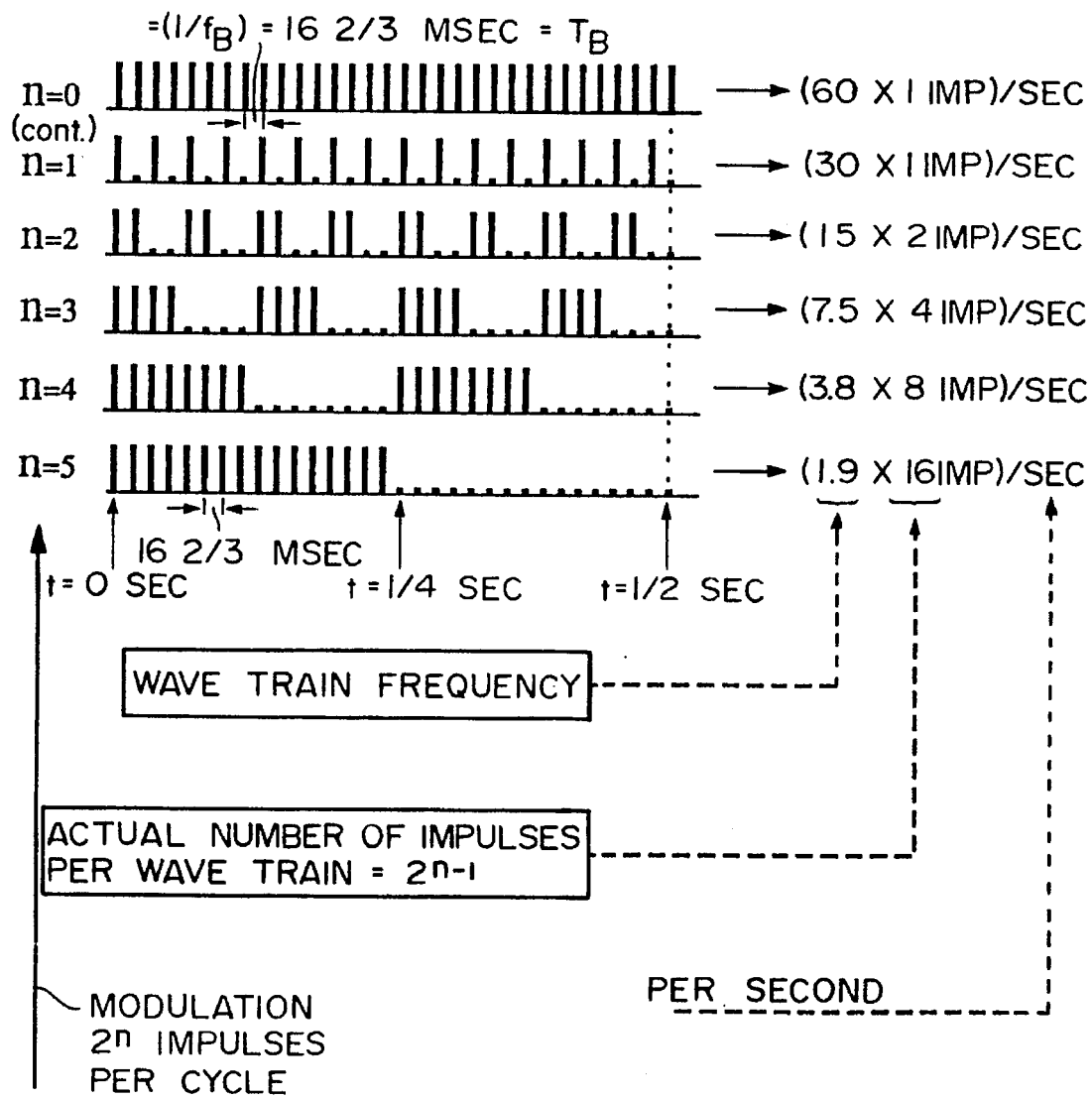
Figure 18D:
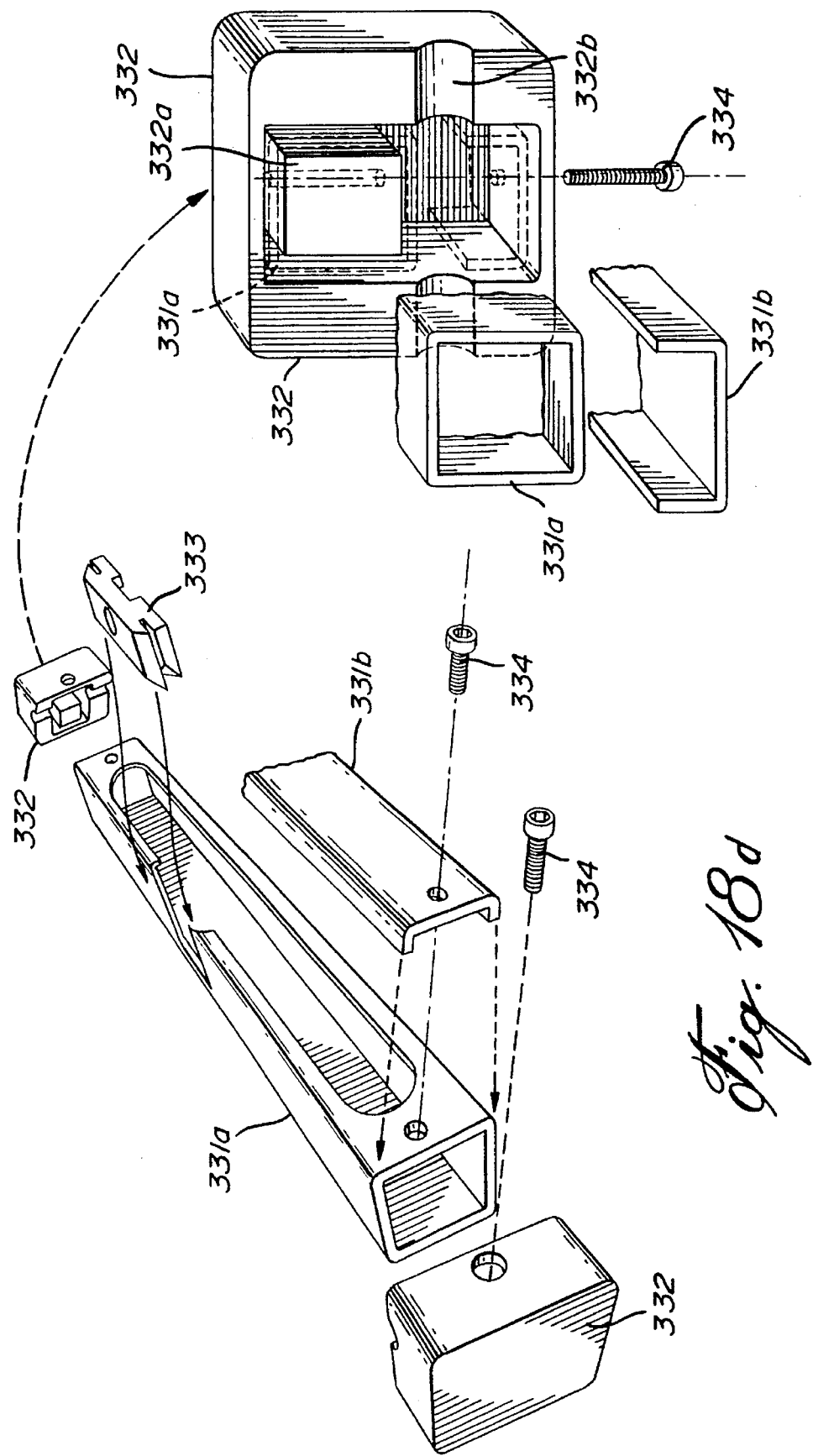

FIG. 7 is a side view of the said MINI-4A local applicator described herein;

FIG. 8 is a perspective illustration of 4 modes of the present invention, e.g. the said MINI-4A, REBONE-4A, MAXI and the MAXI-2A modes all of which include the said MBI-3000 controller;

FIGS. 9a and 9b show illustrations of the front and rear panels of the MBI-3000 bioelectric controller;

FIG. 10 is a perspective illustration of an embodiment of the present invention;

FIG. 11 is a perspective illustration of an embodiment of this invention where the connections of applicators are shown;

FIGS. 12, 12a, and 12b are perspective illustrations of JAM-8A and the MAXI-2A modes including the MBI-3000 controller, and two examples of applications to horse;

FIGS. 13a and 13b are perspective illustrations of various applications to horses of the MAXI-2A and JAM-8A modes of the present invention (not showing the MBI-3000);

FIG. 14 is a perspective view of a miniaturized embodiment of the present invention, that is the REBONE-PM mode which includes the MBI-1000 controller-generator;

FIG. 15 shows an example of an actual application of the REBONE-PM mode to the shoulder;

FIGS. 16, 16a and 16b are illustrations of a miniaturized embodiment of the present invention and its main accessories described with respect to FIG. 14, except for the ferrite magnet 12 used to detect the fields manually or by hearing;

FIG. 16c is an illustration of the MBI-101 field detector positioned between the REBONE-PM applicators of the MBI-1000 showing the configuration used to measure the pulsating field of the REBONE-PM mode;

FIG. 17 is an illustration of the sequential pulses for different modulation "n" values, for a basic frequency, $f_b$, of 60 pulses per second;

FIG. 18a shows a partly exploded perspective illustration of the MAXI applicator showing the MAXI assembly inner and outer parts held together by means of two blocks into which the parts are fixed by means of special screws, see FIG. 18d for further details);

FIGS. 18b is a partly exploded perspective illustration of the construction details of the MAXI assembly box showing how the winding is connected to the lead connector A3M with the strain release block;

FIG. 18c is a fragmented perspective view of details of construction of the specially developed MAXI wall for holding and protecting the MAXI coil winding made up of 58 turns of insulated aluminum wire;

FIG. 18d is an exploded view of the strain release block

Figures 20C, 20D:
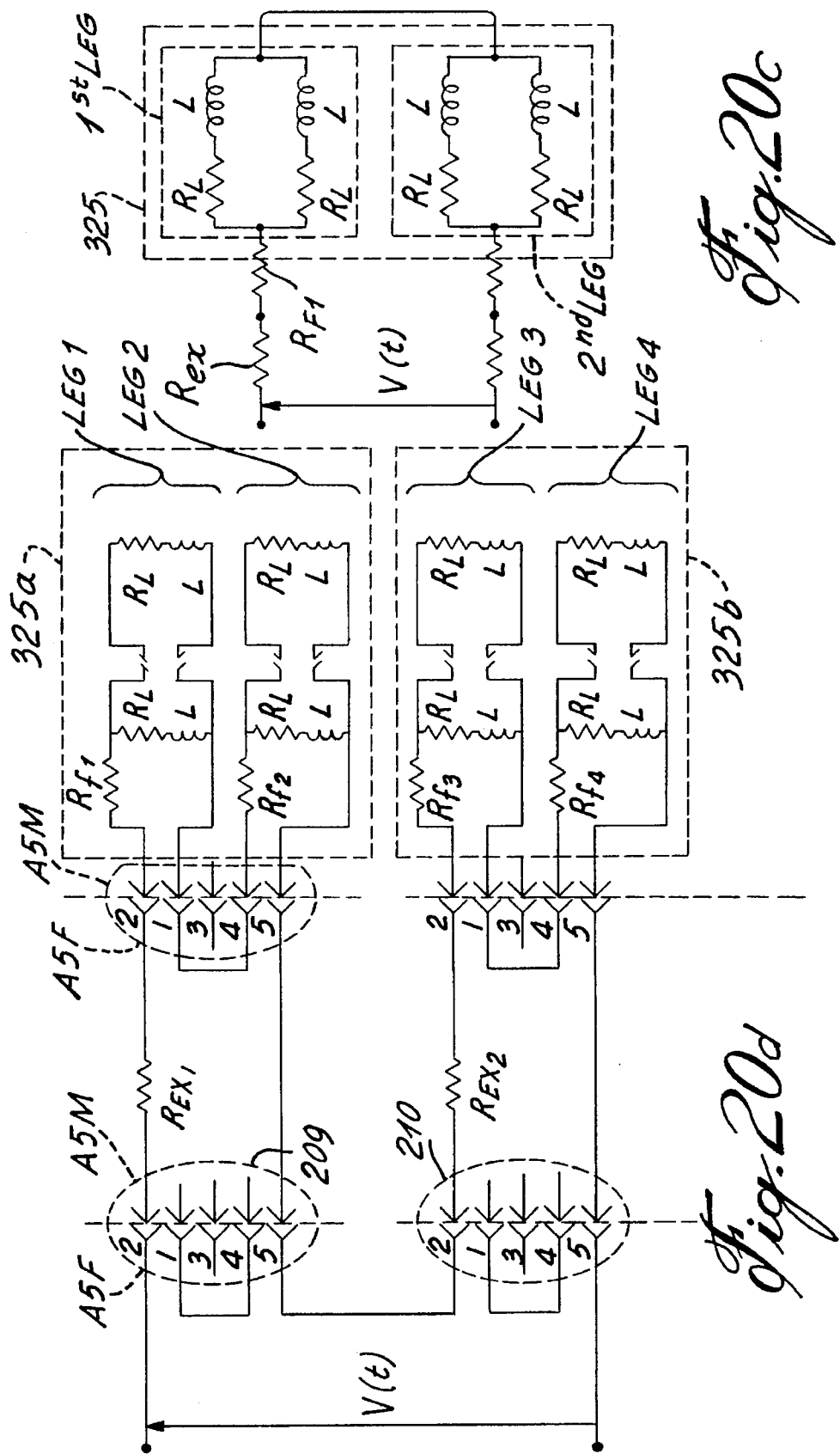
Figure 23:
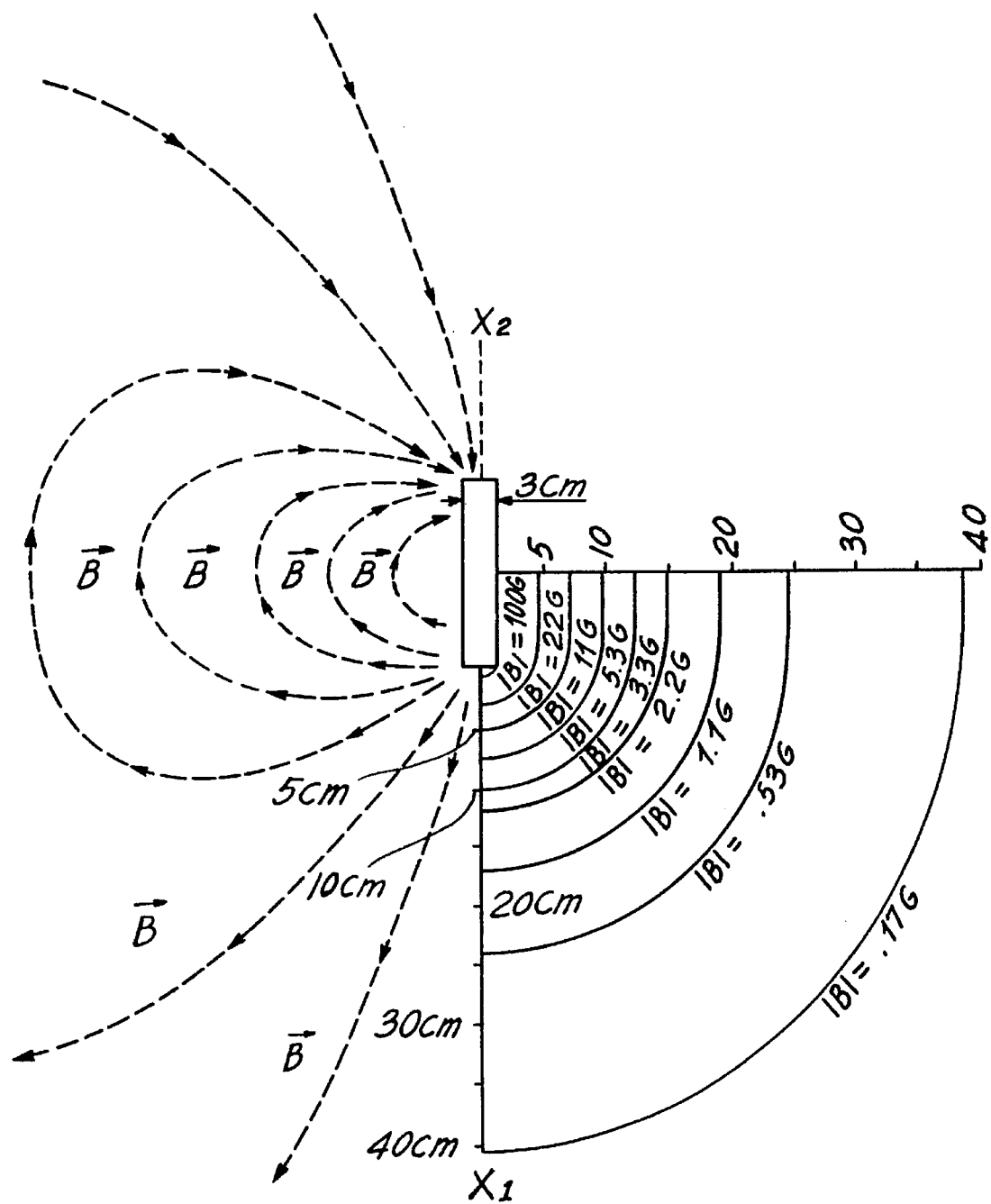
Figures 24A, 24B:
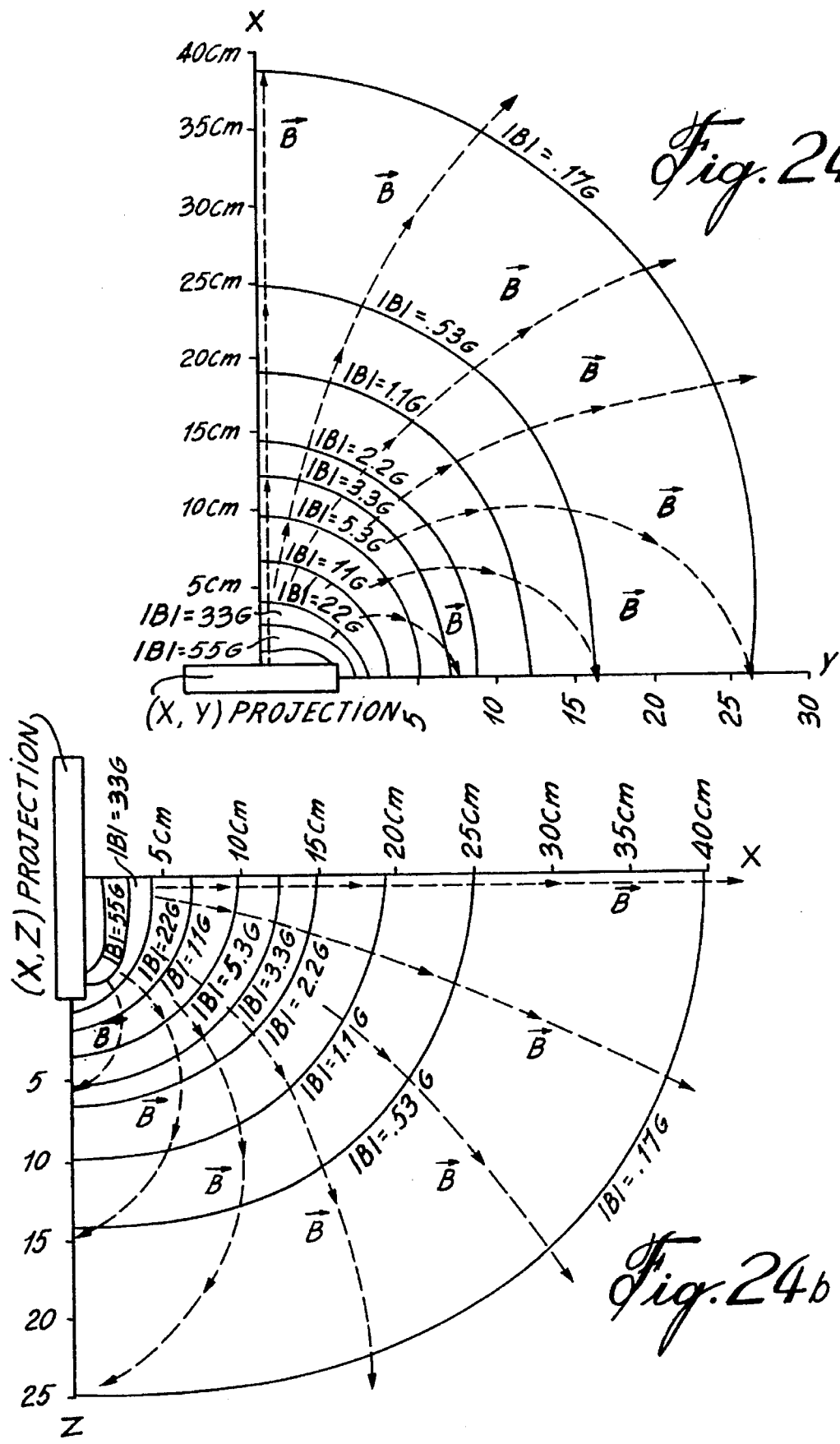
Figure 25A:
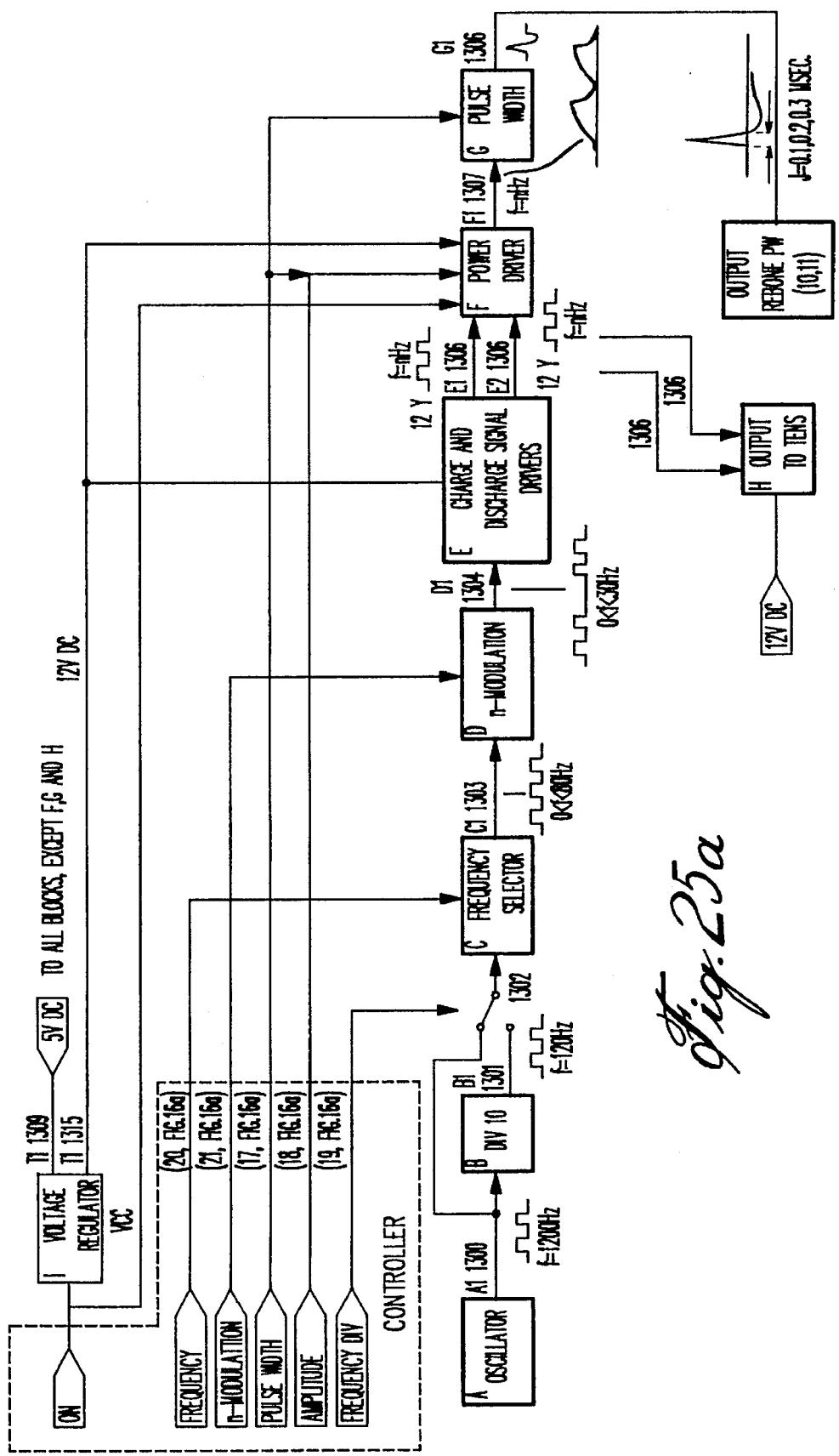
Figure 26A:
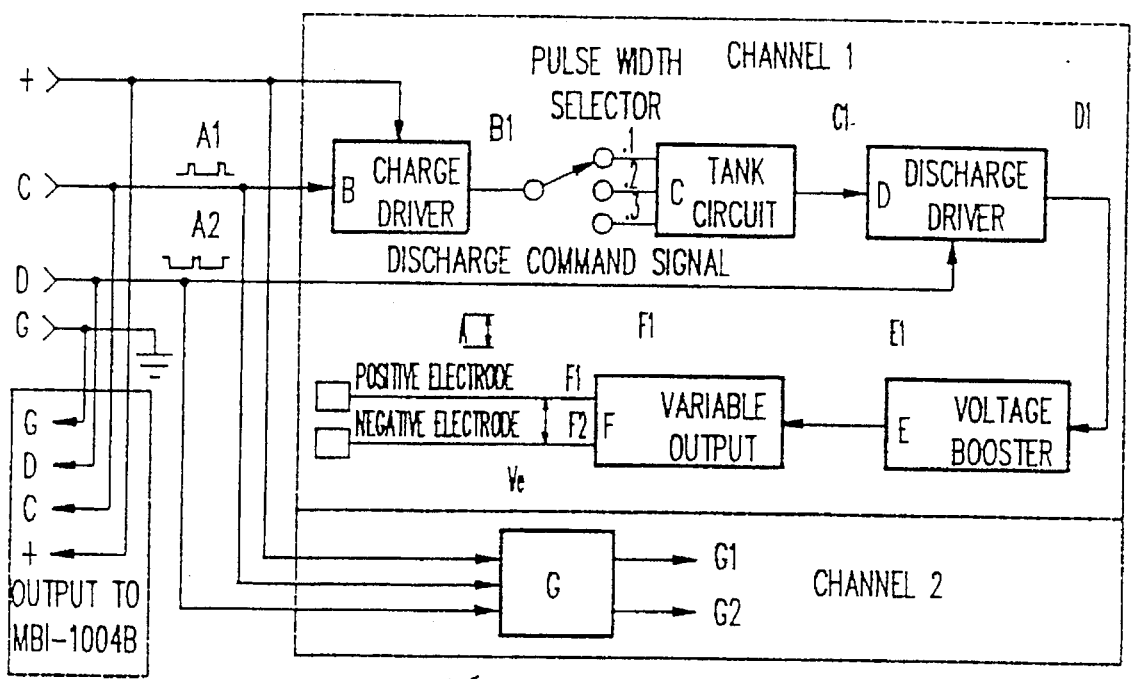
Figure 26B:
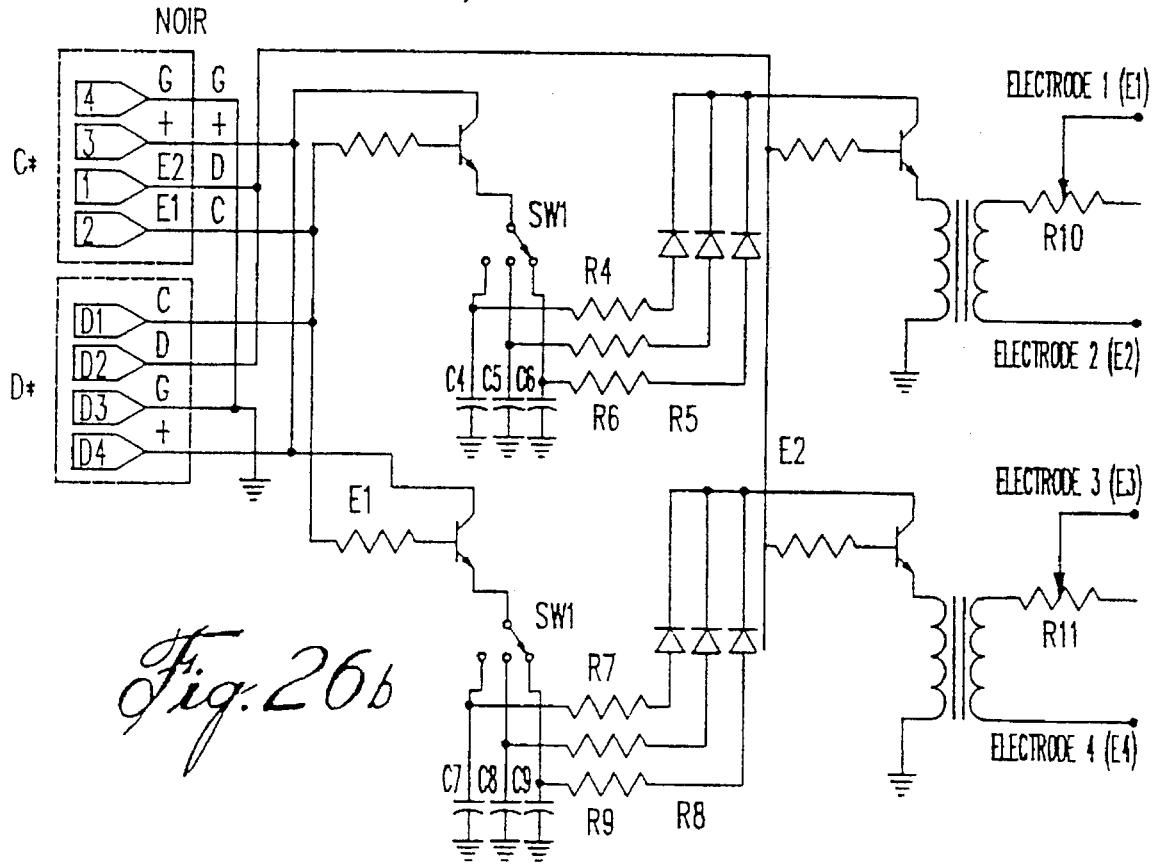
Figure 26C:
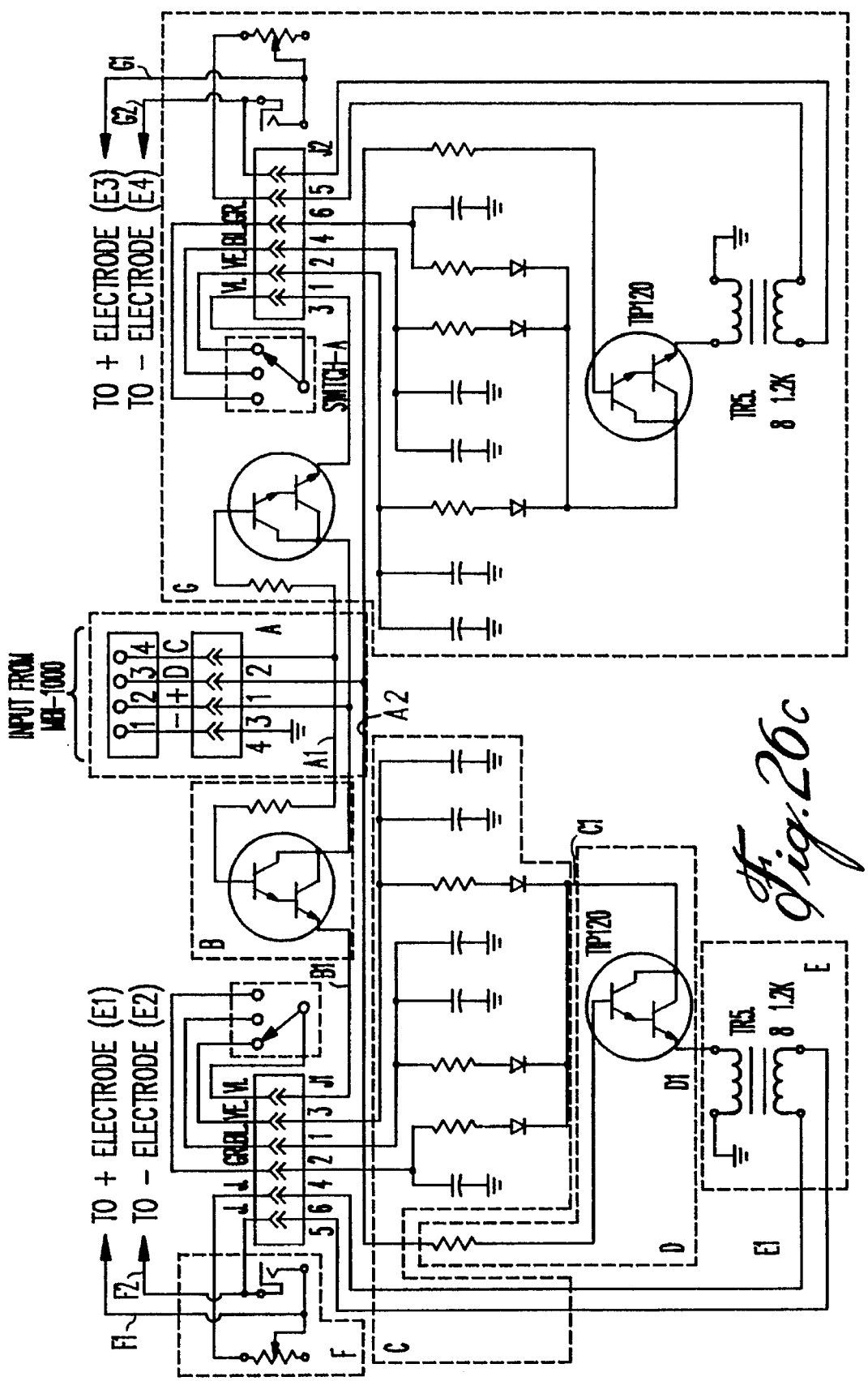
Figure 26E:
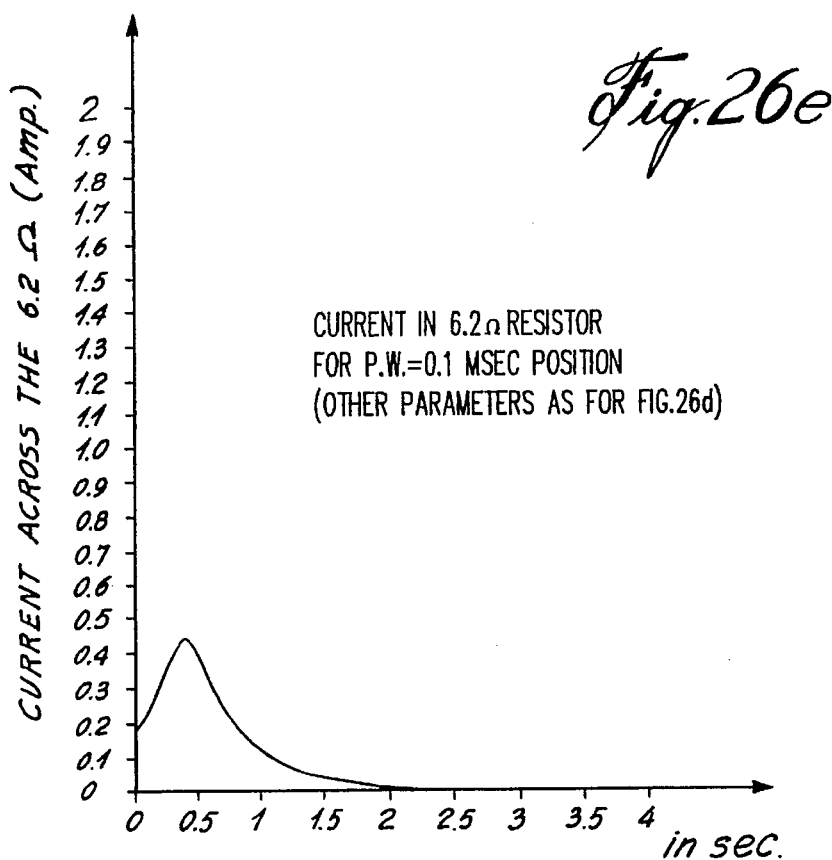
Figure 26D:
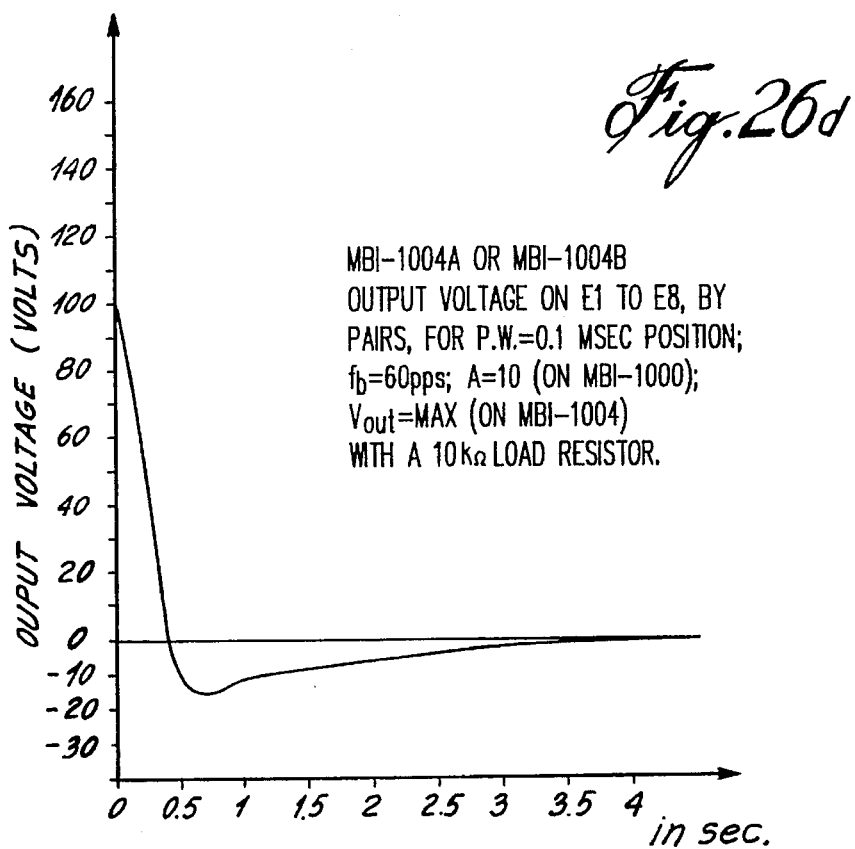
Figure 26F:
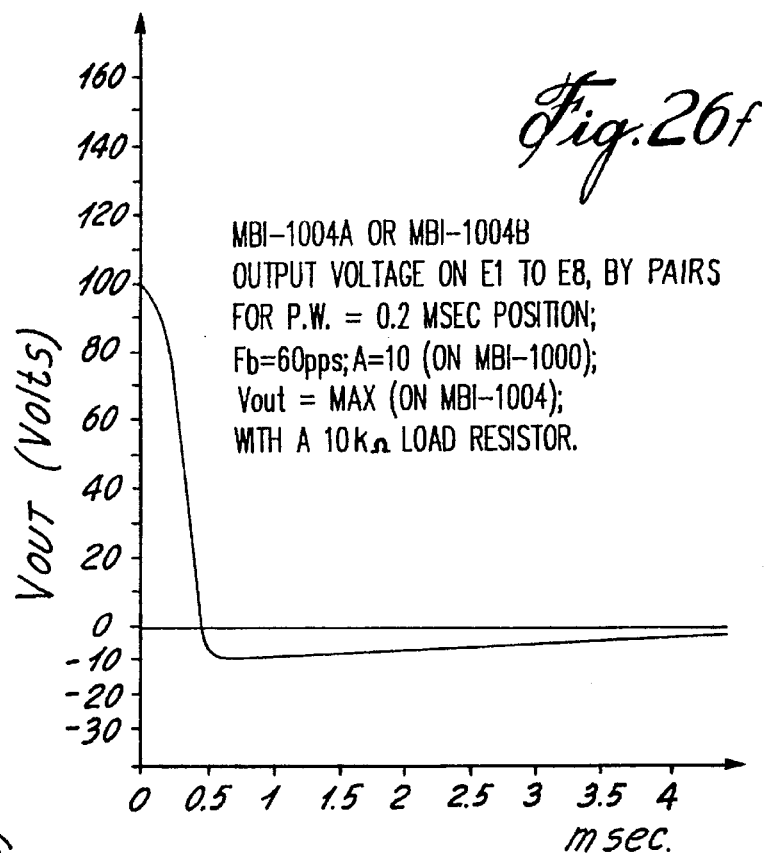
Figure 26G:
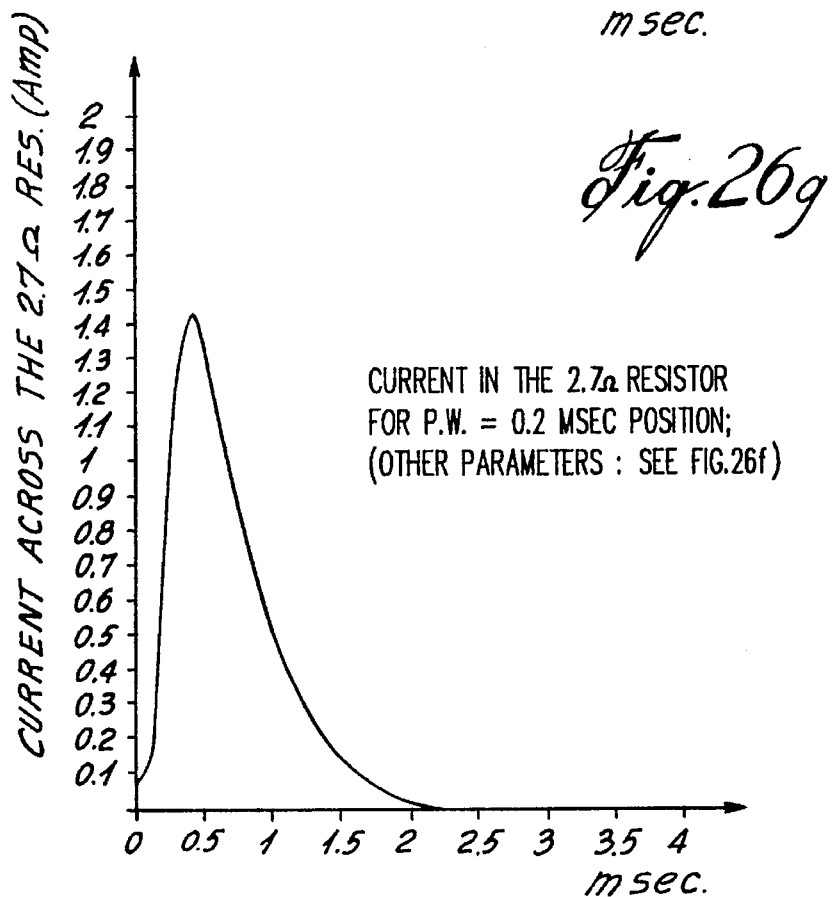
Figure 26H:
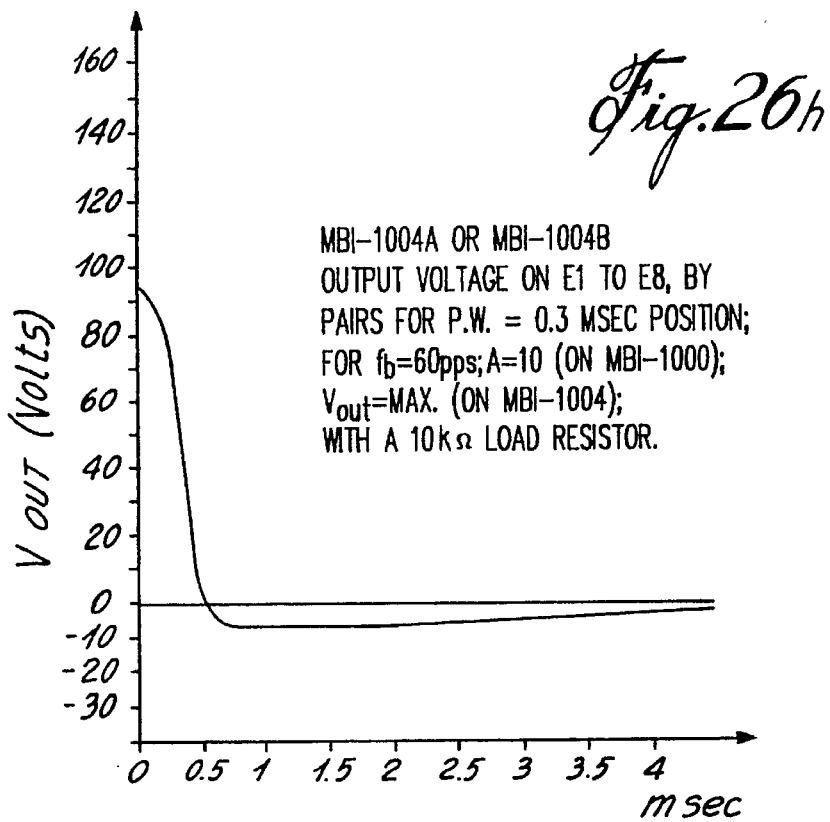
Figure 26I:
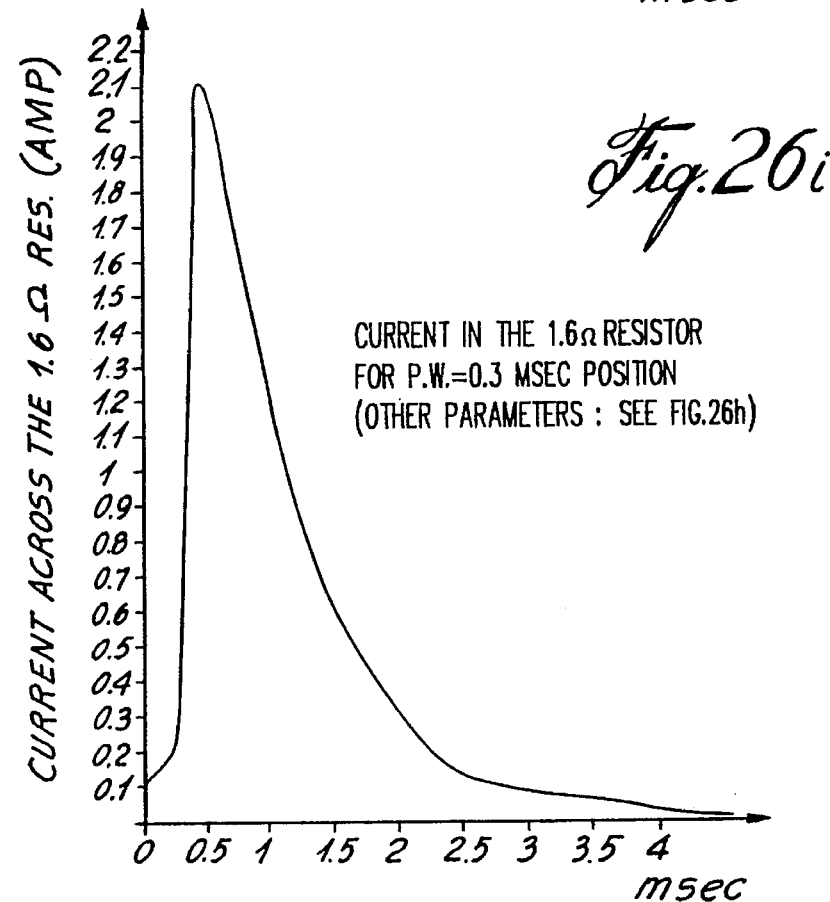
Figure 27A:
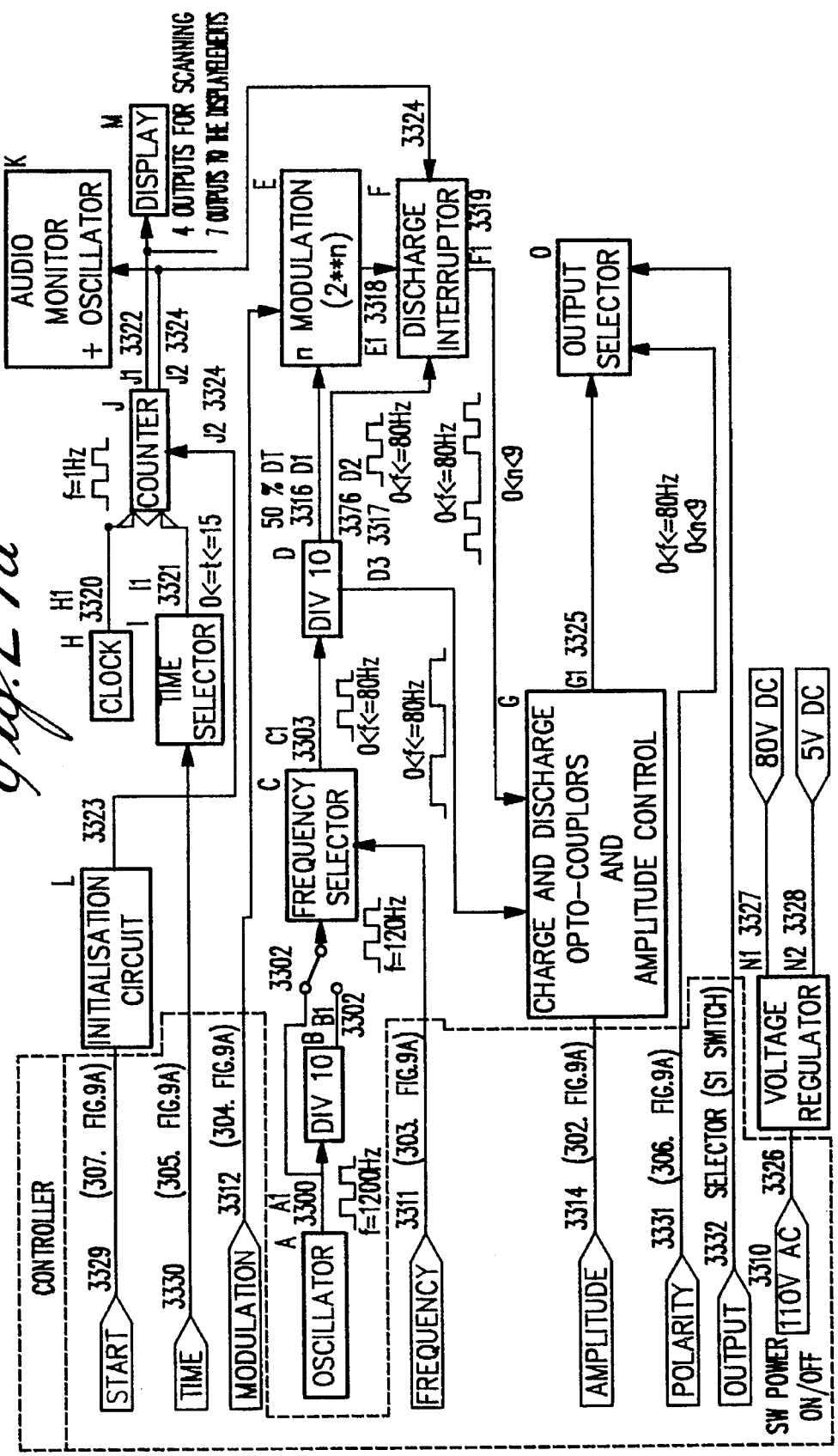
Figure 27B:
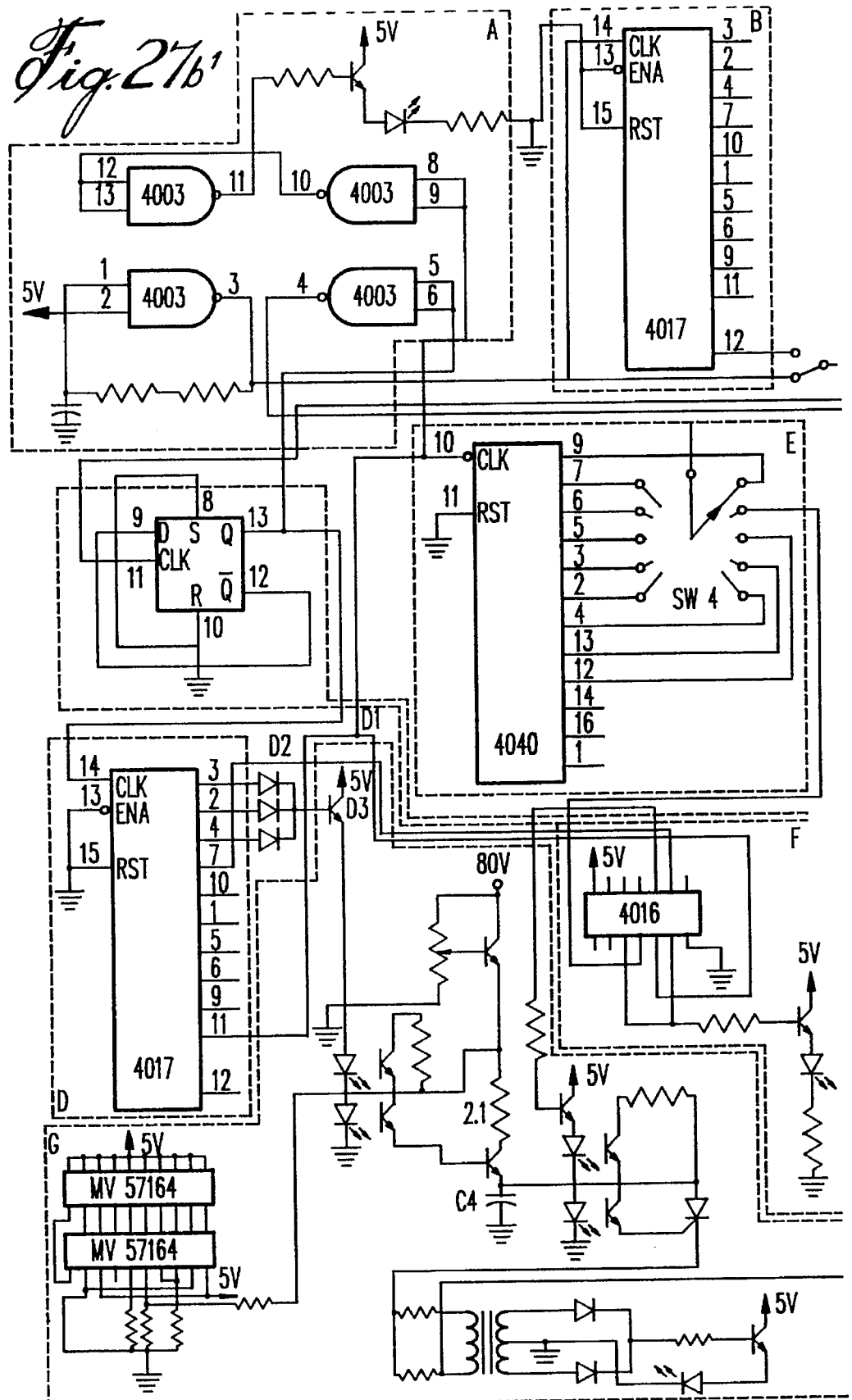
Figure 27C:
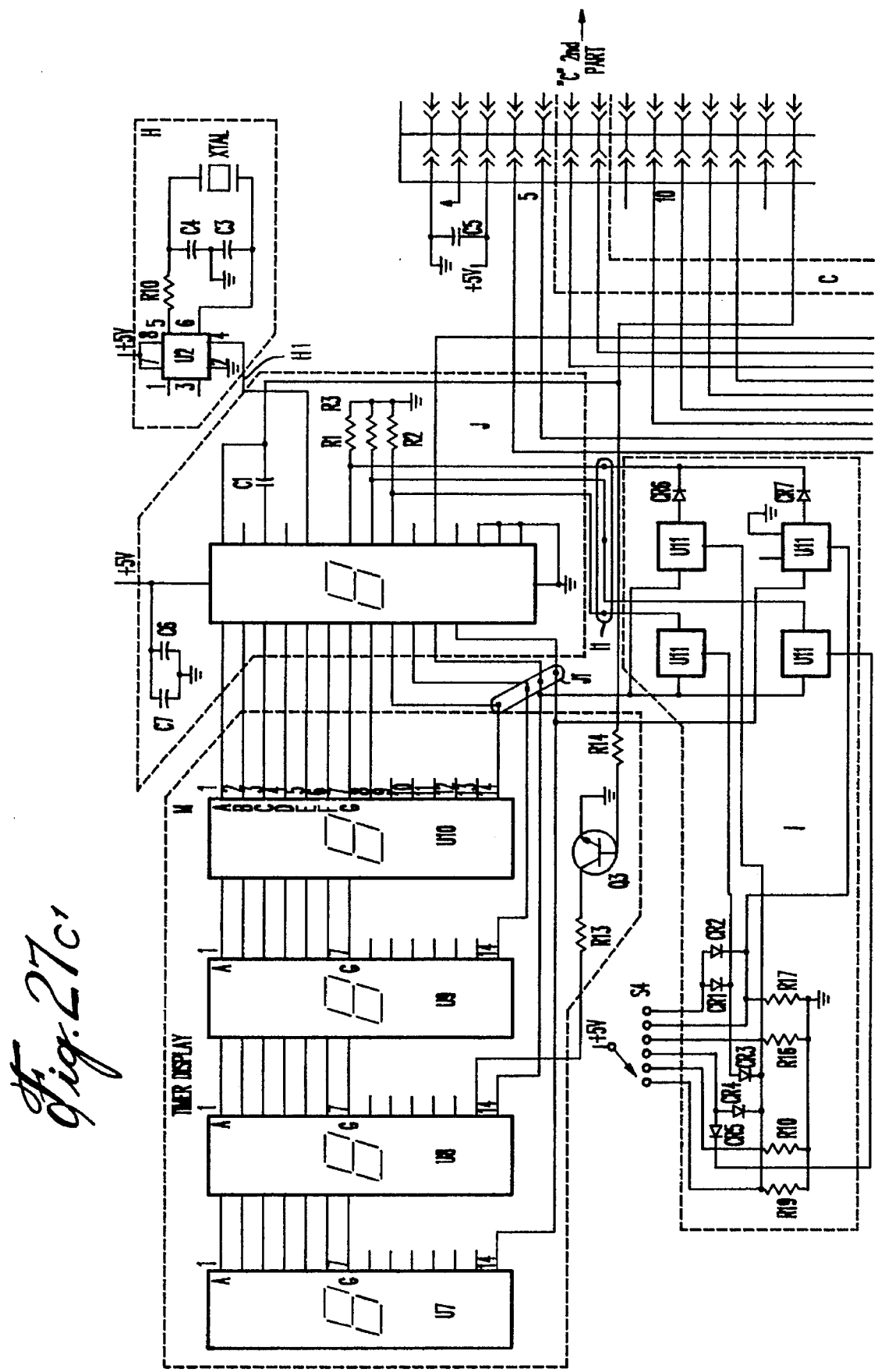
Figure 27D:
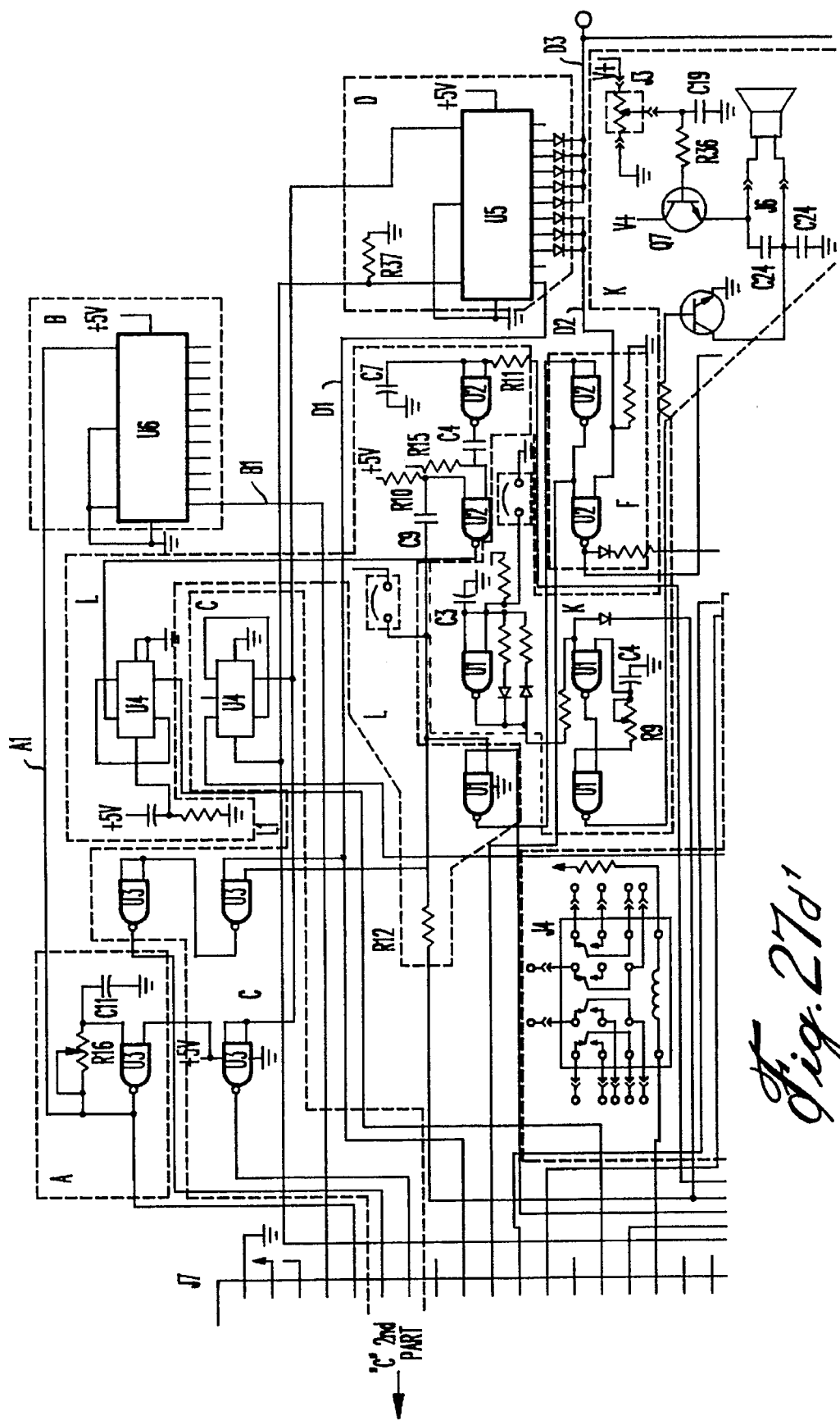
Figure 27E:
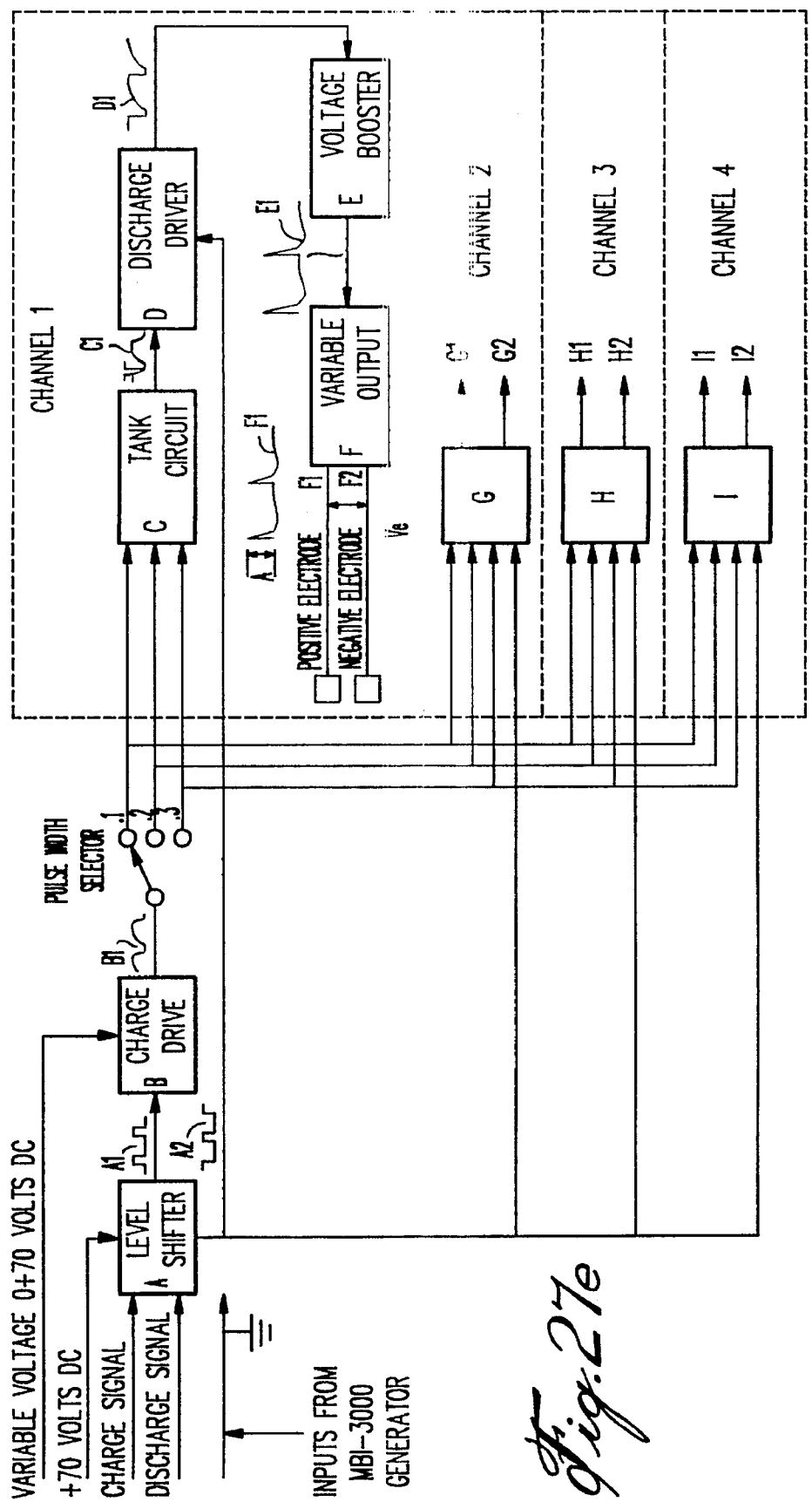
Figure 27G:
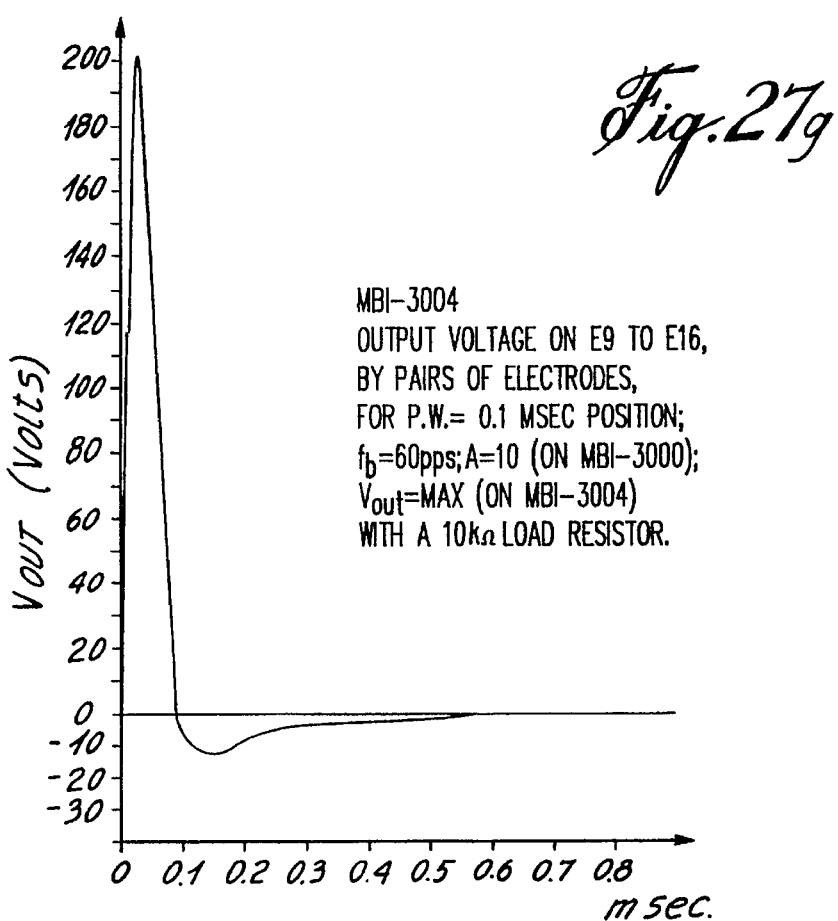
Figure 27H:
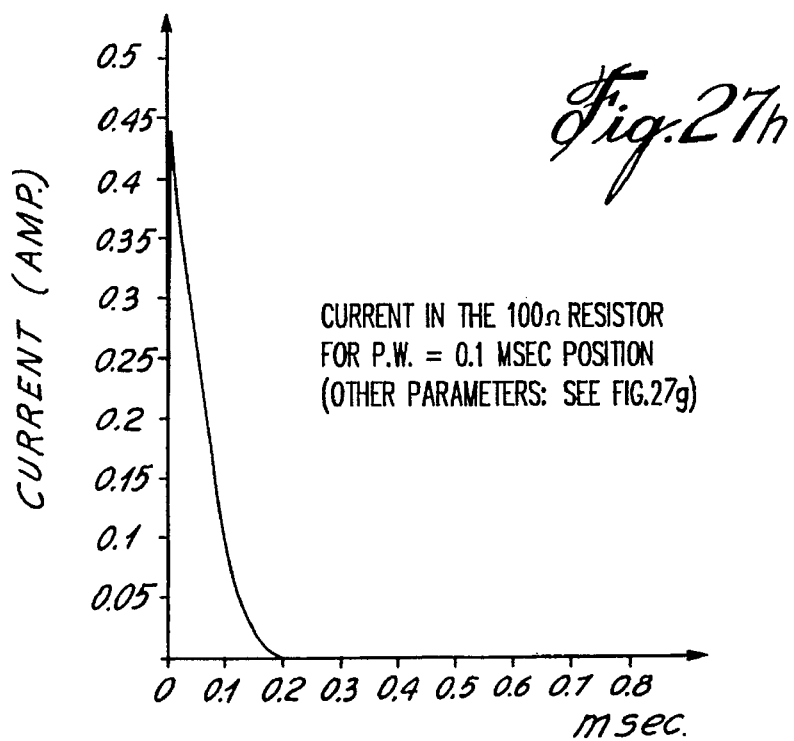
Figure 27I:
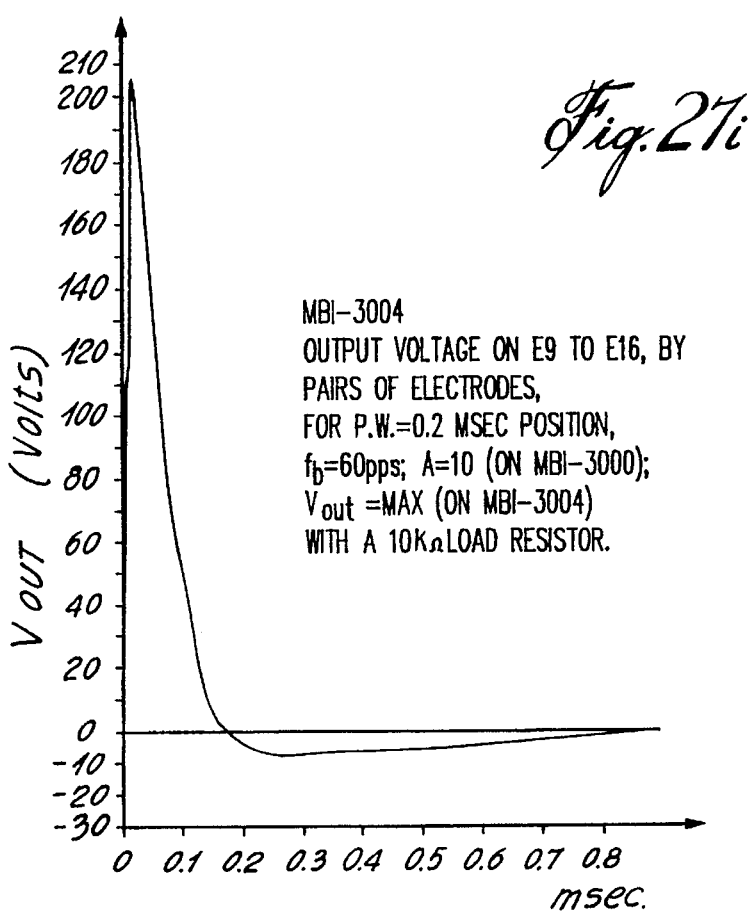
Figure 27J:
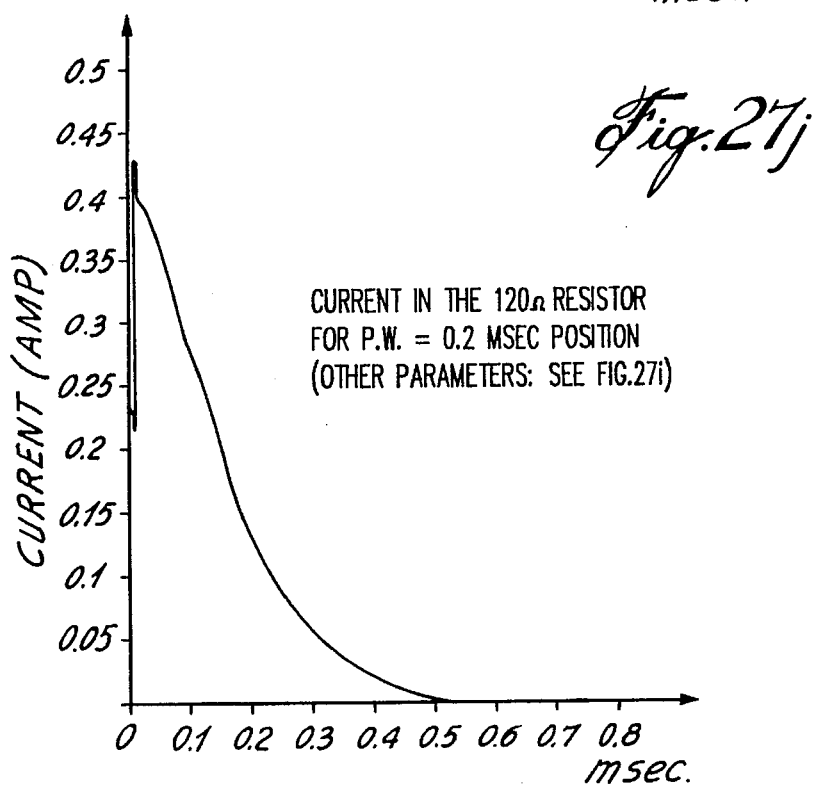
Figure 27M:
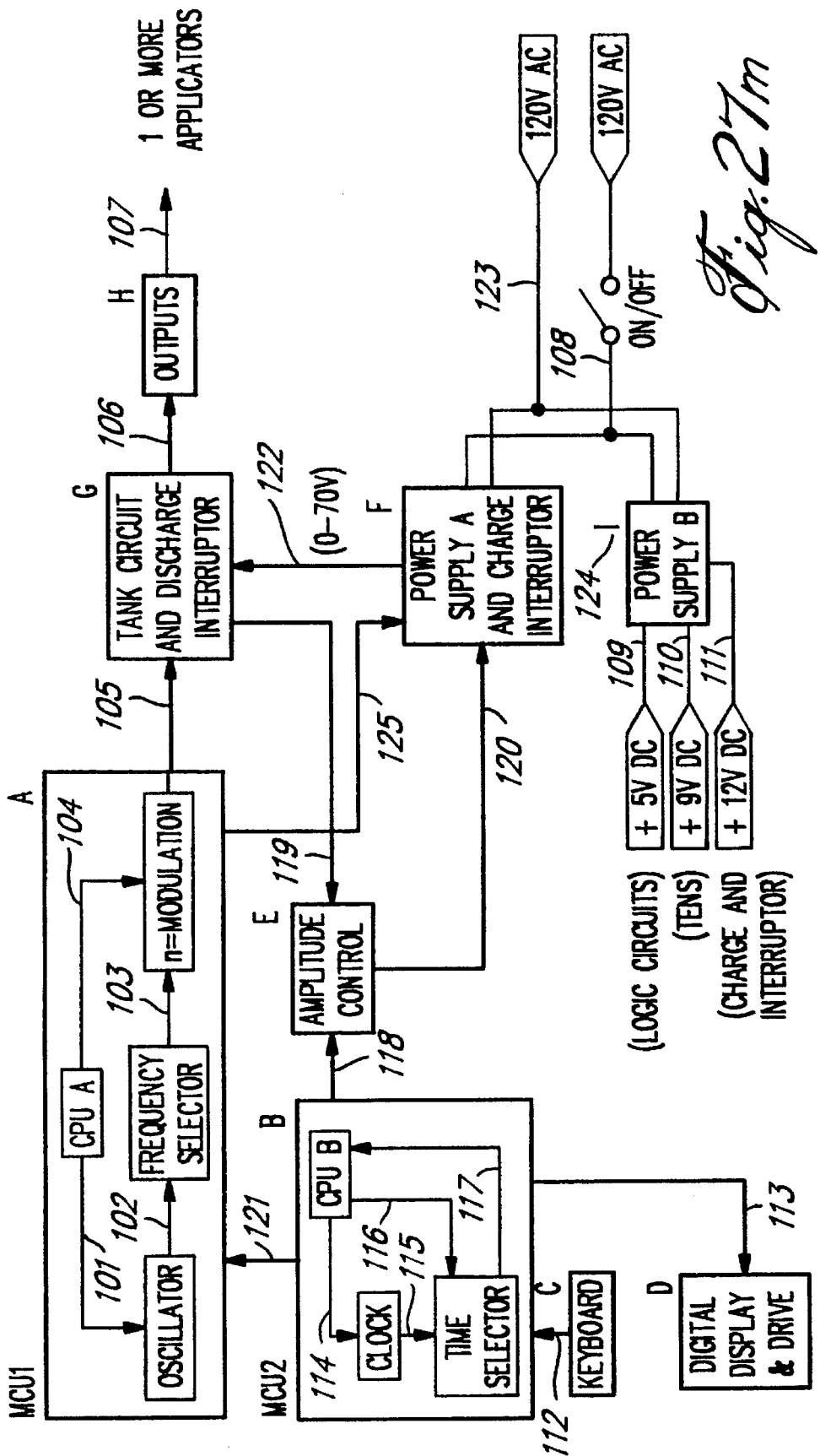
Figure 28A:
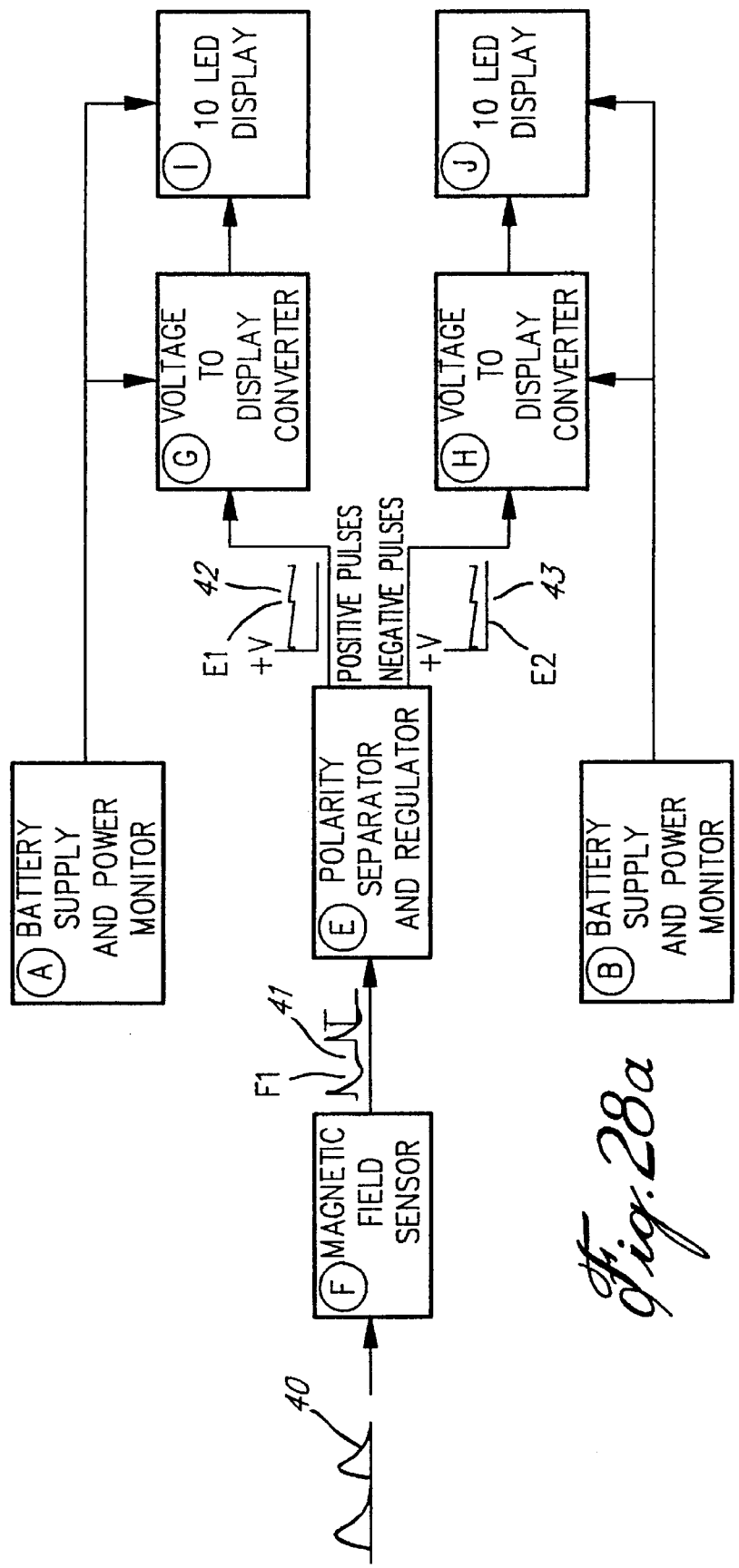
Figure 28B:
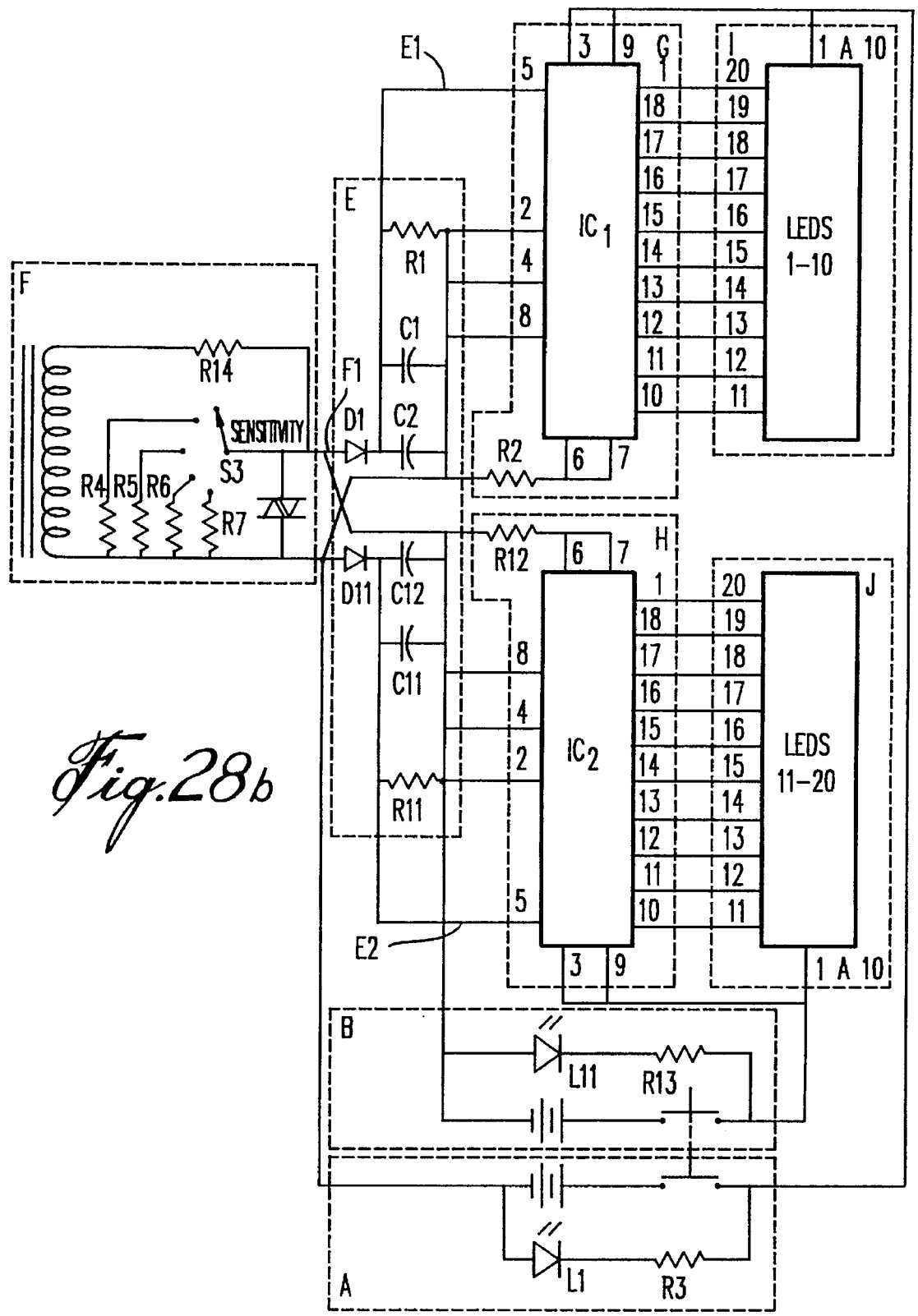
Figure 30:
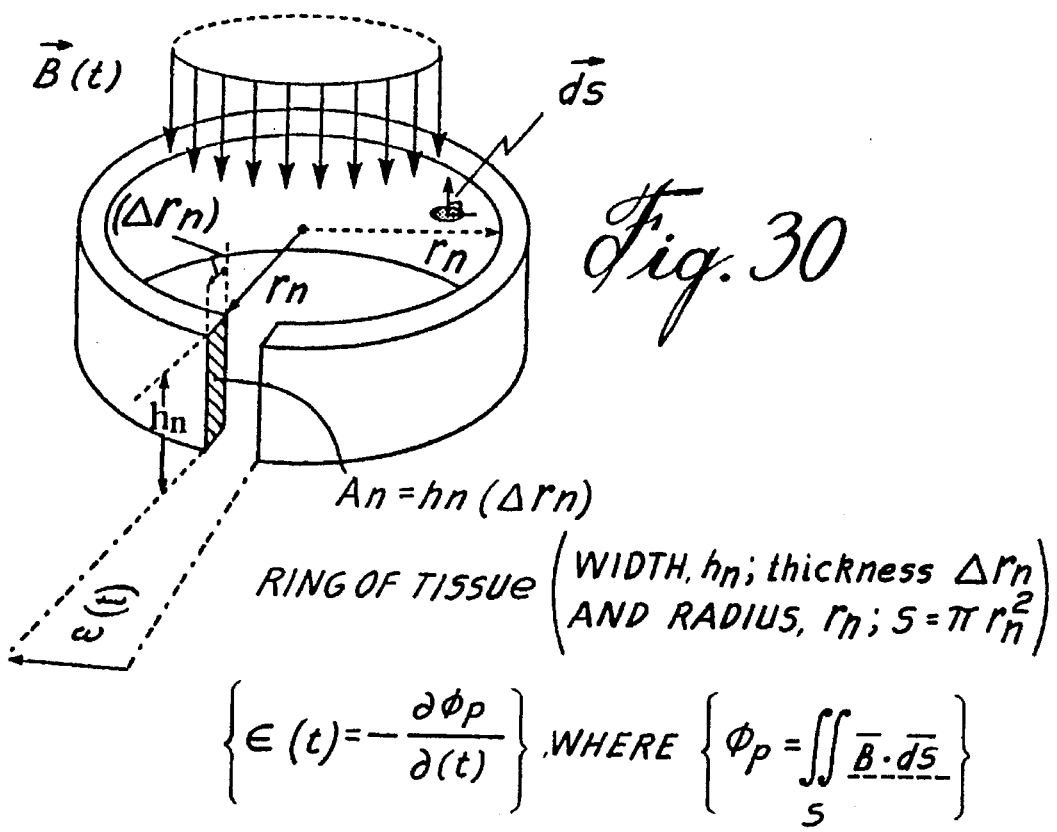
Figure 31:
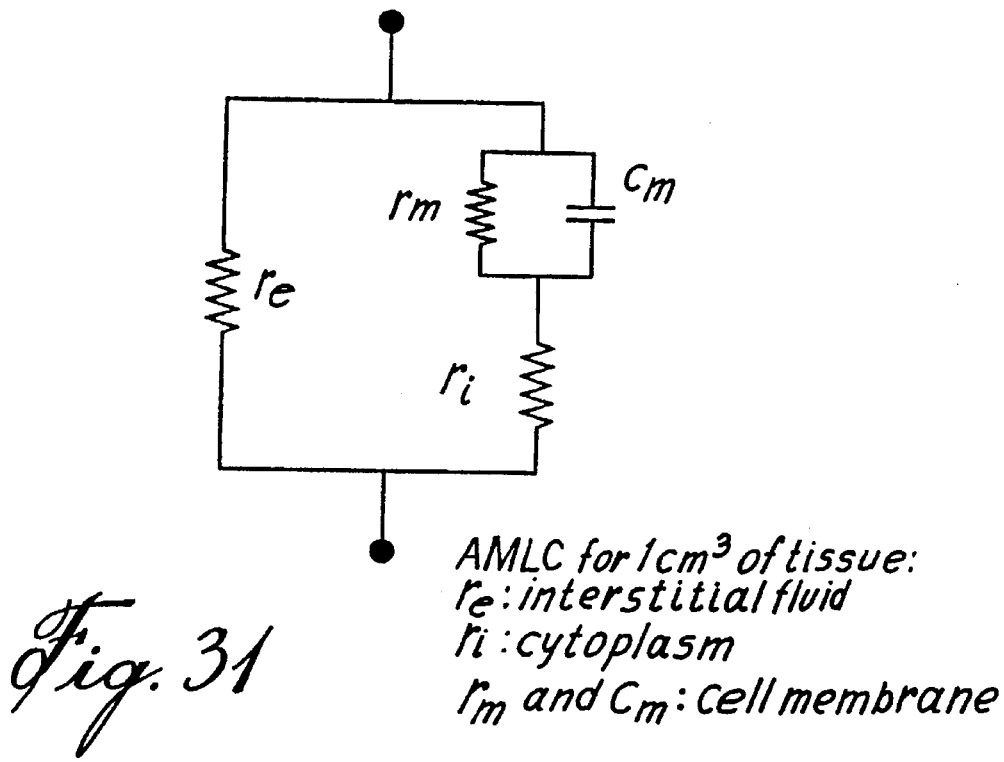

FIGS. 19a, b, c and d show various construction details of a MAXI-2A pair of applicators; the MAXI-2A applicator includes a winding composed of 29 turns of aluminum were with a protective plastic tubing, and twisted masking tape adhering on both sides is taped around said tubing;

FIG. 19e shows the equivalent electrical circuit of two pairs of MAXI-2A applicators and the very low frequency equivalent circuit of the 12 foot extensions used to connect each pair of MAXI-2A to the MBI-3000 controller/generator via the connectors;

FIG. 20a shows a perspective illustration of one pair of JAM-8A leg pads;

FIG. 20b shows the parallel connected pair of MOYI-8A coils which is introduced in the special pockets of the pad shown in FIG. 20a;

FIG. 20c shows the equivalent electrical circuits for the JAM-8A pair of pads, or the 2 legs equivalent circuit, the lead resistance ($R_{F1}$) and the resistance of extension leads ($R_{ex}$);

FIG. 20d shows the electrical equivalent circuit of 4 legs pads or two pairs of leg pads of the type shown in FIG. 20a;

FIG. 21a shows the REBONE-4A applicators;

FIG. 21b shows the applicator windings of the two REBONE-4A applicators of FIG. 21a;

FIG. 22a, b, c and d show the construction details of the MINI-4A applicator;

FIG. 23 is a Field Pattern Chart (FPC) of the MINI-4A;

FIGS. 24a and 24b are Field Pattern Charts (FPC) of the REBONE-4A applicator;

FIG. 25a is a block diagram of the MBI-1000 controller/generator;

FIGS. $25b^1$ and $25b^2$ are detailed circuit diagrams of the MBI-1000 controller/generator;

FIG. $25c^1$ and $25c^2$ illustrate another example of the detailed circuit diagram of the MBI-1000;

FIG. 26a shows a block diagram of the MBI-1004A or the MBI-1004B electrode interface used in combination with the MBI-1000 controller/generator;

FIG. 26b shows a detailed circuit diagram of the MBI-1004A or the MBI-1004b electrode interface;

FIG. 26c shows an other example of detailed circuit diagram of the MBI-1004A or MBI-1004B electrode interface;

FIGS. 26d, 26f and 26h show various output voltages of the MBI-1004A or MBI-1004B for a resistive load of 10 k$\Omega$, with other conditions as specified in these drawings;

FIGS. 26e, 26g and 26i show the current respectively flowing in the resistors placed before the small output transformer of the MBI-1004A or MBI-1004B circuit (FIG. 26b and 26c), with other conditions as specified in these drawings;

FIG. 27a is a block diagram of the MBI-3000 controller;

FIGS. $27b^1$ to $27b^3$ are detailed circuit diagrams of the MBI-3000 controller;

FIGS. $27c^1$ and $27c^2$ and $27d^1$ and $27d^2$ are schematic diagrams of the MBI-3000 controller;

FIG. 27e is a block diagram of the MBI-3004 electrode interface;

FIG. 27f is a detailed circuit diagram for the MBI-3004 electrode interface;

FIGS. 27g, 27j and 27k show various output voltages of the MBI-3004 interface for a resistive load of 10 k$\Omega$, with other conditions specified in these Figures;

FIGS. 27h, 27j and 27l show the current respectively flowing in the 100$\Omega$, 120$\Omega$, and 133$\Omega$ resistors placed before the small output transformer of the MBI-3004 circuit (FIG. 27f), with other conditions as specified in these drawings;

FIG. 27m is a block diagram of a controller-generator Ultima-100T, having the same functions and power output as those of the MBI-3000 described herein, and having further unique feature like, for examples, important weight reduction and having new programming means using two so-called CPV(Central Processing Units) and practical membrane switches for programming conditioning parameters;

FIG. 28a is a block diagram of the MBI-101 of the field detector;

FIG. 28b is a detailed circuit of the MBI-101 field detector;

FIG. 29 is a schematic diagram of the Analog Model of Living Cells (AMLC) based on the electric impedance values measured on various living tissues;

FIG. 30 is a perspective view showing the configuration a modeled ring of tissue with parameters and variables used by the author of the present invention to develop a scientific expression of the voltage and current pulses induced in biological tissues as a function of known cellular and tissular electrical parameters; and, FIG. 31 is a schematic diagram showing the Analog Model of Living Cells (AMLC) for one cubic centimeter of biological tissue with electrical characteristics of the cell membranes, the cytoplasm and the interstitial fluid;

MODES FOR CARRYING OUT THE INVENTION

Figure 1A:
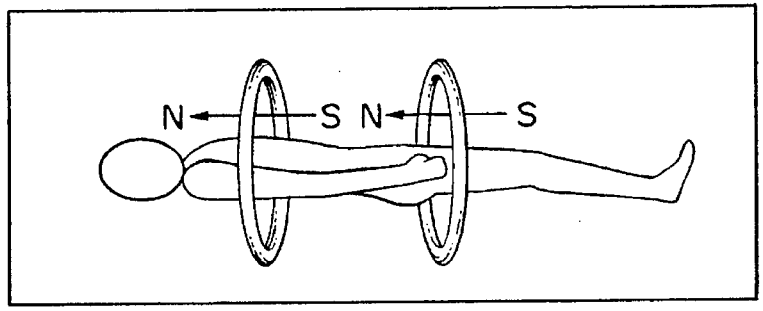
FIG. 1 a to 1y are pictorial diagram which illustrates different configurations of applicators used in the present invention as applied to human beings.
Figure 1B:
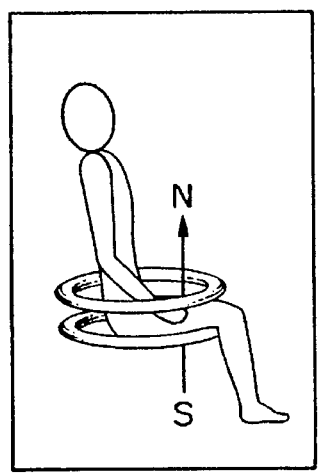
Figure 1C:
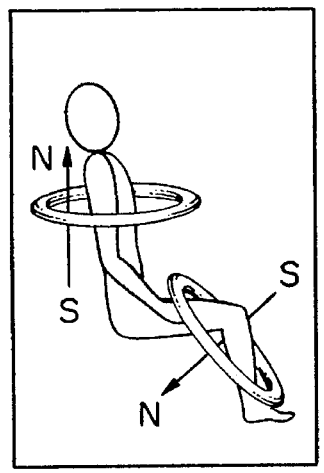
Figure 1D:
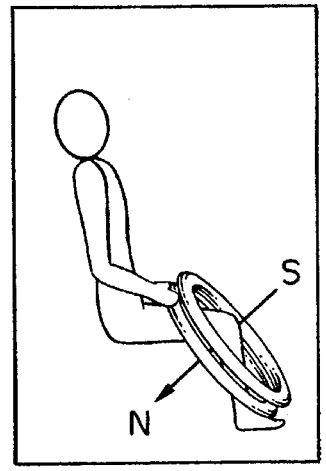
Figure 1E:
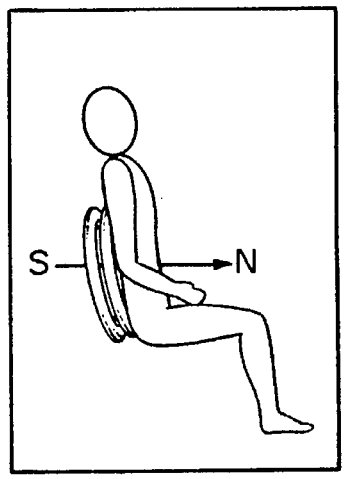
Figure 1F:
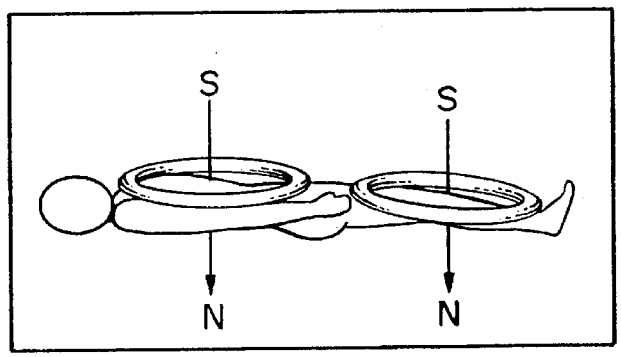
Figure 1S:
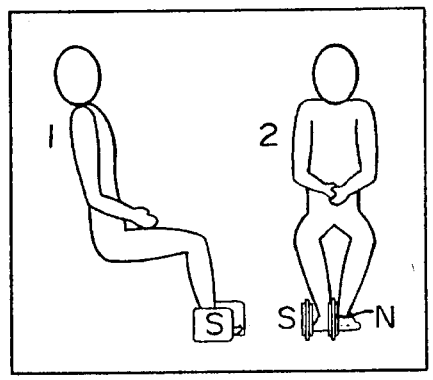
Figure 1T:
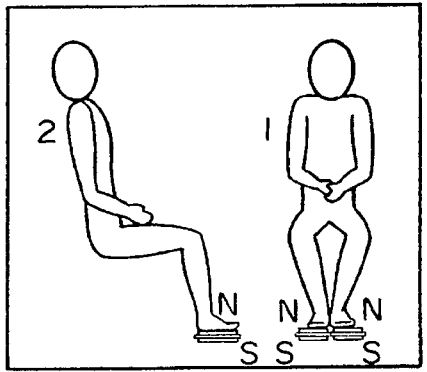
Figure 1U:
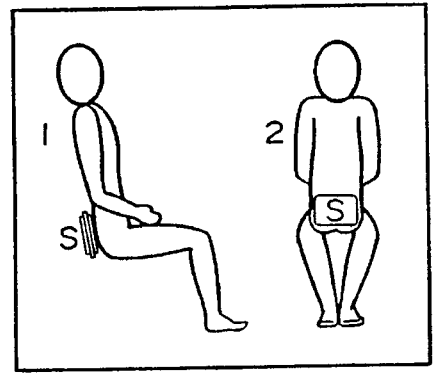
Figure 1V:
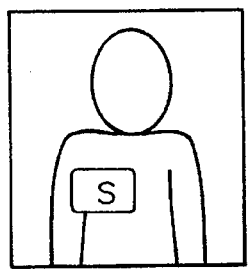
Figure 1W:
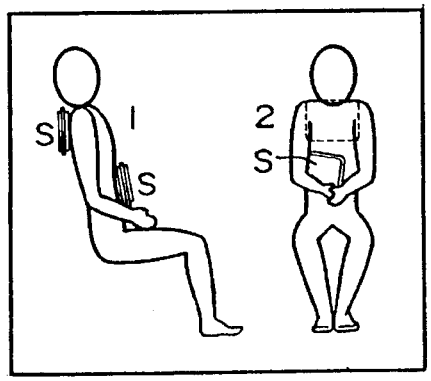
Figure 1X:
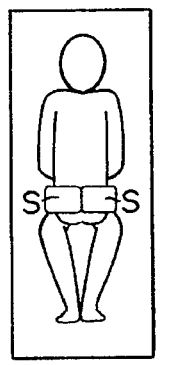
Figure 1Y:
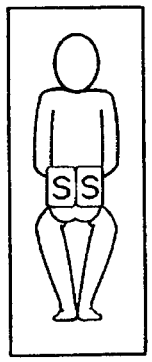

Referring now to FIGS. 1a to 1z, there are shown perspective illustrations of different configurations of the MAXI-2A and REBONE-4A or REBONE-PM pairs of coil applicators of the present invention.

More specifically, FIGS. 1a, b, c, d, e, f, $g^1$, $g^2$, $h^1$, $h^2$, and i show different perspective illustrations of configurations of a pair of MAXI-2A coil applicators used by man, with the north (N) and south (S) polarities oriented in different ways.

FIGS. 1, k, L, m, n, o, p, q, r, s, t, u, v, w, x and y show different perspective illustrations of configurations of the REBONE-4A or REBONE-PM coil applicators used in the present invention with the north (N) and south (S) polarities oriented as shown in these drawings.

Referring now to FIGS. 2(a) and (b), there is shown a simplified version of the front and rear panels of the said MBI-3000 generator/controller means used in the present invention. Following is a brief legend of these two Figures where elements are identified by the numbers $1r$, $2r$, $3r$ . . . , to $18r$. These numbers are used only in reference to FIG. 2a and FIG. 2b. The series of numbers used throughout the present document for referring to the said MBI-3000 means are shown in FIG. 9A and FIG. 9B.

LEGEND of FIG. 2(a)

$1r$. Power switch;
$2r$. AMPLITUDE (A) or Conditioning intensity: e.g. 6 bars lit=Amplitude 6; 4 bars lit=Amplitude 4;
$3r$. PULSE FREQUENCY ($f_b$);
$4r$. PULSE FREQUENCY, ($f_b$), divider (by 10);
$5r$. MODULATION (n): physiological effects of the conditioning: (n=2): anti-pain, anti-stress, anti-inflammatory., (n=3): improved blood circulation, (n=3): stimulation of normal cell regeneration;
$6r$. TIMER (T): length of the conditioning session;
$7r$. POLARITY (N or S): always in the North (N) position, except for various wounds;
$8r$. Switch: signals the start of the session;
$9r$. Applicator selector: (Left., REBONE-4A);
$10r$. Indicator light: OFF=Rings; ON=REBONE-4A (see #$16r$, rear panel);
$11r$. and $12r$. Indicator lights: should blink "ON" and "OFF" during the conditioning session, except when $f_b$=60 pulses/sec;

LEGEND of FIG. 2(b)

$13r$. Control knob of sound signal indicating that the session is in progress (adjustable loudness);
$14r$. Outlet for the said REBONE-4A applicators;
$15r$. Outlet for the said MAXI-2A (rings);
$16r$. Switch: Right position (R) for the rings: signal light in OFF position (see #$10r$ front Left position (L) for the REBONE-4A: signal light ON (see #$10r$ front panel);
$17r$. Applicator selector (Right, MAXI-2A): Always in position 1 (0.5 ms), except for 2 pairs of MAXI-2A. (0.8 ms);
$18r$. Super-TENS output (to said MBI-3004);

Still referring to FIGS. 2a and 2b examples of use of an embodiment of the present invention follow:

N. B. In all cases, said conditioning consists of inducing physiological effects, 5-2-10 Conditioning means: Amplitude 5, Modulation 2, Time 10 minutes (or A5, n2, T10)

Global Conditioning means: One ring around the knees and the other around be chest Local Conditioning means: said REBONE-4A applicators on the area to be conditioned Pad Conditioning means: said REBONE-4A applicators A: AMPLITUDE
USE THE SAME AMPLITUDE FOR THE FIRST WEEK OR TWO (3 TO 5 SESSIONS LASTING 5 OR 10 MINUTES)
to the BODY: A=5 to 8 with the rings (said MAXI-2A) and 3 to 5 with the pads (at 5 for 5 minutes)
to the HEAD: A=1 to 3 with the pads (1 to 3 on the neck: at 3 for 5 minutes)

n: MODULATION
n=0 or 1:
To help cases involving bone fractures (after 2–3 sessions at n=2), bursitis of the shoulder, muscle tone, recent sprains, and to help stabilize the subject's condition in certain cancer cases.
EXAMPLE FOR A CANCER CASE: 1st week at 6-2-10, 2nd week at 6-1-15, 3rd week at 6-0-20 to 30 (maximum conditioning: 1 hour/day)
n=2: RELAXING EFFECT: anti-stress, anti-inflammatory, sedative (for example:rheumatism, arthritis, stomach ulcers, chronic migraines, hypertension)
n=3: STIMULATING EFFECT, normal cell regeneration, blood circulation (wounds, burns, eczema, stomach ulcers after 4 sessions at n=2, varicose veins, swelling).
Always control the pain with n=2 before moving on to n =3.
n=4, n=5:
Chronic migraines, stimulation of hair growth (2 weeks at n=2, 2 weeks at n=5 and then n=4) (to induce the 3 physiological effects)
n=6: Muscular tone (only to induce the 3 physiological effects)

T: TIME
Normal conditioning:
BODY: rings for 10–15 minutes, pads for 1–5 minutes
HEAD & NECK: pads for 1–5 minutes
POLARITY: NORTH polarity is on the side with the rivet heads (N or S Polarity label) (N is calming)
ALWAYS place N on the area to be conditioned (REBONE) or direct it towards the subject's head (rings). Use the SOUTH polarity on an open wound (S is stimulating). When healing has begun, switch to N. NORTH/SOUTH: deep conditioning; NORTH/NORTH: surface conditioning; SOUTH/SOUTH: surface conditioning (open wound). After healing, use NORTH/NORTH or NORTH/SOUTH.

SAMPLE SESSIONS: (A, n, T)
Every other day: rings for 10 min., pads for 5 min.
Every 3 days: 1st day: rings for 10 min.; 2nd day: pads for 10 min.; 3rd day: rest.
Pads only: Every day for the first 4 or 5 days, then every other day. After 4 to 6 weeks, rest for a few days or a week.
Very nervous or sick person: Rings and pads (2-2-10)
Children: dngs, pads (2-2-5) twice a week may be enough.
Head, neck (pads 1-2-3) 2 or 3 consecutive days, then every other day.

SOME SPECIAL CASES
Very elderly or infirm person: (A1-2, n2, T5–10 min.) with the rings.
Diabetics: Monitor your glucose level (by yourself or your physician).
People taking cortisone: Amplitude should not exceed 3 with large ring applicators.

People taking gold salts or antibiotics: Amplitude should not exceed 2 with rings. 3 weeks after these medications have been discontinued: return to normal amplitudes. Shock conditioning immediately after an ACCIDENT or a cut: pads (5-2-10 and 5-3-5) one after the other: (5-3-10) on the next 3 or 4 days; then every other days.

In case of doubt concerning a conditioning, use 4-2-10 with the rings.

Commonly used PARAMETERS (A, n, T)

In general: BODY: Rings (5 to 8-2-10); Pads (3 to 5-2-5)

HEAD:Pads (1 to 3-2-5); NECK: Pads (1 to 3-2-5)

Polarized water: 10-2-1 (or A10, n2, T 1 minute)

IMPORTANT:-Discover the Amplitude (A) that works best for you—Your motivation or will to recover is very important: it's the key to long-term success.

Referring now to the drawings, and more specifically to FIGS. 2c, d and e, there are shown illustrations of the three factors involved in the holistic approach (named RESC) used in the present invention referred to as the RESC or the RHUMART System:

1) The Motivation of the RESC experimentor;
2) The Advisor teacher or mentor; and
3) The RESC or RHUMART Conditioner (including the said MBI-1000 or the MBI-3000 Controller and a choice of an appropriate combination of applicator(s), and/or muscular modes.

In this drawing, the dotted lines and arrows indicate the interdependence and/or inter-relationship between these three fundamental factors involved in the holistic RESC process described herein.

The advisor, teacher or mentor is a person who has a great experience with the use of the present invention including the basic scientific experimental METHOD described herein.

Still referring to FIG. 2d, this drawing illustrates the working principle of the RESC method involving the RESC experimentor, the advisor, teacher or mentor, and the RESC Conditioner including the 8 different modes of the present invention illustrated in FIG. 4; and various combinations of said modes as for examples those shown in FIG. 4.

With the help of the said advisor and the proper use of the RESC Conditioner, the RESC experimenter gradually learns how to maintain, develop and/or improve his own physical, mental and/or social condition (named health in its widest sense possible)

More, specifically, the RESC experimenter chooses an initial set of conditioning parameters (Amplitude (A) of the RHUMART impulses. Modulation (n) of the so called RHUMARF impulse train, characteristic of the desired physiological effect. and Duration or Rme (T) of the conditioning session) after reading the detailed operating procedures described herein. He then takes his first RESC session, and if he can tolerate it well, he takes 3 to 4 sessions with the said initial parameters every second day. If he feels better after these initial sessions, he can continue with the same parameters but, if he does not feel better or if he experiences increased pain and/or a slight aggravation of symptoms, then he should use his own experience and that of his advisor (teacher or mentor) to analyse the cause of such discomfort, based on the three physiological effects induced by RESC Conditioning, and he should then choose a new set of conditioning parameters.

This latter decision process of the RESC experimentor is well illustrated in FIG. 2e.

Referring now to the RESC diagram (FIG. 2d), and to the DIAGRAM OF ORGANIZATION IN MAN FIGS. 2L(a) to 2L(e), it is shown that the RESC method teaches a specific scientific experimental method to every person who wishes to improve positive thinking, health and happiness using the present invention.

Consider the following simple diagram of this method applied to RESC conditioning shown in FIG. 2e.

Initially, one must receive the proper training to use the RESC conditioner, from his advisor, mentor or teacher who is experienced with this technique.

With proper training, the RESC experimenter chooses the initial conditioning parameters: Amplitude (A), Modulation (n), Duration of RESC session and choice of applicators or modes, according to the guidelines presented herein.

In other words, he decides on his first experiment with his RESC conditioner (hypothesis #1, FIG. 2e) using one set of initial parameters. He compares his state of well being or health before, and one day after the use of his conditioner.

Depending on how he feels about his health, he continues with the same parameters for 3 or 4 RESC sessions or he modifies the parameters for the second session. Unless he feels really bad, he should use the same parameters for at least 3 or 4 consecutive sessions. Each RESC session can be regarded as a scientific experiment where the user is the experimenter. His mentor can help or guide him if he needs further training to use his conditioner.

After each session (or one day after), the user-experimenter uses his own mental reflection, the results of his previous conditioning sessions and the experience of others who have mastered this technique to decide on a possible new set of RESC conditioning parameters.

After a certain number of said sessions, which varies with each individual, the experimenter improves his health and happiness. He should therefore improve his attitude and become much more positive about his health and life in general.

FIG. 2d also illustrates the great importance of positive thinking and proper thinking in general of the RESC experimenter who wishes to "set" his Brain, Nervous System and cells of all types in better "working conditions".

With successive RESC sessions, the experimenter gradually improves the mental perception of his own body (partly due to reduced pain and improved sleep) and he rediscovers Self-Confidence which is the basis of positive thinking, and this helps him further improve his own health and happiness with the RESC Conditioner as illustrated in FIG. 2e.

Referring now to FIG. 2f, it shows two embodiments of this invention which use a choice of two different pairs of coil applicators 320 or 340 with an optional table, and portable suitcase to transport the said MBI-3000 Controller 300, REBONE-4A applicators 320, electrical extension cords and accessories of the said MBI-3000. A pair of REBONE-4A applicators (connected in series) and a pair of MAXI-2A applicators (connected in parallel) are shown on either side of the said MBI-3000 Controller.

FIG. 2g shows how the said embodiment of this invention can be transported in the handy case shown and on a man's shoulder the pair of MAXI-2A global applicators is shown.

Referring now to FIG. $2h^1$ and $2h^2$, there is shown another example of configuration to use the embodiment for global conditioning (left) and for conditioning a shoulder (center).

Referring now to FIG. 2i, there is shown still another configuration for using global RESC conditioning, simultaneously by two adults, with the double-ring applicators, MAXI-2A. The said MBI-3000 Controller and two pairs of REBONE-4A regional applicators are shown between the two users of the said AHS-C mode.

Referring now to FIG. 2j, there are shown 5 different said modes of this invention including (from left to right) the global MAXI applicator (330), a pair of MINI-4A local applicators (310) with rotating and flexible supporting arms (named BF-2) placed in cylindrical holes on the appropriate table. Between the two BF-2 arms, the said MBI-101 new field detector (30) is shown. A pair of said REBONE-4A (320) is visible on the left of the said MBI-3000 Controller (300) under which we can see the said MBI-3004 mode (360, 300) and small electrodes and leads to connect them to the MBI-3004. Finally two pairs of MAXI-2A double-ring applicators (340) are shown.

Referring now to FIGS. $2k^1$ and $2k^2$ there is shown the two muscular modes, the MBI-3004 with 4 pairs of electrodes (left), and on the right, we can see the MBI-1000 Controller (15), with a cover, and a pair of REBONE-PM local applicators (10,11) used with the MBI-1000 Controller, and on the right and lower right of this illustration, the MBI-1004A-B (or MBI-1004A plus MBI-1004B), mode (15,26,27) including the MBI-1004A-B Controller, with 4 pairs of special flexible and reusable electrodes are seen.

Referring now to FIGS. $2L^1$, $2L^2$, $2L^3$ and $2L^4$, there is shown the Diagram of Organization in Man from the author of the present invention, illustrating how the RHUMART system of this invention can be useful to help increase man's survival, development and health.

The present invention produces regenerative bioelectricity of the type generated by the nervous system and which stimulates cell and tissue healing mechanisms and can reduce PAIN AND STRESS and therefore improve sleep quality and the Quality of Life in general. In this diagram, the two main constituents of man, The BODY and the SPIRIT or MIND which are interdependent and interrelated by means of man's actions (or movements of body or parts thereof) and conscious and subconscious thoughts and the TEN senses mentioned herein after (NOTE 7).

The physiological and/or natural regenerative bioelectricity induced by the present invention is one of the 6 NECESSARY factors or conditions for MAN'S SURVIVAL. The other five necessary survival factors are the following: the GENETIC CODE. NUTRITION, GRAVITY, POSITIVE THINKING and the TEN SENSES listed herein after. The interrelations of these survival factors with man and its surrounding environment are shown in the FIG. $2L^4$.

Still referring to FIG. $2L^4$, as further description and details of the said Diagram of man, follows a series of 12 explanatory NOTES (1 to 12):

NOTE 1: THE STRUCTURE OF KNOWLEDGE is oriented towards an ever more general and abstract conceptualization, according to Jean Piaget.

Man, moreover, cannot understand a new concept unless all its elements are already present within him. Predicting the overall behavior of a system is impossible, based solely on knowledge of its components, and something is understandable only through its history.

NOTE 2: THE NATURE OF THOUGHT. The basis of knowledge rests on the concept that ACTION is a stage preceding thought, and thought itself is a process of interiorizing a man's actions during his life.

Thoughts are physical entities since they can be detected outside the body. "THOUGHTS ARE THINGS" according to many renowned scientists. Indeed thoughts are electromagnetic wave patterns.

NOTE 3: EXAMPLES OF PSYCHOLOGICAL CONTROL
  1. Biofeedback
  2. Hypnosis
  3. Sleep
  4. GSR (Galvanic skin response
  5. Vasodilation
  7. Heart rate
  8. Blood pressure
  9. Breathing rate
  10. Body temperature
  11. Hypothalamic and hypophyseal activity
  12. Hormones
  13. Cell division
  14. Growth
  15. Reproduction
  16. Homeostasis NOTE 4: CONTROL FACTORS IN MAN'S SURVIVAL, SUR (1 to 7)
  1. The genetic code of life on earth
  2. Appropriate food (including medication) (Note 11)
  3. Regenerative bioelectricity (e.g.: RHUMART Conditioning)
  4. Gravity (mechanical and piezoelectrical effects)
  5. Conscious and subconscious thoughts (Notes 2, 3, 9 and 10)
  6. The ten senses (Note 7)
  7. Various electromagnetic radiations (Notes 8 and 12)

NOTE 5: THERE ARE THREE FUNDAMENTAL WAYS TO LEARN
  1. Personal thinking (and intuition)
  2. The experience of other $\Sigma 1,2,3$=CONVICTION
  3. One's own experience NOTE 6: THINKING OR ACTING
  Habitually thinking without acting will cause the human mind (and the brain) to atrophy and lead to its domination by external thoughts and disturbances.

NOTE 7: THE TEN SENSES, SE (1 to 10)
  1. Sight
  2. Hearing
  3. Smell
  4. Taste
  5. Touch
  6. Hunger
  7. Thirst
  8. Pleasure (e.g.: sex)
  9. Fear (e.g.: stress)
  10. Pain (physical, psychological)

NOTE 8: ATMOSPHERIC RADIATION, RA (1 to 4)
  1. High-energy rays (gamma rays, X-rays, etc.)
  2. Visible, ultraviolet and infrared rays
  3. Non-ionizong radiation (microwaves, shortwaves, VHF, UHF, HF, RF)
  4. Electric and magnetic storms, Schumann's resonances, 1952.

NOTE 9: EXTERNAL INFLUENCES ON THE SUBCONSCIOUS, PS (1 to 5)
  1. Subliminal thoughts
  2. Suggestions under hypnosis
  3. Thoughts stimulated by various mental processes
  4. Foreign thoughts (active spirits)
  5. Thoughts stimulated by consciousness
  6. Thoughts generated by ACTION NOTE 10: EXTERNAL INFLUENCES ON CONSCIOUSNESS, PC (1 to 3)
  1. Foreign thoughts
  2. Thoughts stimulated by various mental processes
  3. Thoughts stimulated by the subconscious
  4. Thoughts generated by ACTION NOTE 11: THE BODY'S IMMEDIATE ENVIRONMENT, EN (1 to 5)
  1. Metals, dust, pollutants, gases, ions, $CO_2$, $O_2$, $O_3$, $H_2O$, $H_2$ 2. Electric and magnetic fields, gravity
3. Animals, vegetables, medication
4. Artificial radiation (Note 12)

NOTE 12: ARTIFICIAL RADIATION, RAA (1 to 12)
1. Radio
2. Television
3. Microwaves
4. VHF
5. UHF
6. HF
7. LF
8. VLF
9. Ultraviolet
10. Visible
11. X-rays
12. etc. . .

It is noticed that, FIGS. $2L^1$–$L^4$ are in agreement with the field theory of modern quantum physics applied to man and its environment in that all aspects and components of man and its environment are interdependent and interrelated, as shown by the arrows in these diagrams. The said diagram of MAN, FIG. $2L^1$–$L^4$, summarizes the general organization and functioning of man so as to better understand how the present invention can help man maintain and/or recover his health.

This diagram shows the relationship between the most important Factors of Organization and Control in man.

Here and now, we are mainly concerned with the Development and Health of Man as related to the said RESC Conditioning method of this invention.

Previously, we have discussed how the Scientific Experimental Method applies to RESC Conditioning. Now, we want to help you visualize the RESC procedure illustrated in FIG. 2e, using the Simplified "Diagram of Man" or Man's Diagram presented in FIGS. $2L^1$–$L^4$.

Any scientific experiment such as a RESC session can be regarded as a positive-action-cycle. Indeed, one can visualize the choice of initial RESC parameters (as well as the subsequent choices) as a psychosomatic event involving both the human mind and body which are both represented as large octagons in the said "Diagram of Man."

The choice of specific wave parameters used in the present invention involves the steps of learning by personal reflection, from the experiences of others and by the operating RESC procedures described in referring to FIG. 2e. This is the first step of the scientific experimentation which involves mainly Thinking and Analysis of previous results and experiences.

The second important step of the RESC method is to adjust the parameters according to how the user himself feels about his health after one or more conditioning sessions. This step involves Action-generated thoughts fed back to the higher brain perception centers via one or more of THE SAID 10 SENSES illustrated in the said "DIAGRAM OF MAN".

When the user has reached a conclusion on a new set of parameters, he must "ingest" or "incorporate" this new set of parameters and verify if it is consistent with everything he knows, and decide how he feels about his conclusion. If he feels well and has no headache, upset stomach or any other symptom which could reveal that his conclusion is not right for him, then he should use this set of parameters in his next RESC session.

After a few months of self training, the RESC Conditioning method can help the user to improve his mental perception of his own body as illustrated in FIG. 2d.

With the mental perception of a relaxed and pain-free body, the candidate for better Health with the present invention will rediscover Self-Confidence, which is the basis of Positive Thinking. This will help him control his own Health and Happiness through successive Positive-Action Cycles, including said RESC Conditioning sessions described herein.

Referring now to FIG. 2m there is illustrated the interdependence of the basic electrophysiological effects produced by the present invention, e.g. improvement of blood circulation, anti-stress, anti-inflammatory, anti-pain and stimulation of normal regeneration.

On the cause-effect links of these electrophysiological effects, we wish to point out the followings:

the resonance between the RHUMART wave and that of the human nervous system produces a relaxing effect on the nervous system (a reduction in resting muscle tone); this, in turn, engenders a reduction in pain and stress;

the relaxation of the nervous system causes vasodilation in the area treated, resulting in a reduction of peripheral resistance and improved blood circulation. The reduction of peripheral resistance lightens the heart's workload and tends to normalize systemic blood pressure. This can help a person to control his hypertension;

the improved blood circulation helps to control inflammation and normalize local temperature, and also has a beneficial effect on cellular nutrition. It thus stimulates normal cell regeneration and repair in general.

The type of bioelectrical asymmetry induced by the present invention is a very effective means of stimulating normal cell regeneration. Moreover, as a result of the work done by a group of researchers at Purdu University in the United States, it is now recognized that cell mitosis is immediately preceded by a "calcium ion explosion" that probably creates cellular ASYMMETRY just before the division;

the specific waveform of the human nerve impulse is almost indistinguishable from that of the present invention;

The calcium ion ($Ca^{++}$) current impulses that are associated with synaptic transmission are almost identical, in intensity ($<20$ $\mu A/cm^2$) as well as in waveform, to the current and voltage impulses of the present invention;

On the importance of bioelectrical signals to the control of natural cellular phenomena, we know, for example, that the very first signal received by the egg after it is fertilized is bioelectrical and causes a so called CALCIUM ION $CA^{++}$ EXPLOSION. It iS this signal that causes a reversal of polarity in the ovular membrane as soon as it is penetrated by the first spermatozoon. Access is thereby denied to all of the other spermatozoa for a period of three minutes except for those lucky twin or triplet spermatozoa that reach the fertilized egg at the same time.

In FIG. 2m, the n=2 and n=3 modulation values refer to the impulse bundles illustrated in FIG. 17 herein.

Referring now to FIG. 2n, there are shown the four stages of development of most diseases or health problems. The first stage, after the cause or the perturbation agent, is the identification of the physical or psychological parameter which is disturbed. The second phase is the PHYSIOLOGICAL STRESS that is the short term consequence of the physical or psychological disturbance of the said parameter. The third phase is a specific disease or health problem that is the direct result of PROLONGED OR INTENSIVE STRESS. The fourth and final stage is the chronic disease(s) or health problem(s) that develop(s) from various combinations of prolonged homeostatic disturbances.

The above definitions and causal relationships are of extreme importance because we can visualize and understand better how the present invention can help man for actively, improving almost any health problem by means of the three basic physiological effects that reduces the PHYSIOLOGICAL STRESS related to almost any disease or health problem. Indeed, even in some cancer cases for example, RHUMART MAY REDUCE THE STRESS that is known to cause (or prevent self-healing of) numerous cancer cases. Therefor this invention can reinforce the body's natural defense and healing mechanisms.

Referring now to FIG. 2p there is shown an example of the 4 phases of health perturbation and more specifically, that of Lyme disease. In this actual example, the 4 levels of disturbances are very well defined and easy to understand. This case clearly show that a single and well known cause, the parasite of Lyme disease (of the Syphilis family), can eventually cause numerous well known diseases such as arthritis, diarrhea, cardiac problems, and meningitis which can still later on degenerate in a debilitating chronic condition characterized by chronic cardiac problems and chronic meningitis all together present at the same time, and which can even cause the person's death.

in the preceding example, we see that serious inflammation is a stage preceding the development of many diseases, and since this invention has the capacity to help reduce or control, if not eliminate completely, the inflammation or PHYSIOLOGICAL STRESS, it is clear that this system could improve the prognosis of Lyme disease in numerous cases, especially if the present invention is used early enough to reinforce the defense and healing mechanisms before their complete deplation by the long term devastating effects of Lyme disease.

Referring now to FIG. 2q there is shown an other example of the 4 phases of health perturbation, that of an accident of various types (automobile, surgical, sports or on-the-job), from examples of perturbation agents or accident causes to the development of chronic health problems. The large arrow on the left hand side show the scale and the direction of time from the causes or physical agents to the final effects or chronic (or mortal) health problems. Numerous typical accidents are chosen as examples in this "block diagram".

Referring now to FIG. 2r there is shown the example of the 4 phases of thought disturbances, from examples of perturbation agents to chronic health problems. The examples chosen on the right hand side column of this "block diagram" show how negative and/or suppressive attitude towards a person (which attitude can be a person's own attitude towards himself) can eventually lead to major chronic health problems in the long term including such problems as chronic migraines, cardiovascular problems or even death. Many such degenerative processes were found by the present author to be reversible with the proper use of the present invention, BY ACTING ON THE SAID PHYSIOLOGICAL STRESS RELATED TO MOST DISEASES OR HEALTH PROBLEMS, in contrast with the prior an which is aimed at treating specific diseases or problems. The long term effect of reducing or controlling said physiological STRESS being the strengthening of one's self-defense and healing mechanisms which often leads to reversal of many degenerative processes.

FIGS. 3a, b, c show general waveforms used in the present invention and the graphical definition of the different parameters, $k_\epsilon$, $\tau_r$, $B_{max}$, $i_{max}$, $S_1$ and $S_2$ related to these impulse waveforms.

The critical damping waveform of the magnetic impulses used in this invention is given by the following equation:

$$B(t) = K_B t \exp(-t/\tau_r)$$

where t is the time, $K_B$ is a constant, exp ( ) means the natural or exponential function, and $\tau_r$ is as defined in FIGS. 3a, 3b, 3c.

We have shown that the maximum magnetic field, $B_{max}$ is given by the equation:

$$B_{max} = \left\{ \frac{(k_\epsilon \tau_r / e)}{(n_p s_p \cos\theta)} \right\}$$

where $k_\epsilon$, $\tau_r$ are as defined above, e=2.71828 . . . (the base of natural logarithms), $n_p s_p$=sensitivity factors of the magnetic field measurement coil probe, $n_p$=the number of turns of wire (or living tissue) wound in the said probe, $s_p$=the average area covered by a single loop of wire in the probe, $\cos\theta$=the cosine of the angle between the main axis of the probe and the direction of the magnetic field to be measured ($\cos\theta$=1, for $\theta$=0, and $\cos\theta$=0, for $\theta=\pi/2$).

The induced bioelectric voltage waveform typically used in this invention is given by: $\epsilon(t) = k_\epsilon (1 - t/\tau_r) \exp(-t/\tau_r)$, where $\epsilon(t)$ and $\tau_r$ are as defined above, and t is the time, as graphically shown in FIGS. 3b and 3c.

FIG. 3d shows actual oscilloscope pictures of the said bioelectric impulses used in the present invention. The top three (3) photographs show the basic current impulse waveform, i(t), which has the same waveform as that of the magnetic field impulse, B(t); and just below in the same top three (3) photographs, the waveform of the induced voltage impulse, $\epsilon(t)$, is shown. The bottom three (3) photographs show different impulse series, trains or sequences of the same waveforms, i(t). B(t) and $\epsilon(t)$, for different values of the MODULATION, n, (n=1, 2 and 3) as further described herein.

Referring now to FIG. 3e there is shown the equivalent circuit of a pulse shaping circuit including a capacitor or combinations of capacitors which are charged to a voltage $V_o$ before being discharged by electronic control means through a total discharge resistive means, $R_T$, which is composed of the equivalent resistive means of said combinations of applicators, the total resistance $R_F$ of connecting leads of said applicators and discharge resistive means. $R_j$, calculated so as to obtain a critical or nearly critical damping of said conditioning pulses produced by said electromagnetic conditioning applicators for a selected value of pulse width, $T_j$, using one or more of said combinations of applicators having an equivalent inductance, $L_{eq}$; and wherein any of the component of this R, R, C circuit can be changed so as to cause the peak amplitude of said conditioning pulses to decrease by not more than approximately 75%.

Referring now to the drawings, and more specifically to FIG. 4, there are shown examples of combinations of the controllers/generators, conditioning applicators circuit interface means and field detector. "Modes" of this invention are defined as different combinations of conditioning applicators, interfaces and generators means. These different modes of the present invention are well illustrated in the numerous drawings of the present document and described in full details herein after.

Referring now to FIG. 5, there are illustrated the MBI-1004A and the MBI-1004B modes including the MBI-1000 controller/generator. The combination of the MBI-1004A and MBI-1004B has been named the MBI-1004A-B for convenience. The said MBI-1000

Controller 15 supply the selected signals to the said MBI-1004A.B through the connector 25. The maximum amplitude of (voltage) impulses is predetermined by the control 18 of the miniaturized Controller 15. The pulse width is selected directly with the slide switch in the middle of the said MBI-1004A or the MBI-1004B (indicates 0.1, 0.2 and 0.3 msec). The electrode pairs (E1, E2), (E3, E4), (E5, E6), and (E7, E8) made of flexible conductive rubber are connected with 2 to 6 feet of wire leads to the banana type double contact connector 29: and the intensity of maximum current flowing through a pair of electrodes (e.g. E1, E2) is predetermined by means of the intensity control (28a) placed to the left of the said connector 29 and similarly for the other three channels (2, 3 and 4).

Referring now to FIGS. 6a and 6b there is shown a preferred embodiment of the said MBI-3004 Mode including the MBI-3004 Electrode Interface (360) and the said MBI-3000 bioelectric Controller/generator (300) (FIG. 6b), both of which are described in greater details herein after. The said MBI-3004 interface is connected to the rear panel of the MBI-3000, under the beeper knob 207 (FIG. 9B). Essentially, the series of pulses generated by the said MBI-3000 are discharged as illustrated in FIG. 17 and FIG. 3b, through one or more of the 4 pairs of electrodes (E9, E10), (E11, E12) etc. (similar to those used with the said MBI-1004A.B interface) connected to the MBI-3004 electrode outlets 364. The pulse width control 361 and the pulse current intensity controls 362 are shown in FIG. 6a.

Referring now to FIG. 7, there is shown the said MINI-4A local applicator used with the said MBI-3000 Controller/generator and connected to the outlet 204 as illustrated in FIG. 8. This example of MINI-4A applicator is approximately 15 cm long and 2.5 cm in diameter, and it is described in great details hereinafter (for example, see FIG. 22).

Referring now to FIG. 8, there is shown a perspective illustration of 4 Modes or embodiments of the present invention, e.g. the MINI-4A, the REBONE-4A, the MAXI and the MAXI-2A Modes each of which include the said MBI-3000 Controller. Extension leads to connect the said coil applicators to the said MBI-3000 are not shown in this Figure (they are illustrated in FIGS. 19 and 20).

One embodiment of the present invention used for Couples (AHS-C) composed of the same elements as the said AHS-B illustrated in FIG. 10 and FIG. 11, plus one pair of MAXI-2A double-ring coil applicators and one pair of said REBONE-4A regional applicators, all of which can connected and used it combination with the MBI-3000 coil Controller/generator Referring now to FIGS. 12a and 12b, there is shown the embodiment of the present invention used for example in equine applications and named AHS-E composed of one said MBI-3000 generator/controller, one pair of said MAXI-2A coil applicators and one pair of said JAM-8A coil applicators. These Figures also show where to connect these applicators to the MBI-3000 generator. FIG. 12 and 12 show various applications or positioning of the applicators for equine or "harness world" applications. The general operation procedures are as described herein for human applications.

The use of JAM-8A pads 325 described in FIG. 12 is similar to that of REBONE-4A coil applicators described herein for human applications. These applicators 325 are connected to the outlets 204 and 205 of the MBI-3000. When using one pair of the MAXI-2A applicators on the horse orient the polarity of the applicator so that the field penetration is at maximum unless you want to give a conditioning session mainly for superficial muscles and biological materials.

As shown in FIGS. 12a, 12b, 13a and 13b, two pairs of JAM-8A can be used simultaneously with one MBI-3000 generator/controller. Simultaneously to the use of two pairs of said applicators one can use the MBI-3004 electrode interface connected to the MBI-3000 generator in order to condition one or several horses at the same time.

Referring to FIG. 14, there is shown a photograph of a preferred embodiment named AHS-M of the present invention including accessories and a handy suitcase. On the left of this picture there is shown a practical chronometer 14 generating an alarm signal and a 60 Hz-115 VAC to 12 VDC adapter 13 which is required to power the said MBI-1000. In the center of this picture, there is the MBI-1000 generator/controller,, and one pair of said REBONE-PM coil applicators is seen on the right-hand side of this picture, more detailed illustration of this AHS-M is shown FIGS. 16, 16a and 16b described hereinafter.

In FIG. 15, there is shown an example of a human application of the miniaturized REBONE-PM Mode on the shoulder including the said MBI-1000 Controller/generator 15.

In FIGS. 16, 16a and 16b, there is shown an illustration of a miniaturized embodiment of the present invention (AHS-M) and its main accessories described with to FIG. 14 except for the ferrite magnet 12 used to detect the field manually or by hearing.

In FIG. 16b there is shown an illustration of the said MBI-101 field detector positioned between said REBONE-PM applicators 10, 11 of the said MBI-1000, showing the configuration used to measure the pulsating field generated by the said REBONE-PM mode.

Referring to FIG. 17, there is shown an illustration of the sequential pulses for different modulation "n" values. Simplified definition of MODULATION (304, FIG. 9A and 21, FIG. 16a). Modulation is the process of blocking out or eliminating a series of pulses within the basic set of pulses, $f_b$ (in which the number of regular, consecutive, pulses is determined by the PULSE FREQ. dial 20 (or 303) and the Frequency Divider 19 (or 303). For example, if the frequency divider is in position 1 and the PULSE FREQ. dial is at 60 pulses per second, the said MBI-1000 or the said MBI-3000 Controller/generator will create a regular series of 60 pulses per second.

The following is the significance of the settings from 1 to 9 and "CONT" (Continuous) around the M, ODULATION dial (21 or 304)

| | |
|---|---|
| n = 0 (CONT.): | none of the basic pulses are blocked; regular stimulation; |
| n = 1 | 1 out of every 2 pulses is blocked; |
| n = 2 | 2 out of every 4 pulses are blocked; |
| n = 3 | 4 out of every 8 pulses are blocked; |
| n = 4 | 8 out of every 16 pulses are blocked; |
| n = 5 | 16 out of every 32 pulses are blocked; |
| n = 6 | 32 out of every 64 pulses are blocked; |
| n = 7 | 64 out of every 128 pulses are blocked; |
| n = 8 | 128 out of every 256 pulses are blocked; |
| n = 9 | 256 out of every 512 pulses are blocked; |

Generally speaking, for any whole number n, 2 exponent (n−1), (written $2^{n-1}$) consecutive pulses out of every $2^n$ pulses in the set of regular pulses will be blocked by the MODULATION dial (or n-MODULATION);

Referring now to FIG. 18a there is shown a perspective illustration of the said MAXI applicator (330) showing the MAXI assembly inner (331b) and outer (331a) pans (aluminum extrusions) held together by means of two blocks (332) into which the said parts are fixed by means of special screws (334), See FIG. 18d for further details;

FIG. 18c shows an exploded view of details of construction of the specially developed MAXI wall 337 for holding and protecting the MAXI coil winding 336 made up of 58 turns of #11 AWG insulated (electrically) Aluminum wire;

FIGS. 18b and d are perspective illustrations of construction details of the MAXI assembly box (331a, 331b and 332) showing how the said winding 336 is connected to the lead connector A3M with strain release block 333 which sides into the Aluminum extrusion 331a; the latter being held to the inner Aluminum extrusion 331b by means of two screws 334 ($S_1$ and $S_2$) which pass in the hole of block 332, through the hole of 331b, by the side of the wall 337 and 337a, through the hole of 331a before reaching the screwing hole in the inner part 332a of said block 332 as further detailed in FIG. 18d;

The winding (336) is fixed to the two sheets (337) with "CONTACT" glue or similar product in order to give just the right flexibility and solidity to the MAXI (330). The electrical cord (339) to connect the applicator (330) to the Controller (300) is properly secured in the outer extrusion to (331a) by means of a standard known strain release rubber like attachment.

The electrical resistance ($R_L$) of the winding (336) is in the range of 0.45 $\Omega$, and the low frequency inductance of the said winding is in the range of 1.75 mH. The length of the MAXI (330) is approx. 25 cm, and its diameter approx. 50 cm.

Referring now to FIG. 19a, b, c, d, there are shown construction details a pair (340) of said MAXI-2A applicator; the MAXI-2A applicator 341 includes a winding 341 a composed of approximately 29 turns of aluminum wire (gage #11 AWG for example) with a protective plastic tubing 342, and twisted masking tape 342a adhering on both sides is taped around said tubing 342; the two ends of said winding (341) are fixed to ta connecting electrical cable (343). This connecting cable is passed twice in the cushion like structure (344) made of leather and rivetted similarly to the said REBONE-4A applicator (320) described herein after (FIG. 21). The distance between the two MAXI-2A applicators 341 can be adjusted at will by pulling the two applicators apart or by pushing the connecting cable (343) into the leather cushion (344). The length of the connecting cable can vary, and is chosen to allow the separation of the ring applicators to vary between zero and two to three feet or more.

Finally, the windings 341 and 342a are incapsulated in a layer of leather or other material and the two edges of the leather bands (345) are solidly fixed with rivets approximately one inch apart (approx. 70 rivets are required for each MAXI-2A applicator having a diameter of approximately 50 cm.

In general terms, the equivalent inductance $L_{eq}$ of a MAXI-2A double-ring applicator is given by (L/2±M), where L is the inductance of one MAXI-2A winding (341) and M is the mutual inductance between the two windings. In this example, $L \approx 1.06$ mH. Therefore, $L_{eq} \approx 0.53$ mH when the mutual inductance, M, is much smaller than the inductance L. This is the case when the two windings are far enough apart (more than 25 cm for example).

FIG. 19e shows the equivalent electrical circuit of two pairs (340a and 340b) of MAXI-2A applicators (340) and the very low frequency equivalent circuit of the 12 foot extensions used to connect each pair (340) of MAXI-2A to the said MBI-3000 Controller/generator (300) via the #202 and 203 (A3M and A3F type) connectors;

Referring now to FIG. 20, there is shown a perspective illustration of construction details of the said JAM-8A pair (325) of pads. This pair of pads are flexibly attached to the leg for example by means of VELCRO bands. The distance between the two pads (326a and 326b) is adjustable by means of a flat wooden piece (327) in which a rope can be threaded with one end of the said rope fixed to the piece (327). Each winding is composed of approx. 29 turns of Aluminum wire (gage 11 AWG) coated with an electrical insulation material, having an inductance $L \approx 0.33$ mH and a resistance $R_L \approx 0.12 \Omega$. The windings are approx. three inches ($\approx 7.5$ cm) wide by approx 15 inches (38 cm) long.

FIG. 20b shows the parallel connected pair (326) of MOYI-8A coils which is introduced in the two special pockets of each pad 326a or 326b.

FIG. 20c shows the equivalent electrical circuits for the said JAM-8A pair 325 of pads, or the 2 LEG equivalent circuit, the lead resistance ($R_{F1}$) and the resistance of extension leads ($R_{ex}$);

FIG. 20d shows the electrical equivalent circuit of 4 LEG pads or two pairs 325a and 325b of LEG pats of the type shown in FIG. 20a, the lead resistances $R_{11}$, $R_{12}$, $R_{13}$ and $R_{14}$; and the resistance $R_{ex1}$ and $R_{ex2}$ of the two extensions used to connect each pair of pads to the said MBI-3000 generator/Controller, via the connectors 209, 210 (of the A5M and A5F types);

FIGS. 21a, b, c show the said REBGNE-4A (320) and the REBONE-PM (10, 11) applicator windings with examples of physical dimensions. In a REBONE-4A mode, the two REBONE-4A coils are serially connected in a pair; for the REBONE-PM mode, the two coils are parallel connected in a pair;

Referring now to the FIG. 21b, there are shown construction details of the REBONE-4A applicator (320) serially connected pairs of which are used with said MBI-3000 Controller/generator, and FIG. 21b shows details of the REBONE-PM applicator (10 or 11) a parallel connected pair of which is used with said MBI-1000 Controller; The shape of these ceils is as shown in the FIG. 21b and the dimensions are approx. 7.3 cm wide by 12.7 cm long (these are the dimensions of the coil windings.) The other characteristics of the said REBONE-4A are as follows; number of turns, N, is approx. 64 of copper wire #18 AWG; inductance of coil, approx. 0.70 mH; electrical resistance of winding, approx. 0.46 $\Omega$; size of external rectangular pieces made of leather approx. 12.5 cm by 18 cm (both pieces of leather being liked with rivets approx. 2.5 cm distant to each other). The other characteristics of the said REBONE-RM are as follows: number of turn, N, is approx. 64 of copper wire #22 AWG; electrical inductance of coil, approx. 0.80 mH; electrical resistance of coil, approx. 1.09 $\Omega$; size of external rectangular pieces, made of leather to protect the windings (11), approx. 12.5 cm by 18 cm (both pieces of learner being fixed with rivets approx. 2.5 cm distant to each other).

Referring now to FIGS. 22 (a), (b), (c) and (d) there are shown construction details and specifications of the said MINI-4A coil applicator (310). A few characteristics of the said MINI-4A are as follows: DC electrical inductance, approx. 0.30 mH; DC electrical resistance, approx. 0.01 $\Omega$; approximately 93 turns of copper wire #12 AWG. Generally, the MINI-4A applicators are serially connected in pairs (in series within a pair) to the said MBI-3000 Controller-generator through the outlets 204 and 205.

Referring now to FIG. 22, there is shown an example of Field Pattern Chart (FPC) of the said MINI-4A coil applicator (310) where isomagnetic-field lines are shown (IBI= 100 G, 22 G, 11 G, 5.3 G, 3.3 G, 2.2 G, 1.1 G, 0.53 G and 0.17 G, where IBI is the maximum intensity of the magnetic field (peak value) and G means Gauss, the unit of magnetic field, $1G = 10^{-4}$ to $Wb/m^2$ and the direction of the field is indicated by arrows in this Figure. A different example of Field Pattern Chart (FPC) for the said REBONE-4A coil applicator (320) is shown in FIGS. 24a and 24b. Isomagnetic-field lines of different IBI values and the direction of the field are indicated in the same fashion as described just before in referring to FIG. 23.

Figure 25B:
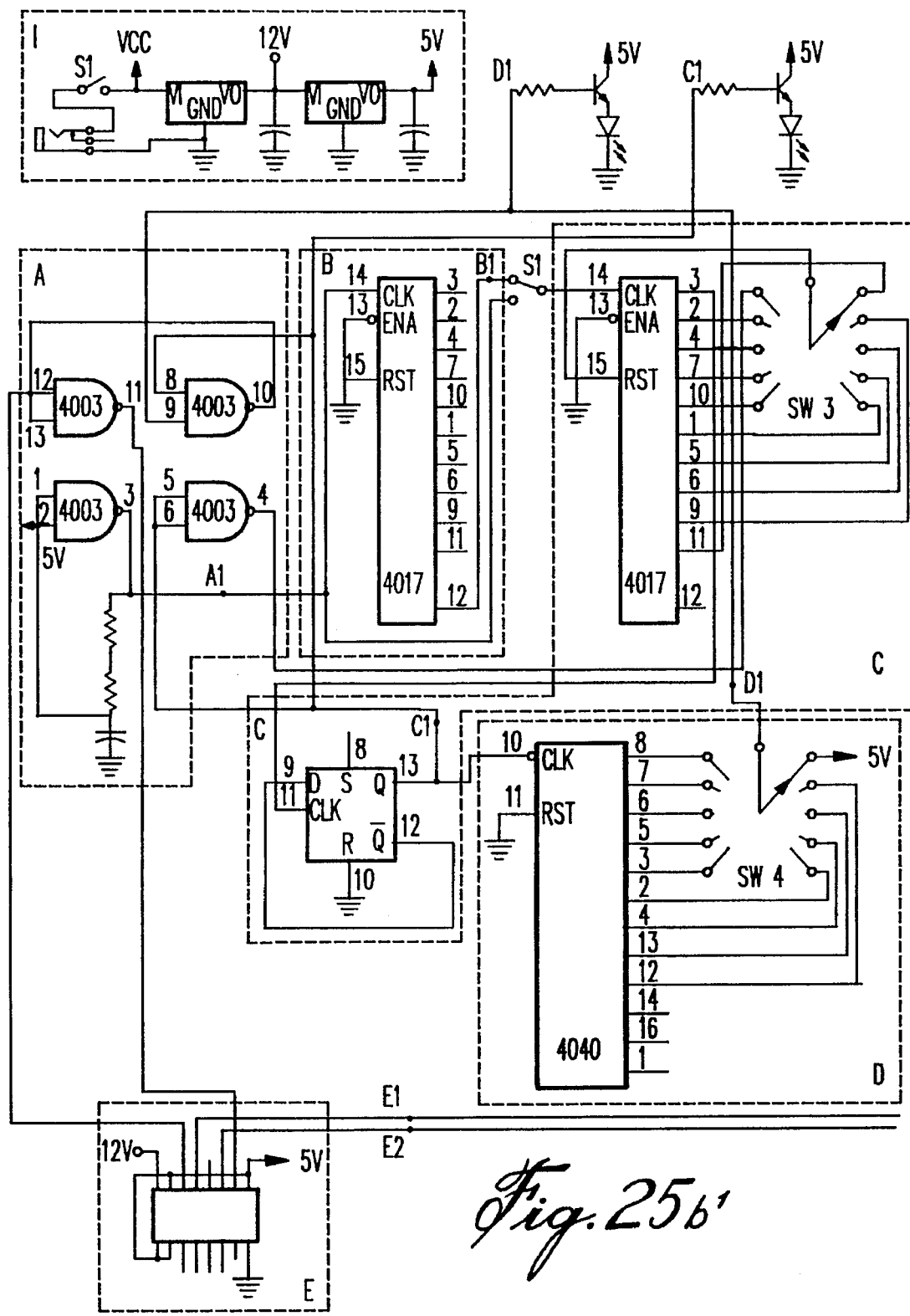
Figure 25C:
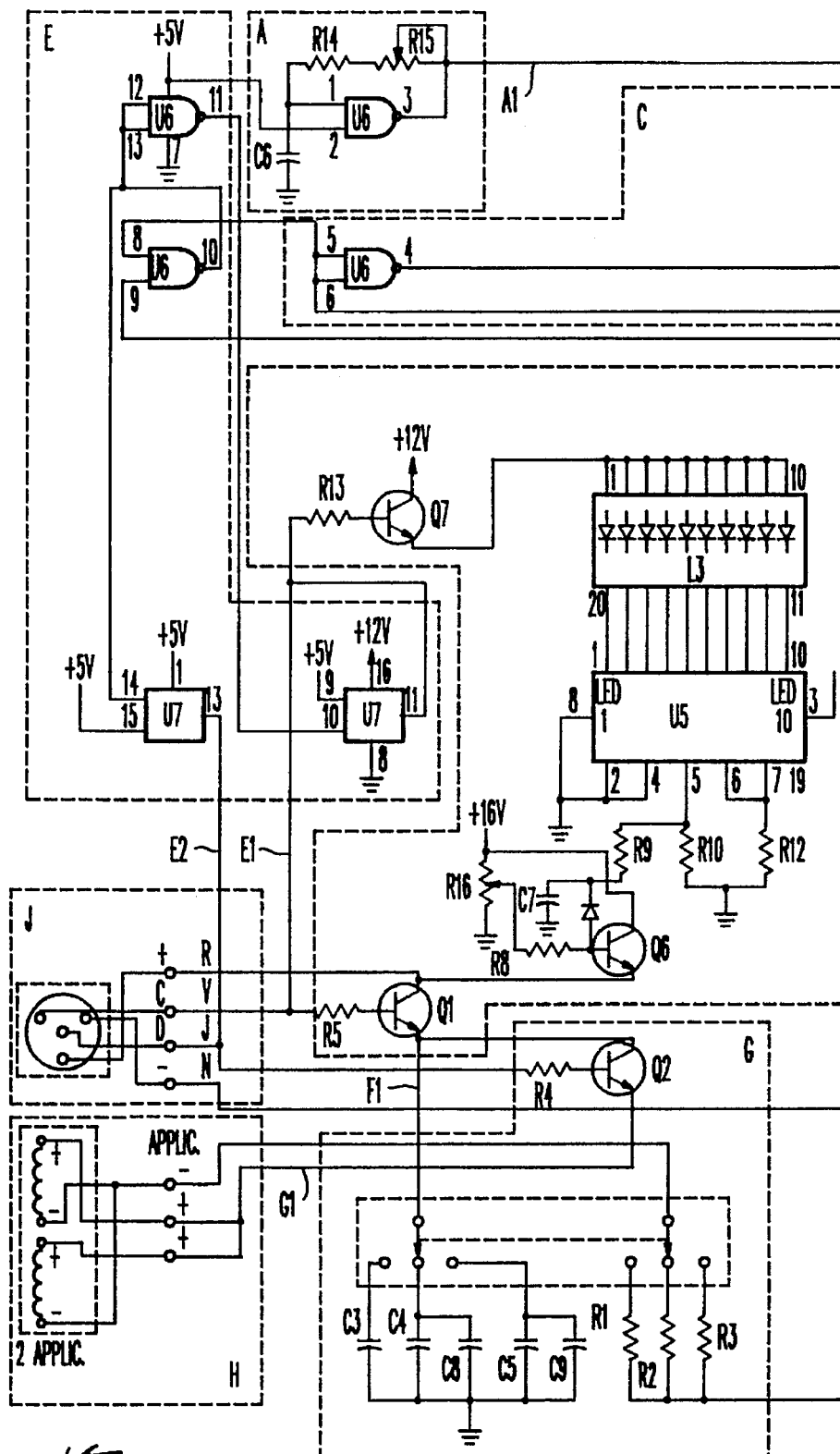

Referring now to FIGS. 25a, 25$b^1$, and 25$b^2$, there are shown a block diagram of MBI-1000 Controller (15) and a detailed circuit diagram of this controller (15). The blocks in the block diagram (FIG. 25a) are identified A, B, C, D, E, F, G, H and I; and the outputs of these blocks, which correspond to the outputs of the A to I dotted line blocks in the detailed circuits diagram of FIGS. 25$b^1$ and 25$b^2$, are identified A1, B1, C1, D1, E1, F1, G1, H1 and L1.

Still referring to FIGS. 25a, 25$b^1$ and 25$b^2$, here is a detailed description of the blocks A to I of these Figures:

BLOCK a: oscillator

This section uses an RC network with NAND gates to create a 1200 Hz square wave at the output 1300. For example, the known IC #4093 is used for this purpose with two resistors and a capacitor as shown in FIG. 25b;

BLOCK B; FREQUENCY DIVER (+10)

This section uses a programmable decade counter to divide the frequency of the input 1300 by ten. For example the known IC#4017 is used for this purpose (FIGS. 25$b^1$ 25$b^2$ and 19, FIGS. 16, 16a and 16b);

BLOCK C: Frequency Selector

This section uses a programmable decade counter to divide the frequency of the input 1302 as predetermined by the control 1311 (or 20, FIGS. 16a and 16b). The output 1303 of this section is a. square wave with a frequency of 0, 6.6, 7.5, 8.6, 10, 12, 15, 20, 30 or 60 Hz, when the control (19, FIG. 16a and 16b) is at 1. For example, the known, IC#4017 and 4013, and the ten position switch 20 are used for this purpose, as shown in FIG. 25$b^1$ and 25$b^2$;

BLOCK D: N—Modulation($2^n$)

This section uses a 12 bit binary counter that divides the frequency of the input 1303 as predetermined by the control 1312 (or 21, FIGS. 16a and 16b). This signal 1304 has a frequency of approx 0.115, 0.23, 0.47, 0.95, 1.9, 3.8, 7.5, 15 or 34 Hz when the control (19,, FIG. 16a) is at the 1 position. When the latter control is in the divide by 10 (+10) position, the frequency of the signal 1304 is divided by ten. For example, the known IC#4040 and the ten position switch 21 ate used for this purpose, as shown in FIG. 25$b^1$ and 25$b^2$;

BLOCK E: Charge and Discharge signal drivers

This section uses NkND gates to divide the input 1304 into two signals, one being the charge (E1) and the other being the discharge (E2) signal. These two signals have a phase shift of 180 degrees, and they are passed through a low-to-high voltage lever shifter to obtain a square wave with a peak value of 12 volts. For example, the known IC40109 is used for this purpose, as shown in FIGS. 25$b^1$ and 25$b^2$;

BLOCK F: Power Driver and Amplitude Control

For example, this section uses two Darlington transistors (for example, of the type TIP-140); one to charge one of the three capacitors $C_1$, $C_2$ or $C_3$ of approx. 25.41 µ. F, 119.64 µF or 264.7 µF shown in the block (of FIG. 26b, and the other Darlington transistor to discharge the capacitor through the pair of parallel connected applicators, of the REBONE-PM the (10,11) which are serially connected to one of the three resistors $R_1$ (6.13 Ω). The transistors are controlled by the input signals 1305 and 1306; and the switch S6 shown in block F of FIG. 25$b^1$ and 25$b^2$ allows for the combination of $R_1$ with $C_1$, $R_2$ with $C_2$, and $R_3$ with $C_3$. The inputs 1305 and 1306 have a phase shift of 180 degrees between each other, so that when the charge transistor is ON, the discharge transistor is OFF, and vice versa. The amplitude of the charging signal is predetermined by the control 1314 (18, FIGS. 16, 16a and 16b) which changes the value of the variable resistor (connected to the 2N3053 transistor shown in block F of FIGS. 25$b^1$ and 25$b^2$ which in turn changes the block value of the voltage of the charged capacitor ($C_1$, $C_2$, $C_3$).

For example, the BAR-LED amplitude display circuit is composes of a 2N2222 transistor connected to a 10 kΩ resistor amplitude display driver, IC #3914 and a BAR-LED display unit, MV57164 which are connected to various resistors, 1 µf capacitor and to a IN914 diode as shown in FIGS. 25$b^1$ and 25$b^2$;

BLOCK G: Pulse Width

The section allows for choosing one of the three combinations, $C_1$, with $R_1$, $C_2$ with $R_2$ or $C_3$ with $R_3$ (where $C_1$, $C_2$ and $C_3$ are the capacitors to be charged and then discharged through the parallel pair of coil applicators (10,11) connected in series with the resistors $R_1$, $R_2$ and $R_3$) as predetermined by the control 1313 (17, FIGS. 16, 16a and 16b);

BLOCK H: Outputs

This section is the parallel pair of coil applicators (10, 11) connected to the MBI-1000 Controller/generator. An example of preferred embodiment of this coil is the REBONE-PN applicator described herein (FIG. 21b).

BLOCK I: Voltage Regulator

This section includes 5 V and 12 V (approx.) voltage regulators to regulate the input voltage 1310 (23, FIGS. 16, 16a and 16b). The output 1309 is applied to all Blocks except F, G and H. The output 1315 is applied to the Block F. The input voltage 1310 can range between 12 and 15 VDC. For example, this section uses two regulators (7812 and 7805) combined with a 2.2 µF and 0.1 µF capacitors.

Referring now to FIG. 25b, there are shown in the Light Emitting Diode (LED) display circuits to visualize the signals C1 (LEDS to the right of the control 20, FIGS. 16, 16a and 16b), D1 (LED to the right of the n-Modulation control 21, FIGS. 16, 16a and 16b), and the discharge signal E2 (the BAR-LED unit composed of 10 LEDs which are positioned to the right of the control 18, FIGS. 16, 16a and 16b, and underneath the small circular windows where we can read the number 2, 4, 6, 8 and 10 indicating the actual peak amplitude delivered to the applicators (10, 11).

In FIG. 25a, the circuits to visualize the signals C1 and D1 are in the upper right hand side of this diagram, and the circuit to visualize the signal E2 is shown in the Block F.

FIGS. 25$c^1$ and 25$c^2$ is a second example of detailed circuit diagram of the MEI-1000;

FIG. 26a shows a block diagram of the MBI-1004A or the MBI-1004B electrode interfaces used in combination with the MBI-1000 controller-generator;

Now referring to FIG. 26b, there is shown a detailed circuit diagram of the MBI-1004A and MBI-1004B electrode interfaces (also named MBI-1004A-B) (shown in FIG. 5. These interfaces are connected to the MBI-1000 controller (15) by means of a special connector (25, FIGS. 16, 16a and 16b labeled "C" in FIG. 26b) with the G (ground),+(variable DC voltage $V_0$), C (charge) and D (discharge signals corresponding to the same signals G,+C and D of the MBI-1000 circuit of FIGS. 25$b^1$ and 25$b^2$ (see #25).

The said interlace MBI-1004B is very similar to the said MBI-1004A interlace and it is connected and driven through the latter using the same charging and discharging signals C and D described above and the same G and $V_0$ "signal". These two said interfaces are connected in parallel through the MBI-1004A interlace.

The circuits of the said MBI-1004A and that of the MBI-1004B use two Darlington transistors each (of type TIP140 for ex.) as already described above in the description of the detailed circuit of the MBI-1000 Controller. So the charge and discharge circuits of the MBI-1004A.B need not be described in details except for the section of these circuits which are different from that of the MBI-1000. The basic difference is seen in the right side of the circuits (at the discharging level) where the charged capacitors are discharged through a variable resistance R10 or R11 (for adjusting the output current) serially connected to a pair of reusable or disposable flexible electrodes (E1, E2) or (E3, E4) (applied directly on the skin with a conducting gel) connected to the high voltage side of a small transformer (ex.: type JJ10807) of which the primary side is serially connected to the discharging resistor R4, R5 or R6 for the first channel and to R7, R8 or R9 for the second channel (through type 1N4003 diodes).

The pulse width of the conditioning signal is adjusted by means of a three position switch shown in the center of FIG. 5 which allows for choosing a pulse width using the three different combinations of resistor-capacitor $R_4C_4$, $R_5C_5$, or $R_6C_6$ for the said first channel and $R_7C_7$, $R_8C_8$ or $R_9C_9$ for the second channel of the said electrode interface MBI-1004A or MBI-1004B.

FIG. 26c shows an other example of detailed circuit diagram of the said MBI-1004A or MBI-1004B electrode interlace;

Referring now to FIG. 26a and 26c there is shown the block diagram and one example of detailed circuit of the said MBI-1004A or the MBI-1004B.

Receiving the signals from the said MBI-1000 generator, the said MBI-1004A and MBI-1004B work by the controls of the said MBI-1000 controller-generator for frequency and modulation settings and amplitude of working voltage ($V_o$).

The only controls we have here are the "PULSE WIDTH SELECTOR" and the output current regulator (R10 and R11 of FIG. 26b).

The four wire cable connecting the unit to the said MBI-1000 carries four signals: Variable supply voltage "+" (0–15 volts), the charge switching signal "C", the discharge switching signal "D" and the ground "G". There is an output connector on the said MBI-1004A to allow the MBI-1004B to be connected in parallel;

Following is a description of the blocks of FIGS. 26a and 26c:

Block B- CHARGE DRIVER

Block B receives the switching signal A1 that will make the NPN transistor MPSU45 switch the supply voltage to the following block, thus providing the charging current on the capacitors of the tank circuit;

Signal B1 shows the waveform of the charging voltage applied to the following block;

Block C- TANK CIRCUIT

The "pulse width selector" will match an "RLC" network to get a predetermined pulse width $T_j$ required to the output of the unit;

When the previous block provides the voltage of charge, the capacitor has enough time to charge to a point close to the supply voltage. When the following block switches the stocked charges, to the ground, the current will flow through a matched resistor giving the desired pulse width $T_j$ of the said Critical Damping pulses.

Three diodes are used to isolate each circuit from each other to eliminate the addition of the capacitor value;

Signal C1 will vary said $T_j$ depending on the selected RC;

Block D- DISCHARGE DRIVER

Receiving signal A2 the NPN transistor TIP120 will switch the stocked charges in the selected capacitor-towards the ground through the following block;

Signal D1 shows the resulting voltage to the entrance of the following block;

Block E- VOLTAGE BOOSTER

This circuit is a high ratio transformer that will boost the voltage by a factor of 150. The nominal input impedance of this circuit is 8 Ω and the output impedance is 1,2 kΩ. The other use of this circuit is to provide electrical insulation with the electronic circuit. Signal E1 is the output signal before the current regulator;

Block F- VARIABLE OUTPUT

Block F is there to allow correct adjustment of the output current. As the formula E=RI, the signal E1 being roughly constant, varying the value of the variable resistor will vary the current in the output loop. Signal F1 is the output waveform of the first channel and the amplitude of the current flowing between the pair of output electrodes will vary with the variable resistor. $V_e$ is the voltage applied between the positive and the negative electrodes. F1 and F2 represent respectively the+and the–electrodes in this diagram; (E1 to E8 are used in other sections of this document to refer to the electrodes of the Said MBI-1004A.B);

Block G- CHANNEL 2

Block G includes circuits similar to those of block B to block F for a second channel. G1 is the output waveform of the second channel. $V_e$ is the voltage generated between the positive and the negative electrodes. G1 and G2 represent respectively the+and the–electrodes in this diagram.

FIGS. 26d, 26f and 26h show various output voltages of the said MBI-1004A or MBI-1004B for a resistive load of 10 kΩ, with other conditions as specified in these drawings;

FIGS. 26e, 26g, and 26i show the current flowing in the 6.2 Ω, 2.7 Ω, and 1.6 Ω resistors placed before the small output transformer (TRS: 8 Ω, 1.2 kΩ) of the said MBI-1004A or MBI-1004B circuit (FIG. 26b and 26c), with other conditions as specified in these drawings;

Referring now to FIGS. 27a and 27b, there are shown a block diagram of the said MBI-3000 Controller-generator (300) and a detailed circuit diagram of this controller 300. The said blocks in the block diagram (FIG. 27a) are identified A, B, C, D, E, F, G, H, I, J, K, L, M, N and O; and the outputs of these blocks, which corresponds to the outputs of the A to O dotted line blocks in the detailed circuit diagram of FIG. 27b, are identified A1, B1, C1, D1, E1, F1, G1, H1, J1, K1, L1, M1, N1 and O1.

Still referring to FIGS. 27a and 27b, a detailed description of the said Blocks A to O of these two Figures follows:

BLOCK A: Oscillator

This section uses an RC network with NAND gates to create a 1200 Hz square wave at the output 3300. For example, the known IC #4093 with two resistors (1 kΩ and 24kΩ) and a 0.µ F capacitor is used as shown in block A of FIG. 27b;

BLOCK B: Frequency DIVIDER (÷10)

This section uses a programmable decade counter to divide the frequency of the input 3300 by ten. For example, the known IC #4017 is used for this purpose (FIGS. 27b and 3 divide by ten (÷10) switch 303, FIG. 9A);

BLOCK C: Frequency Selector

This section uses a programmable decade counter to divide the frequency of the input 3302 as predetermined by the control 3311 (or 303, Pulse Freq., FIG. 9A). The output 3303 of this section is a square wave with a frequency of 0, 6.6, 7.5, 8.6, 10, 12, 15, 20, 30 or 60 Hz, when the control 303, (÷10), FIG. 9A is in the 1 position (left). When the divider is in the ÷10 position, all frequency are divided by ten. For example, the known ICs #4017 and 4013, and a ten position switch are used for this purpose, as shown in FIG. 27b;

BLOCK D: Frequency Divider (÷10)

This section uses a programmable decade counter that is set to divide by ten the frequency of the input 3303. The output D3 or 3317 is the charge signal. The outputs D1 or 3316 and D2 or 3376 are similar square wave signals with a frequency ranging between 0 and 60 Hz. For example, the known IC #4017 is used for this purpose as shown in the dotted block D of FIG. 27b;

BLOCK E: n—Modulation ($2^n$)

This section uses a 12 bit binary counter that divides the frequency of the input 3316 as predetermined by the control 3312 (304, FIG. 9A). The output 3318 has a frequency ranging between 0 and 30 Hz when the control (frequency divider 303, lower switch of FIG. 9A) is in position 1 (on the left position). When the latter control is in the Divide by ten (÷10) position, the frequency of the said signal 3318 is divided by ten. For example, the known IC #4040 and a ten position switch are used for this purpose, as shown in FIGS. $27b^1$–$27b^3$;

BLOCK F: Discharge interrupter

This section uses two analog switches. The first one is used to realize the Modulation of the discharge signal 3376 (D2). The second switch is used to interrupt the output when the "session" time selected in section I (or control 305, FIG. 9A) has run off. This signal interruption is done by the input 3324 coming from the counter (block J). For example, the IC#4016 is used 1or this purpose, as shown in FIGS. $27b^1$–$27b^3$. This section also included a small LED circuit (2N2222 and LED) to allow visualization of the signal;

BLOCK G: CHARGE AND DISCHARGE OPTO-COUPLERS AND AMPLITUDE CONTROL

This section uses opto-couplers to isolate the power stage from the rest of the electronics. One opto-coupler is used to charge the capacitor $C_4$ (FIG. 27b). This coupler is controlled by the charge signal 3317 (FIG. 27a). The other opto-coupler switches ON an SRC (silicon control Rectifier, FIG. $27b^1$–$27b^3$. When the SRC is ON, the charged capacitor is connected to the output. The inputs 3317 and 3319 of this block, G, have a phase shift of 180 degrees (180°) between them so that when the Charge opto-coupler is ON, the Discharge opto-coupler is OFF and vice versa. The amplitude is predetermined by the control 3314 (or 302 FIG. 9A) which changes the value of the variable resistor (AMP, 50 kΩ, FIG. $27b^1$–$27b^3$) which turns changes the peek value of the voltage of the charged capacitor, $C_4$. Two opto-couplers (2N222 and MTC2), two transistors (TIP642), a variable resistor (AMP, 50 kΩ) to allow for amplitude selection and various resistor, as shown in FIG. $27b^1$–$27b^3$, are used for the purpose of the present block G Also, in this section, there is shown the amplitude displays circuit composed of a display driver LM3914 and a BAR-LED display MV57184 (in the left block G) which display can be seen above the amplitude control in FIG. 9A.

Finally, the $C_4$ capacitor (100 μF, 160 V) is discharges through the SRC, the load discharge resistor, $R_D$ (4Ω, 10 W) and the Conditioning applicator(s) (REBONE-4A, MINI-4A, MAXI, MAXI-2A or JAM-8A type) connected to the MBI-3000 as shown in FIG. 8. Across the discharge resistor, $R_D$, there is a simple circuit to visualize the conditioning signal in the lower part of the start session switch shown in FIG. 9A as 307 switch;

BLOCK H: CLOCK

This section uses a one second/one minute precision clock and reference generator to give a square wave of 1 Hz of output 3320. For example, the known IC #7213 and various resistor and capacitors are used for this purpose, as shown in FIG. $27b^1$–$27b^3$;

BLOCK I: TIME on SESSION DURATION SELECTOR

This section uses analog switch to load the stage J with the selected time of session, as predetermined by the control 3330 (or 305, FIG. 9A). For example, the known IC#4016, various resistors and the switch S5 is used for this purpose, as seen in FIG. $27b^1$–$27b^3$;

BLOCK J: REMAINING TIME COUNTER

This section uses a 4 digit CMOS up/down counter/display driver to display the remaining time of the Conditioning session and stop the output when the time selected at stage I has run off. For example, the known IC#7217B is used for this purpose (FIG. $27b^1$–$27b^3$) and this counter generates 4 outputs for scanning 7 outputs to the display elements of section M.

BLOCK K: AUDIO-MONITOR OF CONDITIONING SIGNAL

This section uses an oscillator of 800 Hz which is modulated by a 0.5 Hz square wave. The 0.5 Hz square wave is taken from the clock (block H as input 3320 to the section K. This modulated 800 Hz signal 80 Hz can also be used for example) is fed to a speaker which gives a "Beep" signal for 1 second every 2 seconds. For example, the known ICs #4013 and 4093, a few resistor (10 kΩ) to allow for selection of sound intensity (control 207, FIG. 9B) are used for the purpose of this section K;

BLOCK L: INITIALIZATION OF SESSION CIRCUIT

This section uses a J-K flip-flop. When the input 3329 (307, FIG. 9A) is high, the output 3323 loads section J and starts the counting down of remaining session time and it also initiates the actual RHUMART Conditioning session. For example, the known IC#4027 is used for this purpose (FIG. $27b^1$–$27b^3$);

BLOCK M: DISPLAY OF REMAINING TIME

This section uses four 7-segment-display to display the remaining time of the Conditioning session in minutes (first two digits) and seconds (last two digits). For example, the known display, MAN-4710A, is used for this purpose (FIG. $27b^1$–$27b^3$);

BLOCK N: VOLTAGE REGULATOR

This section uses two transformers. One that transforms the input 3326 (from 3310 or 301, FIG. 9A) into 80 Volts DC output 3327; and the other that transforms the same input 3326 into the 5 Volts DC output 3328.

The signal 3310 (or 3326) is the output of an ON/OFF switch to apply the 110–120 VAC (when the power supply switch 351. FIG. 9B is in the left position, 115 V) or the 220–240 VAC (when the said switch 351 is in the right position, 230 V). The output 3327 (80 Volts) is used in block G only, and the output 3328 (5 Volts) is used in all other blocks of FIG. 27a and 27b; For examples, the transformers 167J55 and 166G6 are used for the 115 VAC power supply and a known LED indicates that the power is ON;

BLOCK O: OUTPUT SELECTOR

This section uses various plugs to connect the output coil applicators. This section also contains a polarity control 33311 (or 306, FIG. 9A) and an output control as determined by controls 3332 (201,206 and 308 in FIG. 9B and 9A). The LED indicator 309 (FIG. 9A) indicated that the switch 221 (FIG. 9B) is in position LEFT APPLICATORS (REBONE-4A, MINI-4A or JAM-8A), and when this indicator 309 is OFF (or not emitting light), it means that the switch 221 (FIG. 9B) is in the position RIGHT APPLICATORS (MAXI or MAXI-2A). The said applicators are described herein and other compatible applicators could be used with the MBI-3000 Controller/generator.

Referring now to FIG. 27g there is shown a block diagram of a new controller-generator herein referred to as Ultima- 100T having the same functions and power output as those of the MBI-3000 described herein and having further unique features like, for examples, important weight reduction and elimination of the auto-transformer used in the MBI-3000 embodiment. It has a new programming means using two CPUs (Central Processing Units), and practical membrane switches for programming the conditioning parameters (amplitude or intensity of the impulses, frequency, modulation, polarity and duration of the conditioning impulses). In FIG. 4, the MBI-3000 controller-generator can be replaced by the Ultima-100T embodiment since it produces the same power of the impulses and it is compatible with or easily adaptable to the coil applicators, electrodes and electrode interlaces used in combination with the MBI-3000.

Still referring to FIG. 27g there is shown a block diagram of the Ultima-100T programmable controller-generator. The detailed description of each block of the diagram and of its input and output is given below:

BLOCK A: This section is essentially composed of a programmable microcontroller CPU "A" that manages most of the logic functions of the Ultima-100T. Its programmation is mainly composed of signal delay loops which give the combined frequency 103 and the modulation 104 signals 105 and 125 which partly control blocks F and G described below. This block A receives its input commands 121 from the membrane keyboard 112, after their interpretation (or transformation) by the block B described just after. The CPU "A" gives the signals 101 and 104 to control the oscillator and n-modulation blocks respectively.

BLOCK B: This block is essentially composed of a programmable microcontroller CPU "B" that manages the informations or signals 112 received from the keyboard, block C; and which thereafter will give operating command signals 121 to the Block A, digital display command signals 113 to block D and the desired amplitude level 118 of the output signal to the applicators.

BLOCK C: This block is a membrane keyboard or an equivalent keyboard with the same functions, which serves to give the input values 112 of the conditioning parameters to the CPU "B" for their interpretation in block B before their use in block A.

BLOCK D: This block is a digital display unit and its drivers. It is composed, for example, of Light-Emitting-Diodes (LEDs) and DEL display having seven sections. This block receives its input codes 113 from block B and distributes them among the display.

BLOCK E: This block is composed, for example, of an electronic potentiometer and a voltage comparator. The voltage to which the capacitor or tank-circuit of block G is charged is sampled 119 and compared to the desired voltage 118 (proportional to the amplitude of the conditioning signals) which is selected on the keyboard (block C). When these two voltages 118 and 119 are equal, the power supply "A" of block F, serving to charge the said tank-circuit, is electronically disconnected by means of the signal 120 given by the voltage comparator of block E.

BLOCK F: This block is a power supply designed in a so called switching-mode which allows for reducing heat production to the smallest possible value by means of energizing the power supply only when necessary. This switching-mode increases the efficiency of the power supply. When the block A gives its command signal 125, the power supply A generates repeted current impulses untill the voltage 119, to which the capacitor or tank-circuit is charged, reaches the desired value 118. This is when the signal 120 from the comparator of block E stops the charging operation of the tank-circuit.

BLOCK G: This block is essentially composed of the capacitor or tank-circuit and of the discharge circuit into the output circuit. The output circuit is composed of one or more coil applicators and the discharge resistance of appropriate value to cause the critical or quasi-critical damping of the conditioning signals, or of the electrode and the electrode interface circuit means to generate the proper conditioning signals. For example, switching is performed by means of power MOSFET transistors in the "HIGH SIDE" mode and the combined frequency and modulation signal 105 from block A. The charge interruption signal 122 comes from block F.

BLOCK H: For example, the output signal 107 can be sent through a known ¼" PHONE JACK connector. The discharge resistance can be incorporated in the coil applicators by means of an electrically resistive wire which is connected serially with the coil winding made of copper, aluminun or of another low weight and electrically conductive wire.

BLOCK I: This block serves as power supplies 109, 111 and 110 for all blocks (A, B, etc.) containing logic circuits (using +5 Volts), for switching circuits of blocks F and G (using +12 Volts) and for the electrode interface circuit means (using +9 Volts) of the MBI-1004A or MBI-3004 type described herein.

Referring now to FIGS. $27c^1$–$c^2$, $27d^1$–$27d^2$ there is shown an other example of the detailed circuit diagram shown in FIG. $27b^1$–$b^3$ and described above. In particular, the output section showing the Right Applicator Selector and the Local and Global Applicator outputs (shown just above the voltage regulator) are more detailed and are compatible with the controls of the said MBI-3000 shown in FIGS. 9A and 9B. In the central part of this diagram, there is shown the major connector JT that is used to interconnect the two printed circuit PC102-6 and PC 201-2. The detailed description of this circuit is similar to that of FIG. $27b^1$–$27b^3$ above, except for the following modifications:

Block F- DISCHARGE INTERRUPTER

This section uses NAND GATES to modulate the said discharge signal 3316 and to interrupt the output when the time selected in section I is elapsed. This interruption is done by the input 3324;

Block G- CHARGE AND DISCHARGE SWITCHES

This section uses bipolar transistors to charge capacitors C22 and/or C21 to a level determined by a variable voltage regulator. The said signal 3314 controls the voltage regulator while said signal 3317 controls the charge switch. The discharge switch is made-up of a power MOSFET controlled by signal 3319;

Block K- AUDIO MONITOR

When said signal 3324 is active, this section uses NAND gates to generate a signal of 240 Hz which is modulated by another of 0.75 Hz creating an audible tone of 0.5 second every 1.5 second. The output goes to the monitor speaker through an amplifier and a volume level control;

Block L- INITIALIZATION CIRCUIT

This section uses a D flip-flop instead of a J-K flip-flop.

Block N- VOLTAGE REGULATOR

This section uses ONE transformer with two primaries and two secondaries. Power is applied through the ON/OFF power switch 301 and the 115–230 VAC selector 351 on lines 3310 and 3326. Said signal 3327 is 77 VDC for block G only and signal 3328 is 5 VDC for all blocks;

Block O- OUTPUT SELECTOR

This section sends output signals to connectors through polarity switch 3331 (306, FIG. 9A) and coil selector 3332 and pulse width selector (206, FIG. 9B). The applicators used can be of the type MINI-4A, REBONE-4A, JAM-8A, MAXI and MAXI-2A;

There is no mention of an output to the said MBI-3004. These outputs are the following: C and D which are the so called charge and discharge signals; "+" which is the variable D.C. voltage supplied to the said MBI-3004; and "G" is the ground.

Referring now to FIG. 27e there is shown the block diagram of the said MBI-3004 electrode interface. The MBI-3004 is the slave of the said MBI-3000 controller-generator for every settings except for selecting the pulse width and the current of the output signal. Controls like frequency and modulation selection, maximum amplitude and duration of session are preselected on the said MBI-3000.

Block A- LEVEL SHIFTER:

This block receives the two control signals for operation of this circuit interface and converts the low 5 volts logical signal from the said MBI-3000 to the level of 15 volts. To do so, we use a dual operational amplifier chip in a comparator mode sensing every time the input voltage reaches the preset threshold (1.5 volts here). The gain of the amplifiers without a feedback loop being in the range of 200,000, the output of the amplifier alternate between 0 and 15 volts depending on the input amplitude. The signals below 1.5 volts not being detected, this circuit ensures the said MBI-3004 to be free of any line noise induced in the cable which connects the said MBI-3000 controller-generator to the said MBI-3004 interlace.

A supply voltage of 15 volts is provided to the operational amplifier by a zener diode (CR13) biased by a resistor to the 75 volts supply. The CR14 diode avoid any feedback effect which could perturbate the MBI-3000 controller-generator.

The output signal of this block (A1 and A2) will be used to switch the MOSFET transistors of the blocks B and D.

Block B- CHARGE DRIVER:

The block B receives the switching command A1 that will allow the MOSFET transistor to drive the PNP transistor Q6 that will charge the selected capacitor to the voltage providing by the amplitude control of the said MBI-3000. Resistor R26 is used to limit the charge current of the capacitor. Signal B1 shows the charging voltage applied to the capacitors. The signal shape may vary depending on the capacitor value selected by means of the "pulse width selector".

Block C- TANK CIRCUIT:

The "pulse width selector" will connect the RC networks of this block to the charging source of block B. The three combinations of capacitor and resistor will give pulse widths of 0.1, 0.2 and 0.3 millisecond;

The capacitor is charged to its nominal value, it is discharged thereafter by means of the driver transistor of the following block through the matched resistor producing the critical Damping shape of the output signal. The diodes CR1 to CR3 are used to insulate the 3 network assemblies from each other. Signal C1 illustrates the voltage being switched by the next block;

Block D- DISCHARGE DRIVER:

The MOSFET transistor Q1 will be switched "on" and "off" by the A2 signal from block A. It will drive the charges stocked in the capacitor to the ground through the output transformer of the next block;

Block E- VOLTAGE BOOSTER:

This circuit is a high ratio transformer that will boost the voltage by a factor of 150. The nominal input impedance of this circuit is 8Ω. and the output impedance is 1,2 KΩ. The other use of this circuit is to provide electrical insulation from the electronic circuit. Signal E1 is the output signal before the current regulator;

Block F- VARIABLE OUTPUT:

Block F is there to allow correct adjustment of the output current. As the formula E=RI, the signal E1 being roughly constant, varying the value of the variable resistor varies the current in the output loop. Signal F1 is the output waveform of the first channel and the amplitude of the current flowing between pairs of output electrodes will vary with the variable resistor;

Block G- CHANNEL 2:

Block G includes circuits similar to those of block C to F for a second channel. G1 and G2 are the outputs to the electrodes in this diagram;

Block H- CHANNEL 3:

Block H includes circuits similar to those of blocks C to F for a third channel. H1 and H2 are the outputs to the electrodes in this diagram;

Block I- CHANNEL 4:

Block I includes circuits similar to those of blocks C to F for a fourth channel. I1 and I2 are the outputs to the electrodes in this diagram. (In the present document, the electrodes of the MBI-3004 are referred to as E9 to E16).

Referring now to FIG. 27g, there is shown an example of detailed circuit diagram for the said MBI-3004 interlace shown in FIG. 2k and FIG. 6a. The said MBI-3004 is a 4 channel electrode interlace used in combination with the said MBI-3000 controller-generator.

The said MBI-3004 electrode interlace is connected to the outlet 208, FIG. 9B. Examples of use of this interlace are given herein and the description of the MBI-3004 circuit, FIG. 27f is very similar to that of the said MBI-1004A or MBI-1004B described above, except that it has 4 channels in the same interlace 360 (FIG. 6a) instead of 2 channels for each interface 26 (MBI-1004A, FIG. 5a) or 27 to (MBI-1004B, FIG. 5b). The main differences between the circuit of FIG. 27g (MBI-3004) and that of FIG. 26b are the following: (1) the output transformers TRS 60-282-φ (T1, T2, T3 and T4, FIG. 27g); (2) the output switching transistors TIP140 (FIG. 26b) have been replaced by four IRFD120 transistors connected to the said output transformers 60-282-φ; (3) the time constants of the RC ($R_4C_4$, $R_5C_5$, $R_6C_6$) used for the MBI-1004A or MBI-1004B are different from the time constants ($R_1$, $C_1$, $R_2C_2$ and $(R_3+R_4)C_4$ used for the MBI-3004 (FIG. 27f). The output connector J4 brings the conditioning signal to the 4 pairs of electrodes connected in series with variable resistors (similar to R10 and R11 of FIG. 26b) allowing for adjustment of peak current flowing through each pair of electrodes connected to the electrode outlets 364 (FIG. 6a). The said variable resistors (approx. 0–25 kΩ) are adjusted using the controls 362 (FIG. 6a) for each of the 4 channels labelled 1, 2, 3 and 4 in FIG. 6a. It is generally assumed that the Amplitude (A) on the MBI-3000 controller 300 or on the MBI-1000 controller 15 are set at maximum value for the operation of the MBI-3004 and the MBI-1004A or MBI-1004B in combination with the said controllers 300 and 15 respectively. The connector J3 (FIG. 27f) is the site 208 where the MBI-3004 (FIG. 6a) is connected to the MBI-3000 Controller (shown in FIG. 6b, 9A and 9B), just below the beeper control 207 (FIG. 9B) having 5 pins and one ground connector). The +75 Volts D.C. regulated supply is taken from the MBI-3000 (through the connector J3). Various charge and discharge switching signals (C and D signals) are taken from the MBI-3000 main logic circuit, through the J3 connector.

Finally, it is important to notice that the voltage used to charge the capacitors C1 to C12 (FIG. 27f) is selected with the amplitude control 302 (FIG. 9A) and the currents flowing between the two electrodes of each of the 4 pairs (E9 to E16) are adjusted with the controls 362 (FIG. 6a) of the MBI-3004 as described above.

FIGS. 27g, 27i and 27k show various output voltages of the MBI-3004 interface for a resistive load of 10 kΩ, with other conditions specified in these Figures;

FIGS. 27h 27j and 27L, show the current flowing in the 100Ω, 120Ω, and 133Ω resistors placed before the small output transformer (TRS: 60-282-ϕ) of the said MBI-3004 circuit (FIG. 27f) with other conditions specified in these drawings;

Referring now to FIGS. 28a and 28b there are shown a block diagram of the said MBI-101, Field Detector 30 (shown in FIG. 16g) and a detailed circuit diagram of this detector. The first section F of this diagram includes the field detection coil (≈1800 turns of small wire, #26 AWG) used to detect the magnetic field impulses generated around the said conditioning coil applicators, and an overload protection circuit and a Gain control (31, FIG. 16c). The input of this block is the magnetic field impulses 40 and its output 41 is the induced voltage across this 1800 turn core coil detector. The core of the detecting device is approx. 4 inch long. The gain selection 31 (FIG. 16c) is achieved with a slide switch S3 (type SP5T) allowing for connecting one of the resistors R4, R5, R6 or R7 or a short circuit in series with the resistor R14, in order to make a voltage divider of the detected signal so that the displays (section I and J) are not saturated, as shown in FIG. 28b; a 32 Volt DIAC (0.5 watt rating) is used for overload protection, just before the output of the block F;

The section E of these drawings (FIG. 28a and 28b) separate the positive (+) and the negative (−) pulses detected by section F so that the input of this section is a biphasic pulse and its two output E1 and E2 are one positive (+) and one negative (−) pulse for each biphasic pulse detected. For example, two silicon rectifier of the type IN4004, two 10 Ω resistors and four 1 µF capacitors are used (as shown in FIG. 28b) for this purpose;

The sections G and H convert the positive 42 and negative 43 analog pulses into a proportional and linear digital signal that can drive two linear arrays of 10 LED each, LEDs #1 to 10 and LEDs #11 to 20, of the type MV57164. These two arrays of LEDs are shown as blocks I and J on FIG. 28a and 28b; a 2 kΩ resistance is used in series with each of the 20 LEDs of the display. The analog to digital converter/driver used to convert the + and − pulses are of the type and configuration shown in FIG. 28b (IC1 and IC2 of the type LM3914 from National Semiconductor);

Finally, the sections A and B of the detailed circuit (FIG. 28b) serve to connect the DC power supply (two 9.8 Volt dry cells serially connected for each of section A and B) to activate the different circuits of sections G, H, I and J. For example, these sections A and B are composed of two known switches, two 5.6 kΩ resistors and two ESBR3931 light emitting diodes (LEDs). The latter LEDs serve as battery state indicator for each of the two independent circuits for measuring the said positive and negative voltage pulses.

The RHUMART Physics—A

The RHUMART Impulse and Its Measurement

Definition of the Impulse Variables:

| | |
|---|---|
| $t$: | time |
| $i(t)$: | electric current in the coil applicator |
| $\vec{B}(t)$: | magnetic field created near the coil applicator |
| $|\vec{B}(t)|$: | amplitude or modulus of $\vec{B}(t)$, the magnetic field vector |
| $\epsilon(t)$: | bioelectric potential induced in an open loop with surface "S" according to the law of electromagnetic induction |

$$\epsilon(t) = -\frac{\partial \Phi_p}{\partial(t)} \quad \text{where} \quad \Phi_p = \int_s \int \vec{B} \cdot \vec{ds} \quad \text{and} \quad |\vec{B}(t)| \propto i(t)$$

Law of induction      Magnetic flux      BIOT-SAVARD'S Law

The symbol (.) between $\vec{B}$ and $\vec{ds}$ denotes the scalar product of the two vectors $\vec{B}$ and $\vec{ds}$, to calculate $\Phi_p$ it is therefore necessary to consider only the component of $\vec{B}$ which is parallel to $\vec{ds}$.

Note that, according to mathematical convention, the vector $\vec{ds}$ is perpendicular (⊥) to the surface S. The induced potential $\epsilon(t)$ is therefore equal to the partial derivative of $\Phi_p$, with respect to time preceded by the symbol (−): this is one of MAXWELL'S equations for electromagnetism. $\Phi_p$=the component of the magnetic flux which is perpendicular to the surface "S", around which the bioelectric potential $\epsilon(t)$ is induced.

In general, the maximum magnetic field density, $B_{max}$, of the type used in the present invention, as measured with a probe (without a ferromagnetic core) may be expressed as follow:

$$B_{max} = \left\{ \frac{(k_\epsilon \tau_r / e)}{(n_p s_p \cos\theta)} \right\}$$

This is called the "$B_{max}$" equation, where:

$k_\epsilon$ and $\tau_r$ are defined as in FIG. 3c;

$k_\epsilon$=the initial value of $\epsilon(t)$, at $t=0$; and $\tau_r$=the width of the impulse;

$e \approx 2.718$, the base of natural logarithm;

$(k_\epsilon \tau_r / e)$=the surface under the voltage curve $\epsilon(t)$ induced at the probe terminals between $t=0$ and $t=\pi_r$, (or between $t=\tau_r$ and $t=\infty$);

$(n_p s_p)$=the sensitivity factor of the measurement probe;

$n_p$=the number of turns of wire in the said measurement probe;

$S_p$=the average area covered by each loop of wire (or tissue) in the said probe;

cos θ=the cosine of the angle between the main axis of the probe and the direction of the magnetic field to be measured (=1 when θ=0, and =0 when θ=π/2).

RHUMART Physics—B

Absolute Measurement of the RHUMART Field Using Man as the Detector or the magnetic field probe With reference to FIG. 3c, the magnetic field may be calculated as follows:

1) Using an oscilloscope and taking care to minimize artifacts, measure the electric potential $\epsilon(t)$ induced between the hands of a person placed inside the MAXI applicator powered by the MBI-3000 controller-generator.

2) Use the following experimental values:

$k_\epsilon \cong 0.5$ Volts; $\tau_r \cong 0.5$ msec;

$\theta = 0$ when the probe axis is parallel to the field $\vec{B}$;

$n_p = 1$ (one loop formed by the arms and shoulders); and $s_p = 700$ cm$^2$ (or 20 cm×35 cm of loop surface).

3) The peak value of the magnetic field is calculated using the 2nd Law of cellular Conditioning (See Section "D" of the said RHUMART physics herein after):

$$\begin{aligned} B_{max} &= (k_\epsilon \tau_r / e)/(n_p s_p) \cos\theta \\ &\cong 0.5 \frac{(0.5 \times 10^{-3})}{2.718} /(1 \times 700 \times 1) \\ &\cong 0.13 \times 10^{-6} \text{ Wb/cm}^2 \\ &\cong 0.13 \times 10^{-2} \text{ Wb/m}^2 \text{ (Weber per square meter)} \end{aligned}$$

And since 1 Wb/m$^2$ = 10$^4$ gauss; $B_{max}$ = 13 gauss (peak amplitude). The peak magnetic field density of the impulse produced using the maximum amplitude of the bioelectric generator MBI-3000—an impulse lasting less than one millisecond. Since the earth's magnetic field has a magnitude of approximately 0.7 gauss, the measured field is approximately 20 times that of the earth's magnetic field.

Using a measuring probe with precisely determined $n_p$ and $s_p$ parameters, it is thus possible to measure the magnetic field.

RHUMART Physics, "D"

The 5 Electromagnetic LAWS of physiological cell conditioning

Introduction

The following 5 laws of physiological cell conditioning were developed by the author of the present invention in the course of research into regenerative bioelectricity.

Before discussing the laws themselves, it will be useful to illustrate the variables and parameters of the optimal pulse waveforms used for cellular conditioning. FIG. 3c provides a graphic representation of the impulses of the present invention.

Using MAXWELL'S equations for electromagnetism and the Analogical Model of Living Cells illustrated in FIG. 29, we can formulate the 2$^{nd}$, 3$^{rd}$ and 4$^{th}$ LAWS of physiological conditioning. We begin with the definition of the impulse in the coil applicator generated by one of the bioelectric controller-generators:

1st LAW:

The electric current, i(t), flowing through the coil applicator may be defined mathematically as follows:

$$i(t) = k_i t e^{-t/\tau_r}$$

where $k_i = i_{max}(e/\tau_r)$; $i_{max} \cong 0.707 \, V_o/R_T$;

where $\tau_r$ and $i_{max}$ are defined in FIG. 3c and where $R_T$ = discharge resistance and $V_o \propto A$ (amplitude on the controller-generator).

2$^{nd}$ LAW:

The magnetic field impulse, $B(t)$, created near the coil applicator may be defined as follows:

$$B(t) = k_B t e^{-t/\tau_r} = \left( \frac{k_\epsilon}{n_p s_p \cos\theta} \right) t e^{-t/\tau_r}$$

where $$k_B = |\vec{B}_{max}| \left( \frac{e}{\tau_r} \right) ; |\vec{B}_{max}| = \left( \frac{k_\epsilon \tau_r}{e} \right) /n_p s_p \cos\theta$$

where $\tau_r$ and $k_\epsilon$ are defined as in FIG. 3c;

and $n_p s_p$ = the sensibility factor of the measurement probe;

and where $\cos\theta = 1$ when $\vec{B}$ is $\Psi$ to the induction surface S.

3$^{rd}$ LAW:

The bioelectric potential, $\epsilon(t)$ induced in a open loop of surface S by the magnetic field impulses may be expressed as follows:

$$\epsilon(t) = k_\epsilon (1 - t/\tau_r) e^{-t/\tau_r}$$

where $\tau_r$ and $k_\epsilon$ are defined in FIG. 3c.

4$^{th}$ LAW:

In order to calculate the maximum microcurrent impulse induced in the human body, $i_{imax(t)}$ we must refer to the Analogical Model of Living Cells (AMLC), developed by the author of the present invention (see FIG. 29)

4A: $\quad i_{imax(t)} \leq C_{me} \dfrac{d}{dt} [\epsilon(t)]$ disregarding $Z_p$ and $R_i$ (and for $R_e \gg Z_m$);

where: $\epsilon(t)$ is defined by the 3$^{rd}$ LAW above;

$$\frac{d}{dt}:$$

derivative with respect to time;

$C_{me}$: equivalent electric capacitance of all cell membranes in the bioelectric induction circuit; by substituting $\epsilon(t)$, (3$^{rd}$ LAW) and taking the mathematical derivative, the 4$^{th}$ LAW becomes:

4B: $\quad i_{i\,max}(t) \leq \left( \dfrac{k_\epsilon C_{me}}{\tau_r} \right) \left[ -2 + \dfrac{t}{\tau_r} \right] \cdot e^{-t/\tau_r}$ 4C: And since the maximum microcurrent will be induced at t=0, we can conclude that:

$$|i_{i\,max}(t=0)| = i_{i\,max\,0} \leq \frac{2 k_\epsilon C_{me}}{\tau_r}$$

Taking the experimental values of the so called arm-to-arm experiment with the said MBI-3000 controller-generator and the MAXI applicator, we have:

$k_\epsilon \cong 0.5$ Volts; $C_{me} \cong 1 \mu F$; $\tau_r = 0.5$ msec.

Thus the, $i_{i\,max\,0} \leq 2$ mA, (disregarding ($R_i$ and $Z_p$).

This current is less than the smallest current perceivable by the subject in the arm-to-arm experiment, which is approximately 3 mA. Since the cross section of a human arm is approximately 50 cm$^2$, we can conclude that:

$$i_{i\,max\,0} \leq \frac{2\,mA}{50\,cm^2}, \text{ or } i_{i\,max\,0} \leq 40\,\frac{\mu A}{cm^2}$$

If we take into account the resistance $(R_i+2Z_p)\cong 250\,\Omega$ in series with the capacitance $C_{me}$ (a simplified model of Dr. Roland A. Drolet's arm-to-arm experiment), knowing that for the impulse used:

$$Z_{C_{me}} = \frac{1}{j\omega C_{me}} \cong (R_i+2Z_p)$$

since the said impulse is in resonance with the cell membrane (in fact $2\tau_r \cong$ the width of the human body's own nerve impulse, which makes it possible to transmit the maximum energy from the coil applicator to living cells), we arrive at the following major conclusion:

$$i_{i\,max\,0} < 20\,\mu A/cm^2$$

where $i_{i\,max\,0}$ the maximum "arm-to-arm" current density, taking $R_i$ and $Z_p$ (and therefore $R_i+Z_p$) into account.

where $R_i$=intracellular resistance in series with $C_{me}$; and $Z_p$=polarization impedance at the interface of the large hand-held cylindrical electrodes. Therefore:

4E: $\quad i_{i\,max\,0} \leq 1\,mA;\, i.e.\, \left(20\,\frac{\mu A}{cm^2} \cdot 50\,cm^2\right)$ (maximum arm-to-arm current) which is exactly the same as the experimental value arrived at by Dr. Roland A. Drolet in his arm-to-arm experiment.

TECHNICAL NOTE:

$$Z_c \cong \frac{\Delta V}{\Delta i} \cong \frac{k_\epsilon}{i_{max\,0}} \cong \frac{0.5}{2 \cdot 10^{-3}} = 250\,\Omega$$

where $Z_c$ is the impedance of an electric capacitance; by virtue of the definition of capacitance itself, we may therefore conclude that:

$$Z_c = \frac{1}{j\omega C} = \frac{1}{2\pi f_e \cdot 10^{-6}} \cong 250\,\Omega$$

where $f_e$ IS THE EQUIVALENT RESONANCE FREQUENCY DEFINED BY THE AUTHOR.

From this last equation we can calculate $f_e$:

$$f_e = 10^6/(2\pi \cdot 250) \cong 637\,Hz$$

The human nerve impulse lasts for approximately 1.5 msec, which means that the "equivalent resonance frequency" of the human nervous system is approximately 666 Hz; this is almost identical to the frequency $f_e$ of the said RHUMART impulse used in the present invention.

We can therefore conclude that the said impulses are in resonance with the human nervous system from the said arm-to-arm experiment and the Analogical Model of Living Cells (AMLC) described herein.

The 5th LAW of Physiological Cell Conditioning

5th LAW: The mathematical expression of the tissular ($j_t$) and intracellular ($j_c$) microcurrent impulse density induced in a ring of tissue with radius $r_n$, whose standardized electric impedance for 1 cm$^3$ of tissue is $z_n$ according to the AMLC, (see FIG. 30 and 31) is based on the following scientific principles:

Based on the first three LAWS discussed above, the AMLC illustrated in FIGS. 29 and 31, and the tissue ring specifications illustrated in FIG. 30, it was demonstrated by the author that, whether or not $\tau_r$ equals $r_i c_m$, or:

$$f_r = \frac{1}{r_i c_m}\,;\,\text{and}\,f_r \neq 1/r_i c_m$$

$j_t$ and $j_c$, were expressed using the following equations developed by the author of the present invention: ($\tau_r$=or $\neq r_i c_m$):

THE WAVEFORM of the current densities induced in the human body were expressed by the following simple equation:

$$j=j_o f(t);\,\text{WAVEFORM OF THE CURRENT INDUCED}$$

where:

j=the density of the current induced $j_o$=the initial density of the current induced (at t=0);

f(t)=$f_1(t)$, $f_2(t)$, $f_3(t)$, or $f_4(t)$: the time functions as defined below;

and t=the time elapsed since the start of the impulse.

More specifically, the author has shown that the densities of the current induced by the sad RHUMART regenerative modes are expressed as follows:

5$^{th}$ LAW $\left\{\begin{array}{l} j_t = j_{ot} f_1(t) \\ j_c = j_{oc} f_2(t) \end{array}\right\}$ $\left[\begin{array}{l}\text{Where the physiological impulses are in resonance} \\ \text{with the interior resistance } r_i \text{ combined with the} \\ \text{membrane capacitance } c_m \text{ of the cells; that is, when:} \\ f_r = \frac{1}{\tau_r} = \frac{1}{r_i c_m} \end{array}\right]$ $\left\{\begin{array}{l} j_t = j_{ot} f_3(t) \\ j_c = j_{oc} f_4(t) \end{array}\right\}$ $\left[\begin{array}{l}\text{Where the physiological impulses are in resonance} \\ \text{with the cell membrane; that is, when:} \\ f_r = f_m = \frac{1}{\tau_m c_m}\,,\,\text{and for all other values of } f_r, \\ \qquad\qquad\text{except for } f_r = 1/r_i c_m \end{array}\right]$ where:

$j_t$=the total current density induced in the tissue, including the current induced in the interstitial fluid;

$j_c$=the current density induced through the cell membranes;

$j_{ot}$=initial current density induced in the tissue at t=0;

$j_{oc}$=initial current density induced in the cells at t=0;

$f_i(t)$=(where i=1 to 4) the time functions as defined below.

The said initial current densities ($j_{ot}$ and $j_{oc}$) induced at t=0 are represented by the following two equations (for all values of $f_r$:)

$$j_{ot} = \frac{|\vec{B}_{max}| r_n(ef_r)}{2} \left[\frac{1}{r_e} + \frac{1}{r_i}\right],\quad\text{(tissular)}$$

$$j_{oc} = \frac{|\vec{B}_{max}| r_n(ef_r)}{2} \left[\frac{1}{r_i}\right],\quad\text{(cellular)}$$

where $|\vec{B}_{max}|$, $r_n$, e, $f_r$, $r_e$ and $r_i$ are defined as follows:

$|\vec{B}_{max}|$=maximum magnetic field intensity; $r_n$, $r_e$ and $r_i$ are defined in FIGS. 30 and 31; e≅2.71828 . . . =base of natural logarithm;

$$f_r = \frac{1}{\tau_r},$$

where $\tau_r$ = the width of the said impulse, e.g. the time required for the field to go from 0 to $|\vec{B}_{max}|$.

THE TIME FUNCTIONS

The following time functions $f_i(t)$, where i=1 to 4, have been defined with a view to simplifying the mathematical expression of the $5^{th}$ LAW of physiological cell conditioning:

$$f_1(t) = [C_1 t^2 + C_2 t + 1] \exp(-f_r t)$$

$$f_2(t) = [D_1 t^2 + D_2 t + 1] \exp(-f_r t)$$

$$f_3(t) = [A_1 t + A_2] \exp(-f_r t) + A_3 \exp(-t/r_i c_m)$$

$$f_4(t) = [B_1 t + B_2] \exp(-f_r t) + B_3 \exp(-t/r_i c_m)$$

Were exp( ) means the exponential function ("e" to the power), e≅2.718 . . .

The constants $C_1$, $C_2$, $D_1$, $D_2$, $A_1$, $A_2$, $A_3$, $B_1$, $B_2$ and $B_3$ appearing in the TIME-FUNCTION EQUATIONS are defined as follows:

$$C_1 = a_{im}^2(1+\alpha_1)/2; \quad C_2 a_{im}(\alpha_1 - 1)$$

$$D_1 = a_{im}^2(1+\alpha_2)/2; \quad D_2 a_{im}(\alpha_2 - 1)$$

$$A_1 = f_r(f_r - a_{ime})/(f_r - a_{im})$$

$$A_2 = (f_r^2 - 2a_{im}f_r + a_{im}a_{ime})/(f_r - a_{im})^2$$

$$A_3 = a_{im}(a_{im} - a_{ime})/(f_r - a_{im})^2$$

$B_1$, $B_2$, $B_3$ are identical to $A_1$, $A_2$ and $A_3$, with the substitution of $a_{ime}$ by $f_m(=1/r_m c_m)$ in the equations for $A_1$, $A_2$ and $A_3$, we may now define $B_1$, $B_2$, $B_3$ as follows:

$$B_1 = f_r(f_r - f_m)/(f_r - a_{im})$$

$$B_2 = (f_r^2 - 2a_{im}f_r + a_{im}f_m)/(f_r - a_{im})^2$$

$$B_3 = a_{im}(a_{im} - f_m)/(f_r - a_{im})^2$$

With the help of the following mathematical equations, it is possible to calculate all of the constants listed above as a function of the parameters defined in said AMLC model developed by the author of this invention:

$$a_{im} = (r_i + r_m)/r_i \tau_m \cong \left(\frac{1}{r_i c_m}\right); \text{ for } (r_m \gg r_i);$$

$$a_{ime} = \left(\frac{r_e + r_i + r_m}{\tau_m(r_e + r_i)}\right) \cong \frac{1}{c_m(r_i + r_e)};$$

$$\alpha_1 \cong r_i/(r_e + r_i); \; (0 < \alpha_1 < 1); \; (\alpha_1 \neq 1);$$

$$\alpha_2 = f_m/a_{im} \cong r_i/r_m; \text{ for } (r_m \gg r_i);$$

$$f_r = \frac{1}{\tau_r}; \; f_{im} = a_{im}; f_m = \frac{1}{\tau_m} = \frac{1}{r_m c_m}$$

NOTE: It is interesting to note that the expressions of initial current density, $j_{ot}$ and $j_{oc}$ may be greatly simplified by replacing $|\vec{B}_{max}|$ with its measured value:

$$|\vec{B}_{max}| = \left(\frac{k_\epsilon \tau_r}{e}\right) l n_p s_p \cos\theta$$

We then have:

$$j_{ot} = \frac{k_\epsilon r_n}{2n_p s_p \cos\theta} \left[\frac{1}{r_e} + \frac{1}{r_i}\right], \quad \text{(tissular)}$$

and $$j_{oc} = \frac{k_\epsilon r_n}{2n_p s_p \cos\theta} \left[\frac{1}{r_i}\right], \quad \text{(cellular)}$$

POWER SUPPLIED TO THE MBI-3000 AND POWER ABSORBED BY THE USER (in $\mu W/cm^2$)

(a) Power supplied to the MBI-3000

$$P = VI \cong 115 \times 0.5 = 57.5 \text{ watts}$$

(b) Energy absorbed by the subject with the MAXI and the MBI-3000 generator:

$$P_{abs} \leq P_{MAXI} = \frac{1}{2} L_{MAXI}(i_{max})^2$$

with specific examples of L and $i_{max}$ values, we have $$P_{abs} \leq \frac{(2 \times 10^{-3})(6.37)^2}{2} \cong 40 \frac{mW}{MAXI}, \text{ (peak)}$$

Taking the surface of the MAXI as equal to $(\pi r^2) = \pi \times 25^2 = 625 \; \pi cm^2$; we can calculate the (peak) power flow absorbed by the subject per square centimeter. i.e.:

$$40 \frac{mW}{MAXI} \times \frac{MAXI}{625 \pi \; cm^2} \cong 20.41 \; \mu W/cm^2$$

therefore $P_{abs} < 20.41 \; \mu W/cm^2$ (peak); for $n \geq 0$.

The average power absorbed with the MODULATION n=0 is equal to $20/13.2 \cong 1.5 \; \mu W/cm^2$.

For n>1, the peak power absorbed is the same as for n=0, i.e.

$P_{abs} \leq 20.41 \; \mu W/cm^2$ (peak); but for $n \geq 1$, the AVERAGE ENERGY ABSORBED m such cases is equal to $(10/26.4) \cong 0.37 \; \mu W/cm^2$.

The peak energy absorbed, as calculated above with the formula $$P_{abs} \leq P_{MAXI} = \frac{1}{2} L_{MAXI}(i_{max})^2$$

agrees with the peak energy actually absorbed, as measured in the so called "HAND-TO-HAND" experiment with one adult in the MAXI, which is connected to the MBI-3000 Controller.

* In this experiment, we have the relationship:

$$\frac{P_{absorbed}}{S_{arms}} \leq \left\{\frac{k_\epsilon \; i_{max}}{S_{arms}}\right\}$$

Where:

$k_\epsilon$ is the initial value of induced voltage across the hands;

$i_{max}$ is the maximum current induced in the arms and $S_{arms}$ is the average cross section of one arm.

Experimentally, with the maximum amplitude (A) on the MBI-3000 Controller, we have measured the following values:

$k_\epsilon \cong 0.5$ Volt [initial value of $\epsilon(t)$]

$i_{max}$=2 mA (after correction for the electrode impedance and measured across a negligible resistance (of 1Ω) between the two hands of the subject in the MAXI)

Knowing that the typical cross section of an arm is approximately 50 cm², we can calculate the experimental value of peak energy absorbed as follows:

$$P_{abs} \leq \left( \frac{0.5 \text{ Volt} \times 2 \text{ mA}}{50 \text{ cm}^2} \right) = 20 \text{ μW/cm}^2, \text{ (peak)}$$

$P_{abs} \leq 20$ μW/cm², (peak value)

(c) Energy transmitted to the user with the MBI-3000

Using the values calculated in (a) and (b) above for the power supplied to the controller and the power absorbed by the subject-user, we have:

$$\% \text{ transmission} \leq \frac{40 \text{ mW}}{57.5 \text{ W}} \text{ (peak)} = 0.07\% \text{ (peak); with one MAXI.}$$

N.B. We could also calculate the power absorbed by the subject with the MBI-3000 and the other applicators, using the same formula as for the MAXI. The JAM-8A, REBONE-4A and MINI-4A would respectively produce increasingly greater energy densities absorbed (per cm²), since energy is more concentrated in these applicators. Thus, for difficult cases where a greater energy density is required in a small area to be conditioned, a pair of MINI-4A or REBONE-4A applicators should be used.

Power supplied to the MBI-1000 and energy absorbed by the subject (in μW/cm²)

(a) Power supplied to the MBI-1000

$P_{a1} = V_o I \cong 12 \times 0.3 \cong 4$ Watts; (or 16 V×0.25 A)

(S) ENERGY ABSORBED BY THE SUBJECT USING THE MBI-1000

For example, with $V_0$=16 and $R_T$=2.26, we have:

$i_{mj} \cong 0.736 \ V_o/R_T = 0.736 \ (16/2.26) = 5.21 \text{A}$ (an other example could be $V_o$=11 and $R_T$=2.66) and $$(i_{max})_{per \ reb.} = \frac{i_{mj}}{2} = \frac{5.21}{2} \cong 2.60 \text{ Amperes}$$

So, $$P_{reb} \leq \frac{L_{reb} i_{max}^2}{2} = \frac{(0.68 \times 10^{-3})(2.6)^2}{2} = 2.3 \text{ mW}$$

The (peak) power absorbed by the subject is therefore less than or equal to 2.3 mW (peak) for each REBONE-PM, or 4.6 mW (peak) for the two REBONE-PMs together. Given that the MBI-1000 emits impulses of approximately 0.75 msec each (2.5 $\tau_r$) every 16,67 msec (for $f_b$=60 imp./sec), the MEAN POWER absorbed is therefore less than:

$$\left( 2.3 \frac{\text{mW}}{\text{reb}} \times \frac{0.75}{16.66} = 0.104 \frac{\text{mW}}{\text{reb}} = 104 \frac{\text{μW}}{\text{reb}} = 208 \frac{\text{μW}}{2 \text{ reb}} \right)$$

In other words, with the MODULATION dial set at CONT. (continuous), or n=0, a subject using two REBONE-PMs absorbs less than 200 μW of mean power. When the dial is set at n≧1 only half as much mean power is absorbed since half of the impulses emitted by the MBI-1000 are blocked.

If we consider the surface of the REBONE-PM to be approximately 3"×5" or 7.5 cm ×12.5 cm (≅94 cm²), we can calculate the peak power flow absorbed by the subject per cm² as follows:

$$2.3 \frac{\text{mW}}{\text{reb}} \times \frac{\text{reb}}{94 \text{ cm}^2} \cong 0.024 \frac{\text{mW}}{\text{cm}^2} \text{ or 24 μW/cm}^2 \text{ (peak)}$$

Thus, at MODULATION =0 (CONT.) 1.1 μW/cm² of mean power is absorbed.

For MODULATION n ≧ 1, the corresponding figures are;

12 μW/cm² (peak) and 0.55 μW/cm² of mean power is absorbed by the subject.

(c) ENERGY TRANSMITTED TO THE SUBJECT USING THE MBI-1000

Using the values calculated in (a) and (b) above for POWER SUPPLIED and POWER ABSORBED by the subject, we can conclude that:

$$\% \text{ transmitted} = \frac{4.6 \text{ mW}}{4.0 \text{ W}} = 1.2\% \text{ (peak)}$$

or ≅0.006% of the power supplied is actually transmitted to the subject, since the mean energy absorbed is approximately 20 times smaller than the peak energy transmitted.

d) Battery, operation of the MBI-3000: similarly to (b) and (c) above, the MBI-3000, generator can operate on batteries. All it requires is a continuous D.C. voltage of approximately 110 to 115 volts (±5%) provided by one or more batteries. Condensers can be charged (with a 12 Volt battery, for example) and connected in series with electronic switches to create a continuous voltage of 120 V (10 condensers charged to 12 volts and connected in series). This may prove practical for using RHUMART systems in Africa, for example, where there is often neither 115 V nor 230 VAC power supply.

The descriptions in (b) and (c) above may vary, depending on the condition of the car battery and the power of the alternator. Current may also be reduced if other car accessories are used at the same time (eg. headlights, windshield wipers, heater, etc.) so it is more accurate to use a known DC voltage supply like that of known batteries.

RHUMART ELECTRICAL ENGINEERING SECTION

DEFINITION OF SYMBOLS t: time;

t': t/$T_j$, where $T_j$ is defined below;

$k_n$: parallel or series factor: $k_n$=N for N applicators in series, and $k_n$=1/N for N applicators in parallel, L: inductance of one applicator;

$L_{eq}$: $k_n L$;

$R_L$: DC resistance of the coil of one applicator;

$R_F$: resistance of the wire to the applicator;

$R_{LF}$: $R_L + R_F$;

$R_{eq}$: $k_n R_{LF}$;

$R_j$: resistance to place in series, with the applicators to obtain Critical Damping;

$R_T$: $R_j + R_{eq} = R_j + k_n R_{LF} = R_j + k_n(R_L + R_F)$ total damping resistance;

$C_j$: capacitance to place in series with the applicator to obtain Critical Damping;

$V_o$: value of the voltage on the charging capacitor at t=0;
$T_j=\tau_r$: time for which the current in the coil is at peak value $$\left(\frac{di}{dt}=0\right)$$

$T_{jc}$: time for which the voltage across the applicator crosses the zero voltage base line;
$I_{mj}$: value of the peak current in the applicator or combination of applicators;
$I_{mjs}$: value of the peak current in the applicator or combination of applicators when the voltage, $V_o=10$ Volts;
NOTE: For the MBI-1000, $V_o \approx 0$ to 11 volts ($V_o$ is proportional to the Amplitude 18, FIG. 16a) For the MBI-3000, $V_o \approx 0$ to 65 volts ($V_o$ is proporbonal to the Amplitude 302, FIG. 9A);
$(k_{\in +}/k_{\in -})$: quotient of the applicator voltage at t=0, over the voltage when $$\frac{d^2i}{dt^2}=0,$$

inflection point of current curve;
$i_{js}(t)$ : the standard current curve: for $V_o=10$ Volts;
$V_{aw}(t)=V_{coil\ (s)}(t)$: the voltage curve across the applicator(s);

$$V_{Leq}(t)=L_{eq}\left(\frac{di}{dt}\right):$$

the voltage curve across the pure $L_{eq}$ of the applicator(s);
i'(t): di/dt;
$T_{jj}$: $T_{jc}+T_j$;
BRIEF DESCRIPTION OF THE PULSE SHAPING CIRCUIT and expressions for the current pulses in each applicator for "N" identical applicators serially or parallel connected to one of the

RESC CONTROLLERS

Referring now to FIGS. 3a. b, c, d and e, there is shown the RHUMART waveform for the current pulses i(t), FIG. 3c, flowing through any of the "N" identical RHUMART applicators serially or parallel connected to one of the RESC Controllers (MBI-1000 or MBI-3000). This current pulse i(t) generates a magnetic field pulse, B(t), FIG. 3a; c and d, within and in the close surroundings of the said applicators. The intensity of this pulse B(t) is directly proportional to the intensity of the current pulse i(t). The waveform of the induced voltage pulse, $\in(t)$, is shown in FIG. 3b, c and d. FIG. 3d shows a photographic reproduction of all these waveforms measured as explained in Sections "A" and "B" of the RHUMART physics summarized herein before. This FIG. 3d shows the measured waveforms for n=1, n=2, and n=3 MODULATION values selected on the RESC Controller, 304 (FIG.9A) or 21 (FIG. 16, 16a and 16b). The pulse bundles for other "n" Modulation values are illustrated in FIG. 17.

Referring now to FIG. 3e, there is shown the equivalent circuit 101 of the "N" identical applicators serially or parallel connected. For the series case, $R_{eq}$ is equal to $NR_L$, and $L_{eq}$ is equal to NL. For the parallel case, $R_{eq}$ is equal to $R_L/N$, and $L_{eq}$ is equal to L/N, where $R_L$ and L are the DC resistance and the inductance of one of the identical applicators serially or parallel connected to one of the RESC Controllers.

$R_F$ is the equivalent resistance of the extensions and leads interconnecting the applicators together. $C_j$ is the capacitive means being sequentially charged (when $K_1$ is closed and $K_2$ open) and discharged (when $K_1$ is open and $K_2$ closed) by the so called Charge and Discharge circuits of the RESC Controller.

The actual magnetization circuit comprises a magnetization coil (applicator) or a combination of "N" such identical coils (applicators) connected in series or in parallel. The capacitive means, $C_j$, feeds the said coil or combination of coils with a Conditioning (or treatment) pulse current, $i_{eq}(t)$, to obtain a desired magnetic field characteristic when the said current pulse is discharged through the said coil or combination of such coils. A damping resistive means, $R_j$, is serially connected to the said coil or combination of coils (in series with the said $R_F$). The pulse current has a rise time $\tau_r$ or $T_j$ for reaching a maximum pulse current intensity, $i_m$ or $i_{max}$, delivered by the capacitive means $C_j$ and a damped fall time of a value such that the second derivative of the current waveform is null at a time twice the said rise time ($\tau_r$ or $T_j$).

THE PULSE CURRENT WAVEFORM IS EXPRESSED BY THE THREE EQUATIONS:

$$i_{eq}(t)=-(R_T/2L_{eq})^2 C_j V_o t \exp(-R_T t/2L_{eq});$$

$$i_{ns}(t)=i_{eq}(t); \text{ for "N" identical applicators in series;}$$

$$i_{np}(t)=i_{eq}(t)/N; \text{ for "N" identical applicators in parallel;}$$

WHERE:

$i_{eq}(t)$=current pulse delivered by the generator/controller;
$i_{ns}(t)$=the current pulse flowing in any of the "N" applicators in series;
$i_{np}(t)$=the current pulse flowing in any of the "N" applicators in parallel;
$R_T$=total series resistance value including said damping resistance means, $R_j$, the resistance of the extentions and leads and the equivalent D.C. resistance, $R_{eq}$ of the said coil or combination of coils (applicators);
$L_{eq}$=equivalent inductance of the said coil or combination of "N" identical coils serially or parallel connected;
$V_o$=voltage to which the capacitive means $C_j$ is charged before being discharged in the said coil or combination of coils;
$C_j$=capacitance of the capacitive means;
e=constant $\approx 2.71828$;
exp=exponential function meaning "e to the power" where e=2.71828 . . . .

RHUMART QUALITY CONTROL EQUATIONS

Equations for the "Critical Damping" papameters In the critical damping equations below, there is a factor "$k_n$," which is named "the parallel or series or in parallel. If the applicators are in parallel, the factor $k_n$ is equal to 1/N. If the applicators are in series, the factor $k_n$ is equal to N.

1) Time where the current in applicator(s) is maximum, ($T_j$):

$$T_j=\frac{2 L_{eq}}{R_T}=\frac{2 k_n L}{R_j+k_n R_{LF}}$$

2) Capacitance for the circuit, ($C_j$):

$$C_j=\frac{2 T_j}{R_T}=\frac{2 T_j}{R_j+k_n R_{LF}}$$

3) Peak current ($I_{mj}$) with the generator at amplitudes ($V_o$):

$$I_{mj} = \frac{C_j V_o}{e T_j} = \frac{2 V_o}{e R_T} = 0.7357588 \frac{V_o}{R_T} = 0.736 \frac{V_o}{R_T}$$

4) First time derivative of applicators current at t=0:

$$\left( \frac{di}{dt} \right)_{t,0} = \frac{V_o}{L_{eq}} = \frac{V_o}{k_n L}$$

5) Time where the voltage across the applicator(s) crosses the zero value, $T_{jcoil(s)}$:

$$T_{jcoil(s)} = \frac{2 k_n L}{R_j - k_n R_{LF}} = T_{jc}$$

6) Quotient of the applicator(s) voltage at t=0, over the voltage when $d^2i/dt^2=0$; the inflection point of the current curve:

$$\left( \frac{k_{e+}}{k_{e-}} \right)_{coil(s)} = \frac{T_{jc}}{T_j} e^{(1+T_{jc}/T_j)}$$

7) Quotient of $T_{jc}$ and $T_j$ defined in (5) and (1) above:

$$\frac{T_{jc}}{T_j} = \frac{1 + (R_{eq}/R_j)}{1 - (R_{eq}/R_j)},$$

8) From equation (7) above, it can be shown the that:

$$R_{eq} = R_j \frac{(T_{jc}/T_j - 1)}{(T_{jc}/T_j + 1)};$$

leading to an indirect method for measuring $R_{eq}$, from $T_{jc}$, $T_j$, $R_j$, at critical damping.

B) Equations for the "CRITICALLY DAMPED", the "OVER DAMPED", and the "UNDER DAMPED" RHUMART waveforms.

To draw the graphics for the "critical damping and the nearly critical damping" cases, computation were made with the following equations.

To determine which set of equations to use, the following condition must be resolved first:

when $$\sqrt{L_{eq} C_j} < T_j$$

use equations of case C below*;
when $$\sqrt{L_{eq} C_j} > T_j$$

use equations of case A below*;
when $$\sqrt{L_{eq} C_j} = T_j$$

use equations of case B below*; where $T_j = 2 L_{eq}/R_T$
*Case A and C below define equations applicable for "Nearly Critical Damping" situations, and Case B is the case of "Critical Damping.

Case A: OVER DAMPING ($\sqrt{L_{eq} C_j} > T_j$):

$$i_j(t) = V_o C_j \left( \frac{\lambda_1 \lambda_2}{\lambda_2 - \lambda_1} \right) [e^{\lambda_1 t} - e^{\lambda_2 t}]$$

$$v_{aw}(t) = V_o C_j \left( \frac{\lambda_1 \lambda_2}{\lambda_2 - \lambda_1} \right) [(R_{eq} + L_{eq}\lambda_1)e^{\lambda_1 t} - (R_{eq} + L_{eq}\lambda_2)e^{\lambda_2 t}]$$

$$v_{L_{eq}}(t) = L_{eq} V_o C_j \left( \frac{\lambda_1 \lambda_2}{\lambda_2 - \lambda_1} \right) [\lambda_1 e^{\lambda_1 t} - \lambda_2 e^{\lambda_2 t}] = L_{eq} \frac{\partial i_j}{\partial t}$$

where $$\lambda_{1,2} = -\frac{1}{T_j} \pm \sqrt{\frac{1}{T_j^2} - \frac{1}{L_{eq} C_j}} \; ; \text{ where } T_j = 2 L_{eq}/R_T$$

Case B: CRITICAL DAMPING ($\sqrt{L_{eq} C_j} = T_j$)

$$i_j(t) = \frac{V_o}{L_{eq}} t e^{-t/T_j};$$

$$\frac{\partial i_j}{\partial t} = \frac{V_o}{L_{eq}} \left( 1 - \frac{t}{T_j} \right) e^{-t/T_j}$$

$$v_{aw}(t) = V_o \left( 1 - \frac{t}{T_{jc}} \right) e^{-t/T_j}$$

$$v_{L_{eq}}(t) = V_o \left( 1 - \frac{t}{T_j} \right) e^{-t/T_j}$$

where $$T_j = 2 L_{eq}/R_T$$

Case C: UNDER DAMPING ($\sqrt{L_{eq} C_j} < T_j$)

$$i_j(t) = \frac{V_o}{\omega_n L_{eq}} e^{-t/T_j} \sin\omega_n t = \frac{V_o T_j}{L_{eq}(\pi/2)} e^{-t/T_j} \sin \frac{\pi t}{2 T_j} \; ;$$

$$\frac{\partial i_j}{\partial t} = \frac{V_o}{L_{eq} \omega_n} e^{-t/T_j} \left[ \omega_n \cos\omega_n t - \frac{1}{T_j} \sin\omega_n t \right];$$

or:

$$\frac{\partial i_j}{\partial t} = \frac{V_o}{L_{eq} \omega_n} e^{-t/T_j} \left[ 1 - \frac{1}{T_j \omega_n} tg\omega_n t \right] \omega_n \cos\omega_n t$$

also, for "nearly critical damping":

$$\omega_n = 2\pi f_n = \frac{2\pi}{T_n} = \frac{2\pi}{4 T_j} = \frac{\pi}{2 T_j} \; ;$$

and $$\omega_n t = \left( \frac{\pi}{2} \right) \frac{t}{T_j} = \left( \frac{\pi}{2} \right) t'; \text{ where } t' = t/T_j$$

$$v_{aw}(t) = \frac{V_o}{\omega_n} e^{-t/T_j} \left[ \omega_n \cos\omega_n t - \frac{1}{T_{jc}} \sin\omega_n t \right]$$

$$v_{L_{eq}}(t) = \frac{V_o}{\omega_n} e^{-t/T_j} \left[ \omega_n \cos\omega_n t - \frac{1}{T_j} \sin\omega_n t \right]$$

where $$\omega_n = \sqrt{\frac{1}{L_{eq} C_j} - \frac{1}{T_j^2}}$$

ELECTRICAL CHARACTERISTICS of APPLICATIORS AND APPLICATOR COMBINATIONS (and extensions)

| | Applicator | Parameters | WIRE of WINDING #12, Cu | WIRE of WINDING #11, Aluminum |
|---|---|---|---|---|
| I. | [ MAXI (one coil) ] | $L = 1.75$ mH; $N = 58$ turns; $R_F = 0.16\ \Omega$; (12' lead, Cu #18) | $R_L = 0.45\ \Omega$; $R_{LF} = 0.61\ \Omega$ | $R_L = 0.61\ \Omega$; $R_{LF} = 0.77\ \Omega$ |
| II. | [ MAXI-2A (one coil) ] | $L = 1.06$ mH; $R_F = 0.17\ \Omega$; (12' lead, Cu #18) | $R_L = 0.24\ \Omega$; $R_{LF} = 0.41\ \Omega$ | $R_L = 0.32\ \Omega$; $R_{LF} = 0.49\ \Omega$ |
| III. | [ MAXI-2A (2 coils) in parallel ] | $L_{eq} = 0.53$ mH; $N = 29$ turns; $R_F = 0.17\ \Omega$; (12' lead, Cu #18) | $R_{eq} = 0.12\ \Omega$; $R_{LF} = 0.29\ \Omega$ | $R_{eq} = 0.61\ \Omega$; $R_{LF} = 0.33\ \Omega$ |
| IV. | [ MINI-4A (one coil) ] | $L = 0.30$ mH; $N = 93$ turns; $R_F = 0.05\ \Omega$; (6'8" lead, Cu #16) | $R_L = 0.01\ \Omega$; $R_{LF} = 0.06\ \Omega$ | |
| V. | [ REBONE-4A one coil (Cu, #18 AWG) winding ] | $L = 0.70$ mH; $N = 64$ turns; $R_F = 0.03\ \Omega$; (50" lead, Cu #16) | $R_L = 0.46\ \Omega$; $R_{LF} = 0.49\ \Omega$ | |
| VI. | [ MOYI-8A one coil in JAM-8A leg applic. ] | $L = 0.33$ mH; $N = 29$ turns; $R_F = 0.05\ \Omega$; (6' lead, Cu #16) | $R_L = 0.12\ \Omega$; $R_{LF} = 0.17\ \Omega$ | $R_L = 0.16\ \Omega$; $R_{LF} = 0.21\ \Omega$ |
| VII. | [ JAM-8A 4 LEG PADS in series FIG. 20c ] | $L_{eq} = 0.66$ mH; $R_F = 0.44\ \Omega$; Cu leads: $(2 \times 12')$ #18 + $4 \times (6'$ #16) | $R_{eq} = 0.24\ \Omega$; $R_{LF} = 0.68\ \Omega$ | $R_{eq} = 0.32\ \Omega$; $R_{LF} = 0.76\ \Omega$ |
| VIII. | [ REBONE-PM one coil (Cu, #22 AWG) winding ] | $L = 0.80$ mH; $N = 64$ turns; $R_F = 0.19\ \Omega$ | $R_L = 1.09\ \Omega$; $R_{LF} = 1.28\ \Omega$ | |
| IX. | [ EX-33 or EX-55 extensions, 12 feet long ] | (Cu, #16 AWG) ----> $R_{ex} = 0.09\ \Omega$; (Cu, #18 AWG) ----> $R_{ex} = 0.12\ \Omega$; for a 6 foot extension: $R_{ex} \longrightarrow (R_{ex}/2)$ | | |

EXAMPLES OF CRITICAL DAMPING DESING CALCULATIONS

| Name | $L_{eq}$ (mH) | $R_L$ (ohms) | $R_F$ (ohms) | $R_{LF}$ (ohms) | $T_j$ (ms) | $T_{jc}$ (ms) | $R_i$ (ohms) | $C_i$ (µF) | $I_{m/s}$ for ($V_0 = 10$) (A) | $\left(\dfrac{k_{\leftarrow+}}{k_{\leftarrow-}}\right)$ coil(s) | $\dfrac{T_{ic}}{T_i}$ |
|---|---|---|---|---|---|---|---|---|---|---|---|
| MAXI | 1.75 | 0.61 | 0.16 | 0.77 | 0.3 | 0.35 | 10.90 | 51.43 | 0.63 | 9.91 | 1.15 |
| (one coil) | 1.75 | 0.61 | 0.16 | 0.77 | 0.5 | 0.64 | 6.23 | 142.86 | 1.05 | 12.56 | 1.28 |
| (Al wire #11) | 1.75 | 0.61 | 0.16 | 0.77 | 0.8 | 1.23 | 3.61 | 365.71 | 1.68 | 19.63 | 1.54 |
| MAXI-2A | 1.06 | 0.32 | 0.17 | 0.49 | 0.3 | 0.35 | 6.58 | 84.91 | 1.04 | 10.08 | 1.16 |
| (one coil) | 1.06 | 0.32 | 0.17 | 0.49 | 0.5 | 0.65 | 3.75 | 235.85 | 1.74 | 12.98 | 1.30 |
| (Al wire #11) | 1.06 | 0.32 | 0.17 | 0.49 | 0.8 | 1.27 | 2.16 | 603.77 | 2.78 | 21.09 | 1.59 |
| MAXI-2A | 0.53 | 0.16 | 0.17 | 0.33 | 0.3 | 0.37 | 3.20 | 169.81 | 2.08 | 11.43 | 1.23 |
| (2 coils //) | 0.53 | 0.16 | 0.17 | 0.33 | 0.5 | 0.73 | 1.79 | 471.70 | 3.47 | 16.86 | 1.45 |
| (Al wire #11) | 0.53 | 0.16 | 0.17 | 0.33 | 0.8 | 1.59 | 1.00 | 1207.55 | 5.55 | 39.72 | 1.99 |
| MOYI-BA | 0.33 | 0.16 | 0.05 | 0.21 | 0.2 | 0.23 | 3.09 | 121.21 | 2.23 | 9.80 | 1.15 |
| (one coil) | 0.33 | 0.16 | 0.05 | 0.21 | 0.3 | 0.37 | 1.99 | 272.73 | 3.35 | 11.56 | 1.24 |
| (Al wire #11) | 0.33 | 0.16 | 0.05 | 0.21 | 0.5 | 0.73 | 1.11 | 757.58 | 5.58 | 17.28 | 1.47 |
| 4 LEG PADS | 0.66 | 0.32 | 0.44 | 0.76 | 0.2 | 0.26 | 5.84 | 60.61 | 1.12 | 12.95 | 1.30 |
| (8 coils) | 0.66 | 0.32 | 0.44 | 0.76 | 0.3 | 0.46 | 3.64 | 136.36 | 1.67 | 19.14 | 1.53 |
| (Al wire #11) | 0.66 | 0.32 | 0.44 | 0.76 | 0.5 | 1.18 | 1.88 | 378.79 | 2.79 | 67.67 | 2.36 |
| MINI-4A | 0.3 | 0.01 | 0.05 | 0.06 | 0.2 | 0.21 | 2.94 | 133.33 | 2.45 | 8.02 | 1.04 |
| (one coil) | 0.3 | 0.01 | 0.05 | 0.06 | 0.3 | 0.32 | 1.94 | 300.00 | 3.68 | 8.38 | 1.06 |
| (Cu wire #12) | 0.3 | 0.01 | 0.05 | 0.06 | 0.5 | 0.56 | 1.14 | 833.33 | 6.13 | 9.17 | 1.11 |
|  | 0.38 | 0.01 | 0.05 | 0.06 | 0.2 | 0.21 | 3.74 | 105.26 | 1.94 | 7.88 | 1.03 |
|  | 0.38 | 0.01 | 0.05 | 0.06 | 0.3 | 0.31 | 2.47 | 236.84 | 2.91 | 8.15 | 1.05 |
|  | 0.38 | 0.01 | 0.05 | 0.06 | 0.5 | 0.54 | 1.46 | 657.89 | 4.84 | 8.74 | 1.09 |
| REBONE-4A | 0.7 | 0.46 | 0.03 | 0.49 | 0.2 | 0.23 | 6.51 | 57.14 | 1.05 | 10.11 | 1.16 |
| (one coil) | 0.7 | 0.46 | 0.03 | 0.49 | 0.3 | 0.38 | 4.18 | 128.57 | 1.58 | 12.20 | 1.27 |
| (Cu wire #18) | 0.7 | 0.46 | 0.03 | 0.49 | 0.5 | 0.77 | 2.31 | 357.14 | 2.63 | 19.48 | 1.54 |
| REBONE-PM | 0.8 | 1.09 | 0.19 | 1.28 | 0.1 | 0.12 | 14.72 | 12.50 | 0.46 | 10.64 | 1.19 |
| (one coil) | 0.8 | 1.09 | 0.19 | 1.28 | 0.2 | 0.29 | 6.72 | 50.00 | 0.92 | 17.40 | 1.47 |
| (Cu wire #22) | 0.8 | 1.09 | 0.19 | 1.28 | 0.3 | 0.58 | 4.05 | 112.50 | 1.38 | 35.77 | 1.92 |

EXAMPLES OF USES OF PREFERRED EMBODIMENTS

Referring to various FIGURES of the present document, examples of uses are given for the following BASIC EMBODIMENTS OF THIS INVENTION:

The MBI-1000

The MBI-1004A.B

The MBI-3000

The MBI-3004

The MBI-101 Field Detector

As you will see, we have based the examples of Conditioning parameters, (A, n, T) Amplitude (A), Modulation (n) and Time (T), on the desired physiological effect rather than on the specific disease or health problem to be dealt with.

Indeed, the user should always refer to the following physiological effect in order to choose the (A, n, T) parameters, and in particular, the simplified guide to choose the Modulation, n, is as follows:

$n = 3$, to stimulate blood circulation;

$\begin{cases} n = 2, & \text{to relax the nervous system and induce} \\ & \text{anti-inflammatory and pain-killing effects;} \\ n = 3, & \text{to stimulate normal cellular repair and regeneration.} \end{cases}$ General precautions (MBI-3000 and MBI-1000)

The RHUMART technique may alter sleep patterns, particularly when applied to the expertmentor's head in the late evening.

Choose a comfortable position during a RESC session (generally seated or lying down.) You need not undress.

When using the MBI-3000 controller, never cover an applicator with a blanket or other insulating fabric, since it could overheat. It is normal for the temperature of the applicator to rise slightly (less than 3° C.) after a long conditioning session at high dosage.

The conditioner can be operated continuously, but this is not advisable, especially at maximum output.

For the first five to ten sessions with the MBI-3000, you should use the system every other day. Conditioning may be given every three days thereafter. When well tolerated, local or "regional" Conditioning (with MINI-4A or REBONE-4A) may be taken every day.

Experimenters suffering from chronic degeneration conditions may not show stable improvement until after the fifteenth or even the twentieth session. Nevertheless, often positive effects are felt from the very first sessions. In rare cases, 6 to 8 months of conditioning may be required before reaching a stable improvement.

It is normal that an experimenter's symptoms become somewhat more pronounced after the first two to four applications. This is not a reason to discontinue the conditioning course. The experimenter is undergoing the initial phase of adaptation to RESC conditioning and will usually show improvement shortly.

If, after the first, second or third session, a user feels sharp, constant pain in the area of application, discontinue RESC conditioning and visit a physician as soon as possible. Such a reaction to conditioning is abnormal.

A weak dosage applied at a distance from the affected area is recommended for the following: arterial embolism, intermittent claudication, diabetic angiopathy, angina (pectoris) accompanied by coronary insufficiency and preinfarctus syndrome. RESC™ is used only to induce physiological effects and not to "treat" or cure these health problems.

1. There is no absolute contraindication to RESC Conditioning when used according to the present document.

2. Results reported in recent years by numerous users of the RESC conditioner have shown the safety and usefulness of this system to help reduce the physiological STRESS related to numerous health problems such as:

implanted cardiac pacemakers (ex.: global applications with large rings)

pregnancy with various health problems (ex.: pain and circulation problems)

diabetes (ex.: various circulation and health problems)

internal haemorrhage (ex.: associated with menstruations)

mycosis (with parasites)

multiple sclerosis at various stages tumors and cancers at various stages.

The RESC technique induces mainly physiological effects similar to those of physical exercise to help all kinds of health problems. It must be specified that this cell conditioner is not represented to be a medical device and no representation to the contrary is allowed by the author here and now.

Various types of cases involving the above conditions and hundreds of others have shown improvement when the user followed the guidelines given herein.

The following is an actual example of a setting up and quality control procedure for the said MBI-1000 system in FIG. 14, 15 and 16a.

FIG. 15 illustrates the uses of the MBI-1000 and FIG. 16, 16a and 16b show its main components. Examples: The REBONE-PM applicators are labelled (10) and (11), while the 12 volt adapter is labelled (13).

1. Referring now to FIGS. 16, 16a and 16b, follow this step by step procedure. Plug the adapter (13)
2. Connect the 12 volt power supply cord (23) to the MBI-1000 controller.
3. Place the switch (16) in the REB position to supply to the controller.
4. Turn the AMPLITUDE dial (18) clockwise as far as it will go.
5. Turn the Pulse Width switch (17) to position 0.3 msec. (on the right hand side).
   the pulse freq. divider switch (19) to position 1.
   the pulse freq. dial (20) to position 60 imp./sec.
   and the Modulation dial (21) to position 2.
6. Make sure that all of the LED indicator lights are on. You will see one to the right of the PULSE FREQ. dial (20), another to the right of the n-MODULATION dial (21), and a sense of ten small lights (LED) to the right of the AMPLITUDE control dial (18).

If one or more of the LED indicator lights to the right or the AMPLITUDE dial (18) are not lit, it is possible that either:

the voltage supplied by the adapter (13) is insufficient to allow the MBI-1000 Controller to deliver full power to the REBONE-PM applicators (10 and 11 ) or the Controller is defective 7. Now verify that the appropriate RHUMART field impulses are being emitted by the REBONE-PM applicators. They are connected to your MBI-1000 Controller.

Turn the AMPLITUDE dial to the maximum setting.

Hold the small magnet (12) between your thumb and index finger less than one centimeter from each applicator. Move the magnet slowly, perpendicular to the surface of the applicator.

While varying the MODULATION (21), check to see that the vibrations felt in your fingertips correspond to the rhythm of the blinking LED indicator light to the fight of the MODULATION dial (21).

8. FIG. 1 (J to Z) and FIG. 15 illustrate how to place the applicators (10, 11) for use on different pans of the body. Elastic or VELCRO straps may be used to hold the applicators in place.

9. Polarity (N or S):

North (N) or South (S) polarity is indicated in the centre of each side of every applicator.

When using a single applicator:

the North (N) pole is directed toward the region to be conditioned;

the South (S) pole is directed toward the region to be conditioned only when you wish to apply the benefits of physiological conditioning to lesions of any kind.

When two (2) applicators are used:

Direct the North pole of one applicator toward the area to be conditioned (arm head, knee, etc.) and direct the South pole of the other applicator toward the other side of the same anatomical region. In this way the RHUMART fields of both applicators add up.

When you wish to condition surface areas only, the two North poles or the two South poles should be used facing each other, in this way the effects of the two applicators are in opposition to each and only the region immediately surrounding the applicators are conditioned.

EXAMPLES of USE of said MBI-1000

Now that you have studied the general precautions, setting up and quality control procedures described herein, you are ready to follow these simplified instructions to select the parameters for the MBI-1000 Controller.

Referring now to FIGS. 16, 16a and 16b, first plug the adapter into a standard outlet (115 volts, 60 Hz). A special car adapter is also available as an option from your distributor. This option makes it possible to plus the RESC Conditioner into the standard cigarette lighter found in most cars.

1, Positioning the Controls of the MBI-1000 Controller

Referring to the illustration of the Miniature RESC Conditioner shown in FIG. 16a, set the controls as follows:

the power switch (16) in the REB position.

the PULSE WIDTH switch (17) in position 0.3 msec the PULSE FREQ Divider (19) in position 1 the PULSE FREQUENCY dial (20) in position 60 imp./sec.

Place the REBONE-PM applicator on the desired location.

2, LENGTH of the Conditioning Session (T)

The timer (14) allows you to determine the length of your conditioning session.

T=10 minutes (generally)

T=5 minutes: for the first session to the head (or) for the first two to three sessions to induce physiological effects in the case of serious lesions (e.g. varicose ulcers)

T=15 minutes for difficult cases after 15 days of conditioning when well tolerated by the subject T=20 to 30 minutes in exceptional cases, such as certain stubborn cases of shoulder bursitis or terminal cancer (that is, to induce only physiological effects, and not to treat or cure the disease).

3, AMPLITUDE (A) (#18, FIG. 16, 16a and 16b)

A=4.5 to 7.5 near the brain

A=4.5 to 9.0 to induce physiological effects to help healing of various lesions and to improve blood circulation (begin with A=4.5).

Keep A constant for three consecutive sessions. When conditioning lesions do not exceed ten minutes, and isolate the lesion with sterilized material.

A=8.0 to 12 to induce physiological effects in most cases (A=12 is the maximum intensity)

Keep A constant for at least 3 consecutive sessions if well tolerated.

4, MODULATION (#21, FIG. 16. 16a and 16b)

Select the appropriate modulation (n) for various applications as follows:

n=0 or 1: to help in cases involving bone fractures, (alter 2 or 3 sessions at n=2), certain stubborn cases of shoulder bursitis, and certain cases of terminal phase cancer: that is, to induce only physiological effects only and not to treat or cure the problem.

n=2: to help in cases involving stress, hypertension, pain, inflammation, active rheumatism, chronic migraine and stomach ulcers (4 sessions at n=2, then use n=3);

A sedative effect (assimilation, with n<3: see Physiological Effects on the next page): That is, to induce only physiological effects only, and not to treat or cure the problem.

n=3: to help in cases of poor blood circulation, various lesions, burns, eczema, ulcers (4 sessions at n=2, then switch to n=3 for stomach ulcers), psoriasis, varicose veins, edema (swelling, recent sprains), inactive rheumatism;

A general stimulating (dissimilation with n≧3; see Physiological Effects on the next page): That is to induce only physiological effects only, and not to treat or cure the problem.

n=4: stimulation of hair growth with the physiological effects of RESC conditioning.

n=4 or 5: for the initial sessions to the head in order to help cases of chronic migraine (before using n=2) and stress: That is, to induce only physiological effects only, and not to treat or cure the problem.

NOTE: Avoid using n=3 on the head, except to improve blood circulation or to stimulate normal cell regeneration in cases of partial paralysis; (That is, to induce physiological effects, and not to treat or cure the problem.)

5, Sedative and stimulating Physiological Effects: (sedative for n<3 and stimulating for n≧3)

Said RHUMART or RESC waves are also useful for inducing the following physiological effects:

a) a sedative effect associated primarily with the process of assimilation in sympathicotonia, asthenic neurosis, neurasthenia, contractures, arthrosis, spondyloarthritis and active rheumatism;b) a stimulant effect associated primarily with the process of dissimilation in parasympathicotonia (vagotonia), depressive neurosis, asthma and inactive rheumatism.

A combination of stimulation and relaxation modes is useful in cases involving pain and inadequate nutrition in the extremities (n=2 for 5 minutes and n=3 for 5 minutes, for example). The reader is invited to consult a good medical dictionary for an explanation of the problems associated with assimilation and dissimilation.

6, POLARITY OF COIL APPLICATORS

In general, the north pole (N) of a coil applicator should be directed toward the area to be conditioned, However, in the case of lesions, the south pole (S) should be directed toward the region to be conditioned.

7, Begin the conditioning session by placing the power switch in the REB posit on. Choose the parameters and place the REBONE-PMs in the desired position.

8, Verify the presence, the intensity (or AMPLITUDE), the frequency and the polarity of the said impulses using the new MBI-101 compact and handy Field Detector.

NOTE: It is useful to demonstrate the presence of the said impulses with the said magnet or with the new MBI-101 Field Detector. These devices serve as extensions of man's senses: TOUCH and HEARING in the case of the magnet, and SIGHT in the case of the new FIELD DETECTOR.

MBI-1004A-B: STEP by STEP EXAMPLES OF USE

Referring now to the FIGS. 5a, 5b and 5c, follow the instructions below numerical order:

1. Plug the MBI-1004A into the outlet 25 of the said MBI-1000 Controller, and the said MBI-1004B into the said MBI-1004A (using the four-pin mini-plug described hereinafter.)

2. Follow the instructions given herein before for SETTING UP and QUALITY CONTROL with of the said MBI-1000 Controller.

3. On the said MBI-1004A and the MBI-1004B, turn the four current intensity control knobs counter-clockwise to zero and set the two (2) PULSE WIDTH dials to 0.3 msec (milliseconds). Push the REB/TENS switch on the said MBI-1000 Controller to the said TENS position.

4. Turn the AMPLITUDE (A) dial on the said MBI-1000 Controller clockwise to the maximum position.

On the said MBI-1000 Controller, set the PULSE FREQUENCY DIVIDER switch to ÷10, the PULSE FREQUENCY switch to 60, and the MODULATION dial to n=0 (CONT). Also set the timer, provided separately, to 15 minutes. Begin the RHUMART Super-TENS session by connecting the said MBI-1000 to an AC 115 V power supply or battery.

6. Plug one or more pairs of electrodes into the said MBI-1004A and the MBI-1004B next to the four current intensity control knobs and apply a conductive gel (the type used for ECGs or TENS) to the electrodes in order to improve skin contact.

7. Place each pair of electrodes at opposite ends:
of the muscle (or its motor endplate)
of the limb OR
of the part of the body you wish to stimulate.
Be very careful that you never place the electrodes on opposite sides of the cardiac region
This is very important in order to avoid excessive, stimulation of the heart and/or the cardiac region.

8. Gradually increase the intensity of the current impulses by slowly turning the control knobs 1, 2, 3 and/or 4 of the said MBI-1004A and 1004B in a clockwise direction. When you begin to feel pain, reduce the intensity slightly to a comfortable level.

9. Use the timer included with the said MBI-1000 to time the session for 1, 2, 10 or even 15 minutes. The length of the session should be based on the individual tolerance level and the intensity of the conditioning desired.

10. After a few minutes you may adjust the modulation of the impulses described herein using the MODULATION dial on the said MBI-1000. BUT FIRST, reduce the impulse intensity to zero by turning either the intensity control(s) on the said MBI-1004A and the MBI-1004B or the AMPLITUDE dial on the said MBI-1000 in a counter-clockwise direction.

11. Next, move the PULSE FREQUENCY DIVIDER on the said MBI-1000 to position 1 (it was in position ÷10 before) and the MODULATION dial to position n=2, for example, to achieve a relaxing effect. Gradually increase the intensity until it starts to be painful, and then reduce it to a comfortable level.

IMPORTANT

Always reduce the intensity of the RHUMART current to zero before changing the position of the PULSE FREQUENCY DIVIDER or the MODULATION dial on the said MBI-1000.

12. Begin again at step 3, experimenting with different PULSE FREQUENCIES, MODULATIONS, session lengths and PULSE WIDTHS.

13. If you wish, start again at step 3 after moving the pair of electrodes to the opposing ends of a different muscle, limb or part of the body. Never place the electrodes on opposite sides of the cardiac region.

14. It is also possible to hold group sessions with 2, 3, or 4 people using each pair of electrodes. Start again at step 3, with each group holding hands between one pair of electrodes connected to said MBI-1000A or MBI-1004B. The person on the left of each group holds the left electrode against the palm of his left hand, while the person on the right of the group holds the right electrode against the palm of his right hand.

In this way it is possible for 16 people at a time to enjoy the benefits of the said MBI-1004 A.B (MBI-1004A and MBI-1004B) used with the said MBI-1000.

MBI-3000:

The following is an actual example of a SETTING UP procedure for the said MBI-3000 shown in FIG. 8:

After reading the general precautions given hereinbefore, you are ready to begin using the MBI-3000 controller with your choice of said coil applicators (MAXI, MAXI-2A, MINI-4A or REBONE-4A or JAM-8A all described herein after).

Follow the instructions below in numerical order:

1, Referring to FIGS. 8 to 13 herein, choose the applicators you wish to use. Each part of said MBI-3000 controller has been given a different number (FIGS. 9A and 9B) while the applicators are identified by a name.

2, FIGS. 8 and 9 show the said MBI-3000 controller. FIG. 9 is a view of its front panel, while FIG. 9B shows its rear panel. Looking at FIG. 9B, plug the power supply cord (352) into a standard outlet (115 volts, 60 Hz for North America; 230 volts, 50 Hz for Europe), making sure to use the proper adapter if you are using the standard 115 volt plug in a 230 volt outlet; then place the power supply option switch (351) at the proper setting (115 or 230 V). The Fuse (353) is a 0.5 Ampere "slow blow" type.

3, Choosing coil Applicators for said MBI-3000

Referring now to FIG. 8, Choose the proper applicator according to the volume, or the dimensions, of the region of the person in which you wish to apply cellular conditioning. The effective size of the region covered by each coil applicator is as follows:

The pair of said MINI-4A: for concentrated physiological conditioning in a spherical area approximately 5 cm in diameter for each MINI-4A;

The pair of said REBONE-4A: for concentrated conditioning in an area approximately 10 cm wide by 15 cm long and about 10 cm deep, per applicator; see FIG. 1 (j to z) for examples of REBONE-4A applicator positioning.

The pair of said JAM-8A: for conditioning in an area approximately 15 cm wide, 40 cm long and 15 cm in depth, for each applicator at hight intensities (each JAM-8A "leg unit" contains two JAM-8A applicators); see FIG. 12 and 13 for examples of JAM-8A applicator positioning;

The said MAXI: for overall conditioning of the torso, midriff or legs. The empty cylinder is 50 cm in diameter and 25 cm high. Conditioning with this applicator at high intensities should not exceed 10 minutes every second day unless, after at least one month's use, the experimenter has shown the ability to tolerate more RESC™ conditioning;

The pair of said MAXI-2A: giant rings, each 50 cm in diameter, used for overall conditioning of the torso, midriff and/or both legs at the same time. To get the equivalent of a MAXI application, simply place the two rings on top of each other to form an empty cylinder approximately 25 cm long, making sure to use the proper polarity: See FIG. 1 (a to j) and FIGS. 12 and 13 for examples of MAXI-2A applicator positioning.

4. Setting the controles on the MBI-3000

With the selected coil applicator(s) connected to the MBI-3000 as indicated in FIG. 8 (REBONE-4A applicators can be connected in the same outlet as the MINI-4A, and vice versa—they both come in pairs); referring to FIG. 9A, press the POWER button (301), turn the AMPLITUDE dial (302) clockwise as far as it will go, set the FREQUENCY (303) to 60 imp/sec and the switch below the dial (303) to 1, i.e. (the left position), set the MODULATION (304) to 2, the MAG. TIME (305) to 10 minutes, and the POLARITY (306) to N. Set the rear panel switch (201, FIG. 9B) to left (L) or right (R), depending on whether you intend to use the applicators connected on the left or right of the rear panel as follows:

(a) If you are using the applicators on the right, the SELECTOR (206) should be in position 1 (0.5 msec impulse width) with a whole body applicator (MAXI or pair of MAXI-2A) connected in (202) and nothing connected in (203). When two (2) whole body applicators are being used at once, the SELECTOR (206) should be turned clockwise as far as it will go (third position); and the MBI-3000 will generate approximately 90% of the intensity produced when only one whole body applicator (MAXI or pair of MAXI-2A) is used.

(b) If you are using the applicators connected on the left (204) or (205), the front panel selector (308, FIG. 9A) acts as control. In position 1, one applicator is fed; in position 1-2, the two applicators connected in outlet (204) are fed; in position 1-3 or 1-4, three or four of the applicators connected in outlets (204) and (205) are fed. The LED indicator light (309) tells you the position of the L-R switch on the rear panel (201): the light will come on when the switch (201) is sending power to the left applicators (204 alone or 204 and 205), and it will be off when the right applicators (202 alone or 202 and 203) are being fed.

5, Turn the BEEPER (207), FIG. 9B, clockwise so that you can hear the signal indicating that conditioning is in progress. Press the button (307) to START the conditioning session.

6, Check if the LED indicator lights above the control buttons (302, 303 and 304) in FIG. 9A are on (including the light bar located above the AMPLITUDE dial (302) and watch the timer readout above the MAG. TIME (305) to see that it is working: the time should be decreasing one second at a time from the conditioning period of time selected, i.e. 10 minutes in this trial operation.

7. Check if the light in the START button (307) is blinking at the same rhythm as the light in the MODULATION dial (304). If it is, then all is normal and the current is being fed to the selected applicator(s). If not, the circuit is open somewhere. Make sure the SELECTOR (206) or (308) is not set for applicators that are not connected to the said MBI-3000. For example, if the SELECTOR (308) is on 1–3 or 1–4 and no applicator is connected in the outlet (205) on the rear panel, or if the SELECTOR (206) is set to 1,2 (0.5 msec) or 1,2 (0.8 msec) and no applicator is connected in (203) on the rear panel, the system will not work because the current circuit is open.

If all the connections are good and the START light (307) is not on, check for the presence of a magnetic field near the applicator, using the said MBI-101 field detector or the simple magnet (ferrite) supplied with the unit. Hold the said magnet between your thumb and forefinger, perpendicular to the direction of the magnetic field, and you'll feel a slight vibration if the field is present (proportional in strength to the AMPLITUDE (A)).

A simple way of checking the presence of the field: aim the magnet toward the centre of your ear and "listen" to the said magnetic field by moving closer to the energized applicator. Vary the MODULATION (304) and you will hear different magnetic impulse and/or impulse bundle frequencies, depending on the selected basic frequency and modulation.

8, Referring to different Figures, between 1 and 13, decide where you want to place the RHUMART applicators on different parts of the body. For the said MINI-4A applicators, place them similarly to the REBONE-4A positioning (FIG. 1, j to z for examples) except that the MINI-4A is positioned at approximately half an inch from the skin.

Position the MAXI as described in the present procedure.

9, Polarity (N or S):

North (N) or South (S) polarity is indicated on each side (or on each end) of every applicator. When only one applicator is being used, the North pole is directed towards the area to be conditioned, except in the case of physiological conditioning of sores, when the South (S) pole is applied to the affected area (with the MAXI or MAXI-2A, generally, the North pole is directed towards the person's head); when two (2) applicators are used on either side of a limb, a shoulder or the head, the North of one applicator is placed on one side of the area to be conditioned and the South pole of the other applicator is placed on the other side of the conditioned limb, shoulder or head. This way, the conditioned area benefits more effectively from the magnetic field of both applicators. When conditioning predominantly near the surface, the two North or two South poles should be placed facing each other. On the head, it is advisable to start with low intensity superficial conditioning that is with facing North or South poles, and a low amplitude, A (A$\leq$2 with MINI-4A or REBONE-4A applicators and A$\leq$3 with MAXI and MAXI-2A applicators).

EXAMPLES of USE of said MBI-3000

(referring to FIGS. 9A and 9B)

Now that you are familiar with the general precautions, as well as the setting up and quality-control procedures described herein before, you are ready to follow the simplified instructions to select the conditioning parameters of the said MBI-3000.

1, Setting the MBI-3000 controls (FIGS. 9A and 9B)

(a) press the POWER button (301) (the power cord must be previously connected to the proper power outlet, 115 VAC or 230 VAC);

(b) set the PULSE FREQUENCY (303) to 60 imp/sec and the switch below it to 1 (i.e. to the left);

(c) set the POLARITY (306) to N;

(d) set the SWITCH (201, FIG. 9B) to L or R, depending on whether you intend to use the applicators connected on the left or the right of the back panel of the MBI-3000;

(e) set the APPLICATOR SELECTOR (308, FIG. 9A or 206, FIG. 9B) to the proper position (as explained in Section 4.2.4 (a) and (b) above, for the MBI-3000);

(f) turn the BEEPER knob (207, FIG. 9B) clockwise so that you can hear, the signal indicating that conditioning is in progress; the signal comes on as soon as the START button (307, FIG. 9A) is pressed, and remains on until the session (305) is finished (when the chronometer above MAG. TIME reaches zero).

2, Look at FIGS. 1 to 13 above, to see examples of how different applicators are used for conditioning different areas of the body (including the examples a–z of ring and pad positions).

3, Duration of conditioning session or MAG. TIME:

The MAG. TIME button (305) determines the duration of a conditioning session (T):

T=10 minutes, usually;

T=5 minutes for the first 2 or 3 sessions on the head or on a serious sore (to induce physiological effects in a case of varicose ulcers, for example);

T=15 minutes, for difficult cases after 15 days of conditioning course;

T=20 to 30 minutes in exceptional cases of recalcitrant bursitis of the shoulder and some terminal-phase cancers (that is, to induce physiological effects in these cases and not to treat or cure them).

4, AMPLITUDE (A), (302, FIG. 9A)

A=3 to 5 with the said MAXI or MAXI-2A near the brain (A=1 to 2 with the said MINI-4A or the REBONE-4A);

A=3 to 6 with the MAXI or the MAXI-2A to induce physiological effects similar to those of physical exercise in cases of various sores and circulation problems (A=1 to 2 with the MINI-4A or the REBONE-4A); maintain the same AMPLITUDE for at least 3 consecutive sessions if the user can tolerate it.

A=6 to 8 with the said MAXI or the MAXI-2A to induce physiological effects to help most conditions (A=2 to 4 with the MINI-4A or REBONE-4A); maintain the same AMPLITUDE for at least 3 consecutive sessions if the user can tolerate it.

A=10 to 12 with the said MAXI or the MAXI-2A to induce physiological effects in difficult cases that do not respond to lower amplitudes (A) (A=4 to 6 with the MINI-4A or the REBONE-4A), but only after 3 to 4 weeks of conditioning; increase gradually and maintain the same AMPLITUDE for at least 3 consecutive sessions, if the user can tolerate it.

NOTE: Place the end of the said MINI-4A about 0.5" from the affected area. Increase the suggested Amplitude (A) by 1 when two applicators (or two pairs of applicators) are "energized" at the same time by the said outlets (204 and 205 or 202 and 203. FIG. 9B).

5, MODULATION (304, FIG. 9A)

Set the modulation (n) as follows:

n=0 or 1: in cases of bone fractures, after 2 or 3 sessions at n=2; also for stubborn cases of bursitis of the shoulder and for some terminal phase cancers (that is to induce only physiological effects similar to those of physical exercise to help these cases and not to treat or cure them.

n=2: in cases of stress, hypertension, pain, inflammation, active rheumatism, chronic migraine, stomach ulcers (4 sessions at n=2 and then try n=3), and when this invention is used as a relaxant or sedative; that is to induce only physiological effects similar to those of physical exercise to help these cases and not to treat or cure them.

n=3: in cases of circulation problems and various sores and burns, eczema, ulcers (start with 4 sessions at n=2 in cases of stomach ulcers), psoriasis, varicose veins, overall cell regeneration, oedema (swellings, recent sprains), inactive rheumatism, and as a general stimulant; that is to induce only physiological effects to help these cases and not to treat or cure them.

n=4: to stimulate hair growth with the said physiological effects.

n=4 or 5: for a first session on the head, in cases of chronic migraine (before using n=2) and in stress cases; that is to induce only physiological effects in these cases and not to treat or cure them.

NOTE: Avoid using n=3 on the head, except to improve circulation or to stimulate cell regeneration in cases of partial paralysis; after a cerebral embolism (it is suggested to wait approximately 15 days before using the said conditioning); that is to induce only physiological effects in these cases and not to treat or cure them.

6, Sedative and stimulating Physiological Effects: (sedative for n<3 and stimulating for n≧3)

Said RHUMART or RESC waves are also useful for inducing the following physiological effects:

a) a sedative effect associated primarily with the process of assimilation in sympathicotonia, asthenic neurosis, neurasthenia, contractures, arthrosis, spondyloarthritis and active rheumatism;

b) a stimulant effect associated primarily with the process of dissimilation in parasympathicotonia (vagotonia), depressive neurosis, asthma and inactive rheumatism.

A combination of stimulation and relaxation effects is useful in cases involving pain and inadequate nutrition in the extremities (n=2 for 5 minutes and n=3 for 5 minutes, for example). The reader should consult a good medical dictionary for an explanation of the problems associated with assimilation and dissimilation.

7, Polarity (NORTH (N) or SOUTH (S)

Select the polarity (N or S). To summarize, set the POLARITY switch (306) to N and direct the North pole of the applicator toward the affected area, except when conditioning sores, when the South pole is placed on the affected area. Said conditioning may be used for surface or deep conditioning depending on whether the two poles are in opposition (N facing N or S facing S) or working together (N facing S).

8, Begin the session by pressing the START button (307, FIG. 9A) after selecting the said conditioning parameters (AMPLITUDE, MODULATION and MAG. TIME) according to the above instructions.

Make sure the system is working and check the intensity (or AMPLITUDE), frequency and polarity of said impulses with the new MBI-101 Field Detector (18).

N.B. It is usefull to demonstrate the presence of the said impulses to the future experimenter with a fiat magnet or the MBI-101 detector. This involves many of the experimenter's senses (touch and hearing with the magnet, as well as sight with the new MBI-101).

Other examples of uses (MBI-3000)

DEFINITIONS:

(i) One embodiment of this invention includes:

☐ One said MBI-3000 controller-generator (11),

☐ a pair of said rings (MAXI-2A, approx. 50 cm in diameter) (12),

☐ a pair of said REBONE-4A regional applicators (pads) (13),

☐ a case and accessories (ii) Abbreviations of parameters:

Instead of using A=2, n=2, T=10 minutes, the abbreviation (A2,n2,T10) or (2-2-10) is used when referring to a conditioning session.

(iii) Definition of said conditioning parameters:

The power push button on the very left of the said MBI-3000 front panel must be pushed ON.

① 1$^{st}$ knob on the left of the panel (after the POWER push button):

AMPLITUDE (A)

A=Intensity of the conditioning signal

② 2$^{nd}$ knob from the left (after the POWER button): FREQUENCY, ($f_b$, imp/sec)

$f_b$=basic impulse frequency $f_b$=60 impulses per second (often used in Regeneration Modes)

③ 3$^{rd}$ knob from the left (after the POWER button): MODULATION (n) n=Mode or type of conditioning.

The Modulation (n) makes it possible to select the predominant physiological affect of said conditioning.

④ 4$^{th}$ knob from the left: MAG. TIME (T, min) T=duration of a session, in minutes ⑤ POLARITY: NORTH (N) or SOUTH (S)

N or S: direction of magnetic field impulse.

N: the magnetic flux exits from the "N" pole.

S: the magnetic flux returns towards the "S" pole.

1, GLOBAL PHYSIOLOGICAL CONDITIONING with the present embodiment (including the MBI-3000 Controller and a MAXI-2A pair of 50 cm applicator rings).

For various examples of positioning said MAXI-2A and REBONE-4A pairs of coil applicators, refer to FIG. 1 (a to z) herein.

Use the following parameters with one MAXI-2A ring around the chest and the other around the knees (polarity N should be directed towards the subject's head).

A5 to A8, n2, T10 to T15 or (5-8,2,10-15) every second day and (A2 to A5, n2, T10 to T15) every second day for hypersensitive subjects who may find it difficult to adjust to normal parameters (i.e., A5 to A8).

Individuals referred to as "hypersensitive to said conditioning" are often underweight and/or elderly (over 75). These individuals should generally begin at a lower AMPLITUDE (A).

Some young people may also be "hypersensitive" to said conditioning.

At the head level, use the following parameters for global conditioning: A≦2 and T≦5 minutes, or according to the users tolerance.

Jewellery and ferromagnetic objects should be removed for best results. Arms should be kept inside the upper ring with joining hands to close the circuit.

Position of rings: When the user is inside the said MAXI-2A pair of rings, it is suggested that the North (N) polarity is directed towards the subject's head, (see illustrations a to z on the following pages).

POLARITY (N or S): Chosen as described herein before.

2, REGIONAL CONDITIONING with said REBONE-4A" applicators (also referred to as the pads, 320)

These are used on specific areas of the head or body (with the MODULATION (n) depending on the predominant physiological effect desired). See also below for selecting the proper MODULATION.

(a) At the head level (with the REBONE-4A pads) Use A1 to A2, T5 to T10, every second day: start with (A1, n2, T5) for 5 to 6 sessions, every second day; then go on to (A1, n3, T5) to stimulate cell regeneration, if so desired.

(b) Below the shoulders (with "n" according to desired effect using the REBONE-4A applicators). Use A2 to A3 for 10 minutes, every second day; or A5 to A6 for 5 minutes, every second day.

(c) Polarity: Be sure to place the NORTH (N) polarity facing the area to be conditioned, except in the case of burns or open wounds, in which case the SOUTH (S) polarity should face the wound.

Note: The NORTH (N) polarity has a "soothing" effect, while the SOUTH (S) polarity has a "stimulating" effect, in the case of wound healing for example.

(d) For an example of physiological reflexilogy system: place the said REBONE-4A pads under the feet, with the NORTH polarity facing the sole of each foot; this is a spot where the entire body's reflex points converge.

For a reflexilogy session, place a REBONE-4A pad under each foot, and begin by using parameters A2, n2, T10 every second day for 4 to 5 sessions; subsequently, increase to A3 or A4, n2, T10, tolerance permitting. At the beginning, use A≦2 for better tolerance thereafter.

3, COMBINED CONDITIONING MODES: GLOBAL (with the 50 cm rings) and LOCALIZED MODES (with the REBONE-4A pads)

An excellent method is to alternate "global" and "localized" conditioning, that is, one day with the said MAXI-2A rings for global conditioning and the next with the REBONE-4A pads for localized conditioning.

4, SELECTING THE PROPER MODULATION (n) or the PREDOMINANT PHYSIOLOGICAL EFFECT n=MODULATION=choice of predominant effect.

(a) "n2" effects (or predominant ANTI-STRESS effects) For example, n2 enables the experimenter to induce one or more of the following physiological effects:

RELAXATION and/or

PAIN RELIEF and/or

ANTI-INFLAMMATORY EFFECT(S)

(b) Examples of applications of "n2" effects:

RELAXATION effect: people with STRESS related to insomnia and hypertension can help themselves with "n2" physiological effects.

PAIN RELIEF: people with STRESS related to bursitis, sprains, rheumatism or arthritis can help themselves with the said Conditioner using "n2".

REDUCTION OF INFLAMMATION: the said physiological anti-inflammatory effect in musculo-skeletal, arthritic and rheumatismal problems can be induced with modulation "n2".

But, remember, the said conditioning is not specific for one and only disease. It rather strengthens the natural self-defense and healing mechanisms by inducing physiological effects.

(c) "n3" effects (or predominant stimulating effects)

With MODULATION n3, the predominant effects are as follows:

it stimulates normal cellular REGENERATION (a basic physiological effect)

and it stimulates blood CIRCULATION, oxygenation, nutrient absorption and waste product elimination (4 basic physiological effects).

NOTE: Before going on to n3, pain should be controlled using n2; subsequently, for 5 to 6 sessions, alternate between 5 minutes at n3 (n3, T5) and 5 minutes at n2 (n2, T5) during each session, then go on to modulation n3 only and increase the AMPLITUDE (A) slowly, every 3 or 4 sessions, according to tolerance to said conditioning.

In the case of blood circulation problems, take 2 to 4 sessions using (A5, n2, T10, global) before going on to n3: the body should be completely relaxed to help improve the performance and endurance of the cardiovascular system.

(d) Effects of "n4" and "n5" MODULATION:

For example, MODULATIONS n4 and n5 can induce beneficial physiological effects in people suffering from the following problems:

chronic migraines visceral problems glandular problems hypotension (n3 and n4) (hypertension (n2))

hair loss or dryness (n4)

For inducing physiological effects to help resolve glandular and abdominal problems, one can use the large rings and the said REBONE-4A pads, with n5 for the first 5 or 6 sessions, before going on to n4.

Exceptions:

In migraines known to be caused by stress, begin with three global conditioning sessions, using n2 instead of n5.

To induce said physiological effects in people with hair loss problems (baldness, eyebrows, etc.) with the pads, begin by using (A1, n4, T10) for 3 to 4 sessions per week, then try (A2, n4, T10) every second day, if well tolerated.

(e) "n6", "n7", "n8" and "n9" effects are mainly used in the said "Super-TENS" or muscular modes (see the description and examples of use of the said MBI-3004 and MBI-1004 modes herein).

MBI-3004:

The following are actual examples of uses of the said MBI-3004 muscular mode shown in FIG. 6a, and 6b.

Referring now to the illustrations of FIG. 6a, 6b, 9A and 9B, follow the step by step procedure below:

1. Plug the said MBI-3004 into the back of the said MBI-3000 Controller (FIG. 9B), below the BEEPER switch in the upper left-hand corner.

2. Follow the instructions for setting up and quality control procedure of the said MBI-3000 described herein.

3. On the said MBI-3004, turn the four current intensity control knobs counter-clockwise to zero and set the PULSE WIDTH dial to 0.3 msec (milliseconds).

4. Turn the AMPLITUDE dial on the said MBI-3000 Controller to maximum.

5. On the said MBI-3000 Controller, set the PULSE FREQUENCY DIVIDER switch to ÷10, the PULSE FREQUENCY dial to 60, the MODULATION dial to n=0 (CONT.), and the timer (MAG. TIME) to 15 minutes. Begin the Conditioning session by pressing the START SESSION button on the MBI-3000 Controller.

6. Plug one or more pairs of electrodes into the said MBI-3004 below the four current intensity controls and apply a conductive gel to the electrodes; this will help to improve skin contact.

7. Place each pair of electrodes at opposite ends:
   of the muscle (or its motor endplate)
   of the limb OR
   of the part of the body you wish to stimulate.
   Note: Be very careful that you never place the electrodes on opposite sides of the cardiac region This is very important in order to avoid excessive, stimulation of the heart and/or the cardiac region.
8. Gradually increase the intensity of the current impulses by slowly turning the control knobs 1, 2, 3 and/or 4 of the said MBI-3004 in a clock-wise direction. When you begin to feel pain, reduce the intensity slightly to a comfortable level.
9. Adjust the session length (MAG.TIME) on the said MBI-3000 to 1, 2, 5, 10 or even 15 minutes in accordance with your individual tolerance level and the degree of conditioning desired.
10. After a few minutes you may adjust the modulation of the impulses described hereinafter (FIG. 17) using the MODULATION dial on the MBI-3000.
    But first, reduce the current intensity to zero by turning either the intensity control(s) on the MBI-3004 or the AMPLITUDE dial on the MBI-3000 in a counter-clockwise direction.
11. Next, move the PULSE FREQUENCY DIVIDER on the said MBI-3000 to position 1 (it was in position ÷10 before) and the MODULATION dial to position n=2, for example, to achieve a relaxing effect. Gradually increase the intensity until it starts to be painful, and then reduce it to a comfortable level.

IMPORTANT

ALWAYS REDUCE THE INTENSITY OF THE CURRENT TO ZERO BEFORE CHANGING THE POSITION OF THE PULSE FREQUENCY DIVIDER OR THE MODULATION DIAL ON THE SAID MBI-3000.

12. Begin again at step 3, experimenting with different PULSE FREQUENCIES, MODULATIONS, session lengths (MAG. TIME) and (PULSE WIDTH=0.1, 0.2 or 0.3 milliseconds).
13. If you wish, start again at step 3 after moving the pair of electrodes to the opposing ends of a different muscle, limb or part of the body. REMEMBER: NEVER PLACE THE ELECTRODES ON OPPOSITE SIDES OF THE CARDIAC REGION.
14. It is also possible to hold group sessions with 2, 3, 4, 5 or even 6 people using each pair of electrodes. Start again at step 3, with one group holding hands between each pair of said MBI-3004 electrodes.
    The person on the left of each group holds the left electrode against the palm of his left hand, while the person on the right of the group holds the right electrode against the palm of his right hand.
    In this way it is possible for 24 people simultaneously to enjoy the benefits of the said MBI-3004 mode of this invention.
15. At the same time as 24 people use the MBI-3004 mode, two persons may use said regeneration modes with the said MBI-3000 controller. They may use either global MAXI coil applicators and one pair of MAXI-2A or local MINI-4A coil applicators and regional REBONE-4A coil applicators as further described herein. When this invention is used in this fashion, the power in said coil applicators is reduced by less than 1% (when used simultaneously with said MBI-3004 muscular mode).

MBI-101 Detector-Calibrator

Referring now to FIGS. 16, 16a and 16b, there is shown the MBI-101 Magnetic Field Detector-Calibrator described in great details herein. Following are examples of uses of a preferred embodiment of the MBI-101 Detector-Calibrator:

1. option A. In order to verify the presence of the magnetic field emitted by the REBONE-PM applicators, place the two applicators (10, 11) 10 cm apart in a parallel position, with the MBI-101 Field Detector (30) in the middle, as illustrated in FIG. 16b. Make sure that the field and $\vec{B}_1$ and $\vec{B}_2$ are oriented in the same direction.
   option B. Verify the presence of the magnetic field emitted by said coil applicators (ex. MAXI-2A giant rings or the MAXI cylinder) in the same way, after reversing the direction of $\vec{B}_1$ and $\vec{B}_2$ (by turning the applicator, 10 and 11 by 180°).
2. With the Field Detector (30) in the centre of each coil applicators (ex. REBONE-4A, REBONE-PM or MAXI-2A giant ring or MAXI cylinder), press the power switch (32), turning on the battery-operated detector and causing two LEDs (33) to light.
3. Make sure that the gain, or sensitivity switch (31) is in position 5 (max.) for maximum sensitivity.
4. It is now possible to read the directional intensity of the magnetic field (one lit LED, 34 or 35, being equivalent to one (1) gauss) to get $\vec{B}_{max}$ or $\vec{B}_{1,2}$ resulting from the vector sum of the two fields $\vec{B}_1$ and $\vec{B}_2$ generated by the applicators being used.
5. The intensity of the magnetic field induced is directly proportional to the number of rectangular indicator lights (34 and 35) lit up on each side of zero (33).
   Notice that the resulting magnetic field $\vec{B}_{1,2}$ is directional 36: that is, there are more rectangles lit up on the right side (34) than on the left side (35) of the power indicator light in the centre (33). This is because the said impulses, like the natural electric impulse of the human nervous system, are polarized.
6. In this example, each rectangular LED light corresponds to one gauss—the unit of magnetic field of $\vec{B}_{max}$ defined hereinbefore. Thus, when there are ten LED rectangles lit on the right side of zero (33), the maximum field in this direction, $B_{max}$, is ten (10) gauss.
7. In general, the maximum magnetic field intensity, $\vec{B}_{max}$, as measured with a probe (without a ferromagnetic core) is calculated using the $\vec{B}_{max}$ equation described herein (see $2^{nd}$ Law of Physiological Cell Conditioning).

GENERAL WORKING INSTRUCTIONS

Let us first recall a few important features of the present invention in order to give to the user a better understanding of the holistic RESC or RHUMART method of this invention.

Basically, although the RHUMART Method can be used by various clinicians using an holistic approach, it remains essentially an INTEGRATED SELF-HEALTH SYSTEM in which the user must remain in full control of the choice of conditioning parameters in order to get the best possible results. As visualized in the said RESC "triangle" FIG. 2c and FIG. 2d, the user takes advantage of the help of his experienced advisor, teacher or mentor, which helps him maintain his MOTIVATION to heat or to improve his Quality of Life with the method and system of this invention.

In other words, the said RESC factors shown in FIG. 2c (including the RESC Conditioner) are interrelated. In fact, the choice of Conditioning parameters is influence by the experience of the said advisor, as further visualized in FIG. 2d and FIG. 2e.

In FIG. 2d, the working principle of the said RESC phenomenon is well illustrated; and in FIG. 2e the user can visualize how to use the Scientific Experimental Method of this invention to improve his Quality of Life.

The Section "D" of the said RHUMART physics shows how to measure and/or calculate various parameters and waveforms of the current pulses induced in the human body by means of the said Conditioning modes of operation (e.g., the REBONE-PM, MINI-4A, REBONE-4A, JAM-8A, MAXI-2A or the MAXI Mode) described herein.

The parameters and variables shown in FIG. 3a, b, c and d are defined in the said RHUMART physics Sections where various new and useful relationships between these parameters and variable are developed or presented by the author of the present invention.

The range of power (in $\mu W$) and that of power density (in $\mu W/cm^2$) absorbed by the user of the said MAXI and the REBONE-PM Modes of operation of the present invention are calculated herein (after the said RHUMART physics "D"), showing that the power and power density absorbed by the user of this invention are below national and international safety standards, in particular, those of the Guidelines issued by the United States BUREAU OF RADIOLOGICAL HEALTH (BRH) entitled "GUIDELINES FOR THE EVALUATION OF ELECTROMAGNETIC RISK FOR TRIALS OF CLINICAL NMR SYSTEMS". Concerning the safety level of these guidelines, they were intended to prevent submission of IDE (Investigational Device Exemption) in the USA, when they were not necessary to ensure patient safety.

Previous devices by different authors were limited to specific applications with specific parameters. Further more, they did not use the physiological or biological type of signals (Described herein) to Condition the cells of the human body. The present invention uses bioelectric impulses of similar waveform and intensity of Calcium ion ($Ca^{++}$) current impulses which are absolutely essential in the Synaptic Transmission of biological signals that control all organs and functions of the human body. This is one basic reason for which the number of different applications of the present invention is limited only by the imagination of the user. Albert Einstein said: "Intelligence is not the greatest faculty of man, but IMAGINATION is!"

In order to help any condition with the present system and method, one has to understand how the symptoms, physical signs or physiological perturbations of a given condition, disease or health problem relate to the basic three (3) physiological effects described herein. Then the user has his hints as to what range of Conditioning parameters (A,n,T) he should start with, and using the method described herein, he will be able to adapt these parameters to any health condition. In this way, he is enabled to enhance his natural Self-Defence and Healing mechanisms leading to the improvement of his health condition and Quality of Life.

AN HOLISTIC APPROACH

Briefly, the method of this invention uses three basic factors (motivation of user, help of his mentor and the said ELECTROPHYSIOLOGICAL Conditioning system) acting together, the initial Conditioning parameters suggested herein and the adaptation of said parameters to individual needs. In short, this invention is a new AUTO-HEALTH or SELF-HEALTH system.

CHOICE OF PHYSIOLOGICAL CONDITIONING MODES FOR PARTICULAR APPLICATIONS AND CIRCUMSTANCES

The next three (3) pages teaches more on how various embodiments of this invention can be used as an integrated SELF-HEALTH system including one or more of said MBI-1000, MBI-3000 controller-generators, the new MBI-101 field detector, and various applicator and circuit interlace means described herein.

The said MBI-1000 Controller-generator can be used in combination with the REBONE-PM, also called the MBI-1000 Cellular Regeneration mode (or in short, the REBONE-PM Cellular mode), or with the MBI-1004 A.B Muscular mode.

The said MBI-3000 Controller-generator can be used in combination with the MINI-4A, REBONE-4A, JAM-8A, MAXI or MAXI-2A, also called the MBI-3000 Cellular Regeneration modes, (or in short, the MINI-4A, REBONE-4A or with the MBI-3004 Muscular mode.

The said MBI-101 field detector 30 and/or the known ferrite magnet 12 can be used in combination with either the MBI-1000 or the MBI-3000 and any said coil applicator.

Now with these terms introduced, let us indicate to the user which embodiment or physiological mode to use generally and in what type of circumstances.

Generally, the method of this invention stars by using the MBI-3000 CELLULAR CONDITIONING mode with the said MAXI or MAXI-2A applicator described herein for global physiological Conditioning and relaxing the whole body as described herein.

Then one would use the said REBONE-4A or the MINI-4A Cellular mode to condition particular areas or specific spots of the body which are the sites of new and/or old STRESS induced by various known and/or unknown causes and which maintain continuous or intermittent health disturbances such as pain and/or inflammation and/or perturbed sleep. If the stressed or painful area is large enough, one could use the JAM-8A Cellular mode described herein.

The said MINt-4A mode is used for well localized pain and/or stress focuses, as compared to the said REBONE-4A which is used for A SMALL REGION Of the body like, for example, an ankle, a knee, an area of the spine, a wrist, an elbow or a shoulder; with Conditioning parameters as suggested in examples of use given herein to start with and which can be adapted by the user in successive applications, as described herein.

Generally, it is the size of the area or region to be conditioned that will determine which is the best applicator or mode to use. Except that the said REBONE-4A mode is much more powerful than the said REBONE-PM mode in terms of intensity of induced bioelectric impulses.

The said REBONE-PM mode of the said MBI-1000 is much more practical to use than the said REBONE-4A mode when a low intensity of impulses is required (in the head region for example, which is more sensitive), and during long distance trips where the small size and low weight of the said MBI-1000 mode are real advantages over the said REBONE-4A mode.

The said MAXI mode of operation is more practical and easy to use by a person lying in a bed, especially if that person cannot sit or stand up.

The said MAXI-2A mode on the other hand is more practical and easy to use by a person who wishes to take his Conditioning sessions while sitting in a comfortable living-room type of seat or in any simple chair, preferably not made of ferromagnetic material so as not to perturbate the magnetic field impulses.

Generally, it is not recommended to use the said MAXI or the MAXI-2A mode directly centered on the head, except if the amplitude is kept very low, lower than 1.5 for example. On the head region, the said REBONE-4A mode should be used with amplitudes lower than 1.5 or 2.0 in most circumstances, except as suggested herein.

For SMALL CHILDREN, below the age of two (2) to three (3) years, the said REBONE-PM MODE is often the best suited because of the SMALL SIZE of the different organs and parts of the child's body, and also because of the GREATER SENSITIVITY OF RESPONSE in general of children (partly due to their known higher regenerative capacity linked with their young age; this also applies to small and young animals.)

Generally, the said MBI-1004 A-B and the MBI-3004 Muscular modes are used after approximately two to three months of Conditioning with the said regeneration or CELLULAR CONDITIONING modes. The Muscular modes are very useful to strengthen various muscles and especially useful also to help reduce or eliminate newly formed or old oedemas. Especially in sports injuries for example, the Modulation n=2 of the cellular mode is used to help reduce pain; and the Modulation n=3 of the Cellular mode is used to help reduce or eliminate severe or persistent oedemas. The said Muscular modes (MBI-1004A.B or MBI-3004) can also be used to help eliminate oedemas as described herein.

The Muscular modes are also very useful to Condition specific muscles while other nearby muscles and/or pans of the body do need a rest in order to recuperate from vanoux sports, injuries and/or accidents.

As for the use of the said magnet and the MBI-101 Field Detector, it is well explained in the examples of use of the MBI-101, the MBI-1000 and MBI-3000 controller-generators.

Generally, the said magnet is used to feel the approximate intensity and frequency of pulse trains (for experienced users). The said MBI-101 detector is essential to find the direction and intensity of the magnetic field impulses. It has five intensity scales (Gain scales) allowing for the measurement of the intensity of magnetic field impulses generated by all regeneration or cellular modes of the present invention. It is also very compact and versatile and is held in one hand for practical use as further described herein.

Previous detectors were not as compact and versatile to detect and quantitatively measure the physiological magnetic field impulses. With the highest sensitivity scale, each LED (Light Emitting Diode) lit in the so called BAR LED corresponds to one gauss ($10^{-4}$ Wb/m$^2$), a unit of magnetic field in the range of that of the earth.

OTHER APPLICATION EXAMPLES

1. Conditioning

Important: in many cases, the biological effects which are induced from physiological conditioning impulses are dependent on the Amplitude (A) and Modulation value (n) of these impulses and also on the duration (T) and frequency of conditioning sessions.

More specifically, there are so called Amplitude (A) and Modulation-Frequency windows for specific physiological effects to be induced; meaning that the same effects are not necessarily induced when the Amplitude and the Modulation value are below or higher than the limit values of the said windows.

In order to discover these Amplitude and Modulation windows, it is recommended to initiate conditioning with low Amplitudes and the Modulation frequency (n) suggested herein (as illustrated in FIG. 2m); and maintain, reduce or gradually increase the Amplitude using the said RESC procedure (FIG. 2e).

If satisfactory results are not obtained after, say 15 or 20 conditioning sessions, always consider the use of a different Modulation frequency (n), duration and/or frequency of conditioning session; and this by taking the examples given herein into consideration along with your own experience.

Towards the end of a conditioning course, it is recommended to decrease the Amplitude and the duration of session CT) gradually in the last 2 or 3 sessions. That is when you do not feel that you need to take regular conditioning sessions, say, every other day or every third day.

The subjective feelings of the experimenter should always be used as indicators, as explained in the said RESC or RHUMART Method.

Generally, the frequency of said conditioning sessions should vary between one session per day to one per week, one session every other day being adopted by most people.

2. Definition of "PULSE" FREQUENCY

In general, the FREQUENCY of any periodic process is the number of full cycles within a time interval (second).

Herein, "pulse" frequency is the repetition frequency of pulse bundles, in bundles per second. The basic frequency, $f_b$, is the frequency of repetition of pulses in each pulse bundle depending on the frequency of the sinusoidal voltage (or power) supplied to the controller-generator used.

With the present system, the basic frequency, $f_b$, ranges from approximately 0.66 imp./sec. to 60 imp./sec. with a 60 Hz power supply; and between 0.55 to 50 imp./sec. with 50 Hz power supplied to the Controller.

3. RHUMART Physiological Conditioning combined to other types of procedures

RHUMART conditioning can be combined with classical medical procedures such as balneological procedures and chemotherapy (with the exception of antibiotics and bacteriological treatments where RHUMART Conditioning should be interrupted until the termination of these treatments.

The therapies of nature-cure practitioners such as ozone therapy (or negative ion therapy); as well as all homeopathic treatment modalities can be combined with RHUMART Physiological Conditioning.

For the above possibilities of combined procedures, RHUMART conditioning can be used either simultaneously, before or immediately after the procedure combined with the RHUMART technique.

However, during the entire RHUMART Conditioning course, there should be no diagnostic X-rays taken, except at the beginning and at the end of the Conditioning course, for follow-up and diagnostic purposes.

I claim:

1. An electrophysiological conditioning system comprising generator means, said generator means feeding one or more conditioning applicators with specific signals, said specific signals being adjustable so as to generate in combination desired magnetic and electric conditioning field signals, said applicators being electromagnetic and/or electrode conditioning applicators, means to measure effective conditioning magnetic field parameters, said parameters including the intensity and the direction or polarity of the said magnetic field parameters, said means to measure said parameters allowing for precise or desired readjustments of said magnetic field parameters to desired values in predetermined areas or spacial volumes in the space surrounding the said one or more electromagnetic conditioning applicators, said magnetic and electric conditioning field signals have a critical damping or nearly critical damping characteristic waveform, said conditioning system having adjustment means for the adjustment or choice of polarity of the said conditioning signals, said conditioning applicators including one or more electromagnetic coil applicators and one or more pairs of electrodes connected to an associated one of said generator means through predetermined interface circuit means, said conditioning system being characterized in that said interface circuit means allows for independent adjustments of the said electric conditioning field signals to desired values and this independently of the amplitude or intensity of the chosen and effective magnetic conditioning field signals which are provided in combination, said conditioning system being capable of producing said conditioning field signals having a peak amplitude in the range of approximately 0.01 to 5 millivolts per centimeter of voltage per unit length in the close surrounding of said one or more electromagnetic applicators, for the said conditioning signals induced by means of said magnetic field signals in the space surrounding the said one or more electromagnetic coil applicators, and a peak amplitude in the range of approximately 1 to 200 volts between the two electrodes of said one or more pairs of electrodes for the said electric conditioning field signals.

2. A system as claimed in claim 1, further comprising means to secure certain said coil or combinations of coil applicators in a predetermined fixed position.

3. A system as claimed in claim 1 wherein said one or more coil applicators is/are constituted by one or more hollow cylinder(s), each of which is made of two layers of strong thin sheet material held together by fixation means, and an electromagnetic coil or winding having a desired number of turns and being secured between said layers, said coil or winding generating said conditioning fields.

4. A system as claimed in claim 3 wherein said winding is made of coated copper, coated aluminum or a light conductive wire coated with a good electrical insulator having a large mechanical resistance, especially for aluminum coated wire.

5. A system as claimed in claim 3 wherein said fixation means includes an assembly box comprised of one inner and one outer part held together by means of two end blocks into which the said parts are fixed by means of special screws or other means.

6. A system as claimed in claim 5 wherein said inner and outer parts are aluminum parts.

7. A system as claimed in claim 3 wherein said sheets of material are fixed to the said coil or winding by glue or other fixation means in order to provide flexibility and solid bonding of said one or more hollow cylinder coil applicators.

8. A system as claimed in claim 5 wherein said winding is connected to an electrical cord of said coil applicator by means of a strain release like attachment and soldering or fixing said coil to said cord by means of connectors having pressure fixation means or using a known soldering or welding means.

9. A system as claimed in claim 1 wherein said one or more coil applicators is/are one or more circular ring coil applicators, each of which include a winding having a desired number of turns so as to generate said conditioning fields, said winding having protective means, and being made of coated copper, coated aluminum or another light conductive material or compound, said winding being connected and fixed to an electrical cord of said coil applicator by means of soldering, welding or pressure connectors.

10. A system as claimed in claim 9 wherein two or more said circular ring applicators are each interconnected by means of said electrical cord and having an adjustable length using a special lead-length adjuster through which one adjustable length turn of said cord is fed back through said lead-length adjuster and then connected to another of said circular ring coil applicator of two or more of said coil applicators so as to allow the adjustment of the distance between two adjacent ring applicators by pulling them apart or by pushing the said connecting cord into said lead-length adjuster.

11. A system as claimed in claim 1 wherein said one or more coil applicators include one or more quasi-rectangular shaped coreless coils, said quasi-rectangular coil being individual coil(s) or connected with other like coils, said coils having the number and size of turns so as to generate the said conditioning fields, and wherein windings of said coils are made of coated copper, coated aluminum or other low-weight conductive wire.

12. A system as claimed in claim 1 wherein said one or more coil applicators is/are one or more quasi-rectangular shaped coils connected in pairs in a flexible pad having one bending angle near its middle, said flexible pads being connected in pairs by means of a mechanical cable-length adjuster, said adjuster being composed of a cable fixed to one of said pairs of flexible pads and passing through a hole in the other of said pair of flexible pads and fixed to a small solid end plate having a hole big enough to thread the said cable through said end plate before fixing it to the said one flexible pad and the two pairs of said coils in said flexible pad being connected together by means of electrical leads, each said coil having a predetermined number of turns so as to generate the said conditioning fields, and wherein windings of said coils are made of coated copper, coated aluminum or other low-weight conductive wire.

13. A system as claimed in claim 1 wherein said one or more coil applicators is/are linear elongated or "U" or "V" shaped core coil(s) composed of laminated carbon steel with oriented magnetic domains or its equivalent; said laminations being held together with insulating electrical tape and one layer of heat-shrink type of cable, said winding of said coil being made of coated copper, coated aluminum or similar low weight conductive wire, and the number of turns of said winding being predetermined to generate the said conditioning fields, a second layer of heat shrink cable protecting said winding, and an insulating cylindrical box protecting said winding which is connected to an electrical lead through a known strain release means.

14. A system as claimed in claim 13 wherein said coils is/are used individually or in pairs, with the number of turns of said coils so as to generate the said conditioning fields.

15. A system as claimed in claim 3, 9 or 11 wherein said one or more hollow cylinder, circular ring or quasi rectangular shaped coils are large enough to fit around various body articulations, large portions of the human body or of a selected animal for application of said conditioning pulses.

16. A system as claimed in claim 15 wherein each of said one or more cylinder coils are made of two layers of strong thin sheet material held together by fixation means, and a coil having a disired number of turns is secured between said layers and generates said conditioning signals.

17. A system as claimed in claim 16 wherein said winding is made of coated copper, coated aluminum or a light conductive wire coated with a good electrical insulator having a large mechanical resistance, especially for aluminum coated wire.

18. A system as claimed in claim 16 wherein said fixation means includes an assembly box comprised of one inner and one outer part held together by means of two end blocks into which the said pans are fixed by means of special screws or other means.

19. A system as claimed in claim 18 wherein said inner an outer parts are aluminum parts.

20. A system as claimed in claim 18 wherein said winding is connected to an electrical cord of said coil applicator by means of a strain release like attachment and soldering or fixing wires together by means of connectors having pressure fixation means.

21. A system as claimed in claim 16 wherein said sheets of material are fixed to the said winding by glue in order to provide flexibility and solid bonding of said hollow cylinder coil.

22. A system as claimed in claim 9 wherein said one or more circular ring coils include a winding having a desired number of turns so as to generate said conditioning signals, said winding having protective means, and being made of coated copper, coated aluminum or an other light conductive material or compound, said winding being connected and fixed to an electrical cord of said coil applicator by means of soldering or pressure-connectors.

23. A system as claimed in claim 22 wherein two or more said circular ring coils are each interconnected by means of said electrical cord and having an adjustable length using a special lead-length-adjuster through which one adjustable length turn of said cord is fed back through said lead-length-adjuster and then connected to another of said circular ring coil of two or more of said coils so as to allow the adjustment of the distance between two adjacent ring coils by pulling them apart or by pushing the said connecting cord into said lead-length-adjuster.

24. A system as claimed in claim 12 wherein said quasi-rectangular shaped coils are connected by pair in a flexible pad having one bending angle near its middle, said flexible pads being connected in pair by means of a mechanical cable-length adjuster, said adjuster being composed of a cable fixed to one of said pair of flexible pads and passing through a hole in the other of said pair of flexible pads and fixed to a small solid end plate having a hole big enough to thread the said cable through said end plate before fixing it to the said one flexible pad and the two pairs of said coils in said flexible pad being connected together by means of electrical leads, each said coil having a predetermined number of turns so as to generate the proper conditioning signals.

25. A system as claimed in claim 11 or 12 wherein said quasi-rectangular shaped coils are individual coils or connected with other like coils, said coils having the number and size of turns so as to generate the proper conditioning signals.

26. A system as claimed in claim 24 or 25 wherein said windings of said coils are made of coated copper, coated aluminium or other low weight conductive wire.

27. A system as claimed in claim 13 wherein said linear elongated or "U" or "V" shaped core coils are composed of laminated carbon-steel with oriented magnetic domains or its equivalent; said laminations being held together with insulating electrical tape and one layer of heat-shrink type of cable, said winding of said coil being made of coated copper, coated aluminum or similar low weight conductive wire, and the number of turns of said winding being predetermined to generate the proper conditioning signals.

28. A system as claimed in claim 27 wherein said coils are used individually or in pairs, with the number of turns of said coils and said damping resistance being selected so as to generate the proper conditioning signals.

29. A system as claimed in claim 1 wherein said electrodes are made of flexible and conductive material having a desired shape.

30. A method of producing electromagnetic and electrophysiological conditioning signals capable of inducing or amplifying physiological effects of relaxation of the nervous system, stimulation of blood circulation and stimulation of normal cell repair and regeneration, and capable of enhancing the natural self-defense and healing mechanisms of man and animals, said method comprising the steps of:

i) producing pulsating conditioning signals each having a critical damping or nearly critical damping waveform and wherein the value and nature of components of a circuit or a computer means generating the said waveform can be varied so as to decrease the maximum intensity of said conditioning signals by not more then 75% of that generated with critical damping conditions, or a waveform defined by the derivative with respect to time of said critical damping or nearly critical damping waveform.

ii) selecting one or more conditioning applicators to transmit said conditioning signals, said applicators being selected from one or more electromagnetic coil applicators and/or one or more pairs of electrodes connected to one or more controller generator means through predetermined interlace circuit means dependent on a selected one or more of said conditioning applicators, iii) adjusting the intensity of said conditioning pulsating signals to a selected intensity in the range of from 0.1 to approximately 200 µA/cm$^2$, said signals being similar to biological impulses present in the human nervous system, adjusting said intensity in accordance with desired physiological effect and the user's needs, tolerance and response to said conditioning, iv) adjusting the basic frequency or pulse rate of said conditioning signals to a selected frequency or pulse rate in the range of 0.55 Hz or 0.55 pulse per second to 180 Hz or 180 pulses per second, according to the desired physiological effect and the user's needs, tolerance and response to said conditioning, v) selecting the modulation of said conditioning signals according ro the desired physiological effects and the user's tolerence to said conditioning, vi) selecting the duration of said conditioning according to the desired physiological effects and the user tolerance to said conditioning, and vii) selecting the polarity of said conditioning signals from each said conditioning applicator or pairs of said applicators.

\* \* \* \* \*